(12) United States Patent
Thatte et al.

(10) Patent No.: US 12,109,219 B2
(45) Date of Patent: *Oct. 8, 2024

(54) CANNABINOID RECEPTOR MODULATORS

(71) Applicant: Arena Pharmaceuticals, Inc., New York, NY (US)

(72) Inventors: Jayant Thatte, San Diego, CA (US); Anthony C. Blackburn, San Diego, CA (US); Sangdon Han, San Diego, CA (US); Robert M. Jones, San Diego, CA (US); Jae-Kyu Jung, San Diego, CA (US); Antonio Garrido Montalban, San Diego, CA (US); Biman B. Pal, San Diego, CA (US); Jaimie Karyn Rueter, San Diego, CA (US); Sonja Strah-Pleynet, Newton, MA (US); Lars Thoresen, San Diego, CA (US); Yifeng Xiong, San Diego, CA (US); Dawei Yue, San Diego, CA (US); Xiuwen Zhu, San Diego, CA (US)

(73) Assignee: Arena Pharmaceuticals, Inc., New York, NY (US)

( * ) Notice: Subject to any disclaimer, the term of this patent is extended or adjusted under 35 U.S.C. 154(b) by 172 days.

This patent is subject to a terminal disclaimer.

(21) Appl. No.: 16/849,216

(22) Filed: Apr. 15, 2020

(65) Prior Publication Data
US 2021/0060040 A1 Mar. 4, 2021

Related U.S. Application Data

(63) Continuation of application No. 15/427,303, filed on Feb. 8, 2017, now Pat. No. 10,632,134, which is a continuation of application No. 14/001,132, filed as application No. PCT/US2012/026507 on Feb. 24, 2012, now Pat. No. 9,597,340.

(60) Provisional application No. 61/446,727, filed on Feb. 25, 2011.

(51) Int. Cl.
*A61K 31/675* (2006.01)
*A61K 31/416* (2006.01)
*A61K 31/4439* (2006.01)
*A61K 31/497* (2006.01)
*A61K 45/06* (2006.01)

(52) U.S. Cl.
CPC .......... *A61K 31/675* (2013.01); *A61K 31/416* (2013.01); *A61K 31/4439* (2013.01); *A61K 31/497* (2013.01); *A61K 45/06* (2013.01)

(58) Field of Classification Search
CPC .................................................. A61K 31/675
See application file for complete search history.

(56) References Cited

U.S. PATENT DOCUMENTS

| | | | |
|---|---|---|---|
| 5,977,108 A | 11/1999 | Kikuchi et al. | |
| 6,329,402 B1 | 12/2001 | Kikuchi et al. | |
| 6,541,474 B2 | 4/2003 | Kikuchi et al. | |
| 6,630,463 B2 | 10/2003 | Kikuchi et al. | |
| 6,884,808 B2 | 4/2005 | Kikuchi et al. | |
| 7,741,350 B1 | 6/2010 | Luo | |
| 9,492,447 B2* | 11/2016 | Thatte | A61P 35/00 |
| 9,597,340 B2* | 3/2017 | Thatte | A61K 45/06 |
| 9,867,822 B2* | 1/2018 | Thatte | A61P 13/12 |
| 10,632,134 B2* | 4/2020 | Thatte | A61K 31/675 |
| 11,771,695 B2* | 10/2023 | Thatte | A61P 13/12 |
| | | | 514/231.5 |
| 2007/0041994 A1 | 2/2007 | Kerr et al. | |
| 2007/0191362 A1 | 8/2007 | Liotta et al. | |
| 2008/0064740 A1 | 3/2008 | Bolli et al. | |
| 2010/0160288 A1 | 6/2010 | Astles et al. | |
| 2012/0088751 A1 | 4/2012 | Lazzari et al. | |
| 2015/0126477 A1* | 5/2015 | Thatte | A61K 31/416 |
| | | | 514/80 |
| 2017/0143704 A1* | 5/2017 | Thatte | A61P 9/12 |
| 2017/0304327 A1* | 10/2017 | Thatte | A61K 31/4439 |
| 2020/0069681 A1* | 3/2020 | Thatte | A61P 1/02 |
| 2022/0241274 A1* | 8/2022 | Thatte | A61P 3/10 |

FOREIGN PATENT DOCUMENTS

| | | |
|---|---|---|
| DE | 102004054666 | 5/2006 |
| EP | 0838453 | 4/2005 |
| EP | 1177187 | 7/2007 |
| FR | 28752030 | 3/2006 |
| WO | WO 97/02244 | 1/1997 |

(Continued)

OTHER PUBLICATIONS

"PI3K1 Akt Cell Signaling," (2010) www.cellsignal.com.
Alexander et al., (2009) "Cannabinoids in the treatment of cancer" Cancer Letters 285:6-12.
Anand et al., (2008) "Cannabinoid Receptor CB2 localisation And Agonist-Mediated Inhibition Of Capsaicin Responses In Human Sensory Neurons," Pain, doi:10.1016/i.pain.2008.06.007.
Belvisi et al., (2008) "Inhibitory Activity Of The Novel CB2 Receptor Agonist, GW833972A, On Guinea-Pig And Human Sensory Nerve Function In The Airways," British Journal of Pharmacology 1-11.

(Continued)

*Primary Examiner* — John S Kenyon
(74) *Attorney, Agent, or Firm* — Haley Guiliano LLP

(57) ABSTRACT

Provided are certain methods useful in the treatment of cancer comprising administering a compound of Formula Ia and pharmaceutical compositions thereof that modulate the activity of the cannabinoid $CB_2$ receptor;

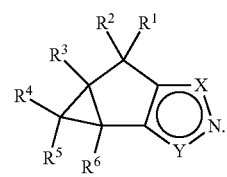

Ia

20 Claims, 12 Drawing Sheets

(56) References Cited

FOREIGN PATENT DOCUMENTS

| WO | WO 2000/064888 | 11/2000 | | |
|---|---|---|---|---|
| WO | WO 04/060882 | 7/2004 | | |
| WO | WO 2005/123677 | 12/2005 | | |
| WO | WO 2006/025069 | 3/2006 | | |
| WO | WO 2006/030124 | 3/2006 | | |
| WO | WO 2006/069242 | 6/2006 | | |
| WO | WO 06/129178 | 12/2006 | | |
| WO | WO 2006/129178 | 12/2006 | | |
| WO | WO 08/003665 | 1/2008 | | |
| WO | WO 08/039645 | 4/2008 | | |
| WO | WO 08/048914 | 4/2008 | | |
| WO | WO 08/053341 | 5/2008 | | |
| WO | WO 08/063781 | 5/2008 | | |
| WO | WO 08/064054 | 5/2008 | | |
| WO | WO 08/079316 | 7/2008 | | |
| WO | WO 08/085302 | 7/2008 | | |
| WO | WO 08/109007 | 9/2008 | | |
| WO | WO 08/119694 | 10/2008 | | |
| WO | WO 08/157500 | 12/2008 | | |
| WO | WO 08/157751 | 12/2008 | | |
| WO | WO 09/009550 | 1/2009 | | |
| WO | WO 09/015169 | 1/2009 | | |
| WO | WO 09/025785 | 2/2009 | | |
| WO | WO 2010/088050 | 8/2010 | | |
| WO | WO 2012/116276 | 8/2010 | | |
| WO | WO 2011/025541 | 3/2011 | | |
| WO | WO-2011025541 A1 * | 3/2011 | ............... | A61P 1/16 |
| WO | WO 2012/116278 | 8/2012 | | |
| WO | WO 2012/116279 | 8/2012 | | |

OTHER PUBLICATIONS

Bingham et al., (2007) "Species-specific In Vitro Pharmacological Effects Of The Cannabinoid Receptor 2 (CB2) Selective Ligand AM1241 And Its Resolved Enantiomers," British Journal of Pharmacology 151:1061-1070.

Boatman et al., (2010) "Potent tricyclic pyrazole tetrazole agonists of the nicotinic acid receptor (GPR109a)," Bioorganic & Medicinal Chemistry Letters, 20:2797-2800.

Bouaboula et al., (1996) "Signaling Pathway Associated With Stimulation Of CB2 Peripheral Cannabinoid Receptor," Eur. J. Biochem. 237:704-711.

Caffarel et al., (2010) "Cannabinoids Reduce ErbB2-Driven Breast Cancer Progression Through Akt Inhibition," Molecular Cancer 2010, 9:196 and Supplement.

Carracedo et al., (2006) "Cannabinoids Induce Apoptosis of Pancreatic Tumor Cells via Endoplasmic Reticulum Stress-Related Genes," Cancer Res 66:6748-6755.

Casanova et al., (2003) "Inhibition Of Skin Tumor Growth And Angiogenesis In Vivo By Activation Of Cannabinoid Receptors," J. Clin. Invest. 111 :43-50 doi: 10.1172/JC1200316116.

Cheng et al., (2008) "Discovery and Optimization of a Novel Series of N-Arylamide Oxadiazoles as Potent, Highly Selective and Orally Bioavailable Cannabinoid Receptor 2 (CB2) Agonists," J. Med. Chem. 51 :5019-5034.

Compton et al., (1992) "Aminoalkylindole Analogs: Cannabimimetic Activity of a Class of Compounds Structurally Distinct from D9-Tetrahydrocannabinols," JPET 263:1118-1126.

Di Marzo et al., (2006) "Plant, Synthetic, And Endogenous Cannabinoids In Medicine," Annu. Rev. Med. 57:553-74.

Diaz et al., (2008) "Design and Synthesis of a Novel Series of N-Alkyl Isatin Acylhydrazone Derivatives that Act as Selective Cannabinoid Receptor 2 Agonists for the Treatment of Neuropathic Pain," J. Med. Chem., 51 :4932-4947.

DiMauro et al., (2008) "Structural Modifications Of N-arylamide Oxadiazoles: Identification Of N-Arylpiperidine Oxadiazoles As Potent And Selective Agonists Of CB2," Bioorganic & Medicinal Chemistry Letters 18:4267-4274.

Ermann et al., (2008) "Arylsulfonamide CB2 receptor agonists: SAR and Optimization of CB2 Selectivity," Bioorganic & Medicinal Chemistry Letters 18:1725-1729.

Galiegue et al., (1995) "Expression Of Central And Peripheral Cannabinoid Receptors In Human Immune Tissues And Leukocyte Subpopulations," Eur. J. Biochem. 232:54-61.

Giblin et al., (2007) "Discovery of 2-[(2,4-Dichlorophenyl)amino]-N-[(tetrahydro-2H-pyran-4-y1)methyl]-4-(trifluoromethyl)-5-pyrimidinecarboxamide, a Selective CB2 Receptor Agonist for the Treatment of Inflammatory Pain," J. Med. Chem. 50:2597-2600.

Goodman et al., (2009) "CB2 selective Sulfamoyl Benzamides: Optimization Of The Amide Functionality," Bioorganic & Medicinal Chemistry Letters 19:309-313.

Graham et al., (2009) "Cannabinoid Receptors: A Brief History And 'What's Hot," Frontiers in Bioscience 14:944-957.

Hanus et al., (1999) "HU-308: A Specific Agonist For CB2, A Peripheral Cannabinoid Receptor," PNAS 96: 14228-14233.

Hosohata et al., (1997) "AM630 Antagonism Of Cannabinoid-Stimulated [$^{35}$S]GTPyS Binding In The Mouse Brain," European Journal of Pharmacology 321: R1-R3.

Ibn-e-Sina, Abu Ali; Al Qaanoon fil Tibb, 1987, p. 327. w/ English translation.

Khan, Mohammad Naimul Ghani; Khazaain al Advia, 1911, Pa 887. w/ English translation.

Khan, Mohammad Najmul Ghani; Khazaain al Advia, 1911, Pa 886. w/ English translation.

Khan, Mohammad Najmul Ghani; Khazaain al Advia, 1911, Pa 889. w/ English translation.

Kikuch et al., (2008) "Pharmacological Evaluation of a Novel Cannabinoid 2 (CB2) Ligand, PF-03550096, In Vitro and In Vivo by Using a Rat Model of Visceral Hypersensitivity," J Pharmacol Sci 106:219-224.

Lozano-Ondoua et al., (2010) "A Cannabinoid 2 Receptor Agonist Attenuates Bone Cancer-Induced Pain And Bone Loss," Life Sciences 86:646-653.

Maresz et al., (2007) "Direct Suppression Of CNS Autoimmune Inflammation Via The Cannabinoid Receptor CB1 On Neurons And CB2 On Autoreactive T Cells," Nature Medicine 13:492-497.

Markt et al., (2009) "Discovery of Novel CB2 Receptor Ligands by a Pharmacophore-Based Virtual Screening Workflow," J. Med. Chem. 52:369-378.

Marx et al., (2009) "Discovery Of a-Amidosulfones As Potent And Selective Agonists Of CB2: Synthesis, SAR, And Pharmacokinetic Properties," Bioorganic & Medicinal Chemistry Letters 19:31-35.

McKallip et al., (2002) "Targeting CB2 Cannabinoid Receptors As A Novel Therapy To Treat Malignant Lymphoblastic Disease," Blood 100:627-634.

Michalski et al., (2008) "Cannabinoids In Pancreatic Cancer: Correlation With Survival And Pain," Int J Cancer. 122:742-750.

Mitchell et al., (2009) "Pyridine-3-carboxamides As Novel CB2 Agonists For Analgesia," Bioorganic & Medicinal Chemistry Letters 19:259-263.

Munro et al., (1993) "Molecular Characterization Of A Peripheral Receptor For Cannabinoids," Nature 365:61-65.

Naguib et al., (2008) "MDA7: A Novel Selective Agonist For CB2 Receptors That Prevents Allodynia In Rat Neuropathic Pain Models," British Journal of Pharmacology 1-13.

Narayanan et al., (2006) "GRC 10622: A Novel Orally Active CB2 Receptor Agonist With Potential Anti-Hyperalgesic Effects," poster submitted at Society for Neuroscience—Oct. 14-18, 2006, Atlanta, Georgia, USA.

Nunez et al., (2004) "Cannabinoid CB2 Receptors Are Expressed by Perivascular Microglial Cells in the Human Brain: An Immunohistochemical Study," Synapse 53:208-213.

Ofek et al., (2006) "Peripheral Cannabinoid Receptor, CB2, Regulates Bone Mass," PNAS 103:696-701.

Ohta et al., (2007) "N-Alkylidenearylcarboxamides As New Potent And Selective CB2 Cannabinoid Receptor Agonists With Good Oral Bioavailability," Bioorganic & Medicinal Chemistry Letters 17:6299-6304.

Ohta et al., (2008) "Imine Derivatives As New Potent And Selective CB2 Cannabinoid Receptor Agonists With An Analgesic Action," Bioorganic & Medicinal Chemistry 16:1111-1124.

(56) References Cited

OTHER PUBLICATIONS

Olea-Herrero et al., (2009) "Inhibition Of Human Tumour Prostate PC-3 cell growth by Cannabinoids R(+)-Methanandamide and JWH-015: Involvement of CB2," British Journal of Cancer 101:940-950.
Omura et al., (2008) "The SAR Studies of Novel CB2 Selective Agonists, Benzimidazolone Derivatives," Bioorganic & Medicinal Chemistry Letters, doi: 10.1016/j.bmcl.2008.04.032.
Page et al., (2007) "New 1,2,3,4-Tetrahydropyrrolo[3,4-b]indole Derivatives As Selective CB2 Receptor Agonists," Bioorganic & Medicinal Chemistry Letters 17:6183-6187.
Page et al., (2008) "Novel Benzimidazole Derivatives As Selective CB2 Agonists," Bioorganic & Medicinal Chemistry Letters 18:3695-3700.
Palazuelos et al., (2008) "The CB2 Cannabinoid Receptor Controls Myeloid Progenitor Trafficking," http://www.jbc.org/cqi/doi/10.1074/jbc.M707960200.
Pasquini et al., (2008) "Investigations on the 4-Quinolone-3-carboxylic Acid Motif. 2. Synthesis and Structure-Activity Relationship of Potent and Selective Cannabinoid- 2 Receptor Agonists Endowed with Analgesic Activity in Vivo," J. Med. Chem. 51 : 5075-5084.
Pisanti et al., (2009) "Use Of Cannabinoid Receptor Agonists In Cancer Therapy As Palliative And Curative Agents," Best Practice & Research Clinical Endocrinology & Metabolism 23:117-131.
Preet et al., (2010) "Cannabinoid Receptors, CB1 and CB2, as Novel Targets for Inhibition of Non- Small Cell Lung Cancer Growth and Metastasis," Published Online First on Nov. 19, 2010 as 10.1158/1940-6207.CAPR-10-0181.
Rinaldi-Carmona et al., (1998) "SR 144528, the First Potent and Selective Antagonist of the CB2 Cannabinoid Receptor," JPET 284:644-650.
Sanchez et al., (2001) "Inhibition of Glioma Growth in Vivo by Selective Activation of the CB2 Cannabinoid Receptor," Cancer Research 61:5784-5789.
Sharma et al., (2010) "Cell Line-Based Platforms To Evaluate The Therapeutic Efficacy Of Candidate Anticancer Agents," Nature Reviews I Cancer 10:241-253.
Shi et al., (2008) "Cannabinoid 2 Receptor Induction By IL-12 And Its Potential As A Therapeutic Target For The Treatment Of Anaplastic Thyroid Carcinoma," Cancer Gene Therapy 15:101-107.
Slipetz et al., (1995) "Activation of the Human Peripheral Cannabinoid Receptor Results in Inhibition of Adenylyl Cyclase," Molecular Pharmacology, 48:352-361.
Stansfield et al., (2007) "Development Of Carboxylic Acid Replacements In Indole-N-acetamide Inhibitors Of Hepatitis C Virus NS5B Polymerase," Bioorganic & Medicinal Chemistry Letters 17:5143-5149.
Valenzano et al., (2003) "Pharmacological And Pharmacokinetic Characterization Of The Cannabinoid Receptor 2 Agonist, GW405833, Utilizing Rodent Models Of Acute And Chronic Pain, Anxiety, Ataxia And Catalepsy," Neuropharmacology 48:658-672.
Van Sickle et al., (2005) "Identification and Functional Characterization of Brainstem Cannabinoid CB2 Receptors," Science 310:329.
Verbist et al., (2008) "5-Sulfonyl-benzimidazoles As Selective CB2 Agonists," Bioorganic & Medicinal Chemistry Letters 18:2574-2579.
Whiteside et al., (2007) "The Role of the Cannabinoid CB2 Receptor in Pain Transmission and Therapeutic Potential of Small Molecule CB2 Receptor Agonists," Current Medicinal Chemistry, 14:917-936.
Worm et al., (2008) "Sulfamoyl Benzamides As Novel CB2 Cannabinoid Receptor Ligands," Bioorganic & Medicinal Chemistry Letters 18:2830-2835.
Wotherspoon et al., (2005) "Peripheral Nerve Injury Induces Cannabinoid Receptor 2 Protein Expression In Rat Sensory Neurons," Neuroscience 135:235-245.
Yao et al., (2008) "Characterization of a Cannabinoid CB2 Receptor Selective Agonist, A-836339, in In Vitro Pharmacological assays and In Vivo Pain Models," JPET Fast Forward. Published on Oct. 17, 2008 as DOI :1 0.1124/jpet. 1 08.145011.
Yao et al., (2008) "In Vitro And In Vivo Characterization Of A-796260: A Selective Cannabinoid CB2 Receptor Agonist Exhibiting Analgesic Activity In Rodent Pain Models," British Journal of Pharmacology 153:390-401.
Zindell et al., (2009) "Morpholine Containing CB2 Selective Agonists," Bioorganic & Medicinal Chemistry Letters, doi: 0.1016/i.bmcl.2009. 02.033.

* cited by examiner

CANNABINOID RECEPTOR MODULATORS

Cannabinoids are a group of extracellular signaling molecules that are found in both plants and animals. Signals from these molecules are mediated in animals by two G-protein coupled receptors, Cannnabinoid Receptor 1 ($CB_1$) and Cannabinoid Receptor 2 ($CB_2$). $CB_1$ is expressed most abundantly in the neurons of the CNS but is also present at lower concentrations in a variety of peripheral tissues and cells (Matsuda, L. A. et al. (1990) *Nature* 346:561-564). In contrast, $CB_2$ is expressed predominantly, although not exclusively, in non-neural tissues, e.g. in hematopoictic cells, endothelial cells, osteoblasts, osteoclasts, the endocrine pancreas, and cancerous cell lines (Munro, S. et al. (1993) *Nature* 365:61-65; and as reviewed in Pacher, P. et al. (2006) *Pharmacol. Rev.* 58(3): 389-462). As such, $CB_1$ is believed to be primarily responsible for mediating the psychotropic effects of cannabinoids on the body, whereas $CB_2$ is believed to be primarily responsible for most of their non-neural effects.

The texts of the references cited in this disclosure are herein incorporated by reference in their entireties. In the event that a definition of a term as incorporated by reference differs from the meaning defined herein, then the meaning provided herein is intended.

Provided is a composition comprising a compound of Formula Ia or a pharmaceutically acceptable salt, solvate, hydrate, and/or N-oxide thereof:

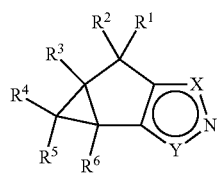

Ia wherein:
$R^1$, $R^2$, $R^3$, $R^4$, $R^5$, and $R^6$ are each independently selected from: H and $C_1$-$C_6$ alkyl;
X is $NR^7$ and Y is $CC(O)N(R^8)R^9$; or
X is $CC(O)N(R^8)R^9$ and Y is $NR^7$,
$R^7$ is —$R^{10}$—$R^{11}$—$R^{12}$—$R^{13}$; wherein:
$R^{10}$ is selected from: $C_1$-$C_6$ alkylene, heteroarylene, and heterocyclylene; or $R^{10}$ is absent;
$R^{11}$ is selected from: —C(O)NH— and $C_1$-$C_6$ alkylene; or $R^{11}$ is absent;
$R^{12}$ is $C_1$-$C_6$ alkylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;
$R^8$ is —$R^{14}$—$R^{15}$—$R^{16}$—$R^{17}$; wherein:
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;
$R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;
$R^{16}$ is $C_1$-$C_6$ alkylene; or $R^{16}$ is absent; and
$R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkyl amino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and
$R^9$ is selected from H, $C_1$-$C_6$ alkyl, and $C_3$-$C_7$ cycloalkyl; or
$R^8$ and $R^9$ together with the nitrogen atom to which they are both bonded form a group selected from: heterocyclyl and heterobicyclyl, each optionally substituted with one or more substituents selected from: Carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl,
and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents.

Also provided is a composition comprising a compound of Formula Ia or a pharmaceutically acceptable salt, solvate, hydrate, and/or N-oxide thereof, one or more known pharmaceutical agents selected from inhibitors of inherent multidrug resistance, anti-emetic agents, agents useful in the treatment of anemia, agents useful in the treatment of neutropenia, immunologic-enhancing agents, and anti cancer agents, and a pharmaceutically acceptable carrier.

Also provided is a method for preparing a composition comprising the step of admixing a compound of Formula Ia or a pharmaceutically acceptable salt, solvate, hydrate, and/or N-oxide thereof, and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents.

Also provided is a method for preparing a composition comprising the step of admixing a compound of Formula Ia or a pharmaceutically acceptable salt, solvate, hydrate, and/or or N-oxide thereof, and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents, and a pharmaceutically acceptable carrier.

Also provided is a composition obtained by any of the methods described herein.

Also provided is a method for the treatment of cancer in an individual in need thereof, comprising administering to said individual, a therapeutically effective amount of a compound of Formula Ia or a pharmaceutically acceptable salt, solvate, hydrate, and/or N-oxide thereof, wherein the cancer is not prostate cancer, leukemia, lymphoma, or a CNS tumor.

Also provided is a method for the treatment of cancer in an individual in need thereof, comprising prescribing to said individual, a therapeutically effective amount of a compound of Formula Ia or a pharmaceutically acceptable salt, solvate, hydrate, and/or N-oxide thereof wherein the cancer is not prostate cancer, leukemia, lymphoma, or a CNS tumor.

Also provided is a method for the treatment of cancer in an individual in need thereof, comprising administering to said individual, a therapeutically effective amount of a compound of Formula Ia or a pharmaceutically acceptable salt, solvate, hydrate, and/or N-oxide thereof, and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents, wherein the cancer is not prostate cancer, leukemia, lymphoma, or a CNS tumor.

Also provided is a method for the treatment of cancer in an individual in need thereof, comprising prescribing to said individual, a therapeutically effective amount of a compound of Formula Ia or a pharmaceutically acceptable salt, solvate, hydrate, and/or N-oxide thereof, and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents, wherein the cancer is not prostate cancer, leukemia, lymphoma, or a CNS tumor.

Also provided is a compound of Formula Ia, or a pharmaceutically acceptable salt, solvate, hydrate, and/or N-oxide thereof, for use in combination with and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents.

Also provided is a compound of Formula Ia, or a pharmaceutically acceptable salt, solvate, hydrate, and/or N-oxide thereof, for use in a method for the treatment of cancer in an individual in need thereof, comprising administering to said individual said compound, wherein the cancer is not prostate cancer, leukemia, lymphoma, or a CNS tumor.

Also provided is a compound of Formula Ia, or a pharmaceutically acceptable salt, solvate, hydrate, and/or N-oxide thereof, for use in a method for the treatment of cancer in an individual in need thereof, comprising prescribing to said individual said compound wherein the cancer is not prostate cancer, leukemia, lymphoma, or a CNS tumor.

Also provided is a compound of Formula Ia, or a pharmaceutically acceptable salt, solvate, hydrate, and/or N-oxide thereof, for use in a method for the treatment of cancer in an individual in need thereof, comprising administering to said individual said compound and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents, wherein the cancer is not prostate cancer, leukemia, lymphoma, or a CNS tumor.

Also provided is a compound of Formula Ia, or a pharmaceutically acceptable salt, solvate, hydrate, and/or N-oxide thereof, for use in a method for the treatment of cancer in an individual in need thereof, comprising prescribing to said individual said compound and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents, wherein the cancer is not prostate cancer, leukemia, lymphoma, or a CNS tumor.

Also provided is one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents for use in combination with a compound of Formula Ia, or a pharmaceutically acceptable salt, solvate, hydrate, and/or N-oxide thereof.

Also provided is one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents for use in a method for the treatment of cancer in an individual in need thereof, said method comprises administering to said individual one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents and a compound of Formula Ia, or a pharmaceutically acceptable salt, solvate, hydrate, and/or N-oxide thereof, wherein the cancer is not prostate cancer, leukemia, lymphoma, or a CNS tumor.

Also provided is one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents for use in a method for the treatment of cancer in an individual in need thereof, said method comprises prescribing to said individual one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents and a compound of Formula Ia, or a pharmaceutically acceptable salt, solvate, hydrate, and/or N-oxide thereof, wherein the cancer is not prostate cancer, leukemia, lymphoma, or a CNS tumor.

Also provided is a pharmaceutical product selected from: a pharmaceutical composition, a formulation, a dosage form, a combined preparation, a twin pack, and a kit; comprising a compound of Formula Ia, or a pharmaceutically acceptable salt, solvate, hydrate, and/or N-oxide thereof, and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents; for treating cancer in an individual, wherein the cancer is not prostate cancer, leukemia, lymphoma, or a CNS tumor.

Also provided is the use of a compound of Formula Ia, or a pharmaceutically acceptable salt, solvate, hydrate, and/or N-oxide thereof, in the manufacture of a medicament for treating cancer in an individual, wherein the cancer is not prostate cancer, leukemia, lymphoma, or a CNS tumor.

Also provided is the use of a compound of Formula Ia, or a pharmaceutically acceptable salt, solvate, hydrate, and/or N-oxide thereof, and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents in the manufacture of a medicament for treating cancer in an individual, wherein the cancer is not prostate cancer, leukemia, lymphoma, or a CNS tumor.

These and other aspects of the invention disclosed herein will be set forth in greater detail as the patent disclosure proceeds.

Figure 1:
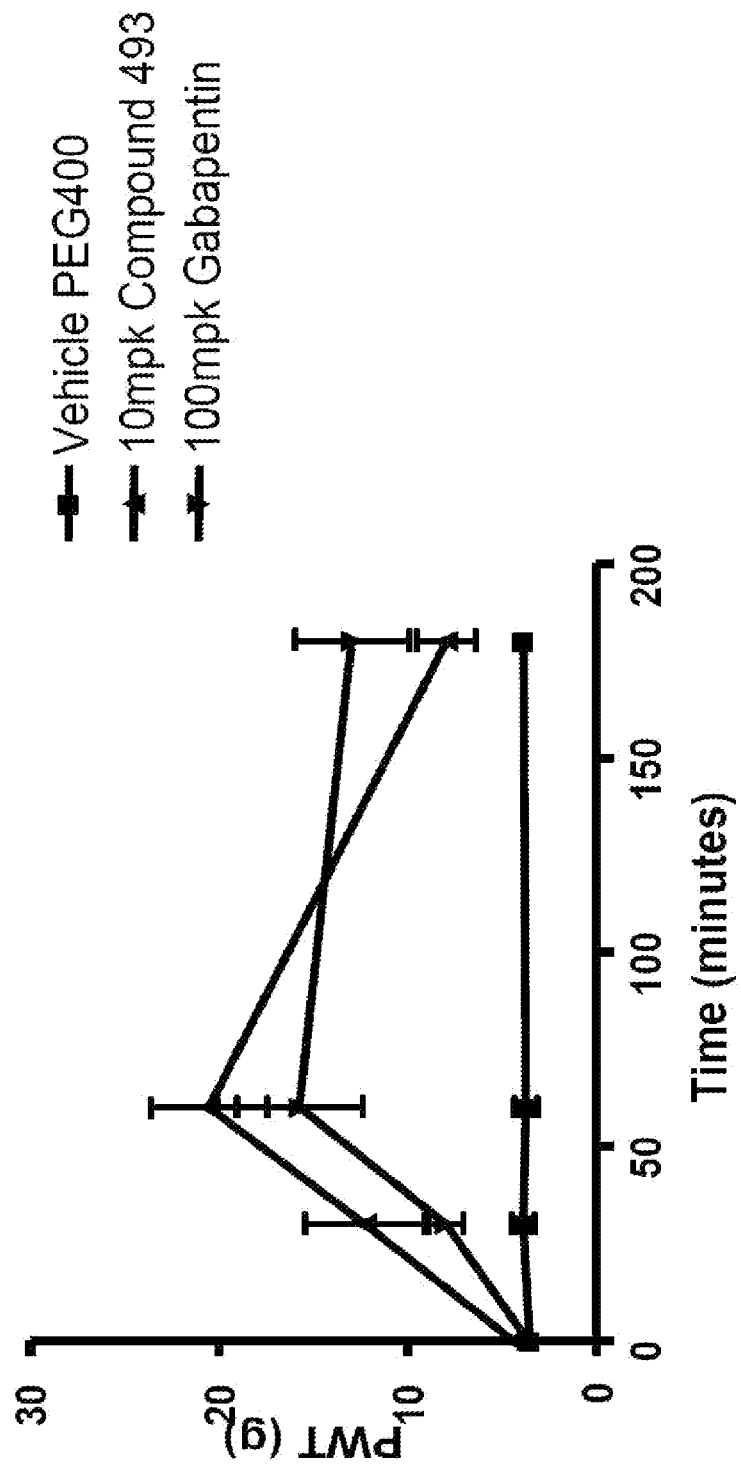
FIG. 1 shows the effect of 10 mg/kg of Compound 493 on paclitaxel-induced allodynia in rats. See Example 5.
Figure 2:
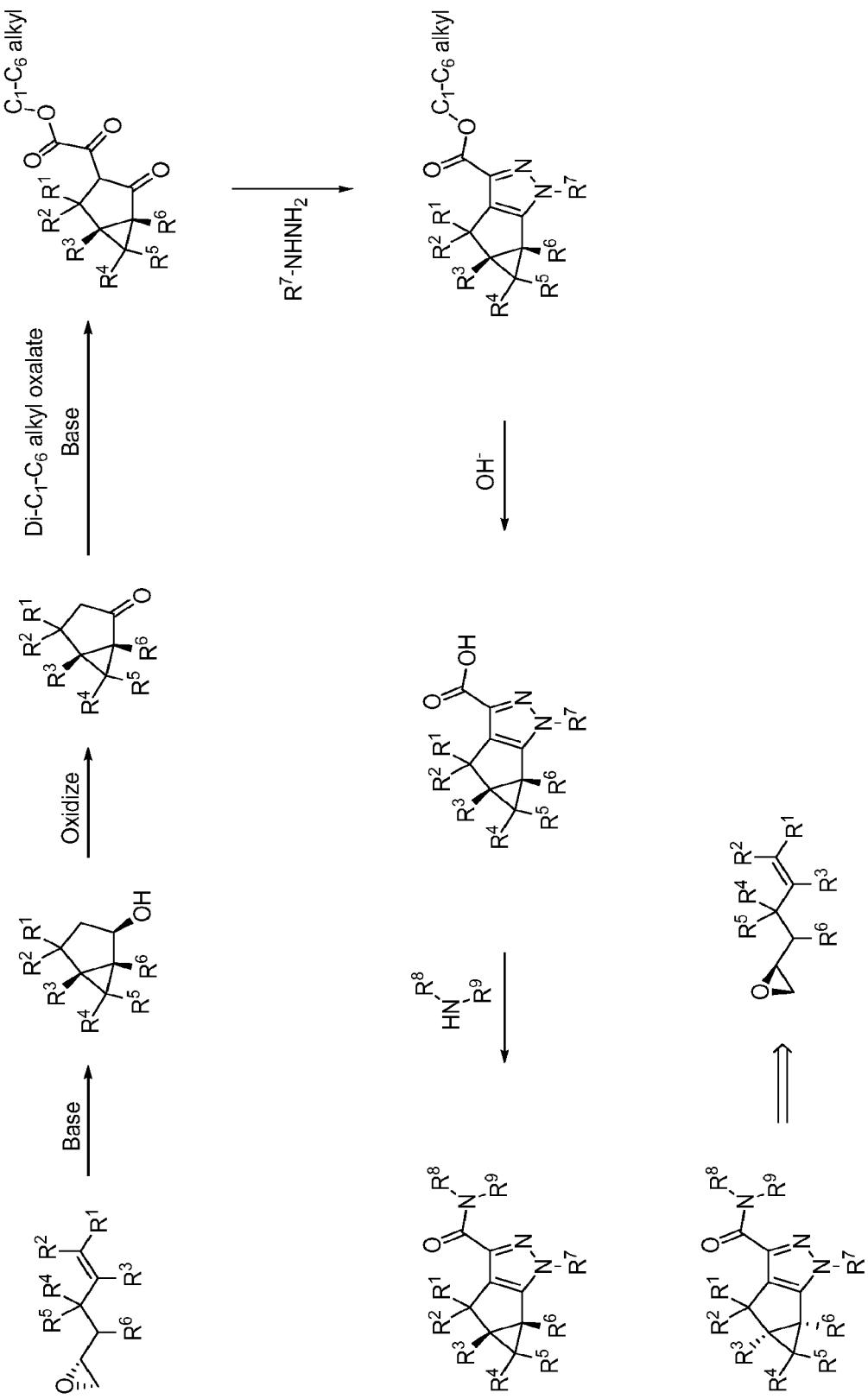
FIG. 2 shows a general synthesis of compounds described herein wherein X is CC(O)N($R^8$)$R^9$ and Y is $NR^7$. First, a 2-(but-3-enyl)oxirane derivative is cyclized by treatment with a base. The resulting bicyclic alcohol is oxidized to the ketone and reacted with a dialkyl oxalate derivative in the presence of a base. The pyrazole ring is then formed by reaction with a substituted hydrazine and the resulting ester is hydrolyzed and coupled with an amine to form compounds described herein.
Figure 3:
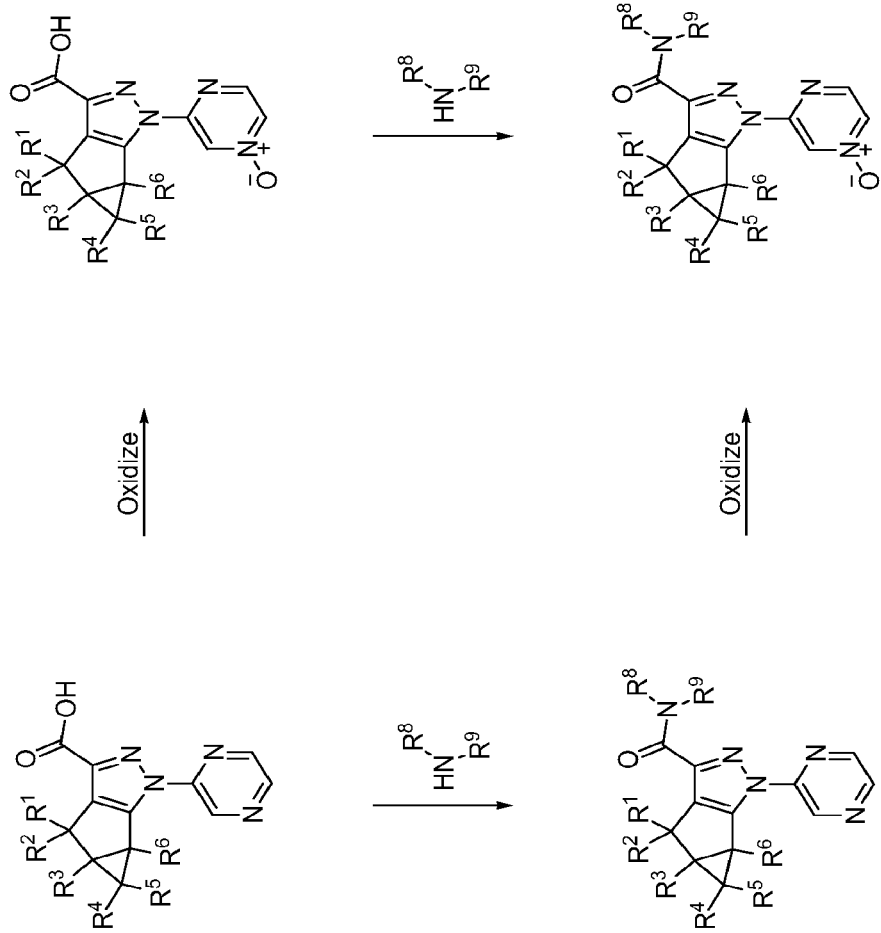
FIG. 3 shows a general synthesis of compounds described herein in which $R^7$ is a 4-oxy-pyrazin-2-yl group.
Figure 4:
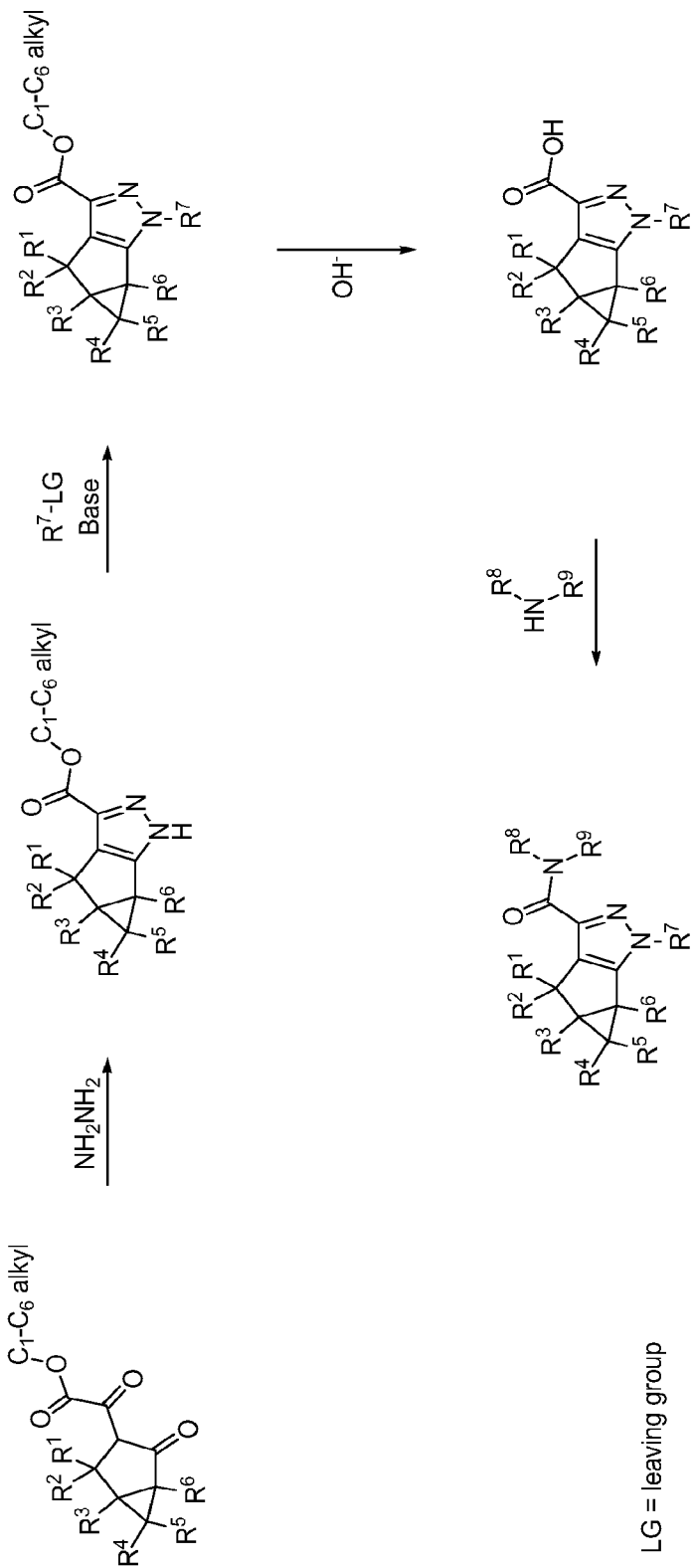
FIG. 4 shows a general synthesis of compounds described herein similar to the one shown in FIG. 2 except the group $R^7$ is introduced subsequent to the formation of a tri-substituted pyrazole.
Figure 5:
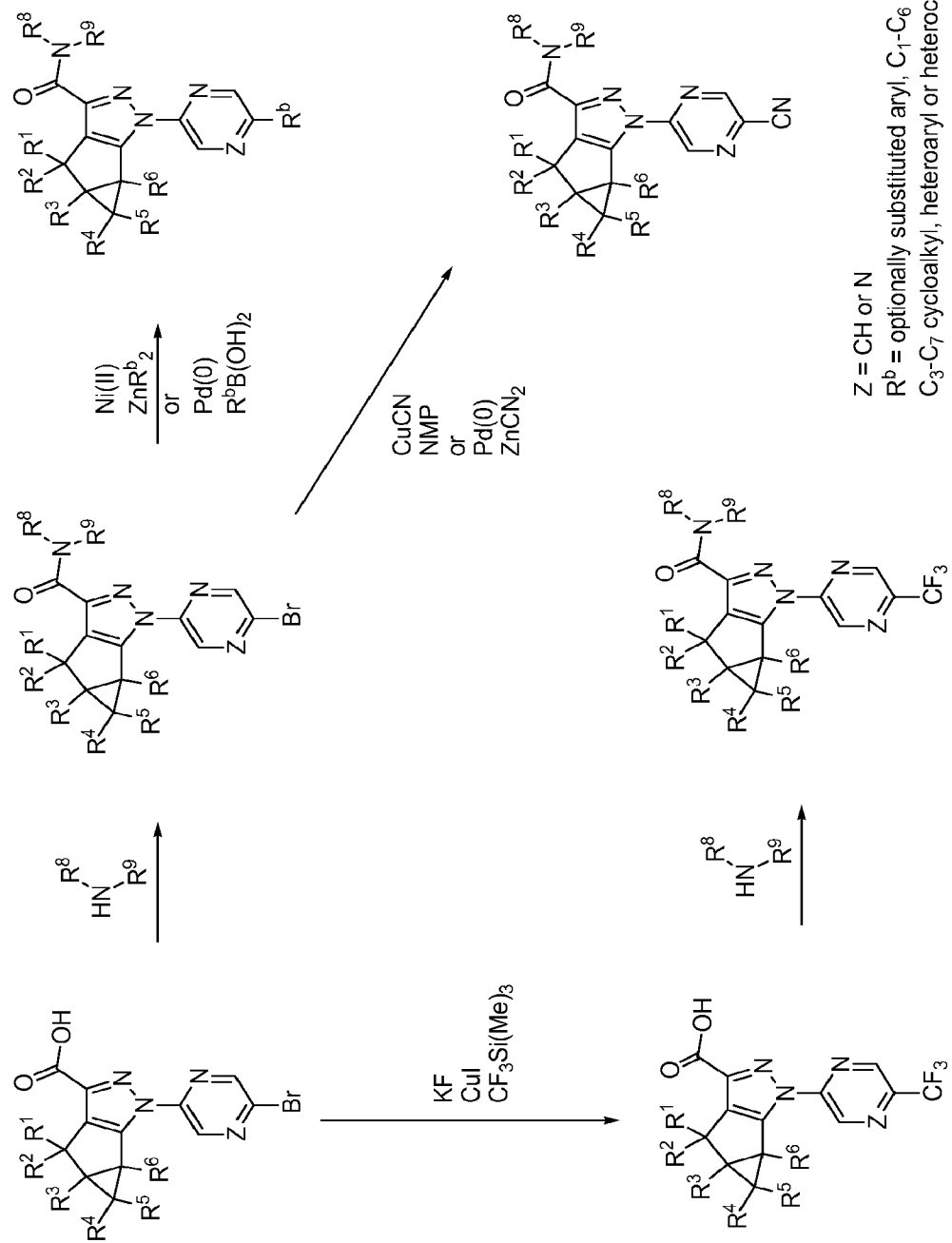
FIG. 5 shows a general synthesis of compounds described herein in which $R^7$ is either a 5-substituted-pyridin-2-yl group or a 5-substituted-pyrazin-2-yl group.
Figure 6:
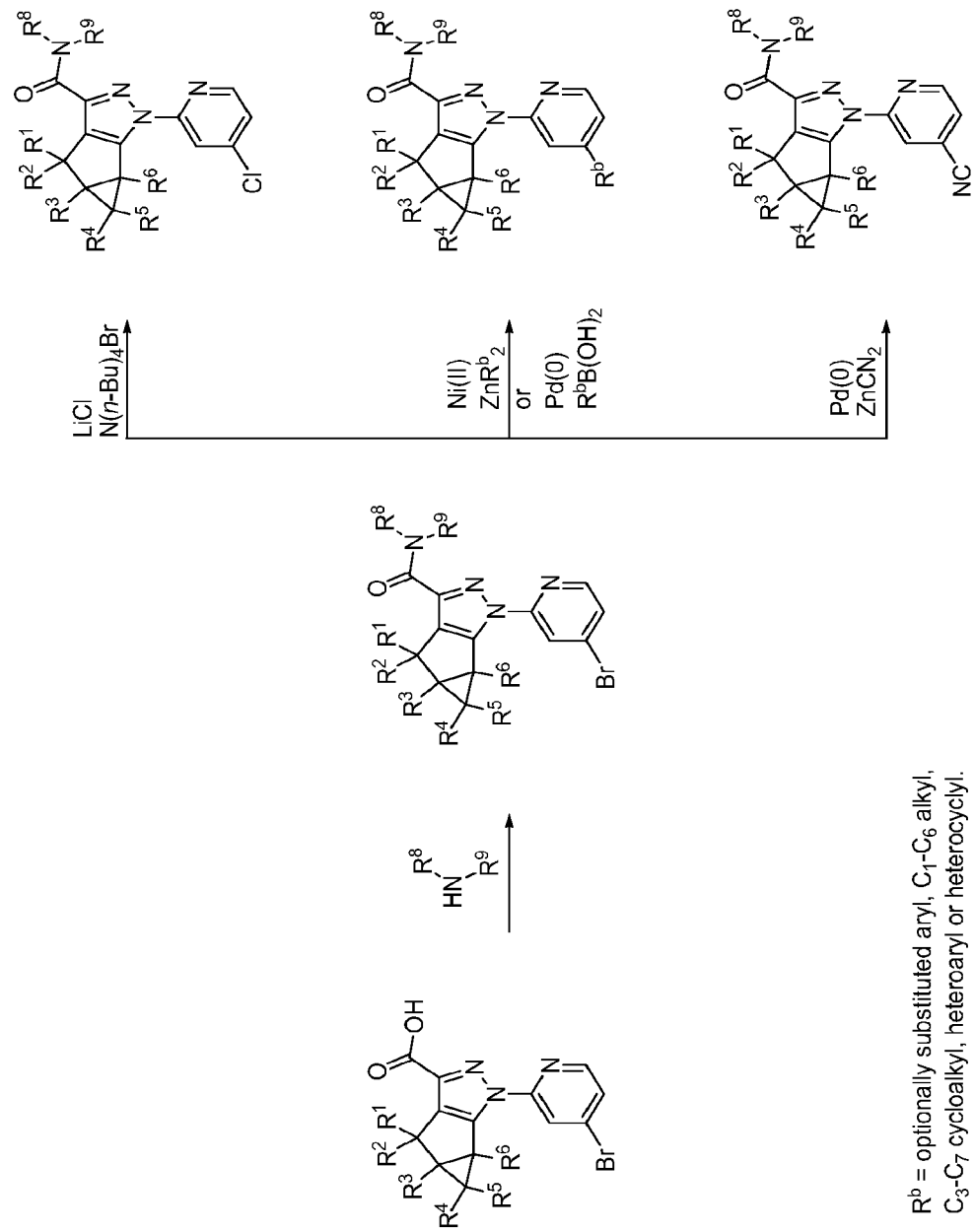
FIG. 6 shows a general synthesis of compounds described herein in which $R^7$ is a 4-substituted-pyridin-2-yl group.
Figure 7:
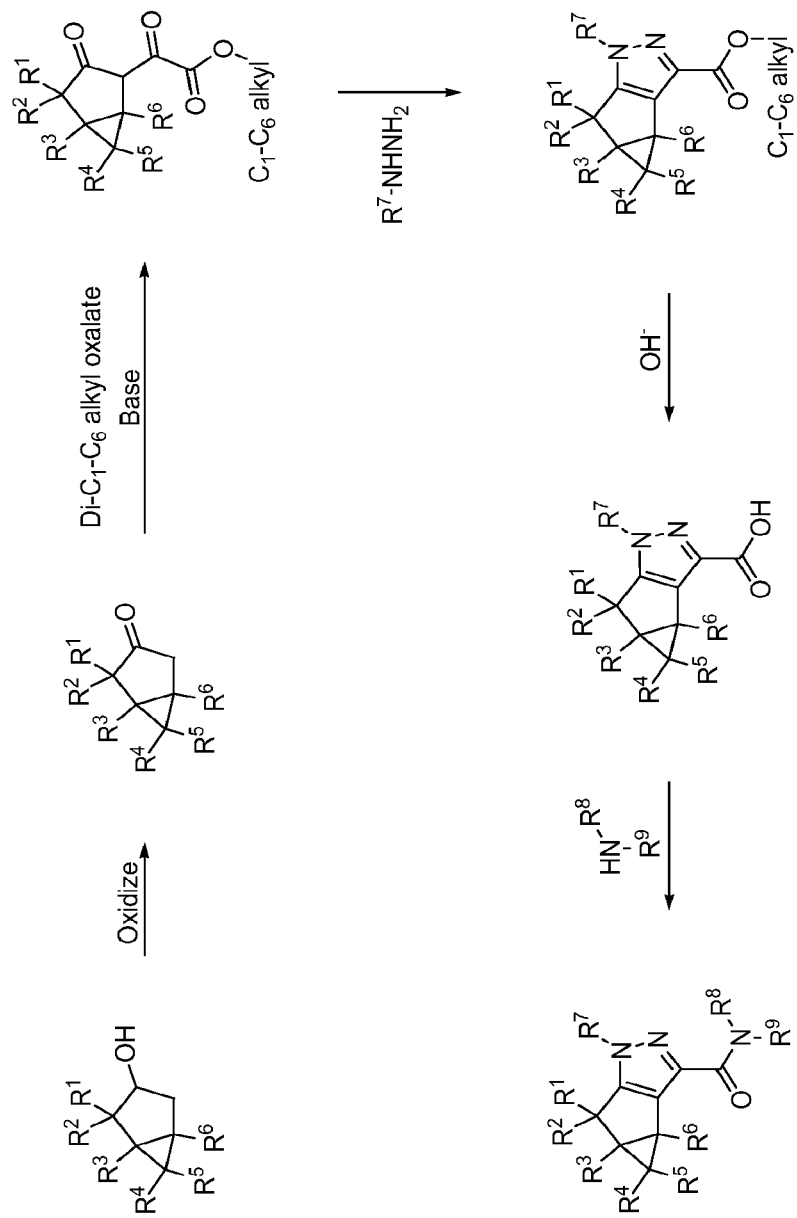
FIG. 7 shows a general synthesis of compounds described herein wherein X is $NR^7$ and Y is CC(O)N($R^8$)$R^9$. First, a bicyclo[3.1.0]hexan-3-ol derivative is oxidized and the resulting ketone is reacted with a dialkyl oxalate derivative in the presence of a base. The pyrazole ring is then formed by reaction with a substituted hydrazine and the resulting ester is hydrolyzed and coupled with an amine to form compounds described herein.
Figure 8:
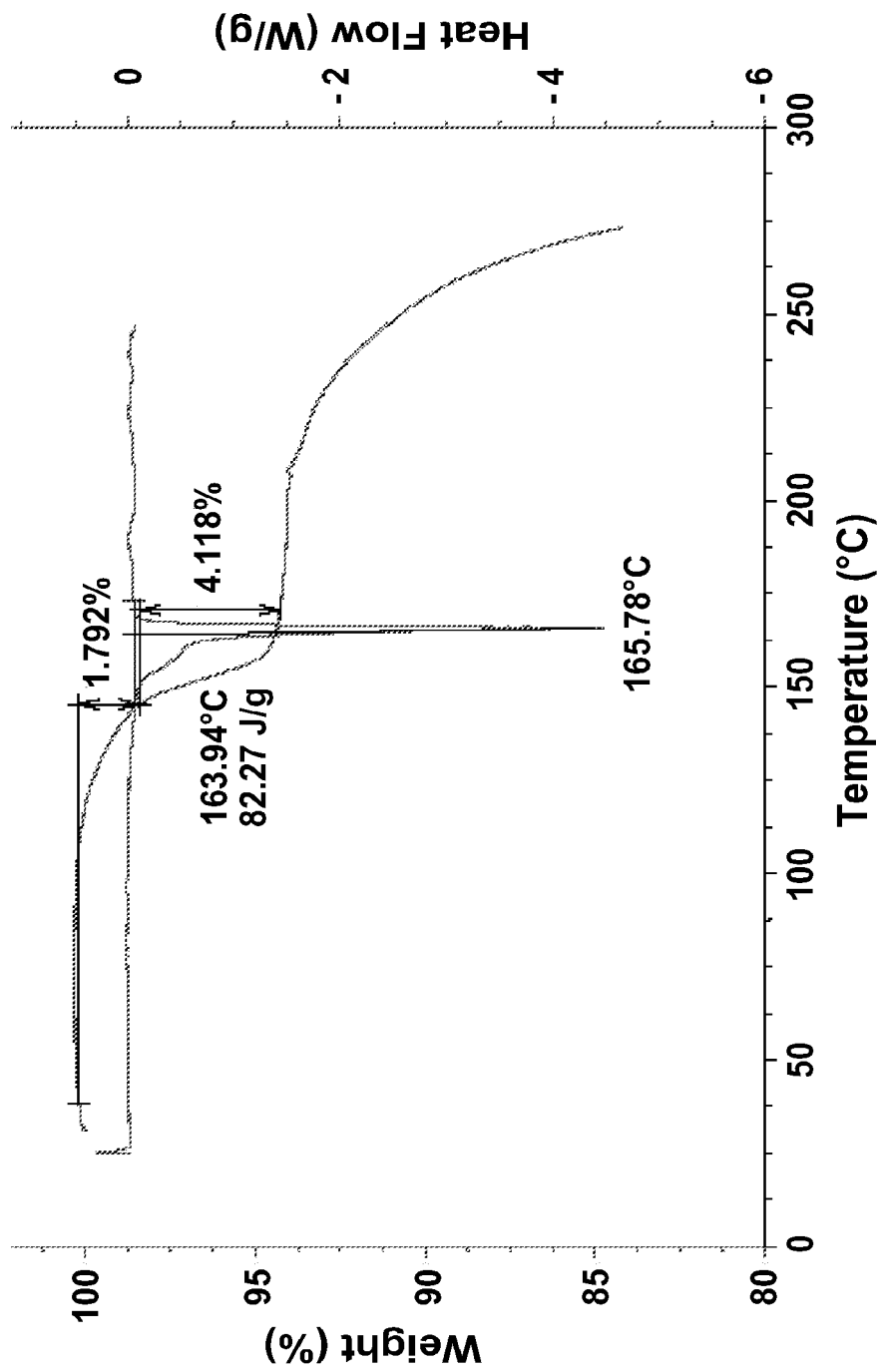
FIG. 8 shows a differential scanning calorimetry (DSC) thermogram for a sample containing a crystalline form of Compound 699 $CH_2Cl_2$ solvate and a thermogravimetric analysis (TGA) thermogram of a sample containing a crystalline form of Compound 699 $CH_2Cl_2$ solvate.
Figure 9:
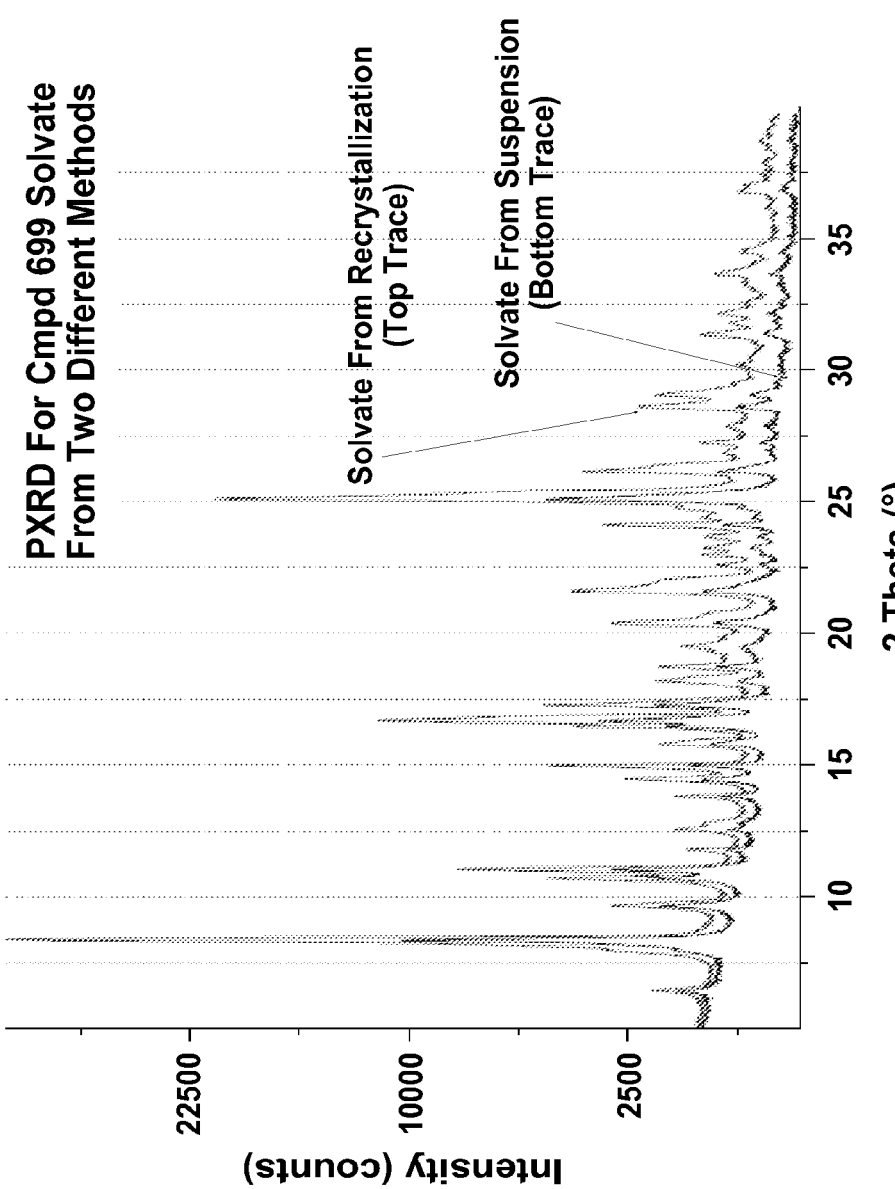
FIG. 9 shows an overlay of a powder X-ray diffraction pattern (PXRD) for a sample containing a crystalline form of Compound 699 $CH_2Cl_2$ solvate obtained from recrystallization using $CH_2Cl_2$/hexane (Top Trace) and a powder X-ray diffraction pattern (PXRD) for a sample containing a crystalline form of Compound 699 $CH_2Cl_2$ solvate obtained by slurrying non-solvated Compound 699 in $CH_2Cl_2$ (Bottom Trace). The PXRD showed the crystalline solvate obtained from the $CH_2Cl_2$ slurry is substantially indistinguishable from the crystalline solvate resulting from recrystallized from $CH_2Cl_2$/hexane.

For clarity and consistency, the following definitions will be used throughout this patent document.

The term "analgesic agent" is intended to mean any biomolecule, drug or active agent that alleviates or prevents pain.

The term "co-analgesic agent" is intended to mean a drug that typically addresses indications other than pain relief, but possesses analgesic action for certain painful conditions.

The term "anti-emetic agent" is intended to mean a drug to treat nausea or emesis, including acute, delayed, late-phase, and anticipatory emesis, which may result from the use of a compound described herein alone, another anticancer agent, or with radiation therapy.

The term "agonist" is intended to mean a moiety that interacts with and activates a G-protein-coupled receptor, for instance a cannabinoid receptor, and can thereby initiate a physiological or pharmacological response characteristic of that receptor. For example, an agonist may activate an intracellular response upon binding to a receptor, or enhance GTP binding to a membrane.

The term "antagonist" is intended to mean a moiety that competitively binds to the receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response in the absence of an agonist or partial agonist.

The term "hydrate" as used herein means a compound described herein or a salt thereof, that further includes a stoichiometric or non-stoichiometric amount of water bound by non-covalent intermolecular forces.

The term "solvate" as used herein means a compound described herein or a salt, thereof, that further includes a stoichiometric or non-stoichiometric amount of a solvent bound by non-covalent intermolecular forces. In some embodiments, the solvents are volatile, non-toxic, and/or acceptable for administration to humans in trace amounts.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds described herein. Accordingly, the compounds described herein can be used in a protective or preventive manner; or compounds described herein can be used to alleviate, inhibit or ameliorate the disease, condition or disorder.

The term "individual" is intended to mean any animal, including mammals, such as mice, rats, other rodents, rabbits, dogs, cats, swine, cattle, sheep, horses, or primates, and in some embodiments, humans.

The term "inverse agonist" is intended to mean a moiety that binds to the endogenous form of the receptor or to the constitutively activated form of the receptor and which inhibits the baseline intracellular response initiated by the active form of the receptor below the normal base level of activity which is observed in the absence of an agonist or partial agonist, or decreases GTP binding to a membrane. In some embodiments, the baseline intracellular response is inhibited in the presence of the inverse agonist by at least 30%, such as by at least 50% and for example, by at least 75%, as compared with the baseline response in the absence of the inverse agonist.

The term "modulate or modulating" is intended to mean an increase or decrease in the amount, quality, response or effect of a particular activity, function or molecule.

The term "pharmaceutical composition" is intended to mean a composition comprising at least one active ingredient; including but not limited to, salts, solvates, and hydrates of compounds described herein, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "therapeutically effective amount" is intended to mean the amount of active compound or pharmaceutical agent that elicits the biological or medicinal response in a tissue, system, animal, individual or human that is being sought by a researcher, veterinarian, medical doctor or other clinician or caregiver or by an individual, which includes one or more of the following:

(1) Preventing the disease, for example, preventing a disease, condition or disorder in an individual that may be predisposed to the disease, condition or disorder but does not yet experience or display the pathology or symptomatology of the disease;

(2) Inhibiting the disease, for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease, for example, ameliorating a disease, condition or disorder in an individual that is experiencing or displaying the pathology or symptomatology of the disease, condition or disorder (i.e., reversing the pathology and/or symptomatology).

The term "$C_1$-$C_4$ acyl" is intended to mean a radical comprising a $C_1$-$C_4$ alkyl group attached to the carbon of a carbonyl group, wherein $C_1$-$C_4$ alkyl has the same definition as found herein. Examples include, but are not limited to acetyl, propionyl, butyryl, isobutyryl, pivaloyl, and the like.

The term "amino" is intended to mean the group —$NH_2$.

The term "aryl" is intended to mean a ring system containing 6 to 10 carbon atoms, that may contain a single ring or two fused rings, and wherein at least one ring is aromatic. Examples include phenyl, indanyl, and naphthyl.

The term "arylamino" is intended to mean a radical comprising an aryl group, attached to a nitrogen, wherein aryl has the same definition as found herein. Examples include, but are not limited to, phenylamino and naphthylamino.

The term "arylcarbonyl" is intended to mean a radical comprising an aryl group, attached to the carbon atom of a carbonyl group, wherein aryl has the same definition as found herein. Examples include, but are not limited to, benzoyl and naphthylcarbonyl.

The term "aryloxy" is intended to mean a radical comprising an aryl group, attached to an oxygen, wherein aryl has the same definition as found herein. Examples include, but are not limited to, phenoxy and naphthyloxy.

The term "$C_1$-$C_6$ alkoxy" is intended to mean a radical comprising a $C_1$-$C_6$ alkyl group attached directly to an oxygen atom, wherein $C_1$-$C_6$ alkyl has the same definition as found herein. Some embodiments contain 1 to 5 carbons. Some embodiments contain 1 to 4 carbons. Some embodiments contain 1 to 3 carbons. Some embodiments contain 1 or 2 carbons. Examples include, but are not limited to methoxy, ethoxy, n-propoxy, isopropoxy, n-butoxy, t-butoxy, isobutoxy, s-butoxy, and the like.

The term "$C_1$-$C_6$ alkoxycarbonyl" is intended to mean a radical comprising a single $C_1$-$C_6$ alkoxy group attached to the carbon of a carbonyl group, wherein $C_1$-$C_6$ alkoxy has the same definition as found herein. The alkoxycarbonyl group may be represented by the following:

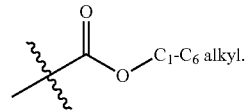

The term "$C_1$-$C_6$ alkyl" is intended to mean a straight or branched carbon radical containing 1 to 6 carbons. Some embodiments contain 1 to 5 carbons. Some embodiments contain 1 to 4 carbons. Some embodiments contain 1 to 3 carbons. Some embodiments contain 1 or 2 carbons. Examples of an alkyl group include, but are not limited to, methyl, ethyl, n-propyl, isopropyl, n-butyl, s-butyl, isobutyl, t-butyl, pentyl, isopentyl, t-pentyl, neopentyl, 1-methylbutyl [i.e., —$CH(CH_3)CH_2CH_2CH_3$], 2-methylbutyl [i.e., —$CH_2CH(CH_3)CH_2CH_3$], n-hexyl, and the like.

The term "$C_1$-$C_4$ alkyl" is intended to mean a straight or branched carbon radical containing 1 to 4 carbons. Some embodiments contain 1 to 3 carbons. Some embodiments contain 1 or 2 carbons. Examples of an alkyl group include, but are not limited to, methyl, ethyl, n-propyl, isopropyl, n-butyl, s-butyl, isobutyl, 1-butyl, and the like.

The term "$C_1$-$C_6$ alkylamino" is intended to mean a radical comprising one $C_1$-$C_6$ alkyl group attached to an NH group, wherein $C_1$-$C_6$ alkyl has the same meaning as described herein. Some examples include, but are not limited to, methylamino, ethylamino, n-propylamino, isopropylamino, n-butylamino, s-butylamino, isobutylamino, t-butylamino, and the like. Some embodiments are "$C_1$-$C_2$ alkylamino."

The term "$C_1$-$C_6$ alkylcarboxamide" is intended to mean a single $C_1$-$C_6$ alkyl group attached to either the carbon or the nitrogen of an amide group, wherein $C_1$-$C_6$ alkyl has the same definition as found herein. The $C_1$-$C_6$ alkylcarboxamido group may be represented by the following:

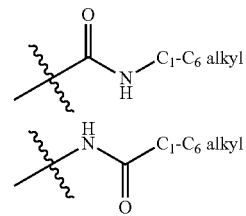

Examples include, but are not limited to, N-methylcarboxamide, N-ethylcarboxamide, N-n-propylcarboxamide, N-isopropylcarboxamide, N-n-butylcarboxamide, N-s-butylcarboxamide, N-isobutylcarboxamide, N-t-butylcarboxamide, and the like.

The term "$C_1$-$C_6$ alkylene" is intended to mean a straight or branched, saturated aliphatic, divalent radical having 1 to 6 carbon atoms. Some embodiments contain 1 to 5 carbons. Some embodiments contain 1 to 4 carbons. Some embodiments contain 1 to 3 carbons. Some embodiments contain 1 or 2 carbons. Examples include, but are not limited to, methylene, ethylene, n-propylene, isopropylene, n-butylene, s-butylene, isobutylene, t-butylene, pentylene, isopentylene, t-pentylene, neopentylene, 1-methylbutylene [i.e., —CH(CH$_3$)CH$_2$CH$_2$CH$_3$], 2-methylbutylene [i.e., —CH$_2$CH(CH$_3$)CH$_2$CH$_3$], n-hexylene, and the like.

The term "$C_1$-$C_6$ alkylsulfonyl" is intended to mean a radical comprising a $C_1$-$C_6$ alkyl group attached to the sulfur of a sulfonyl group, wherein the $C_1$-$C_6$ alkyl radical has the same definition as described herein. Examples include, but are not limited to, methylsulfonyl, ethylsulfonyl, n-propylsulfonyl, isopropylsulfonyl, n-butylsulfonyl, s-butylsulfonyl, isobutylsulfonyl, t-butylsulfonyl, and the like.

The term "$C_5$-$C_{11}$ bicycloalkyl" is intended to mean a radical comprising two fused or bridged, saturated rings containing 5 to 11 ring carbon atoms. Examples of a bicycloalkyl group include, but are not limited to, bicyclo[3.1.1]heptyl, bicyclo[2.2.1]heptyl, and the like.

The term "$C_3$-$C_7$ cycloalkenylene" is intended to mean is intended to mean a mono unsaturated ring di-radical containing 3 to 7 carbons. Some embodiments contain 3 to 6 carbons. Some embodiments contain 3 to 5 carbons. Some embodiments contain 5 to 7 carbons. Some embodiments contain 3 to 4 carbons. Examples include cyclopropenediyl, cyclobutenediyl, cyclopentenediyl, cyclohexenediyl, cycloheptenediyl, and the like.

The term "$C_3$-$C_7$ cycloalkyl" is intended to mean a saturated ring radical containing 3 to 7 carbons. Some embodiments contain 3 to 6 carbons. Some embodiments contain 3 to 5 carbons. Some embodiments contain 5 to 7 carbons. Some embodiments contain 3 to 4 carbons. Examples include cyclopropyl, cyclobutyl, cyclopentyl, cyclohexyl, cycloheptyl, and the like.

The term "$C_3$-$C_7$ cycloalkylamino" is intended to mean a radical comprising a $C_3$-$C_7$ cycloalkyl attached the nitrogen of an amino group, wherein $C_3$-$C_7$ cycloalkyl has the same definition as found herein. Examples include, but are not limited to, cyclopropylamino, cyclobutylamino, cyclopentylamino, cyclohexylamino, and the like.

The term "$C_3$-$C_7$ cycloalkylene" is intended to mean a saturated ring di-radical containing 3 to 7 carbons. Some embodiments contain 3 to 6 carbons. Some embodiments contain 3 to 5 carbons. Some embodiments contain 5 to 7 carbons. Some embodiments contain 3 to 4 carbons. Examples include cyclopropanediyl, cyclobutanediyl, cyclopentanediyl, cyclohexanediyl, cycloheptanediyl, and the like. In some embodiments $C_3$-$C_7$ cycloalkylene is selected from: 1,1-cyclopropanediyl, 1,1-cyclobutanediyl, 1,1-cyclopentanediyl, 1,1-cyclohexanediyl, 1,1-cycloheptanediyl, and the like. In some embodiments $C_3$-$C_7$ cycloalkylene is selected from: 1,2-cyclopropanediyl, 1,2-cyclobutanediyl, 1,2-cyclopentanediyl, 1,2-cyclohexanediyl, 1,2-cycloheptanediyl, and the like.

The term "carbo-$C_1$-$C_6$-alkoxy" is intended to mean a $C_1$-$C_6$ alkyl ester of a carboxylic acid, wherein $C_1$-$C_6$ alkyl has the same definition as found herein. Examples include, but are not limited to, carbomethoxy [—C(O)OCH$_3$], carboethoxy, carbo-n-propoxy, carboisopropoxy, carbo-n-butoxy, carbo-s-butoxy, carbo-isobutoxy, carbo-t-butoxy, carbo-n-pentoxy, carbo-isopentoxy, carbo-t-pentoxy, carboneopentoxy, carbo-n-hexyloxy, and the like.

The term "carboxamide" is intended to mean the group —CONH$_2$.

The term "carboxy" is intended to mean the group —CO$_2$H; also referred to as a carboxylic acid group.

The term "cyano" is intended to mean the group —CN.

The term "$C_2$-$C_8$ dialkylamino" is intended to mean a radical comprising an amino group substituted with two of the same or different $C_1$-$C_4$ alkyl groups, wherein $C_1$-$C_4$ alkyl has the same definition as found herein. Some examples include, but are not limited to, dimethylamino, methylethylamino, diethylamino, methylpropylamino, methylisopropylamino, ethylpropylamino, ethylisopropylamino, dipropylamino, propylisopropylamino, and the like. Some embodiments are $C_2$-$C_4$ dialkylamino.

The term "$C_2$-$C_8$ dialkylsulfonamide" is intended to mean is intended to mean one of the following groups shown below:

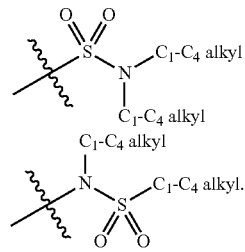

wherein $C_1$-$C_4$ alkyl has the same definition as found herein.

The term "$C_1$-$C_6$ haloalkoxy" is intended to mean a radical comprising a $C_1$-$C_6$ haloalkyl group directly attached to an oxygen atom, wherein $C_1$-$C_6$ haloalkyl has the same definition as found herein. Examples include, but are not limited to, difluoromethoxy, trifluoromethoxy, 2,2,2-trifluoroethoxy, pentafluoroethoxy, and the like.

The term "$C_1$-$C_6$ haloalkyl" is intended to mean a radical comprising a $C_1$-$C_6$ alkyl group substituted with one or more halogens, wherein $C_1$-$C_6$ alkyl has the same definition as found herein. The $C_1$-$C_6$ haloalkyl may be fully substituted in which case it can be represented by the formula $C_nL_{2n+1}$, wherein L is a halogen and "n" is 1, 2, 3, 4, 5 or 6. When more than one halogen is present then they may be the same or different and selected from: fluorine, chlorine, bromine, and iodine. In some embodiments, haloalkyl contains 1 to 5 carbons. In some embodiments, haloalkyl contains 1 to 4 carbons. In some embodiments, haloalkyl contains 1 to 3 carbons. In some embodiments, haloalkyl contains 1 or 2 carbons. Examples of haloalkyl groups include, but are not limited to, fluoromethyl, difluoromethyl, trifluoromethyl, chlorodifluoromethyl, 2,2,2-trifluoroethyl, pentafluoroethyl, and the like.

The term "halogen" is intended to mean to a fluoro, chloro, bromo or iodo group.

The term "heteroaryl" is intended to mean a ring system containing 5 to 14 ring atoms, that may contain a single ring, two fused rings or three fused rings, and wherein at least one ring is aromatic and at least one ring atom is a heteroatom selected from, for example: O, S and N, wherein N is optionally substituted with H, $C_1$-$C_4$ acyl, $C_1$-$C_4$ alkyl, or oxide (i.e., together with an aromatic ring nitrogen form an N-oxide). Some embodiments contain 5 to 6 ring atoms for example (uranyl, thienyl, pyrrolyl, imidazolyl, oxazolyl, thiazolyl, isoxazolyl, pyrazolyl, isothiazolyl, oxadiazolyl, triazolyl, tetrazolyl, thiadiazolyl, pyridinyl, pyrazinyl, pyrimidinyl, pyridazinyl, triazinyl, and the like. Some embodiments contain 8 to 14 ring atoms for example quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl. phenazinyl, phenothiazinyl, phenoxazinyl, benzoxazolyl, benzothiazolyl, 1H-benzimidazolyl, imidazopyridinyl, benzothienyl, benzofuranyl, isobenzofuran, 2,3-dihydrobenzofuranyl, 4H-benzo[1,3]dioxinyl, 3,4-dihydro-1H-isoquinolinyl, 1,4,6,7-tetrahydroimidazo[4,5-c]pyridinyl, 7,8-dihydro-5H-[1,6]naphthyridinyl, 5,6-dihydro-8H-[1,2,4]triazolo[4,3-a]pyrazinyl, benzo[1,3]dioxolyl, pyrazolo[1,5-a]pyrimidinyl, tetrahydroquinolinyl, and the like.

The term "heteroarylene" is intended to mean is intended to mean an aromatic ring di-radical containing 5 to 14 ring atoms that may be a single ring, two fused rings or three fused rings, wherein at least one aromatic ring atom is a heteroatom selected from, for example: O, S, and N, wherein N is optionally substituted with H, $C_1$-$C_4$ acyl, $C_1$-$C_4$ alkyl, or oxide (i.e., together with an aromatic ring nitrogen form an N-oxide). Some embodiments contain 5 to 6 ring atoms for example furandiyl, thiophenediyl, pyrrolediyl, imidazolediyl, oxazolediyl, thiazolediyl, isoxazolediyl, pyrazolediyl, isothiazolediyl, oxadiazolediyl, triazolediyl, thiadiazolediyl, pyridinediyl, pyrazinediyl, pyrimidinediyl, pyridazinediyl, triazinediyl, and the like. Some embodiments contain 8 to 14 ring atoms for example quinolizinediyl, quinolinediyl, isoquinolinediyl, cinnolinediyl, phthalazinediyl, quinazolinediyl, quinoxalinediyl, triazinediyl, indolediyl, isoindolediyl, indazolediyl, indolizinediyl, purinediyl, naphthyridinediyl, pteridinediyl, carbazolediyl, acridinediyl. phenazinediyl, phenothiazinediyl, phenoxazinediyl, benzoxazolediyl, benzothiazolediyl, 1H-benzimidazolediyl, imidazopyridinediyl, benzothienediyl, benzofurandiyl, isobenzofurandiyl, and the like.

The term "heteroaryloxy" is intended to mean a radical comprising a heteroaryl group, attached to an oxygen, wherein heteroaryl has the same definition as found herein. The term "heterobicyclyl" is intended to mean a radical comprising two fused or bridged, non-aromatic rings containing 5 to 11 ring atoms wherein one, two, three or four ring atoms are heteroatoms selected from, for example: O, S, and N, wherein N is substituted with H, $C_1$-$C_4$ acyl or $C_1$-$C_4$ alkyl, and S is optionally substituted with one or two oxygens. Examples of a heterobicyclyl group include, but are not limited to, octahydropyrrolo[1,2-a]pyrazinyl, 1-azabicyclo[2.2.2]octyl, 9-aza-bicyclo[3.3.1]nonyl, and the like.

The term "heterocyclyl" is intended to mean a non-aromatic ring radical containing 3 to 8 ring atoms, wherein one, two or three ring atoms are heteroatoms selected from, for example: O, S, and N, wherein N is substituted with H, $C_1$-$C_4$ acyl or $C_1$-$C_4$ alkyl, and S is optionally substituted with one or two oxygens. Examples of a heterocyclyl group include, but are not limited to, aziridinyl, azetidinyl, piperidinyl, morpholinyl, piperazinyl, pyrrolidinyl, [1,3]-dioxolanyl, thiomorpholinyl, [1,4]oxazepanyl, 1,1-dioxothiomorpholinyl, azepanyl, tetrahydrofuranyl, tetrahydropyranyl, tetrahydrothiopyranyl, 1-oxo-hexahydro-1$\lambda^4$-thiopyranyl, 1,1-dioxo-hexahydro-1$\lambda^6$-thiopyranyl, and the like.

The term "heterocyclylene" is intended to mean a non-aromatic ring di-radical containing 3 to 8 ring atoms, wherein one, two or three ring atoms are heteroatoms selected from, for example: O, S, and N, wherein N is substituted with H, $C_1$-$C_4$ acyl or $C_1$-$C_4$ alkyl, and S is optionally substituted with one or two oxygens. Examples of a heterocyclylene group include, but are not limited to, aziridinediyl, azetidinediyl, piperidinediyl, morpholinediyl, piperazinediyl, pyrrolidinediyl, [1,3]-dioxolanediyl, thiomorpholinediyl, [1,4]oxazepanediyl, 1,1-dioxothiomorpholinediyl, azepanediyl, tetrahydrofurandiyl, and the like.

The term "hydroxyl" is intended to mean the group —OH.

The term "phosphonooxy" is intended to mean the group —OP(O)(OH)$_2$.

The term "ureyl" is intended to mean the group —NH$_2$C(O)NH$_2$.

Administration of the compounds and pharmaceutically acceptable salts, solvates, hydrates, and/or N-oxides thereof described herein as the sole active pharmaceutical agent (i.e., mono-therapy) is described in PCT/US2010/002360, filed Aug. 27, 2010, which is incorporated herein by reference in its entirety.

Provided is a compound of Formula Ia or a pharmaceutically acceptable salt, solvate, hydrate, and/or N-oxide thereof described herein for use in combination with and one or more known pharmaceutical agents selected from one or more known pharmaceutical agents is chosen from inhibitors of inherent multidrug resistance, anti-emetic agents, agents useful in the treatment of anemia, agents useful in the treatment of neutropenia, immunologic-enhancing agents, analgesic agents, and anticancer agents. Also provided is a compound of Formula Ia or a pharmaceutically acceptable salt, solvate, hydrate, and/or N-oxide thereof described herein for use in combination with and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents.

Provided is the use of a compound of Formula Ia or a pharmaceutically acceptable salt, solvate, hydrate, and/or N-oxide thereof described herein in the manufacture of a medicament for treating cancer in an individual. Provided is the use of a compound of Formula Ia or a pharmaceutically acceptable salt, solvate, hydrate, and/or N-oxide thereof described herein, wherein the cancer is not prostate cancer, leukemia, lymphoma, or a CNS tumor.

Provided is the use of a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents in the manufacture of a medicament for treating cancer in an individual. Provided is the use of a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents in the manufacture of a medicament for treating cancer in an individual, wherein the cancer is not prostate cancer, leukemia, lymphoma, or a CNS tumor. Also provided is the use of a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents in the manufacture of a medicament for treating cancer in an individual. Also provided is the use of a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents in the manufacture of a medicament for treating cancer in an individual, wherein the cancer is not prostate cancer, leukemia, lymphoma, or a CNS tumor.

Provided is a composition comprising a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents. Also provided is a composition comprising a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents.

Provided is a composition comprising a compound of Formula Ia or a pharmaceutically acceptable salt, solvate, hydrate, and/or N-oxide described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents, and a pharmaceutically acceptable carrier. Also provided is a composition comprising a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents, and a pharmaceutically acceptable carrier.

Provided is a method for preparing a composition comprising the step of admixing a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents. Also provided is a composition obtained by a method for preparing a composition comprising the step of admixing a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents.

Also provided is a method for preparing a composition comprising the step of admixing a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents. Also provided is a composition obtained by a method for preparing a composition comprising the step of admixing a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents.

Provided is a method for preparing a composition comprising the step of admixing a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents, and a pharmaceutically acceptable carrier. Also provided is a composition obtained by a method for preparing a composition comprising the step of admixing a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents, and a pharmaceutically acceptable carrier.

Also provided is a method for preparing a composition comprising the step of admixing a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents. Also provided is a composition obtained by a method for preparing a composition comprising the step of admixing a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents.

In some embodiments, the compound of Formula Ia, or a pharmaceutically acceptable salt, solvate, hydrate, and/or N-oxide thereof described herein and the one or more known pharmaceutical agents are admixed with a pharmaceutically acceptable carrier.

In some embodiments, the compound of Formula Ia, or a pharmaceutically acceptable salt, solvate, hydrate, and/or N-oxide thereof described herein compound of Formula Ia, or a pharmaceutically acceptable salt, solvate, hydrate, and/or N-oxide thereof and the one or more known pharmaceutical agents are each admixed with a different pharmaceutically acceptable carrier.

The pharmaceutical carrier generally is compatible with the other ingredients in the composition and should be tolerated by the individual recipient. Other physiologically active ingredients can be incorporated into the pharmaceutical composition if desired, and if such ingredients are compatible with the other ingredients in the composition. Conventional excipients, such as binding agents, fillers, acceptable wetting agents, tabletting lubricants, and disintegrants can be used in tablets and capsules for oral administration.

Compositions for oral administration can be in the form of solutions, emulsions, aqueous or oily suspensions, and syrups. Alternatively, the compositions for oral administration can be in the form of dry powder that can be reconstituted with water or another suitable liquid vehicle before use. Additional additives such as suspending or emulsifying agents, non-aqueous vehicles (including edible oils), preservatives, and flavorings and colorants can be added. Compositions for parenteral administration can be prepared by dissolving the compounds in a suitable liquid vehicle and filter sterilizing the solution before filling and sealing an appropriate vial or ampoule. These are just a few examples of the many appropriate methods well known in the art for preparing compositions for oral or parenteral administration.

Provided is a compound of Formula Ia or a pharmaceutically acceptable salt, solvate, hydrate, and/or N-oxide thereof described herein for use in a method for the treatment of cancer in an individual in need thereof, comprising administering to said individual said compound. Also provided is a compound of Formula Ia or a pharmaceutically acceptable salt, solvate, hydrate, and/or N-oxide thereof described herein for use in a method for the treatment of cancer in an individual in need thereof, comprising administering to said individual said compound wherein the cancer is not prostate cancer, leukemia, lymphoma, or a CNS tumor.

Provided is a compound of Formula Ia or a pharmaceutically acceptable salt, solvate, hydrate, and/or N-oxide thereof described herein for use in a method for the treatment of cancer in an individual in need thereof, comprising administering to said individual said compound and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents. Also provided is a compound of Formula Ia or a pharmaceutically acceptable salt, solvate, hydrate, and/or N-oxide thereof described herein for use in a method for the treatment of cancer in an individual in need thereof, comprising administering to said individual said compound and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents, wherein the cancer is not prostate cancer, leukemia, lymphoma, or a CNS tumor. Also provided is a compound of Formula Ia or a pharmaceutically acceptable salt, solvate, hydrate, and/or N-oxide thereof described herein for use in a method for the treatment of cancer in an individual in need thereof, comprising administering to said individual said compound and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents, wherein the cancer is not prostate cancer, leukemia, lymphoma, or a CNS tumor.

Provided is a compound of Formula Ia or a pharmaceutically acceptable salt, solvate, hydrate, and/or N-oxide thereof described herein for use in a method for the treatment of cancer in an individual in need thereof, comprising prescribing to said individual said compound. Also provided is a compound of Formula Ia or a pharmaceutically acceptable salt, solvate, hydrate, and/or N-oxide thereof described herein for use in a method for the treatment of cancer in an individual in need thereof, comprising prescribing to said individual said compound wherein the cancer is not prostate cancer, leukemia, lymphoma, or a CNS tumor.

Provided is a compound of Formula Ia or a pharmaceutically acceptable salt, solvate, hydrate, and/or N-oxide thereof described herein for use in a method for the treatment of cancer in an individual in need thereof, comprising prescribing to said individual said compound and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents. Also provided is a compound of Formula Ia or a pharmaceutically acceptable salt, solvate, hydrate, and/or N-oxide thereof described herein for use in a method for the treatment of cancer in an individual in need thereof, comprising prescribing to said individual said compound and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents, wherein the cancer is not prostate cancer, leukemia, lymphoma, or a CNS tumor. Also provided is a compound of Formula Ia or a pharmaceutically acceptable salt, solvate, hydrate, and/or N-oxide thereof described herein for use in a method for the treatment of cancer in an individual in need thereof, comprising prescribing to said individual said compound and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents. Also provided is a compound of Formula Ia or a pharmaceutically acceptable salt, solvate, hydrate, and/or N-oxide thereof described herein for use in a method for the treatment of cancer in an individual in need thereof, comprising prescribing to said individual said compound and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents, wherein the cancer is not prostate cancer, leukemia, lymphoma, or a CNS tumor.

Provided is one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents for use in combination with a compound of Formula Ia or a pharmaceutically acceptable salt, solvate, hydrate, and/or N-oxide thereof described herein. Also provided is one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents, for use in combination with a compound of Formula Ia or a pharmaceutically acceptable salt, solvate, hydrate, and/or N-oxide thereof described herein.

Provided is one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents for use in a method for the treatment of cancer in an individual in need thereof, said method comprises administering to said individual one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents and a compound of Formula Ia or a pharmaceutically acceptable salt, solvate, hydrate, and/or N-oxide thereof described herein. Also provided is one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents for use in a method for the treatment of cancer in an individual in need thereof, said method comprises administering to said individual one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents and a compound of Formula Ia or a pharmaceutically acceptable salt, solvate, hydrate, and/or N-oxide thereof described herein, wherein the cancer is not prostate cancer, leukemia, lymphoma, or a CNS tumor. Also provided is one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents for use in a method for the treatment of cancer in an individual in need thereof, said method comprises administering to said individual one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents and a compound of Formula Ia or a pharmaceutically acceptable salt, solvate, hydrate, and/or N-oxide thereof described herein. Also provided is one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents for use in a method for the treatment of cancer in an individual in need thereof, said method comprises administering to said individual one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents and a compound of Formula Ia or a pharmaceutically acceptable salt, solvate, hydrate, and/or N-oxide thereof described herein, wherein the cancer is not prostate cancer, leukemia, lymphoma, or a CNS tumor.

Provided is one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents for use in a method for the treatment of cancer in an individual in need thereof, said method comprises prescribing to said individual one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents and a compound of Formula Ia or a pharmaceutically acceptable salt, solvate, hydrate, and/or N-oxide thereof described herein. Also provided is one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents for use in a method for the treatment of cancer in an individual in need thereof, said method comprises prescribing to said individual one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents and a compound of Formula Ia or a pharmaceutically acceptable salt, solvate, hydrate, and/or N-oxide thereof described herein, wherein the cancer is not prostate cancer, leukemia, lymphoma, or a CNS tumor. Also provided is one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents for use in a method for the treatment of cancer in an individual in need thereof, said method comprises prescribing to said individual one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents and a compound of Formula Ia or a pharmaceutically acceptable salt, solvate, hydrate, and/or N-oxide thereof described herein. Also provided is one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents for use in a method for the treatment of cancer in an individual in need thereof, said method comprises prescribing to said individual one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents and a compound of Formula Ia or a pharmaceutically acceptable salt, solvate, hydrate, and/or N-oxide thereof described herein, wherein the cancer is not prostate cancer, leukemia, lymphoma, or a CNS tumor.

Provided is a pharmaceutical product selected from: a pharmaceutical composition, a formulation, a dosage form, a combined preparation, a twin pack, and a kit; comprising a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents; for treating cancer in an individual. Also provided is a pharmaceutical product selected from: a pharmaceutical composition, a formulation, a dosage form, a combined preparation, a twin pack, and a kit; comprising a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents; for treating cancer in an individual, wherein the cancer is not prostate cancer, leukemia, lymphoma, or a CNS tumor. Also provided is a pharmaceutical product selected from: a pharmaceutical composition, a formulation, a dosage form, a combined preparation, a twin pack, and a kit; comprising a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents; for treating cancer in an individual. Also provided is a pharmaceutical product selected from: a pharmaceutical composition, a formulation, a dosage form, a combined preparation, a twin pack, and a kit; comprising a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents; for treating cancer in an individual, wherein the cancer is not prostate cancer, leukemia, lymphoma, or a CNS tumor.

In some embodiments, the pharmaceutical product comprises a pharmaceutical composition.

In some embodiments, the pharmaceutical product comprises a formulation.

In some embodiments, the pharmaceutical product comprises a dosage form.

In some embodiments, the pharmaceutical product comprises a combined preparation.

In some embodiments, the pharmaceutical product comprises a twin pack.

In some embodiments, the pharmaceutical product comprises a kit.

In some embodiments, the kit comprises a first package comprising a compound of Formula Ia or a pharmaceutically acceptable salt, solvate, hydrate, and/or N-oxide thereof described herein or a pharmaceutical composition thereof, and a second package comprising one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents or a pharmaceutical composition thereof. In some embodiments, the kit comprises a first package comprising a compound of Formula Ia or a pharmaceutically acceptable salt, solvate, hydrate, and/or N-oxide thereof described herein or a pharmaceutical composition thereof, and a second package comprising one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents.

Provided is a method for the treatment of cancer in an individual in need thereof, comprising administering to said individual, a therapeutically effective amount of a compound of Formula to or a pharmaceutically acceptable salt, solvate, hydrate, and/or N-oxide thereof described herein. Also provided is a method for the treatment of cancer in an individual in need thereof, comprising administering to said individual, a therapeutically effective amount of a compound of Formula Ia or a pharmaceutically acceptable salt, solvate, hydrate, and/or N-oxide thereof described herein, wherein the cancer is not prostate cancer, leukemia, lymphoma, or a CNS tumor.

Provided is a method for the treatment of cancer in an individual in need thereof, comprising administering to said individual, a therapeutically effective amount of a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents. Also provided is a method for the treatment of cancer in an individual in need thereof, comprising administering to said individual, a therapeutically effective amount of a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents, wherein the cancer is not prostate cancer, leukemia, lymphoma, or a CNS tumor.

Provided is a method for the treatment of cancer in an individual in need thereof, comprising prescribing to said individual, a therapeutically effective amount of a compound of Formula Ia or a pharmaceutically acceptable salt, solvate, hydrate, and/or N-oxide thereof described herein. Also provided is a method for the treatment of cancer in an individual in need thereof, comprising prescribing to said individual, a therapeutically effective amount of a compound of Formula Ia or a pharmaceutically acceptable salt, solvate, hydrate, and/or N-oxide thereof described herein, wherein the cancer is not prostate cancer, leukemia, lymphoma, or a CNS tumor.

Provided is a method for the treatment of cancer in an individual in need thereof, comprising prescribing to said individual, a therapeutically effective amount of a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, analgesic agents, and anticancer agents. Also provided is a method for the treatment of cancer in an individual in need thereof, comprising prescribing to said individual, a therapeutically effective amount of a compound of Formula Ia or a pharmaceutically acceptable salt, solvate, hydrate, and/or N-oxide thereof described herein and one or more known pharmaceutical agents selected from inhibitors of inherent multidrug resistance, anti-emetic agents, agents useful in the treatment of anemia, agents useful in the treatment of neutropenia, immunologic-enhancing agents, and anticancer agents, wherein the cancer is not prostate cancer, leukemia, lymphoma, or a CNS tumor.

In some embodiments, the individual is a human.

In some embodiments, the one or more known pharmaceutical agents are administered to the individual simultaneously, separately, or sequentially.

In some embodiments, the compound of Formula Ia, or a pharmaceutically acceptable salt, solvate, hydrate, and/or N-oxide thereof described herein and the one or more known pharmaceutical agents are administered simultaneously.

In some embodiments, the compound of Formula Ia, or a pharmaceutically acceptable salt, solvate, hydrate, and/or N-oxide thereof described herein and the one or more known pharmaceutical agents are administered separately.

In some embodiments, the compound of Formula Ia, or a pharmaceutically acceptable salt, solvate, hydrate, and/or N-oxide thereof described herein and the one or more known pharmaceutical agents are administered sequentially.

In some embodiments, the amount of the compound of Formula Ia, or a pharmaceutically acceptable salt, solvate, hydrate, and/or N-oxide thereof described herein alone and the amount of the one or more known pharmaceutical agents alone are therapeutically ineffective.

In some embodiments, the combination of a compound of Formula Ia, or a pharmaceutically acceptable salt, solvate, hydrate, and/or N-oxide thereof described herein and the one or more known pharmaceutical agents results in a supra-additive or synergistic effect. A synergistic effect means that the effect observed with the combination therapy is greater than that seen by adding the effect of each compound together. One advantage of using a synergistic combination therapy is that less of each compound is required to achieve a significant effect and so fewer side effects can result from treatment. In some cases, side effects are not seen at the lower doses used. Also, in some cases, the side effect profile of one drug can mitigate or average out the side effect profile of the other drug. For example, one of the drugs may result in increased blood pressure and the other drug results in lowered blood pressure so that the combination therapy does not effect blood pressure. Another potential advantage of combination therapy is that, since less compound is required, the cost of therapy can be reduced.

In some embodiments, the cancer is chosen from astrocytoma, brain cancers, breast cancer, colorectal cancer, glioblastoma multiforme, glioma, intestinal cancer, liver cancer, lung cancer, skin, neuroglioma, pancreatic cancer, and thyroid cancer.

In some embodiments, the cancer is chosen from pancreatic cancer, lung cancer, and breast cancer.

In some embodiments, the cancer is melanoma.

In some embodiments, the breast cancer is estrogen receptor (ER)-negative breast tumor.

In some embodiments, the cancer is not prostate cancer, leukemia, lymphoma, or a CNS tumor.

Suitable pharmaceutical agents that can be used in combination with the compounds described herein include inhibitors of inherent multidrug resistance, anti-emetic agents, agents useful in the treatment of anemia, agents useful in the treatment of neutropenia, immunologic-enhancing agents, analgesic agents, and anticancer agents.

In some embodiments, the analgesic agent is chosen from non-opioid drugs, opioid drugs, and co-analgesic medications.

In some embodiments, the non opioid drug is chosen from non steroidal anti-inflammatory agents, choline magnesium trisalicylate, sulfasalazine, olsalazin, phenacetin, tenoxicam, phenylbutazone, oxyphenthartazone, tapentadol, celecoxib, etoricoxib, lumiracoxib, rofecoxib, parecoxib, and ziconotide.

In some embodiments, the non steroidal anti-inflammatory agent is chosen from acemetacin, acetaminophen, aminoprofen, aspirin, benoxaprofen, bucloxic acid, carprofen, choline magnesium salicylate, choline salicylate, clidanac, diclofenac, diflunisal, diflurisal, etodolac, fenoprofen, fenoprofen calcium, fentiazac, flosulide, flubufen, flufenamic acid, flufenisal, flurbiprofen, fluprofen, ibuprofen, indoprofen, indomethacin, isoxicam, ketoprofen, ketorolac tromethamine, lornoxicam, magnesium salicylate, meclofenamic acid, meclofenamate sodium, mefenamic acid, meloxicam, muroprofen, nabumetone, naproxen, nepafenac, niflumic acid, nimesulide, oxaprozin, oxpinac, piroprofen, piroxicam, pramoprofen, remifenzone, salsalate, salicylsalicylic acid, sodium salicylate, sudoxicam, sulindac, suprofen, tiaprofenic acid, tiopinac, tolfenamic acid, tolmetin, trioxaprofen, zidometacin, and zomepirac.

In some embodiments, the opioid drug is chosen from alfentanil, allylprodine, alphaprodine, anileridine, apomorphine, benzylmorphine, bezitramide, buprenorphine, butorphanol, clonitazene, codeine, desomorphine, dextromoramide, dextropropoxyphene, dezocine, diampromide, diamorphone, dihydrocodeine, dihydrocodeinone enol acetate, dihydromorphine, dilaudid, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodeine, hydrocodone, hydromorphone, hydroxypethidine, isomethadone, ketobemidone, levallorphan, levorphanol, levophenacylmorphan, lofentanil, meperidine, meptazinol, metazocine, methadone, metopon, 6-monoacetylmorphine, morphine, morphine-6-glucuronide, myrophine, nalbuphine, narceine, nicomorphine, norlevorphanol, normethadone, nalorphine, normorphine, norpipanone, noscapine, opium, oxycodone, oxymorphone, papavcretum, papvcrinc, pentazocine, pethidine, phenadoxone, phenomorphan, phenazocine, phenoperidine, piminodine, piritramide, proheptazine, promedol, properidine, propiram, propoxyphene, sufentanil, tilidine, and tramadol.

In some embodiments, the at least one analgesic agent comprises an NSAID and an opiod drug.

In some embodiments, the at least one analgesic agent is chosen from vicodin (acetaminophen and hydrocodone), percocet (oxycodone and acetaminophen), norco (hydrocodone bitartrate and acetaminophen), lorcet (acetaminophen and hydrocodone), darvocet (acetaminophen and propoxyphene), and percodan (aspirin and oxycodone).

In some embodiments, the at least one analgesic agent is at least one co-analgesic medication chosen from antidepressants, anti-anxiety medications, migraine medications, and gabapentin.

In some embodiments, the migraine medication is chosen from alpiropride, dihydroergotamine, dolasetron, ergocornine, ergocorninine, ergocryptine, ergot, ergotamine, flumedroxone acetate, fonazine, lisuride, lomerizine, methysergide oxetorone, and pizotyline.

In some embodiments, the antidepressant is chosen from escitalopram, binedaline, caroxazonc, citalopram, (S)-citalopram, dimcthazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, roliram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

In some embodiments, the anti-anxiety medication is chosen from alprazolam, chlordiazepoxide, clonazepam, clorazepate, diazepam, halazepam, lorazepam, oxazepam, and prazepam, buspirone, and barbituates.

In some embodiments, the or more known pharmaceutical agents is chosen from anticancer agents.

In some embodiments, the anticancer agent is paclitaxel.

In some embodiments, the cancer is chosen from prostrate cancer, pancreatic cancer, lung cancer, and breast cancer.

In some embodiments, the cancer is chosen from pancreatic cancer, lung cancer, and breast cancer.

In some embodiments, the anticancer agent is chosen from acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alfa-2a, interferon alfa-2b, interferon alfa-n1, interferon alfa-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorclin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, and zorubicin hydrochloride.

In some embodiments, the anticancer agent is chosen from 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol; 9-dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+*myobacterium* cell wall sk; mopidamol; multiple drug resistance gene inhibitor; multiple tumor suppressor-1 based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In some embodiments, the anticancer agent is chosen from eribulin mesylate, cabazitaxel, sipuleucel-T, degarelix, raloxifene, topotecan hydrochloride, ixabepilone, lapatinib, erlotinib, gefitinib, abarelix, leuprolide acetate, fulvestrant, letrozole, triptorelin pamoate, herceptin, nolvadex, photofrin, xeloda, letrozole, anastrozole, flutamide, gemcitabine HCl, docetaxel, goserelin acetate, bevacizumab, celecoxib, cetuximab, denosumab, ibandronic acid, thyrotropin alfa, trabectedin, and Pemetrexed.

In some embodiments, the anticancer agent is paclitaxel.

In some embodiments, the inhibitor of inherent multidrug resistance is chosen from LY335979 (Zosuquidar), XR9576 (Tariquidar), OC144-093, R101922 (Timcodar dimesilate), VX853 and PSC833 (valspodar).

The inhibitor of inherent multidrug resistance OC144-093 is: N-[4-[2-[4-[3-ethoxy-1(E)-propenyl]phenyl]-4-[4-(isopropylamino)phenyl]-1H-imidazol-5-yl]phenyl]-N-isopropylamine, the chemical structure is:

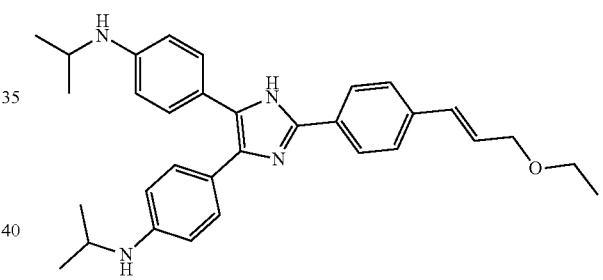

In some embodiments, the anti-emetic agent is chosen from neurokinin-1 receptor antagonists, 5HT3 receptor antagonists, GABAB receptor agonists, corticosteroids, and antidopaminergics.

In some embodiments, the anti-emetic agent is chosen from acetylleucine, alizapride, aprepitant, azasetron, baclofen, benzquinamide, Betamethasone valerate, bietanautine, bromopride, buclizine, clebopride, chlorpromazine, cyclizine, dimenhydrinate, diphenidol, dolasetron, domperidone, dronabinol, flunisolide, fluphenazine, fosaprepitant, granisetron, hydroxyzine, meclizine, methallatal, mesoridazine, metoclopramide, metopimazine, monoethanolamine, nabilone, ondansetron, oxyperndyl, palonosetron, pipamazine, prochlorperazine, promethazine, scopolamine, sulpiride, tetrahydrocannabinol, thiethylperazine, thioridazine, thioproperazine, triamcinolone, trimethobenzamide, tropisetron, and zatisetron.

In some embodiments, the agent useful in the treatment of anemia is chosen from eythropoiesis receptor activators.

In some embodiments, the agent useful in the treatment of anemia is chosen from epoetin alfa, methoxy polyethylene glycol-epoetin beta, darbepoetin alfa, and epoetin theta.

In some embodiments, the agent useful in the treatment of neutropenia is a hematopoietic growth factor.

In some embodiments, the hematopoietic growth factor is chosen from pegfilgrastim and filgrastim.

In some embodiments, the immunologic-enhancing agent is chosen from levamisole, isoprinosine, cyclophosphamide, lentinan, melphalan, muramyl dipeptide, SM1213 (Amiprilose), and zadaxin.

Other pharmaceutical agents are well known, or will be readily apparent in light of the instant disclosure, to one of ordinary skill in the art.

It is understood that the scope of combination-therapy of the compound of Formula Ia or a pharmaceutically acceptable salt, solvate, and hydrate thereof described herein with other pharmaceutical agents is not limited to those listed herein but includes in principle any combination with any pharmaceutical agent or pharmaceutical composition useful for the treatment of diseases, conditions or disorders that are linked to cancer.

Provided are certain compounds as shown in Formula Ia and pharmaceutically acceptable salts, solvates, hydrates, and/or N-oxides thereof:

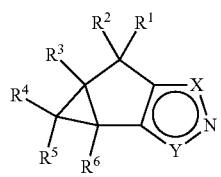

Ia wherein:
$R^1$, $R^2$, $R^3$, $R^4$, $R^5$, and $R^6$ are each independently selected from: H and $C_1$-$C_6$ alkyl;
X is $NR^7$ and Y is $CC(O)N(R^8)R^9$; or
X is $CC(O)N(R^8)R^9$ and Y is $NR^7$;
$R^7$ is —$R^{10}$—$R^{11}$—$R^{12}$—$R^{13}$; wherein:
$R^{10}$ is selected from: $C_1$-$C_6$ alkylene, heteroarylene, and heterocyclylene; or $R^{10}$ is absent;
$R^{11}$ is selected from: —C(O)NH— and $C_1$-$C_6$ alkylene; or $R^{11}$ is absent;
$R^{12}$ is $C_1$-$C_6$ alkylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;
$R^8$ is —$R^{14}$—$R^{15}$—$R^{16}$—$R^{17}$; wherein
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;
$R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;
$R^{16}$ is $C_1$-$C_6$ alkylene; or $R^{16}$ is absent; and
$R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, urcyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and
$R^9$ is selected from H, $C_1$-$C_6$ alkyl, and $C_3$-$C_7$ cycloalkyl; or
$R^8$ and $R^9$ together with the nitrogen atom to which they are both bonded form a group selected from: heterocyclyl and heterobicyclyl, each optionally substituted with one or more substituents selected from: Carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, X, and Y) contained within the generic chemical formulae described herein, for example, Ia and Ie, etc., are specifically embraced by the present invention just as if each and every combination was individually explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein. In addition, some embodiments include every combination of the one or more known pharmaceutical agents either specifically disclosed herein or specifically disclosed in any reference recited herein just as if each and every combination was individually and explicitly recited. Still further, some embodiments of the present invention include every combination of one or more embodiments pertaining to the chemical groups represented by the variables and generic chemical formulae as described herein or every combination of one or more compounds of Formula (Ia) together/in combination with every combination of the one or more known pharmaceutic) agents either specifically disclosed herein or specifically disclosed in any reference recited herein just as if each and every combination was individually and explicitly recited.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents, and the like. Likewise, "substituted with one or more substituents" refers to the substitution of a group with one substituent up to the total number of substituents physically allowed by the group. Further, when a group is substituted with more than one group they can be identical or they can be different.

Compounds described herein can also include tautomeric forms, such as keto-enol tautomers and the like. Tautomeric forms can be in equilibrium or sterically locked into one form by appropriate substitution. It is understood that the various tautomeric forms are within the scope of the compounds described herein.

The present disclosure includes all isotopes of atoms occurring in the present compounds, salts and crystalline forms thereof. Compounds described herein can also include all isotopes of atoms occurring in the intermediates and/or final compounds. Isotopes include those atoms having the same atomic number but different mass numbers. By way of general example, and without limitation, isotopes of hydrogen include $^2H$ (deuterium) and $^3H$ (tritium). Isotopes of carbon include $^{13}C$ and $^{14}C$.

It is understood and appreciated that compounds of Formula Ia and formulae related thereto may have one or more chiral centers and therefore can exist as enantiomers and/or diastereoisomers. The invention is understood to extend to and embrace all such enantiomers, diastereoisomers and mixtures thereof, including but not limited to racemates. It is understood that compounds of Formula Ia and formulae used throughout this disclosure are intended to represent all individual enantiomers and mixtures thereof, unless stated or shown otherwise.

The Group $R^1$:
In some embodiments, $R^1$ is selected from: H and $C_1$-$C_6$ alkyl.
In some embodiments, $R^1$ is H.
In some embodiments, $R^1$ is $C_1$-$C_6$ alkyl.
In some embodiments, $R^1$ is methyl.
In some embodiments, $R^1$ is isopropyl.

The Group $R^2$:
In some embodiments, $R^2$ is selected from: H and $C_1$-$C_6$ alkyl.
In some embodiments, $R^2$ is H.
In some embodiments, $R^2$ is $C_1$-$C_6$ alkyl.
In some embodiments, $R^2$ is methyl.
In some embodiments, $R^2$ is isopropyl.

The Group $R^3$:
In some embodiments, $R^3$ is selected from: H and $C_1$-$C_6$ alkyl.
In some embodiments, $R^3$ is H.
In some embodiments, $R^3$ is $C_1$-$C_6$ alkyl.
In some embodiments, $R^3$ is methyl.
In some embodiments, $R^3$ is isopropyl.

The Group $R^4$:
In some embodiments, $R^4$ is selected from: H and $C_1$-$C_6$ alkyl.
In some embodiments, $R^4$ is H.
In some embodiments, $R^4$ is $C_1$-$C_6$ alkyl.
In some embodiments, $R^4$ is methyl.
In some embodiments, $R^4$ is isopropyl.

The Group $R^5$:
In some embodiments, $R^5$ is selected from: H and $C_1$-$C_6$ alkyl.
In some embodiments, $R^5$ is H.
In some embodiments, $R^5$ is $C_1$-$C_6$ alkyl.
In some embodiments, $R^5$ is methyl.
In some embodiments, $R^5$ is isopropyl.

The Group $R^6$:
In some embodiments, $R^6$ is selected from: H and $C_1$-$C_6$ alkyl.
In some embodiments, $R^6$ is H.
In some embodiments, $R^6$ is $C_1$-$C_6$ alkyl.
In some embodiments, $R^6$ is methyl.
In some embodiments, $R^6$ is isopropyl.

The Group X:
In some embodiments, X is $NR^7$; wherein $R^7$ is —$R^{10}$—$R^{11}$—$R^{12}$—$R^{13}$
In some embodiments, X is $CCONR^8R^9$.
In some embodiments, X is $CC(O)NHR^8$.

The Group Y:
In some embodiments, Y is $NR^7$; wherein $R^7$ is —$R^{10}$—$R^{11}$—$R^{12}$—$R^{13}$
In some embodiments, Y is $CCONR^8R^9$.
In some embodiments, Y is $CC(O)NHR^8$.

The Group $R^7$:
In some embodiments, $R^7$ is —$R^{10}$—$R^{11}$—$R^{12}$—$R^{13}$, or an N-oxide thereof.
In some embodiments, $R^7$ is —$R^{10}$—$R^{11}$—$R^{12}$—$R^{13}$.
In some embodiments, $R^7$ is selected from: aryl and heteroaryl; wherein said aryl and heteroaryl are each optionally substituted with one or two substituents selected from: cyano and halogen.
In some embodiments, $R^7$ is selected from: aryl and heteroaryl; wherein said aryl and heteroaryl are each optionally substituted with one or two substituents selected from: fluoro, chloro, and cyano.
In some embodiments, $R^7$ is selected from: 2,4-difluoro-phenyl, 2,4-dichloro-phenyl, 5-chloro-pyridin-2-yl, 5-cyano-pyrazin-2-yl, pyrazin-2-yl, 5-fluoro-pyridin-2-yl, 4-chloro-pyridin-2-yl, 4-fluoro-pyridin-2-yl, 4-cyano-pyridin-2-yl, and 4-oxy-pyrazin-2-yl.
In some embodiments, $R^7$ is selected from: 2,4-difluoro-phenyl, 2,4-dichloro-phenyl, 5-chloro-pyridin-2-yl, 5-cyano-pyrazin-2-yl, pyrazin-2-yl, 5-fluoro-pyridin-2-yl, 4-chloro-pyridin-2-yl, 4-fluoro-pyridin-2-yl, 4-cyano-pyridin-2-yl, and 4-oxy-pyrazin-2-yl.
In some embodiments, $R^7$ is selected from: 2,4-difluoro-phenyl, 5-bromo-pyridin-2-yl, 4-cyano-phenyl, pyridin-3-yl, pyridin-2-yl, 5-thiazol-2-yl-pyridin-2-yl, 5-trifluoromethyl-pyridin-2-yl, 5-o-tolyl-pyridin-2-yl, 5-dimethylamino-pyrazin-2-yl, 2,4-dichloro-phenyl, 5-isopropyl-pyridin-2-yl, 5-methyl-pyridin-2-yl, 5-(4-methoxy-phenyl)-pyridin-2-yl, 2-fluoro-4-methanesulfonyl-phenyl, 2-fluoro-phenyl, 5-chloro-pyridin-2-yl, 5-bromo-pyridin-3-yl, tert-butyl, 2-methoxy-pyridin-4-yl, 2,2-dimethyl-propyl, tetrahydro-pyran-4-ylmethyl, phenyl, 4-trifluoromethyl-pyridin-2-yl, 6-chloro-pyrazin-2-yl, 1-oxo-hexahydro-1$\lambda^4$-thiopyran-4-yl, 5-morpholin-4-yl-pyridin-2-yl, 6-bromo-pyridin-3-yl, 5-methoxy-pyridin-2-yl, 5,6-difluoro-pyridin-3-yl, 6-methoxy-pyridazin-3-yl, 2-chloro-pyridin-4-yl, 5-cyclopropyl-pyrazin-2-yl, 1,1-dioxo-tetrahydro-1$\lambda^6$-thiophen-3-yl, 1-benzyl-piperidin-4-yl, 6-cyano-pyrazin-2-yl, 2-hydroxy-2-methyl-propyl, 4-fluoro-phenyl, 5-ethyl-pyridin-2-yl, isopropyl, 5-phenyl-pyridin-2-yl, pyridin-4-yl, 2,5-difluoro-phenyl, 3-fluoro-phenyl, pyrimidin-4-yl, 2-(tetrahydro-pyran-4-yl)-ethyl, 3,5-difluoro-pyridin-2-yl, pyrazin-2-yl, tetrahydro-thiopyran-4-yl, 5-p-tolyl-pyridin-2-yl, 4-methoxy-phenyl, 2-morpholin-4-yl-ethyl, 5-cyano-pyridin-2-yl, 5-cyano-pyrazin-2-yl, 6'-methyl-[3,3]bipyridinyl-6-yl, 6-chloro-pyridazin-3-yl, 5-fluoro-pyridin-2-yl, 5-ethyl-pyrazin-2-yl, 6-methoxy-pyrazin-2-yl, 5-dimethylamino-pyridin-2-yl, 1-(4-fluoro-phenyl)-1-methyl-ethyl, 5-pyrimidin-5-yl-pyridin-2-yl, 4-methyl-pyridin-2-yl, 5-methoxy-pyrazin-2-yl, 5-propyl-pyridin-2-yl, 6-chloro-pyridin-3-yl, 5-m-tolyl-pyridin-2-yl, 5-hydroxy-pyrazin-2-yl, cyclopropyl-pyridin-2-yl, 2,6-difluoro-phenyl, 3-fluoro-pyridin-4-yl, 5-isopropyl-pyrazin-2-yl, 5-bromo-pyrazin-2-yl, 5-cyclopentyl-pyridin-2-yl, o-tolyl, 4-fluoro-benzyl, 3-methyl-pyridin-2-yl, 6-methyl-4-trifluoromethyl-pyridin-2-yl, 6-dimethylamino-pyrazin-2-yl, 1,1-dioxo-hexahydro-1$\lambda^6$-thiopyran-4-yl, 5-(4-fluoro-phenyl)-pyridin-2-yl, 5-cyclopropyl-pyridin-2-yl, 6-ethyl-pyrazin-2-yl, 5-methylamino-pyrazin-2-yl, 5-methyl-pyrazin-2-yl, 3-fluoro-pyridin-2-yl, 5-cyclobutyl-pyrazin-2-yl, 5-ethoxy-pyrazin-2-yl, 5-trifluoromethyl-pyrazin-2-yl, 5-cyano-pyridin-3-yl, 5-cyclopropylmethyl-pyrazin-2-yl, 5-pentafluoroethyl-pyrazin-2-yl, 5-heptafluoropropyl-pyrazin-2-yl, 5-chloro-4-methyl-pyridin-2-yl, 5-chloro-4-trifluoromethyl-pyridin-2-yl, 4-bromo-pyridin-2-yl, 4-chloro-pyridin-2-yl, 4-fluoro-pyridin-2-yl, 4-oxy-pyrazin-2-yl, 4-cyclopropyl-pyridin-2-yl, 4-cyano-pyridin-2-yl, 4-methanesulfonyl-pyridin-2-yl, 4-methoxy-pyridin-2-yl, piperidin-4-yl, tetrahydro-pyran-4-yl, 3-methyl-1,1-dioxo-tetrahydro-1$\lambda^6$-thiophen-3-yl, 5-chloro-3-fluoro-pyridin-2-yl, 3-fluoro-5-methoxy-pyridin-2-yl, 2-chloro-4-fluoro-phenyl, 6-fluoro-pyridin-3-yl, 6-cyano-pyridin-3-yl, 3-hydroxy-3-methyl-butyl, 4-iodo-pyridin-2-yl, 1-oxy-pyridin-3-yl, 4-tert-butylcarbamoyl-pyridin-2-yl, and 4-hydroxy-pyridin-2-yl.

In some embodiments, $R^7$ is selected from: 2,4-difluorophenyl, 5-bromo-pyridin-2-yl, 4-cyano-phenyl, pyridin-3-yl, pyridin-2-yl, 5-thiazol-2-yl-pyridin-2-yl, 5-trifluoromethyl-pyridin-2-yl, 5-o-tolyl-pyridin-2-yl, 5-dimethylamino-pyrazin-2-yl, 2,4-dichloro-phenyl, 5-isopropyl-pyridin-2-yl, 5-methyl-pyridin-2-yl, 5-(4-methoxy-phenyl)-pyridin-2-yl, 2-fluoro-4-methanesulfonyl-phenyl, 2-fluoro-phenyl, 5-chloro-pyridin-2-yl, 5-bromo-pyridin-3-yl, tert-butyl, 2-methoxy-pyridin-4-yl, 2,2-dimethyl-propyl, tetrahydro-pyran-4-ylmethyl, phenyl, 4-trifluoromethyl-pyridin-2-yl, 6-chloro-pyrazin-2-yl, 1-oxo-hexahydro-1$\lambda^4$-thiopyran-4-yl, 5-morpholin-4-yl-pyridin-2-yl, 6-bromo-pyridin-3-yl, 5-methoxy-pyridin-2-yl, 5,6-difluoro-pyridin-3-yl, 6-methoxy-pyridazin-3-yl, 2-chloro-pyridin-4-yl, 5-cyclopropyl-pyrazin-2-yl, 1,1-dioxo-tetrahydro-1$\lambda^6$-thiophen-3-yl, 1-benzyl-piperidin-4-yl, 6-cyano-pyrazin-2-yl, 2-hydroxy-2-methyl-propyl, 4-fluoro-phenyl, 5-ethyl-pyridin-2-yl, isopropyl, 5-phenyl-pyridin-2-yl, pyridin-4-yl, 2,5-difluoro-phenyl, 3-fluoro-phenyl, pyrimidin-4-yl, 2-(tetrahydro-pyran-4-yl)-ethyl, 3,5-difluoro-pyridin-2-yl, pyrazin-2-yl, tetrahydro-thiopyran-4-yl, 5-p-tolyl-pyridin-2-yl, 4-methoxy-phenyl, 2-morpholin-4-yl-ethyl, 5-cyano-pyridin-2-yl, 5-cyano-pyrazin-2-yl, 6'-methyl-[3,3]bipyridinyl-6-yl, 6-chloro-pyridazin-3-yl, 5-fluoro-pyridin-2-yl, 5-ethyl-pyrazin-2-yl, 6-methoxy-pyrazin-2-yl, 5-dimethylamino-pyridin-2-yl, 1-(4-fluoro-phenyl)-1-methyl-ethyl, 5-pyrimidin-5-yl-pyridin-2-yl, 4-methyl-pyridin-2-yl, 5-methoxy-pyrazin-2-yl, 5-propyl-pyridin-2-yl, 6-chloro-pyridin-3-yl, 5-m-tolyl-pyridin-2-yl, 5-hydroxy-pyrazin-2-yl, cyclopropyl-pyridin-2-yl, 2,6-difluoro-phenyl, 3-fluoro-pyridin-4-yl, 5-isopropyl-pyrazin-2-yl, 5-bromo-pyrazin-2-yl, 5-cyclopentyl-pyridin-2-yl, o-tolyl, 4-fluoro-benzyl, 3-methyl-pyridin-2-yl, 6-methyl-4-trifluoromethyl-pyridin-2-yl, 6-dimethylamino-pyrazin-2-yl, 1,1-dioxo-hexahydro-1$\lambda^6$-thiopyran-4-yl, 5-(4-fluoro-phenyl)-pyridin-2-yl, 5-cyclopropyl-pyridin-2-yl, 6-ethyl-pyrazin-2-yl, 5-methylamino-pyrazin-2-yl, 5-methyl-pyrazin-2-yl, 3-fluoro-pyridin-2-yl, 5-cyclobutyl-pyrazin-2-yl, 5-ethoxy-pyrazin-2-yl, 5-trifluoromethyl-pyrazin-2-yl, 5-cyano-pyridin-3-yl, 5-cyclopropylmethyl-pyrazin-2-yl, 5-pentafluoroethyl-pyrazin-2-yl, 5-heptafluoropropyl-pyrazin-2-yl, 5-chloro-4-methyl-pyridin-2-yl, 5-chloro-4-trifluoromethyl-pyridin-2-yl, 4-bromo-pyridin-2-yl, 4-chloro-pyridin-2-yl, 4-fluoro-pyridin-2-yl, 4-oxy-pyrazin-2-yl, 4-cyclopropyl-pyridin-2-yl, 4-cyano-pyridin-2-yl, 4-methanesulfonyl-pyridin-2-yl, 4-methoxy-pyridin-2-yl, and piperidin-4-yl.

In some embodiments, $R^7$ is 2,4-difluoro-phenyl. In some embodiments, $R^7$ is 5-bromo-pyridin-2-yl. In some embodiments, $R^7$ is 4-cyano-phenyl. In some embodiments, $R^7$ is pyridin-3-yl. In some embodiments, $R^7$ is pyridin-2-yl. In some embodiments, $R^7$ is 5-thiazol-2-yl-pyridin-2-yl. In some embodiments, $R^7$ is 5-trifluoromethyl-pyridin-2-yl. In some embodiments, $R^7$ is 5-o-tolyl-pyridin-2-yl. In some embodiments, $R^7$ is 5-dimethylamino-pyrazin-2-yl. In some embodiments, $R^7$ is 2,4-dichloro-phenyl. In some embodiments, $R^7$ is 5-isopropyl-pyridin-2-yl. In some embodiments, $R^7$ is 5-methyl-pyridin-2-yl. In some embodiments, $R^7$ is 5-(4-methoxy-phenyl)-pyridin-2-yl. In some embodiments, $R^7$ is 2-fluoro-4-methanesulfonyl-phenyl. In some embodiments, $R^7$ is 2-fluoro-phenyl. In some embodiments, $R^7$ is 5-chloro-pyridin-2-yl. In some embodiments, $R^7$ is 5-bromo-pyridin-3-yl. In some embodiments, $R^7$ is tert-butyl. In some embodiments, $R^7$ is 2-methoxy-pyridin-4-yl. In some embodiments, $R^7$ is 2,2-dimethyl-propyl. In some embodiments, $R^7$ is tetrahydro-pyran-4-ylmethyl. In some embodiments, $R^7$ is phenyl. In some embodiments, $R^7$ is 4-trifluoromethyl-pyridin-2-yl. In some embodiments, $R^7$ is 6-chloro-pyrazin-2-yl. In some embodiments, $R^7$ is 1-oxo-hexahydro-1$\lambda^4$-thiopyran-4-yl. In some embodiments, $R^7$ is 5-morpholin-4-yl-pyridin-2-yl. In some embodiments, $R^7$ is 6-bromo-pyridin-3-yl. In some embodiments, $R^7$ is 5-methoxy-pyridin-2-yl. In some embodiments, $R^7$ is 5,6-difluoro-pyridin-3-yl. In some embodiments, $R^7$ is 6-methoxy-pyridazin-3-yl. In some embodiments, $R^7$ is 2-chloro-pyridin-4-yl. In some embodiments, $R^7$ is 5-cyclopropyl-pyrazin-2-yl. In some embodiments, $R^7$ is 1,1-dioxo-tetrahydro-1$\lambda^6$-thiophen-3-yl. In some embodiments, $R^7$ is 1-benzyl-piperidin-4-yl. In some embodiments, $R^7$ is 6-cyano-pyrazin-2-yl. In some embodiments, $R^7$ is 2-hydroxy-2-methyl-propyl. In some embodiments, $R^7$ is 4-fluoro-phenyl. In some embodiments, $R^7$ is 5-ethyl-pyridin-2-yl. In some embodiments, $R^7$ is isopropyl. In some embodiments, $R^7$ is 5-phenyl-pyridin-2-yl. In some embodiments, $R^7$ is pyridin-4-yl. In some embodiments, $R^7$ is 2,5-difluoro-phenyl. In some embodiments, $R^7$ is 3-fluoro-phenyl. In some embodiments, $R^7$ is pyrimidin-4-yl. In some embodiments, $R^7$ is 2-(tetrahydro-pyran-4-yl)-ethyl. In some embodiments, $R^7$ is 3,5-difluoro-pyridin-2-yl. In some embodiments, $R^7$ is pyrazin-2-yl. In some embodiments, $R^7$ is tetrahydro-thiopyran-4-yl. In some embodiments, $R^7$ is 5-p-tolyl-pyridin-2-yl. In some embodiments, $R^7$ is 4-methoxy-phenyl. In some embodiments, $R^7$ is 2-morpholin-4-yl-ethyl. In some embodiments, $R^7$ is 5-cyano-pyridin-2-yl. In some embodiments, $R^7$ is 5-cyano-pyrazin-2-yl. In some embodiments, $R^7$ is 6'-methyl-[3,3']bipyridinyl-6-yl. In some embodiments, $R^7$ is 6-chloro-pyridazin-3-yl. In some embodiments, $R^7$ is 5-fluoro-pyridin-2-yl. In some embodiments, $R^7$ is 5-ethyl-pyrazin-2-yl. In some embodiments, $R^7$ is 6-methoxy-pyrazin-2-yl. In some embodiments, $R^7$ is 5-dimethylamino-pyridin-2-yl. In some embodiments, $R^7$ is 1-(4-fluoro-phenyl)-1-methyl-ethyl. In some embodiments, $R^7$ is 5-pyrimidin-5-yl-pyridin-2-yl. In some embodiments, $R^7$ is 4-methyl-pyridin-2-yl. In some embodiments, $R^7$ is 5-methoxy-pyrazin-2-yl. In some embodiments, $R^7$ is 5-propyl-pyridin-2-yl. In some embodiments, $R^7$ is 5-m-tolyl-pyridin-2-yl. In some embodiments, $R^7$ is 5-hydroxy-pyrazin-2-yl. In some embodiments, $R^7$ is cyclopropyl-pyridin-2-yl. In some embodiments, $R^7$ is 2,6-difluoro-phenyl. In some embodiments, $R^7$ is 3-fluoro-pyridin-4-yl. In some embodiments, $R^7$ is 5-isopropyl-pyrazin-2-yl. In some embodiments, $R^7$ is 5-bromo-pyrazin-2-yl. In some embodiments, $R^7$ is 5-cyclopentyl-pyridin-2-yl. In some embodiments, $R^7$ is o-tolyl. In some embodiments, $R^7$ is 4-fluoro-benzyl. In some embodiments, $R^7$ is 3-methyl-pyridin-2-yl. In some embodiments, $R^7$ is 6-methyl-4-trifluoromethyl-pyridin-2-yl. In some embodiments, $R^7$ is 6-dimethylamino-pyrazin-2-yl. In some embodiments, $R^7$ is 1,1-dioxo-hexahydro-1$\lambda^6$-thiopyran-4-yl. In some embodiments, $R^7$ is 5-(4-fluoro-phenyl)-pyridin-2-yl. In some embodiments, $R^7$ is 5-cyclopropyl-pyridin-2-yl. In some embodiments, $R^7$ is 6-ethyl-pyrazin-2-yl. In some embodiments, $R^7$ is 5-methylamino-pyrazin-2-yl. In some embodiments, $R^7$ is dichloro-phenyl. In some embodiments, $R^7$ is 5-methyl-pyrazin-2-yl. In some embodiments, $R^7$ is 3-fluoro-pyridin-2-yl. In some embodiments, $R^7$ is 5-cyclobutyl-pyrazin-2-yl. In some embodiments, $R^7$ is 5-ethoxy-pyrazin-2-yl. In some embodiments, $R^7$ is 5-trifluoromethyl-pyrazin-2-yl. In some embodiments, $R^7$ is 5-cyano-pyridin-3-yl. In some embodiments, $R^7$ is 5-cyclopropylmethyl-pyrazin-2-yl. In some embodiments, $R^7$ is 5-pentafluoroethyl-pyrazin-2-yl. In some embodiments, $R^7$ is 5-heptafluoropropyl-pyrazin-2-yl. In some embodiments, $R^7$ is 5-chloro-4-methyl-pyridin-2-yl. In some embodiments, $R^7$ is 5-chloro-4-trifluoromethyl-pyridin-2-yl. In some embodiments, $R^7$ is 4-bromo-pyridin-2-yl. In some embodiments, $R^7$ is 4-chloro-pyridin-2-yl. In some embodiments, $R^7$ is 4-fluoro-pyridin-2-yl. In some embodiments, $R^7$ is 4-oxy-pyrazin-2-yl. In some embodiments, $R^7$ is 4-cyclopropyl-pyridin-2-yl. In some embodiments, $R^7$ is 4-cyano-pyridin-2-yl. In some embodiments, $R^7$ is 4-methanesulfonyl-pyridin-2-yl. In some embodiments, $R^7$ is 4-methoxy-pyridin-2-yl. In some embodiments, $R^7$ is piperidin-4-yl. In some embodiments, $R^7$ is tetrahydro-pyran-4-yl. In some embodiments, $R^7$ is 3-methyl-1,1-dioxo-tetrahydro-1$\lambda^6$-thiophen-3-yl. In some embodiments, $R^7$ is 5-chloro-3-fluoro-pyridin-2-yl. In some embodiments, $R^7$ is 3-fluoro-5-methoxy-pyridin-2-yl. In some embodiments, $R^7$ is 2-chloro-4-fluoro-phenyl. In some embodiments, $R^7$ is 6-fluoro-pyridin-3-yl. In some embodiments, $R^7$ is 6-cyano-pyridin-3-yl. In some embodiments, $R^7$ is 3-hydroxy-3-methyl-butyl. In some embodiments, $R^7$ is 4-iodo-pyridin-2-yl. In some embodiments, $R^7$ is 1-oxy-pyridin-3-yl. In some embodiments, $R^7$ is 4-tert-butylcarbamoyl-pyridin-2-yl. In some embodiments, $R^7$ is 4-hydroxy-pyridin-2-yl.

The Group $R^8$:

In some embodiments, $R^8$ is —$R^{14}$—$R^{15}$—$R^{16}$—$R^{17}$.

In some embodiments, $R^8$ is selected from: 1-hydroxymethyl-2,2-dimethyl-propyl, 2-hydroxy-1,1-dimethyl-ethyl, 1-hydroxymethyl-cyclopropyl, 2-hydroxy-indan-1-yl, 1-hydroxymethyl-cyclobutyl, tert-butyl, 2-hydroxy-1-phenyl-ethyl, 2-hydroxy-1-hydroxymethyl-1-methyl-ethyl, tert-butylamino, 2,2,2-trifluoro-1,1-dimethyl-ethyl, 2-methyl-1-(phosphonooxy)propan-2-yl, 1-methyl-cyclobutyl, 1-hydroxymethyl-2-methyl-propyl, cyano-dimethyl-methyl, 2,2-dimethyl-1-(methylcarbamoyl)-propyl, 3,3-dimethyl-1-(phosphonooxy)butan-2-yl, 2-hydroxy-1-tetrahydro-pyran-4-yl-ethyl, 1,2-dimethyl-propyl, 1-pyridin-2-yl-cyclobutyl, 2-(methylamino)-2-oxo-1-phenylethyl, 2,2-dimethyl-1-pyridin-2-yl-propyl, 1-methoxy-3,3-dimethyl-1-oxobutan-2-yl, 1-(2-amino-3-methylbutanoyloxy)-3-methylbutan-2-yl, 1-(4-carboxybutanoyloxy)-3-methylbutan-2-yl, 3,3,3-trifluoro-1-hydroxymethyl-propyl, 2-fluoro-1,1-dimethyl-ethyl, 2-fluoro-1-fluoromethyl-1-hydroxymethyl-ethyl, 1-fluoromethyl-2,2-dimethyl-propyl, 1-fluoromethyl-cyclobutyl, 1-trifluoromethyl-cyclopropyl, and 1-trifluoromethyl-cyclobutyl.

In some embodiments, $R^8$ is selected from: H, 2-methyl-2-morpholin-4-yl-propyl, 1-hydroxymethyl-2,2-dimethyl-propyl, 2-(tert-butoxycarbonylamino)cyclohexyl, 1-phenyl-cyclopropyl, 5-trifluoromethyl-pyridin-2-yl, 1-methyl-1-phenyl-ethyl, 1-(2-methoxy-ethyl)-pyrrolidin-3-ylmethyl, 1-(methoxycarbonyl)cyclopropyl, tetrahydro-pyran-4-ylmethyl, 1-(tert-butoxycarbonyl)piperidin-4-yl, 1-(4-fluoro-phenyl)-cyclopropyl, 6-methyl-pyridin-3-ylmethyl, 2-hydroxy-1-phenyl-ethyl, 1,3,3-trimethyl-bicyclo[2.2.1]hept-2-yl, 2-hydroxy-1,1-dimethyl-ethyl, 2-(5-hydroxy-1H-indol-3-yl)-ethyl, 1-hydroxymethyl-cyclopropyl, 3-chloro-5-methyl-pyridin-2-yl, 6-fluoro-pyridin-3-yl, 1-(3-fluoro-phenyl)-cyclobutyl, 2-methyl-pyridin-3-yl, 2-hydroxy-1-(tetrahydro-furan-3-yl)-ethyl, 2-(pyridin-3-yloxy)-propyl, carbamoyl-phenyl-methyl, 5-fluoro-2-methoxy-phenyl, 2-methoxy-ethyl, 2,3-dihydroxy-propyl, 1-(tert-butoxycarbonyl)pyrrolidin-3-yl, 2-oxo-2-phenyl-ethyl, 1-(3,3,3-trifluoro-propyl)-azetidin-3-yl, 2-hydroxy-1-pyridin-2-yl-ethyl, 3-hydroxy-pyridin-4-yl, 1-methyl-1-pyridin-4-yl-ethyl, 1-hydroxymethyl-2-3H-imidazol-4-yl-ethyl, 4-hydroxy-3-methoxy-benzyl, 5-fluoro-2-oxo-2,3-dihydro-pyrimidin-4-yl, 1-(4-fluoro-phenyl)-3-hydroxy-propyl, 1-pyridin-4-yl-cyclopropyl, 2-hydroxy-1-pyridin-3-yl-ethyl, 1,1-dimethyl-2-(4-methyl-piperidin-1-yl)-ethyl, 6-cyano-pyridin-3-yl, 5-fluoro-pyridin-2-yl, 2,5-dimethyl-benzyl, 1-isopropyl-piperidin-4-yl, 2-methoxy-1-methoxymethyl-ethyl, 2,3-dimethyl-benzyl, 1-pyridin-2-yl-ethyl, 6-chloro-pyridin-3-ylmethyl, 3-methyl-pyridin-2-yl, 2-hydroxy-indan-1-yl, 1-hydroxymethyl-cyclobutyl, 2-(4-chloro-phenyl)-1,1-dimethyl-ethyl, 3-hydroxy-pyridin-2-ylmethyl, 3-methyl-pyridin-4-yl, 5-tert-butyl-isoxazol-3-yl, 1-(6-methoxy-pyridin-3-yl)-1-methyl-ethyl, 1H-benzoimidazol-2-yl, tert-butyl, 4-phenyl-thiazol-2-yl, 1-(2-fluoro-phenyl)-cyclobutyl, 2,4-dimethoxy-benzyl, 5-bromo-3-methyl-pyridin-2-yl, 4-benzyl-morpholin-2-ylmethyl, 6-trifluoromethyl-pyridin-3-ylmethyl, tetrahydro-furan-3-yl, pyridin-3-ylmethyl, pyrazin-2-yl, piperidin-4-yl, 1-(6-hydroxy-pyridin-3-yl)-1-methyl-ethyl, 1-methyl-1-pyridin-2-yl-ethyl, 1-hydroxymethyl-cyclopentyl, 1-aza-bicyclo[2.2.2]oct-3-yl, 2-hydroxy-cyclopentyl, 2-hydroxy-1-(hydroxymethyl)-propyl, 1-(tert-butoxycarbonyl)piperidin-4-yl)methyl, 3,5-dimethoxy-phenyl, 6-fluoro-4H-benzo[1,3]dioxin-8-ylmethyl, 4,6-dimethyl-pyridin-2-yl, 1,1-dimethyl-2-morpholin-4-yl-ethyl, 2-hydroxy-cyclohexylmethyl, 1-(4-methoxy-phenyl)-cyclopropyl, 1-ethyl-pyrrolidin-2-ylmethyl, indan-1-yl, pyrimidin-4-yl, 2-fluoro-4- methanesulfonyl-phenyl, 6-hydroxy-pyridin-2-yl, cyclobutyl, 1-(3-methoxy-phenyl)-cyclopropyl, 1-(3,3,3-trifluoro-propyl)-pyrrolidin-3-yl, 2-hydroxy-pyridin-3-yl, 4-difluoromethoxy-benzyl, 1-piperidin-1-yl-cyclopentylmethyl, 3-hydroxy-3-methyl-butyl, 1-(4-fluoro-phenyl)-cyclobutyl, 4-methoxy-benzyl, pyridin-2-yl, 2-hydroxy-2-phenyl-ethyl, 2-hydroxymethyl-2,3-dihydro-indol-1-yl, 3-hydroxy-pyridin-2-yl, 4-dimethylamino-tetrahydro-pyran-4-ylmethyl, 2-(4-fluoro-phenyl)-ethyl, 1-(2-methoxy-ethyl)-piperidin-4-ylmethyl, 2-morpholin-4-yl-ethyl, 1-(tert-butoxycarbonyl)-4-carboxypiperidin-4-yl, quinolin-3-yl, 1-morpholin-4-ylmethyl-cyclopentyl, 1,4-dimethyl-1H-pyrrol-2-ylmethyl, 2-hydroxy-2-pyridin-2-yl-ethyl, pyridin-3-yl, 2-dimethylamino-benzyl, tetrahydro-thiopyran-4-yl, 1-m-tolyl-cyclopropyl, 1-(2-methoxy-ethyl)-piperidin-3-yl, 5-methoxy-pyridin-2-ylmethyl, 2-hydroxy-1-pyridin-4-yl-ethyl, 4-methyl-pyridin-2-yl, 4-carboxy-2-fluorophenyl, 6-methanesulfonyl-pyridin-3-yl, 1-o-tolyl-cyclobutyl, 1,1-dimethyl-2-pyrrolidin-1-yl-ethyl, 2,6-dimethoxy-pyridin-3-yl, pyridin-2-yl, 4-hydroxymethyl-tetrahydro-pyran-4-yl, 2-(1H-imidazol-4-yl)-ethyl, 3-fluoro-pyridin-4-yl, 1-carbamoyl-2-phenyl-ethyl, oxazol-4-ylmethyl, 6-methoxy-pyrimidin-4-yl, 1,1-dioxo-hexahydro-1λ$^6$-thiopyran-4-yl, 1-methoxy-1-oxo-3-phenylpropan-2-yl, 1-(2-methoxy-ethyl)-pyrrolidin-3-yl, 1-(6-methyl-pyridin-2-yl)-ethyl, 2-hydroxy-1-(4-hydroxy-phenyl)-ethyl, 2-methoxy-pyridin-4-yl, 1-pyridin-2-yl-cyclopropyl, 1-(tert-butoxycarbonyl)piperidin-3-yl, 3-methyl-pyridin-2-ylmethyl, 3-fluoro-pyridin-2-yl, 1-pyridin-4-yl-cyclobutyl, 2-carboxy-1-(pyridin-3-yl)ethyl, 2-hydroxy-1-methyl-ethyl, 1-(methoxycarbonyl)cyclohexyl, 3-hydroxymethyl-pyridin-4-yl, 2-hydroxy-1-phenyl-ethyl, 3-dimethylamino-tetrahydro-thiophen-3-ylmethyl, tetrahydro-pyran-4-yl, 5-chloro-pyridin-2-yl, 1-carbamoyl-cyclobutyl, 5-fluoro-2-methyl-benzyl, 2-morpholin-4-yl-2-pyridin-3-yl-ethyl, 1-(3-methoxy-phenyl)-cyclobutyl, 5-methyl-pyridin-2-yl, 1-(tetrahydro-furan-2-yl)methyl, 1-dimethylaminomethyl-cyclopentyl, 2-(4-fluoro-phenyl)-1-methyl-ethyl, benzothiazol-2-yl, 1-(2-fluoro-phenyl)-cyclopropyl, 1-(2-methoxy-ethyl)-piperidin-4-yl, 2-hydroxy-1-pyridin-4-yl-ethyl, 1-(3,3,3-trifluoro-propyl)-azetidin-3-ylmethyl, 6-pyrrolidin-1-yl-pyridin-2-ylmethyl, 1,1-dioxo-tetrahydro-1λ$^6$-thiophen-3-yl, 2,3-dimethoxy-benzyl, 3-cyano-5-methyl-pyridin-2-yl, 2,3-dihydro-benzofuran-3-yl, 1-hydroxymethyl-cyclohexyl, 2,5-difluoro-benzyl, 4-dimethylamino-benzyl, 4-hydroxy-1,1-dioxo-tetrahydro-1λ$^6$-thiophen-3-yl, 4-trifluoromethyl-pyridin-2-yl, 5-methyl-thiazol-2-yl, 6-trifluoromethyl-pyridin-3-yl, 5-hydroxy-1H-pyrazol-3-yl, 2-thiomorpholin-4-yl-ethyl, benzo[1,3]dioxol-5-ylmethyl, 2-amino-cyclohexyl, 3-dimethylamino-1-oxo-tetrahydro-1λ$^4$-thiophen-3-ylmethyl, 4-methyl-morpholin-2-ylmethyl, 1-(2-methoxy-phenyl)-cyclopropyl, 2-carboxy-1-(4-fluorophenyl)propan-2-yl, pyridin-2-ylmethyl, pyridazin-3-yl, 4-pyridin-2-yl-thiazol-2-yl, 1-(3,3,3-trifluoro-propyl)-piperidin-4-ylmethyl, 6-chloro-2-methyl-pyridin-3-yl, 6-hydroxy-pyridin-3-yl, 3-trifluoromethoxy-benzyl, 1-morpholin-4-yl-cyclopentylmethyl, 1-pyridin-2-yl-cyclobutylmethyl, indan-1-ylamide, 2-hydroxy-1-hydroxymethyl-1-methyl-ethyl, 5-hydroxymethyl-pyridin-2-yl, 5-fluoro-1-oxy-pyridin-2-yl, 6-methoxy-pyridin-2-yl, 1-methyl-1-pyridin-3-yl-ethyl, 6-methyl-pyridin-3-yl, 2-hydroxy-1-hydroxymethyl-propyl, 2-chloro-pyridin-3-yl, 3-methyl-3H-imidazol-4-ylmethyl, 6-fluoro-pyridin-2-yl, 3-dimethylamino-benzyl, 6-morpholin-4-yl-pyridin-3-yl, 1-o-tolyl-cyclopropyl, 1-(3,3,3-trifluoro-propyl)-piperidin-3-yl, 6-methanesulfonyl-4-methyl-pyridin-3-yl, 2-methyl-quinolin-4-yl, 1-(3,3,3-trifluoro-propyl)-pyrrolidin-3-ylmethyl, benzooxazol-2-yl, 1-methyl-piperidin-4-ylmethyl, 2-(2,6-dimethyl-morpholin-4-yl)-2-methyl-propyl, 1-methyl-piperidin-2-ylmethyl, pyridin-4-ylmethyl, 4-hydroxymethyl-pyridin-2-yl, 5,7-dimethyl-pyrazolo[1,5-a]pyrimidin-2-yl, 6,6-dimethyl-bicyclo[3.1.1]hept-2-ylmethyl, 1-(5-methyl-pyridin-2-yl)-ethyl, 2-fluoro-pyridin-3-yl, morpholin-4-yl, 2-hydroxy-2-pyridin-4-yl-ethyl, pyridin-4-yl, 4-hydroxy-pyridin-2-yl, 3-methoxy-benzyl, 1-oxy-pyridin-2-yl, 1-ethyl-propyl, 6-carboxypyridin-2-yl, 1,2,2,6,6-pentamethyl-piperidin-4-yl, 6-methoxy-pyridin-3-yl, cyclopentyl, morpholin-2-ylmethyl, 1-(tert-butoxycarbonyl)azetidin-3-yl)methyl, 2-dimethylamino-2-pyridin-3-yl-ethyl, 1-(4-methoxy-phenyl)-cyclobutyl, 3-hydroxy-benzyl, tetrahydrofuran-2-ylmethyl, 4-(tert-butoxycarbonyl)morpholin-2-ylmethyl, 1-(3-fluoro-phenyl)-cyclopropyl, 2-o-tolyl-ethyl, 3-hydroxymethyl-1-isobutyl-pyrrolidin-3-yl, 1-(2-methoxy-ethyl)-azetidin-3-yl, 6-morpholin-4-yl-pyridin-2-ylmethyl, 1,1-dioxo-tetrahydro-1λ$^6$-thiophen-3-yl methyl, 2-(4-fluoro-phenoxy)-ethyl, 2,6-dimethyl-pyrimidin-4-yl, 1-hydroxymethyl-2-(3H-imidazol-4-yl)-ethyl, 4-methanesulfonyl-benzyl, 1-pyridin-3-yl-cyclopropyl, 9-methyl-9-azabicyclo[3.3.1]non-1-yl, 2,6-dimethyl-pyridin-3-yl, 4-hydroxy-benzyl, 2-oxo-2-phenyl-ethyl), 1-methyl-1H-pyrazol-3-ylmethyl, pyrimidin-2-yl, 5-methyl-pyrazin-2-yl, 1-(2-methoxy-pyridin-3-yl)-1-methyl-ethyl, 6-methanesulfonyl-2-methyl-pyridin-3-yl, 2-hydroxy-benzyl, 6-bromo-2-methyl-pyridin-3-yl, 2-methoxy-pyridin-3-yl, 1-(4-chloro-phenyl)-cyclobutyl, 2-(pyridine-2-sulfonyl)-ethyl, 1-pyridin-2-yl-cyclopropylmethyl, 1-methyl-1,2,3,4-tetrahydro-quinolin-7-yl, benzyl, 3,5-dimethyl-pyrazin-2-yl, 1-(2-hydroxy-pyridin-3-yl)-1-methyl-ethyl, 1-(ethoxycarbonyl)cyclobutyl, 1-(tert-butoxycarbonyl)pyrrolidin-3-ylmethyl, quinolin-4-ylmethyl, 2-(4-fluoro-phenyl)-1-(2-hydroxy-ethylcarbamoyl)-1-methyl-ethyl, 2-morpholin-4-yl-pyridin-3-yl, 6-methyl-pyridin-2-yl, 3-difluoromethoxy-benzyl, 4-hydroxy-1-methyl-piperidin-4-ylmethyl, 1-(2,5-dimethylpyrrolidine-1-carbonyl)cyclopentyl, 2-methoxy-benzyl, 6-methyl-pyridin-2-ylmethyl, 3-chloro-pyridin-4-yl, 2-carboxypropan-2-yl, 6-chloro-pyridin-3-yl, 2-hydroxy-2-pyridin-3-yl-ethyl, 1-p-tolyl-cyclopropyl, 1-(3,3,3-trifluoro-propyl)-piperidin-4-yl, 4-methoxy-pyridin-2-yl, 3-azepan-1-yl-2,2-dimethyl-propyl, 1-(tert-butoxycarbonyl)azetidin-3-yl, 5-methyl-pyrazin-2-ylmethyl, 1-oxo-hexahydro-1λ$^4$-thiopyran-4-yl, 2-(2-chloro-phenyl)-ethyl, 3-chloro-5-trifluoromethyl-pyridin-2-ylmethyl, 2-hydroxy-1-hydroxymethyl-ethyl, (1-methyl-pyrrolidin-2-yl)-pyridin-2-yl, 5-fluoro-2-hydroxy-phenyl, methyl, 4-(methoxycarbonyl)-1-methylpiperidin-4-yl, 4-hydroxymethyl-1-methyl-piperidin-4-yl, 2-(2-hydroxymethyl-pyrrolidin-1-yl)-ethyl, 1-phenyl-cyclohexyl, 3-methyl-1,1-dioxo-tetrahydro-1λ$^6$-thiophen-3-yl, 1-cyano-cyclohexyl, 1-(5-methyl-[1,2,4]oxadiazol-3-yl)-cyclohexyl, 2-cyanopropan-2-yl, 3-methyl-1-phenylureido, 1-carbamoyl-2,2-dimethyl-propyl, tert-butylamino, 2,2,2-trifluoro-1,1-dimethyl-ethyl, 2,2-dimethyl-1-methylcarbamoyl-propyl, 1-cyclopropyl-ethyl, amino, N-tert-butylmethylsulfonamido, 1,1-dimethyl-prop-2-ynyl, 2-methyl-1-(phosphonooxy)propan-2-yl, 1-tert-butyl-3-methylureido, 4-cyano-tetrahydro-pyran-4-yl, 1-methyl-cyclobutyl, 1-hydroxymethyl-2-methyl-propyl, cyclobutylamino, 1-cyano-cyclopentyl, cyano-dimethyl-methyl, 2,2-dimethyl-1-(methylcarbamoyl)-propyl, phenylamino, 1-hydroxymethyl-propyl, 1-methyl-1-(1H-tetrazol-5-yl)-ethyl, 3,3-dimethyl-1-(phosphonooxy)butan-2-yl), 2-hydroxy-1-tetrahydro-pyran-4-yl-ethyl, 1,2-dimethyl-propyl, 1-pyridin-2-yl-cyclobutyl, 1-hydroxymethyl-2-phenyl-ethyl, 4-methylcarbamoyl-tetrahydro-pyran-4-yl, 1-methyl-1-methylcarbamoyl-ethyl, 2,2-dimethyl-1-morpholin-4-ylmethyl-propyl, 1-methylcarbamoyl-cyclopent-3-enyl, 2-methoxy-2-oxo-1-(pyridin-2-yl)ethyl, methylcarbamoyl-pyridin-2-yl-methyl, 1-methylcarbamoyl-cyclopentyl, 1-(tert-butylcarbamoyl)-2,2-dimethyl-propyl, 2,2-dimethyl-1-(pyridin-2-ylcarbamoyl)-propyl, 1-(pyridin-2-ylcarbamoyl)-cyclobutyl, 1-methylcarbamoyl-cyclobutyl, 2-(methyl-amino)-2-oxo-1-phenylethyl, pyrrolidin-1-yl, piperidin-1-yl, 2,6-dimethyl-piperidin-1-yl, 1-cyclopropylcarbamoyl-2,2-dimethyl-propyl, 2,2-dimethyl-1-(2,2,2-trifluoro-ethylcarbamoyl)-propyl, 1-ethylcarbamoyl-2,2-dimethyl-propyl, 2-hydroxy-1-(tetrahydro-pyran-4-yl)-ethyl, N-cyclobutylmethylsulfonamido, N-phenylmethylsulfona-mido, 1-cyclopropyl-2-hydroxy-ethyl, 1,2,2-trimethyl-pro-pyl, 2-oxo-1-(pyridin-2-yl)-2-(2,2,2-trifluoroethylamino)ethyl, 2,2-dimethyl-1-pyridin-2-yl-propyl, 1-methoxy-3,3-dimethyl-1-oxobutan-2-yl, 1-carboxy-2,2-dimethylpropyl, 1-(hydroxy-methyl-carbamoyl)-2,2-dimethyl-propyl, 1-dimethylcarbamoyl-2,2-dimethyl-propyl, 1-(azetidine-1-car-bonyl)-2,2-dimethyl-propyl, 1-methoxycarbamoyl-2,2-dim-ethyl-propyl, 1-(methoxy-methyl-carbamoyl)-2,2-dimethyl-propyl, 1-tert-butoxycarbamoyl-2,2-dimethyl-propyl, 2,2-dimethyl-1-pyridin-2-yl-propyl, (1,1-dioxo-tetrahydro-1$\lambda^6$-thiophen-3-yl)amino, 1-hydroxycarbamoyl-2,2-dimethyl-propyl, 1-hydroxymethyl-2-methyl-butyl, 1-(2-hydroxy-ethylcarbamoyl)-2,2-dimethyl-propyl, 1,1-bis-hydroxymethyl-propyl, 1-(5-fluoro-pyridin-2-yl)-2,2-dimethyl-propyl, 4-hydroxymethyl-tetrahydro-2H-pyran-4-yl, 1-(2-(tert-butoxycarbonylamino)-3-methylbutanoyloxy)-2-methylpropan-2-yl, 1-(2-amino-3-methylbutanoyloxy)-3-methylbutan-2-yl, 1-(2-amino-3-methylbutanoyloxy)-2-methylpropan-2-yl, 2-hydroxy-1-(tetrahydro-2H-pyran-4-yl)-ethyl, 1-(4-carboxybutanoyloxy)-2-methylpropan-2-yl, 1-(4-carboxybutanoyloxy)-3-methylbutan-2-yl, 1-(4-car-boxybutanoyloxy)-3,3-dimethylbutan-2-yl, 1-(2-amino-3-methylbutanoyloxy)-3,3-dimethylbutan-2-yl, 2-(2-amino-3-methylbutanoyloxy)-1-(tetrahydro-2H-pyran-4-yl)ethyl, 3,3,3-trifluoro-1-hydroxymethyl-propyl, 3-fluoro-1-methoxy-3-methyl-1-oxobutan-2-yl, 1-ethoxy-4,4,4-trif-luoro-1-oxo-3-(trifluoromethyl)butan-2-yl, 2-fluoro-1-hy-droxymethyl-2-methyl-propyl, 1-(2-(tert-butoxycarbonylamino)-3-methylbutanoyloxy)-3,3-dimethylbutan-2-yl, 4,4,4-trifluoro-1-methoxy-1-oxobutan-2-yl, 2-fluoro-1,1-dimethyl-ethyl, 3-fluoro-2-(fluoromethyl)-1-methoxy-1-oxopropan-2-yl, 2-fluoro-1-fluoromethyl-1-hydroxymethyl-ethyl, 3-hydroxy-1-methoxy-2-methyl-1-oxopropan-2-yl, 2-carboxy-1-hydroxypropan-2-yl, 2,2,2-trifluoroethylamino, 1-fluoromethyl-2-methyl-propyl, 1-fluoromethyl-2,2-dim-ethyl-propyl, 3-methyl-oxetan-3-yl, 1-fluoromethyl-cy-clobutyl, 1,1-bis-hydroxymethyl-2-methyl-propyl, 1-trifluo-romethyl-cyclopropyl, 1-methyl-cyclopropyl, and 1-trifluoromethyl-cyclobutyl.

In some embodiments, $R^8$ is selected from: H, 2-methyl-2-morpholin-4-yl-propyl, 1-hydroxymethyl-2,2-dimethyl-propyl, 2-(tert-butoxycarbonylamino)cyclohexyl, 1-phenyl-cyclopropyl, 5-trifluoromethyl-pyridin-2-yl, 1-methyl-1-phenyl-ethyl, 1-(2-methoxy-ethyl)-pyrrolidin-3-ylmethyl, 1-(methoxycarbonyl)cyclopropyl, tetrahydro-pyran-4-ylm-ethyl, 1-(tert-butoxycarbonyl)piperidin-4-yl, 1-(4-fluoro-phenyl)-cyclopropyl, 6-methyl-pyridin-3-ylmethyl, 2-hy-droxy-1-phenyl-ethyl, 1,3,3-trimethyl-bicyclo[2.2.1]hept-2-yl, 2-hydroxy-1,1-dimethyl-ethyl, 2-(5-hydroxy-1H-indol-3-yl)-ethyl, 1-hydroxymethyl-cyclopropyl, 3-chloro-5-methyl-pyridin-2-yl, 6-fluoro-pyridin-3-yl, 1-(3-fluoro-phenyl)-cyclobutyl, 2-methyl-pyridin-3-yl, 2-hydroxy-1-(tetrahydro-furan-3-yl)-ethyl, 2-(pyridin-3-yloxy)-propyl, carbamoyl-phenyl-methyl, 5-fluoro-2-methoxy-phenyl, 2-methoxy-ethyl, 2,3-dihydroxy-propyl, 1-(tert-butoxycar-bonyl)pyrrolidin-3-yl, 2-oxo-2-phenyl-ethyl, 1-(3,3,3-trif-luoro-propyl)-azetidin-3-yl, 2-hydroxy-1-pyridin-2-yl-ethyl, 3-hydroxy-pyridin-4-yl, 1-methyl-1-pyridin-4-yl-ethyl, 1-hydroxymethyl-2-3H-imidazol-4-yl-ethyl, 4-hydroxy-3-methoxy-benzyl, 5-fluoro-2-oxo-2,3-dihydro-pyrimidin-4-yl, 1-(4-fluoro-phenyl)-3-hydroxy-propyl, 1-pyridin-4-yl-cyclopropyl, 2-hydroxy-1-pyridin-3-yl-ethyl, 1,1-dimethyl-2-(4-methyl-piperidin-1-yl)-ethyl, 6-cyano-pyridin-3-yl, 5-fluoro-pyridin-2-yl, 2,5-dimethyl-benzyl, 1-isopropyl-piperidin-4-yl, 2-methoxy-1-methoxymethyl-ethyl, 2,3-dimethyl-benzyl, 1-pyridin-2-yl-ethyl, 6-chloro-pyridin-3-ylmethyl, 3-methyl-pyridin-2-yl, 2-hydroxy-in-dan-1-yl, 1-hydroxymethyl-cyclobutyl, 2-(4-chloro-phenyl)-1,1-dimethyl-ethyl, 3-hydroxy-pyridin-2-ylmethyl, 3-methyl-pyridin-4-yl, 5-tert-butyl-isoxazol-3-yl, 1-(6-methoxy-pyridin-3-yl)-1-methyl-ethyl, 1H-benzoimidazol-2-yl, tert-butyl, 4-phenyl-thiazol-2-yl, 1-(2-fluoro-phenyl)-cyclobutyl, 2,4-dimethoxy-benzyl, 5-bromo-3-methyl-pyridin-2-yl, 4-benzyl-morpholin-2-ylmethyl, 6-trifluoromethyl-pyridin-3-ylmethyl, tetrahydro-furan-3-yl, pyridin-3-ylmethyl, pyrazin-2-yl, piperidin-4-yl, 1-(6-hydroxy-pyridin-3-yl)-1-methyl-ethyl, 1-methyl-1-pyridin-2-yl-ethyl, 1-hydroxymethyl-cyclopentyl, 1-aza-bicyclo[2.2.2]oct-3-yl, 2-hydroxy-cyclopentyl, 2-hydroxy-1-(hydroxymethyl)-propyl, 1-(tert-butoxycarbonyl)piperidin-4-yl)methyl, 3,5-dimethoxy-phenyl, 6-fluoro-4H-benzo[1,3]dioxin-8-ylmethyl, 4,6-dimethyl-pyridin-2-yl, 1,1-dimethyl-2-morpholin-4-yl-ethyl, 2-hydroxy-cyclohexylmethyl, 1-(4-methoxy-phenyl)-cyclopropyl, 1-ethyl-pyrrolidin-2-ylmethyl, indan-1-yl, pyrimidin-4-yl, 2-fluoro-4-methanesulfonyl-phenyl, 6-hydroxy-pyridin-2-yl, cyclobutyl, 1-(3-methoxy-phenyl)-cyclopropyl, 1-(3,3,3-tri-fluoro-propyl)-pyrrolidin-3-yl, 2-hydroxy-pyridin-3-yl, 4-difluoromethoxy-benzyl, 1-piperidin-1-yl-cyclopentylm-ethyl, 3-hydroxy-3-methyl-butyl, 1-(4-fluoro-phenyl)-cy-clobutyl, 4-methoxy-benzyl, pyridin-2-yl, 2-hydroxy-2-phe-nyl-ethyl, 2-hydroxymethyl-2,3-dihydro-indol-1-yl, 3-hydroxy-pyridin-2-yl, 4-dimethylamino-tetrahydro-pyran-4-ylmethyl, 2-(4-fluoro-phenyl)-ethyl, 1-(2-methoxy-ethyl)-piperidin-4-ylmethyl, 2-morpholin-4-yl-ethyl, 1-(tert-butoxycarbonyl)-4-carboxypiperidin-4-yl, quinolin-3-yl, 1-morpholin-4-ylmethyl-cyclopentyl, 1,4-dimethyl-1H-pyr-rol-2-ylmethyl, 2-hydroxy-2-pyridin-2-yl-ethyl, pyridin-3-yl, 2-dimethylamino-benzyl, tetrahydro-thiopyran-4-yl, 1-m-tolyl-cyclopropyl, 1-(2-methoxy-ethyl)-piperidin-3-yl, 5-methoxy-pyridin-2-ylmethyl, 2-hydroxy-1-pyridin-4-yl-ethyl, 4-methyl-pyridin-2-yl, 4-carboxy-2-fluorophenyl, 6-methanesulfonyl-pyridin-3-yl, 1-o-tolyl-cyclobutyl, 1,1-dimethyl-2-pyrrolidin-1-yl-ethyl, 2,6-dimethoxy-pyridin-3-yl, pyridin-2-yl, 4-hydroxymethyl-tetrahydro-pyran-4-yl, 2-(1H-imidazol-4-yl)-ethyl, 3-fluoro-pyridin-4-yl, 1-car-bamoyl-2-phenyl-ethyl, oxazol-4-ylmethyl, 6-methoxy-py-rimidin-4-yl, 1,1-dioxo-hexahydro-1$\lambda^6$-thiopyran-4-yl, 1-methoxy-1-oxo-3-phenylpropan-2-yl, 1-(2-methoxy-ethyl)-pyrrolidin-3-yl, 1-(6-methyl-pyridin-2-yl)-ethyl, 2-hydroxy-1-(4-hydroxy-phenyl)-ethyl, 2-methoxy-pyridin-4-yl, 1-pyridin-2-yl-cyclopropyl, 1-(tert-butoxycarbonyl)pi-peridin-3-yl, 3-methyl-pyridin-2-ylmethyl, 3-fluoro-pyri-din-2-yl, 1-pyridin-4-yl-cyclobutyl, 2-carboxy-1-(pyridin-3-yl)ethyl, 2-hydroxy-1-methyl-ethyl, 1-(methoxycarbonyl)cyclohexyl, 3-hydroxymethyl-pyridin-4-yl, 2-hydroxy-1-phenyl-ethyl, 3-dimethylamino-tetrahydro-thiophen-3-yl methyl, tetrahydro-pyran-4-yl, 5-chloro-pyridin-2-yl, 1-car-bamoyl-cyclobutyl, 5-fluoro-2-methyl-benzyl, 2-morpholin-4-yl-2-pyridin-3-yl-ethyl, 1-(3-methoxy-phenyl)-cy-clobutyl, 5-methyl-pyridin-2-yl, 1-(tetrahydro-furan-2-yl)methyl, 1-dimethylaminomethyl-cyclopentyl, 2-(4-fluorophenyl)-1-methyl-ethyl, benzothiazol-2-yl, 1-(2-fluoro-phenyl)-cyclopropyl, 1-(2-methoxy-ethyl)-piperidin-4-yl, 2-hydroxy-1-pyridin-4-yl-ethyl, 1-(3,3,3-trifluoro-propyl)-azetidin-3-ylmethyl, 6-pyrrolidin-1-yl-pyridin-2-ylmethyl, 1,1-dioxo-tetrahydro-1$\lambda^6$-thiophen-3-yl, 2,3-dimethoxy-benzyl, 3-cyano-5-methyl-pyridin-2-yl, 2,3-dihydro-benzofuran-3-yl, 1-hydroxymethyl-cyclohexyl, 2,5-difluoro-benzyl, 4-dimethylamino-benzyl, 4-hydroxy-1,1-dioxo-tetrahydro-1$\lambda^6$-thiophen-3-yl, 4-trifluoromethyl-pyridin-2-yl, 5-methyl-thiazol-2-yl, 6-trifluoromethyl-pyridin-3-yl, 5-hydroxy-1H-pyrazol-3-yl, 2-thiomorpholin-4-yl-ethyl, benzo[1,3]dioxol-5-ylmethyl, 2-amino-cyclohexyl, 3-dimethylamino-1-oxo-tetrahydro-1$\lambda^4$-thiophen-3-ylmethyl, 4-methyl-morpholin-2-ylmethyl, 1-(2-methoxy-phenyl)-cyclopropyl, 2-carboxy-1-(4-fluorophenyl)propan-2-yl, pyridin-2-ylmethyl, pyridazin-3-yl, 4-pyridin-2-yl-thiazol-2-yl, 1-(3,3,3-trifluoro-propyl)-piperidin-4-ylmethyl, 6-chloro-2-methyl-pyridin-3-yl, 6-hydroxy-pyridin-3-yl, 3-trifluoromethoxy-benzyl, 1-morpholin-4-yl-cyclopentylmethyl, 1-pyridin-2-yl-cyclobutylmethyl, 2-hydroxy-1-hydroxymethyl-1-methyl-ethyl, 5-hydroxymethyl-pyridin-2-yl, 5-fluoro-1-oxy-pyridin-2-yl, 6-methoxy-pyridin-2-yl, 1-methyl-1-pyridin-3-yl-ethyl, 6-methyl-pyridin-3-yl, 2-hydroxy-1-hydroxymethyl-propyl, 2-chloro-pyridin-3-yl, 3-methyl-3H-imidazol-4-ylmethyl, 6-fluoro-pyridin-2-yl, 3-dimethylamino-benzyl, 6-morpholin-4-yl-pyridin-3-yl, 1-o-tolyl-cyclopropyl, 1-(3,3,3-trifluoro-propyl)-piperidin-3-yl, 6-methanesulfonyl-4-methyl-pyridin-3-yl, 2-methyl-quinolin-4-yl, 1-(3,3,3-trifluoro-propyl)-benzooxazol-2-yl, 1-methyl-piperidin-4-ylmethyl, 2-(2,6-dimethyl-morpholin-4-yl)-2-methyl-propyl, 1-methyl-piperidin-2-ylmethyl, pyridin-4-ylmethyl, 4-hydroxymethyl-pyridin-2-yl, 5,7-dimethyl-pyrazolo[1,5-a]pyrimidin-2-yl, 6,6-dimethyl-bicyclo[3.1.1]hept-2-ylmethyl, 1-(5-methyl-pyridin-2-yl)-ethyl, 2-fluoro-pyridin-3-yl, morpholin-4-yl, 2-hydroxy-2-pyridin-4-yl-ethyl, pyridin-4-yl, 4-hydroxy-pyridin-2-yl, 3-methoxy-benzyl, 1-oxy-pyridin-2-yl, 1-ethyl-propyl, 6-carboxypyridin-2-yl, 1,2,2,6,6-pentamethyl-piperidin-4-yl, 6-methoxy-pyridin-3-yl, cyclopentyl, morpholin-2-ylmethyl, 1-(tert-butoxycarbonyl)azetidin-3-yl)methyl, 2-dimethylamino-2-pyridin-3-yl-ethyl, 1-(4-methoxy-phenyl)-cyclobutyl, 3-hydroxy-benzyl, tetrahydro-furan-2-ylmethyl, 4-(tert-butoxycarbonyl)morpholin-2-ylmethyl, 1-(3-fluoro-phenyl)-cyclopropyl, 2-o-tolyl-ethyl, 3-hydroxymethyl-1-isobutyl-pyrrolidin-3-yl, 1-(2-methoxy-ethyl)-azetidin-3-yl, 6-morpholin-4-yl-pyridin-2-ylmethyl, 1,1-dioxo-tetrahydro-1$\lambda^6$-thiophen-3-ylmethyl, 2-(4-fluoro-phenoxy)-ethyl, 2,6-dimethyl-pyrimidin-4-yl, 1-hydroxymethyl-2-(3H-imidazol-4-yl)-ethyl, 4-methanesulfonyl-benzyl, 1-pyridin-3-yl-cyclopropyl, 9-methyl-9-aza-bicyclo[3.3.1]non-1-yl, 2,6-dimethyl-pyridin-3-yl, 4-hydroxy-benzyl, 2-oxo-2-phenylethyl), 1-methyl-1H-pyrazol-3-ylmethyl, pyrimidin-2-yl, 5-methyl-pyrazin-2-yl, 1-(2-methoxy-pyridin-3-yl)-1-methyl-ethyl, 6-methanesulfonyl-2-methyl-pyridin-3-yl, 2-hydroxy-benzyl, 6-bromo-2-methyl-pyridin-3-yl, 2-methoxy-pyridin-3-yl, 1-(4-chloro-phenyl)-cyclobutyl, 2-(pyridine-2-sulfonyl)-ethyl, 1-pyridin-2-yl-cyclopropylmethyl, 1-methyl-1,2,3,4-tetrahydro-quinolin-7-yl, benzyl, 3,5-dimethyl-pyrazin-2-yl, 1-(2-hydroxy-pyridin-3-yl)-1-methyl-ethyl, 1-(ethoxycarbonyl)cyclobutyl, 1-(tert-butoxycarbonyl)pyrrolidin-3-ylmethyl, quinolin-4-ylmethyl, 2-(4-fluoro-phenyl)-1-(2-hydroxy-ethylcarbamoyl)-1-methyl-ethyl, 2-morpholin-4-yl-pyridin-3-yl, 6-methyl-pyridin-2-yl, 3-difluoromethoxy-benzyl, 4-hydroxy-1-methyl-piperidin-4-ylmethyl, 1-(2,5-dimethylpyrrolidine-1-carbonyl)cyclopentyl, 2-methoxy-benzyl, 6-methyl-pyridin-2-ylmethyl, 3-chloro-pyridin-4-yl, 2-carboxypropan-2-yl, 6-chloro-pyridin-3-yl, 2-hydroxy-2-pyridin-3-yl-ethyl, 1-p-tolyl-cyclopropyl, 1-(3,3,3-trifluoro-propyl)-piperidin-4-yl, 4-methoxy-pyridin-2-yl, 3-azepan-1-yl-2,2-dimethyl-propyl, 1-(tert-butoxycarbonyl)azetidin-3-yl, 5-methyl-pyrazin-2-ylmethyl, 1-oxo-hexahydro-1$\lambda^4$-thiopyran-4-yl, 2-(2-chloro-phenyl)-ethyl, 3-chloro-5-trifluoromethyl-pyridin-2-ylmethyl, 2-hydroxy-1-hydroxymethyl-ethyl, (1-methyl-pyrrolidin-2-yl)-pyridin-2-yl, 5-fluoro-2-hydroxy-phenyl, methyl, 4-(methoxycarbonyl)-1-methylpiperidin-4-yl, 4-hydroxymethyl-1-methyl-piperidin-4-yl, 2-(2-hydroxymethyl-pyrrolidin-1-yl)-ethyl, 1-phenyl-cyclohexyl, 3-methyl-1,1-dioxo-tetrahydro-1$\lambda^6$-thiophen-3-yl, 1-cyano-cyclohexyl, 1-(5-methyl-[1,2,4]oxadiazol-3-yl)-cyclohexyl, 2-cyanopropan-2-yl, 3-methyl-1-phenylureido, 1-carbamoyl-2,2-dimethyl-propyl, tert-butylamino, 2,2,2-trifluoro-1,1-dimethyl-ethyl, 2,2-dimethyl-1-methylcarbamoyl-propyl, 1-cyclopropyl-ethyl, amino, N-tert-butylmethylsulfonamido, 1,1-dimethyl-prop-2-ynyl, 2-methyl-1-(phosphonooxy)propan-2-yl, 1-tert-butyl-3-methylureido, 4-cyano-tetrahydro-pyran-4-yl, 1-methyl-cyclobutyl, 1-hydroxymethyl-2-methyl-propyl, cyclobutyl amino, 1-cyano-cyclopentyl, cyano-dimethyl-methyl, 2,2-dimethyl-1-(methylcarbamoyl)-propyl, phenylamino, 1-hydroxymethyl-propyl, 1-methyl-1-(1H-tetrazol-5-yl)-ethyl, 3,3-dimethyl-1-(phosphonooxy)butan-2-yl), 2-hydroxy-1-tetrahydro-pyran-4-yl-ethyl, 1,2-dimethyl-propyl, 1-pyridin-2-yl-cyclobutyl, 1-hydroxymethyl-2-phenyl-ethyl, 4-methylcarbamoyl-tetrahydro-pyran-4-yl, 1-methyl-1-methylcarbamoyl-ethyl, 2,2-dimethyl-1-morpholin-4-yl-methyl-propyl, 1-methylcarbamoyl-cyclopent-3-enyl, 2-methoxy-2-oxo-1-(pyridin-2-yl)ethyl, methylcarbamoyl-pyridin-2-yl-methyl, 1-methylcarbamoyl-cyclopentyl, 1-(tert-butylcarbamoyl)-2,2-dimethyl-propyl, 2,2-dimethyl-1-(pyridin-2-ylcarbamoyl)-propyl, 1-(pyridin-2-ylcarbamoyl)-cyclobutyl, 1-methylcarbamoyl-cyclobutyl, 2-(methylamino)-2-oxo-1-phenylethyl, pyrrolidin-1-yl, piperidin-1-yl, 2,6-dimethyl-piperidin-1-yl, 1-cyclopropylcarbamoyl-2,2-dimethyl-propyl, 2,2-dimethyl-1-(2,2,2-trifluoro-ethylcarbamoyl)-propyl, 1-ethylcarbamoyl-2,2-dimethyl-propyl, 2-hydroxy-1-(tetrahydro-pyran-4-yl)-ethyl, N-cyclobutylmethylsulfonamido, N-phenylmethylsulfonamido, 1-cyclopropyl-2-hydroxy-ethyl, 1,2,2-trimethyl-propyl, 2-oxo-1-(pyridin-2-yl)-2-(2,2,2-trifluoroethylamino) ethyl, 2,2-dimethyl-1-pyridin-2-yl-propyl, 1-methoxy-3,3-dimethyl-1-oxobutan-2-yl, 1-carboxy-2,2-dimethylpropyl, 1-(hydroxy-methyl-carbamoyl)-2,2-dimethyl-propyl, 1-dimethylcarbamoyl-2,2-dimethyl-propyl, 1-(azetidine-1-carbonyl)-2,2-dimethyl-propyl, 1-methoxycarbamoyl-2,2-dimethyl-propyl, 1-(methoxy-methyl-carbamoyl)-2,2-dimethyl-propyl, 1-tert-butoxycarbamoyl-2,2-dimethyl-propyl, and 2,2-dimethyl-1-pyridin-2-yl-propyl.

In some embodiments, $R^8$ is H. In some embodiments, $R^8$ is 2-methyl-2-morpholin-4-yl-propyl. In some embodiments, $R^8$ is 1-hydroxymethyl-2,2-dimethyl-propyl. In some embodiments, $R^8$ is 2-(tert-butoxycarbonylamino)cyclohexyl. In some embodiments, $R^8$ is 1-phenyl-cyclopropyl. In some embodiments, $R^8$ is 5-trifluoromethyl-pyridin-2-yl. In some embodiments, $R^8$ is 1-methyl-1-phenyl-ethyl. In some embodiments, $R^8$ is 1-(2-methoxy-ethyl)-pyrrolidin-3-ylmethyl. In some embodiments, $R^8$ is 1-(methoxycarbonyl) cyclopropyl. In some embodiments, $R^8$ is tetrahydro-pyran-4-ylmethyl. In some embodiments, $R^8$ is 1-(tert-butoxycarbonyl)piperidin-4-yl. In some embodiments, $R^8$ is 1-(4-fluoro-phenyl)-cyclopropyl. In some embodiments, $R^8$ is 6-methyl-pyridin-3-ylmethyl. In some embodiments, $R^8$ is 2-hydroxy-1-phenyl-ethyl. In some embodiments, $R^8$ is 1,3,3-trimethyl-bicyclo[2.2.1]hept-2-yl. In some embodiments, R⁸ is 2-hydroxy-1,1-dimethyl-ethyl. In some embodiments, R⁸ is 2-(5-hydroxy-1H-indol-3-yl)-ethyl. In some embodiments, R⁸ is 1-hydroxymethyl-cyclopropyl. In some embodiments, R⁸ is 3-chloro-5-methyl-pyridin-2-yl. In some embodiments, R⁸ is 6-fluoro-pyridin-3-yl. In some embodiments, R⁸ is 1-(3-fluoro-phenyl)-cyclobutyl. In some embodiments, R⁸ is 2-methyl-pyridin-3-yl. In some embodiments, R⁸ is 2-hydroxy-1-(tetrahydro-furan-3-yl)-ethyl. In some embodiments, R⁸ is 2-(pyridin-3-yloxy)-propyl. In some embodiments, R⁸ is carbamoyl-phenyl-methyl. In some embodiments, R⁸ is 5-fluoro-2-methoxy-phenyl. In some embodiments, R⁸ is 2-methoxy-ethyl. In some embodiments, R⁸ is 2,3-dihydroxy-propyl. In some embodiments, R⁸ is 1-(tert-butoxycarbonyl)pyrrolidin-3-yl. In some embodiments, R⁸ is 2-oxo-2-phenyl-ethyl. In some embodiments, R⁸ is 1-(3,3,3-trifluoro-propyl)-azetidin-3-yl. In some embodiments, R⁸ is 2-hydroxy-1-pyridin-2-yl-ethyl. In some embodiments, R⁸ is 3-hydroxy-pyridin-4-yl. In some embodiments, R⁸ is 1-methyl-1-pyridin-4-yl-ethyl. In some embodiments, R⁸ is 1-hydroxymethyl-2-3H-imidazol-4-yl-ethyl. In some embodiments, R⁸ is 4-hydroxy-3-methoxy-benzyl. In some embodiments, R⁸ is 5-fluoro-2-oxo-2,3-dihydro-pyrimidin-4-yl. In some embodiments, R⁸ is 1-(4-fluoro-phenyl)-3-hydroxy-propyl. In some embodiments, R⁸ is 1-pyridin-4-yl-cyclopropyl. In some embodiments, R⁸ is 2-hydroxy-1-pyridin-3-yl-ethyl. In some embodiments, R⁸ is 1,1-dimethyl-2-(4-methyl-piperidin-1-yl)-ethyl. In some embodiments, R⁸ is 6-cyano-pyridin-3-yl. In some embodiments, R⁸ is 5-fluoro-pyridin-2-yl. In some embodiments, R⁸ is 2,5-dimethyl-benzyl. In some embodiments, R⁸ is 1-isopropyl-piperidin-4-yl. In some embodiments, R⁸ is 2-methoxy-1-methoxymethyl-ethyl. In some embodiments, R⁸ is 2,3-dimethyl-benzyl. In some embodiments, R⁸ is 1-pyridin-2-yl-ethyl. In some embodiments, R⁸ is 6-chloro-pyridin-3-ylmethyl. In some embodiments, R⁸ is 3-methyl-pyridin-2-yl. In some embodiments, R⁸ is 2-hydroxy-indan-1-yl. In some embodiments, R⁸ is (1S,2S)-2-hydroxy-indan-1-yl. In some embodiments, R⁸ is (1S,2R)-2-hydroxy-indan-1-yl. In some embodiments, R⁸ is (1R,2R)-2-hydroxy-indan-1-yl. In some embodiments, R⁸ is (1R,2S)-2-hydroxy-indan-1-yl. In some embodiments, R⁸ is 1-hydroxymethyl-cyclobutyl. In some embodiments, R⁸ is 2-(4-chloro-phenyl)-1,1-dimethyl-ethyl. In some embodiments, R⁸ is 3-hydroxy-pyridin-2-ylmethyl. In some embodiments, R⁸ is 3-methyl-pyridin-4-yl. In some embodiments, R⁸ is 5-tert-butyl-isoxazol-3-yl. In some embodiments, R⁸ is 1-(6-methoxy-pyridin-3-yl)-1-methyl-ethyl. In some embodiments, R⁸ is 1H-benzoimidazol-2-yl. In some embodiments, R⁸ is tert-butyl. In some embodiments, R⁸ is 4-phenyl-thiazol-2-yl. In some embodiments, R⁸ is 1-(2-fluoro-phenyl)-cyclobutyl. In some embodiments, R⁸ is 2,4-dimethoxy-benzyl. In some embodiments, R⁸ is 5-bromo-3-methyl-pyridin-2-yl. In some embodiments, R⁸ is 4-benzyl-morpholin-2-ylmethyl. In some embodiments, R⁸ is 6-trifluoromethyl-pyridin-3-ylmethyl. In some embodiments, R⁸ is tetrahydro-furan-3-yl. In some embodiments, R⁸ is pyridin-3-ylmethyl. In some embodiments, R⁸ is pyrazin-2-yl. In some embodiments, R⁸ is piperidin-4-yl. In some embodiments, R⁸ is 1-(6-hydroxy-pyridin-3-yl)-1-methyl-ethyl. In some embodiments, R⁸ is 1-methyl-1-pyridin-2-yl-ethyl. In some embodiments, R⁸ is 1-hydroxymethyl-cyclopentyl. In some embodiments, R⁸ is 1-azabicyclo[2.2.2]oct-3-yl. In some embodiments, R⁸ is 2-hydroxy-cyclopentyl. In some embodiments, R⁸ is 2-hydroxy-1-(hydroxymethyl)-propyl. In some embodiments, R⁸ is 1-(tert-butoxycarbonyl)piperidin-4-yl)methyl. In some embodiments, R⁸ is 3,5-dimethoxy-phenyl. In some embodiments, R⁸ is 6-fluoro-4H-benzo[1,3]dioxin-8-ylmethyl. In some embodiments, R⁸ is 4,6-dimethyl-pyridin-2-yl. In some embodiments, R⁸ is 1,1-dimethyl-2-morpholin-4-yl-ethyl. In some embodiments, R⁸ is 2-hydroxy-cyclohexyl-methyl. In some embodiments, R⁸ is 1-(4-methoxy-phenyl)-cyclopropyl. In some embodiments, R⁸ is 1-ethyl-pyrrolidin-2-ylmethyl. In some embodiments, R⁸ is indan-1-yl. In some embodiments, R⁸ is pyrimidin-4-yl. In some embodiments, R⁸ is 2-fluoro-4-methanesulfonyl-phenyl. In some embodiments, R⁸ is 6-hydroxy-pyridin-2-yl. In some embodiments, R⁸ is cyclobutyl. In some embodiments, R⁸ is 1-(3-methoxy-phenyl)-cyclopropyl. In some embodiments, R⁸ is 1-(3,3,3-trifluoro-propyl)-pyrrolidin-3-yl. In some embodiments, R⁸ is 2-hydroxy-pyridin-3-yl. In some embodiments, R⁸ is 4-difluoromethoxy-benzyl. In some embodiments, R⁸ is 1-piperidin-1-yl-cyclopentylmethyl. In some embodiments, R⁸ is 3-hydroxy-3-methyl-butyl. In some embodiments, R⁸ is 1-(4-fluoro-phenyl)-cyclobutyl. In some embodiments, R⁸ is 4-methoxy-benzyl. In some embodiments, R⁸ is pyridin-2-yl. In some embodiments, R⁸ is 2-hydroxy-2-phenyl-ethyl. In some embodiments, R⁸ is 2-hydroxymethyl-2,3-dihydro-indol-1-yl. In some embodiments, R⁸ is 3-hydroxy-pyridin-2-yl. In some embodiments, R⁸ is 4-dimethylamino-tetrahydro-pyran-4-ylmethyl. In some embodiments, R⁸ is 2-(4-fluoro-phenyl)-ethyl. In some embodiments, R⁸ is 1-(2-methoxy-ethyl)-piperidin-4-ylmethyl. In some embodiments, R⁸ is 2-morpholin-4-yl-ethyl. In some embodiments, R⁸ is 1-(tert-butoxycarbonyl)-4-carboxypiperidin-4-yl. In some embodiments, R⁸ is quinolin-3-yl. In some embodiments, R⁸ is 1-morpholin-4-ylmethyl-cyclopentyl. In some embodiments, R⁸ is 1,4-dimethyl-1H-pyrrol-2-ylmethyl. In some embodiments, R⁸ is 2-hydroxy-2-pyridin-2-yl-ethyl. In some embodiments, R⁸ is pyridin-3-yl. In some embodiments, R⁸ is 2-dimethylamino-benzyl. In some embodiments, R⁸ is tetrahydro-thiopyran-4-yl. In some embodiments, R⁸ is 1-m-tolyl-cyclopropyl. In some embodiments, R⁸ is 1-(2-methoxy-ethyl)-piperidin-3-yl. In some embodiments, R⁸ is 5-methoxy-pyridin-2-ylmethyl. In some embodiments, R⁸ is 2-hydroxy-1-pyridin-4-yl-ethyl. In some embodiments, R⁸ is 4-methyl-pyridin-2-yl. In some embodiments, R⁸ is 4-carboxy-2-fluorophenyl. In some embodiments, R⁸ is 6-methanesulfonyl-pyridin-3-yl. In some embodiments, R⁸ is 1-o-tolyl-cyclobutyl. In some embodiments, R⁸ is 1,1-dimethyl-2-pyrrolidin-1-yl-ethyl. In some embodiments, R⁸ is 2,6-dimethoxy-pyridin-3-yl. In some embodiments, R⁸ is pyridin-2-yl. In some embodiments, R⁸ is 4-hydroxymethyl-tetrahydro-pyran-4-yl. In some embodiments, R⁸ is 2-(1H-imidazol-4-yl)-ethyl. In some embodiments, R⁸ is 3-fluoro-pyridin-4-yl. In some embodiments, R⁸ is 1-carbamoyl-2-phenyl-ethyl. In some embodiments, R⁸ is oxazol-4-ylmethyl. In some embodiments, R⁸ is 6-methoxy-pyrimidin-4-yl. In some embodiments, R⁸ is 1,1-dioxo-hexahydro-1λ⁶-thiopyran-4-yl. In some embodiments, R⁸ is 1-methoxy-1-oxo-3-phenylpropan-2-yl. In some embodiments, R⁸ is 1-(2-methoxy-ethyl)-pyrrolidin-3-yl. In some embodiments, R⁸ is 1-(6-methyl-pyridin-2-yl)-ethyl. In some embodiments, R⁸ is 2-hydroxy-1-(4-hydroxy-phenyl)-ethyl. In some embodiments, R⁸ is 2-methoxy-pyridin-4-yl. In some embodiments, R⁸ is 1-pyridin-2-yl-cyclopropyl. In some embodiments, R⁸ is 1-(tert-butoxycarbonyl)piperidin-3-yl. In some embodiments, R⁸ is 3-methyl-pyridin-2-ylmethyl. In some embodiments, R⁸ is 3-fluoro-pyridin-2-yl. In some embodiments, R⁸ is 1-pyridin-4-yl-cyclobutyl. In some embodiments, R⁸ is 2-carboxy-1-(pyridin-3-yl)ethyl. In some embodiments, R⁸ is 2-hydroxy-1-methyl-ethyl. In some embodiments, R⁸ is 1-(methoxycarbonyl)cyclohexyl. In some embodiments, R⁸ is 3-hydroxymethyl-pyridin-4-yl. In some embodiments, $R^8$ is 2-hydroxy-1-phenyl-ethyl. In some embodiments, $R^8$ is 3-dimethylamino-tetrahydro-thiophen-3-ylmethyl. In some embodiments, $R^8$ is tetrahydro-pyran-4-yl. In some embodiments, $R^8$ is 5-chloro-pyridin-2-yl. In some embodiments, $R^8$ is 1-carbamoyl-cyclobutyl. In some embodiments, $R^8$ is 5-fluoro-2-methyl-benzyl. In some embodiments, $R^8$ is 2-morpholin-4-yl-2-pyridin-3-yl-ethyl. In some embodiments, $R^8$ is 1-(3-methoxy-phenyl)-cyclobutyl. In some embodiments, $R^8$ is 5-methyl-pyridin-2-yl. In some embodiments, $R^8$ is 1-(tetrahydro-furan-2-yl)methyl. In some embodiments, $R^8$ is 1-dimethylaminomethyl-cyclopentyl. In some embodiments, $R^8$ is 2-(4-fluoro-phenyl)-1-methyl-ethyl. In some embodiments, $R^8$ is benzothiazol-2-yl. In some embodiments, $R^8$ is 1-(2-fluoro-phenyl)-cyclopropyl. In some embodiments, $R^8$ is 1-(2-methoxy-ethyl)-piperidin-4-yl. In some embodiments, $R^8$ is 2-hydroxy-1-pyridin-4-yl-ethyl. In some embodiments, $R^8$ is 1-(3,3,3-trifluoro-propyl)-azetidin-3-ylmethyl. In some embodiments, $R^8$ is 6-pyrrolidin-1-yl-pyridin-2-ylmethyl. In some embodiments, $R^8$ is 1,1-dioxo-tetrahydro-1$\lambda^6$-thiophen-3-yl. In some embodiments, $R^8$ is 2,3-dimethoxy-benzyl. In some embodiments, $R^8$ is 3-cyano-5-methyl-pyridin-2-yl. In some embodiments, $R^8$ is 2,3-dihydro-benzofuran-3-yl. In some embodiments, $R^8$ is 1-hydroxymethyl-cyclohexyl. In some embodiments, $R^8$ is 2,5-difluoro-benzyl. In some embodiments, $R^8$ is 4-dimethylamino-benzyl. In some embodiments, $R^8$ is 4-hydroxy-1,1-dioxo-tetrahydro-1$\lambda^6$-thiophen-3-yl. In some embodiments, $R^8$ is 4-trifluoromethyl-pyridin-2-yl. In some embodiments, $R^8$ is 5-methyl-thiazol-2-yl. In some embodiments, $R^8$ is 6-trifluoromethyl-pyridin-3-yl. In some embodiments, $R^8$ is 5-hydroxy-1H-pyrazol-3-yl. In some embodiments, $R^8$ is 2-thiomorpholin-4-yl-ethyl. In some embodiments, $R^8$ is benzo[1,3]dioxol-5-ylmethyl. In some embodiments, $R^8$ is 2-amino-cyclohexyl. In some embodiments, $R^8$ is 3-dimethylamino-1-oxo-tetrahydro-1$\lambda^4$-thiophen-3-ylmethyl. In some embodiments, $R^8$ is 4-methyl-morpholin-2-ylmethyl. In some embodiments, $R^8$ is 1-(2-methoxy-phenyl)-cyclopropyl. In some embodiments, $R^8$ is 2-carboxy-1-(4-fluorophenyl)propan-2-yl. In some embodiments, $R^8$ is pyridin-2-ylmethyl. In some embodiments, $R^8$ is pyridazin-3-yl. In some embodiments, $R^8$ is 4-pyridin-2-yl-thiazol-2-yl. In some embodiments, $R^8$ is 1-(3,3,3-trifluoro-propyl)-piperidin-4-ylmethyl. In some embodiments, $R^8$ is 6-chloro-2-methyl-pyridin-3-yl. In some embodiments, $R^8$ is 6-hydroxy-pyridin-3-yl. In some embodiments, $R^8$ is 3-trifluoromethoxy-benzyl. In some embodiments, $R^8$ is 1-morpholin-4-yl-cyclopentylmethyl. In some embodiments, $R^8$ is 1-pyridin-2-yl-cyclobutylmethyl. In some embodiments, $R^8$ is 2-hydroxy-1-hydroxymethyl-1-methyl-ethyl. In some embodiments, $R^8$ is 5-hydroxymethyl-pyridin-2-yl. In some embodiments, $R^8$ is 5-fluoro-1-oxy-pyridin-2-yl. In some embodiments, $R^8$ is 6-methoxy-pyridin-2-yl. In some embodiments, $R^8$ is 1-methyl-1-pyridin-3-yl-ethyl. In some embodiments, $R^8$ is 6-methyl-pyridin-3-yl. In some embodiments, $R^8$ is 2-hydroxy-1-hydroxymethyl-propyl. In some embodiments, $R^8$ is 2-chloro-pyridin-3-yl. In some embodiments, $R^8$ is 3-methyl-3H-imidazol-4-ylmethyl. In some embodiments, $R^8$ is 6-fluoro-pyridin-2-yl. In some embodiments, $R^8$ is 3-dimethylamino-benzyl. In some embodiments, $R^8$ is 6-morpholin-4-yl-pyridin-3-yl. In some embodiments, $R^8$ is 1-o-tolyl-cyclopropyl. In some embodiments, $R^8$ is 1-(3,3,3-trifluoro-propyl)-piperidin-3-yl. In some embodiments, $R^8$ is 6-methanesulfonyl-4-methyl-pyridin-3-yl. In some embodiments, $R^8$ is 2-methyl-quinolin-4-yl. In some embodiments, $R^8$ is 1-(3,3,3-trifluoro-propyl)-pyrrolidin-3-ylmethyl. In some embodiments, $R^8$ is benzooxazol-2-yl. In some embodiments, $R^8$ is 1-methyl-piperidin-4-ylmethyl. In some embodiments, $R^8$ is 2-(2,6-dimethyl-morpholin-4-yl)-2-methyl-propyl. In some embodiments, $R^8$ is 1-methyl-piperidin-2-ylmethyl. In some embodiments, $R^8$ is pyridin-4-ylmethyl. In some embodiments, $R^8$ is 4-hydroxymethyl-pyridin-2-yl. In some embodiments, $R^8$ is 5,7-dimethyl-pyrazolo[1,5-a]pyrimidin-2-yl. In some embodiments, $R^8$ is 6,6-dimethyl-bicyclo[3.1.1]hept-2-ylmethyl. In some embodiments, $R^8$ is 1-(5-methyl-pyridin-2-yl)-ethyl. In some embodiments, $R^8$ is 2-fluoro-pyridin-3-yl. In some embodiments, $R^8$ is morpholin-4-yl. In some embodiments, $R^8$ is 2-hydroxy-2-pyridin-4-yl-ethyl. In some embodiments, $R^8$ is pyridin-4-yl. In some embodiments, $R^8$ is 4-hydroxy-pyridin-2-yl. In some embodiments, $R^8$ is 3-methoxy-benzyl. In some embodiments, $R^8$ is 1-oxy-pyridin-2-yl. In some embodiments, $R^8$ is 1-ethyl-propyl. In some embodiments, $R^8$ is 6-carboxypyridin-2-yl. In some embodiments, $R^8$ is 1,2,2,6,6-pentamethyl-piperidin-4-yl. In some embodiments, $R^8$ is 6-methoxy-pyridin-3-yl. In some embodiments, $R^8$ is cyclopentyl. In some embodiments, $R^8$ is morpholin-2-ylmethyl. In some embodiments, $R^8$ is 1-(tert-butoxycarbonyl)azetidin-3-yl)methyl. In some embodiments, $R^8$ is 2-dimethylamino-2-pyridin-3-yl-ethyl. In some embodiments, $R^8$ is 1-(4-methoxy-phenyl)-cyclobutyl. In some embodiments, $R^8$ is 3-hydroxy-benzyl. In some embodiments, $R^8$ is tetrahydro-furan-2-ylmethyl. In some embodiments, $R^8$ is 4-(tert-butoxycarbonyl)morpholin-2-ylmethyl. In some embodiments, $R^8$ is 1-(3-fluoro-phenyl)-cyclopropyl. In some embodiments, $R^8$ is 2-o-tolyl-ethyl. In some embodiments, $R^8$ is 3-hydroxymethyl-1-isobutyl-pyrrolidin-3-yl. In some embodiments, $R^8$ is 1-(2-methoxy-ethyl)-azetidin-3-yl. In some embodiments, $R^8$ is 6-morpholin-4-yl-pyridin-2-yl. In some embodiments, $R^8$ is 1,1-dioxo-tetrahydro-1$\lambda^6$-thiophen-3-ylmethyl. In some embodiments, $R^8$ is 2-(4-fluoro-phenoxy)-ethyl. In some embodiments, $R^8$ is 2,6-dimethyl-pyrimidin-4-yl. In some embodiments, $R^8$ is 1-hydroxymethyl-2-(3H-imidazol-4-yl)-ethyl. In some embodiments, $R^8$ is 4-methanesulfonyl-benzyl. In some embodiments, $R^8$ is 1-pyridin-3-yl-cyclopropyl. In some embodiments, $R^8$ is 9-methyl-9-aza-bicyclo[3.3.1]non-1-yl. In some embodiments, $R^8$ is 2,6-dimethyl-pyridin-3-yl. In some embodiments, $R^8$ is 4-hydroxy-benzyl. In some embodiments, $R^8$ is 2-oxo-2-phenyl-ethyl). In some embodiments, $R^8$ is 1-methyl-1H-pyrazol-3-ylmethyl. In some embodiments, $R^8$ is pyrimidin-2-yl. In some embodiments, $R^8$ is 5-methyl-pyrazin-2-yl. In some embodiments, $R^8$ is 1-(2-methoxy-pyridin-3-yl)-1-methyl-ethyl. In some embodiments, $R^8$ is 6-methanesulfonyl-2-methyl-pyridin-3-yl. In some embodiments, $R^8$ is 2-hydroxy-benzyl. In some embodiments, $R^8$ is 6-bromo-2-methyl-pyridin-3-yl. In some embodiments, $R^8$ is 2-methoxy-pyridin-3-yl. In some embodiments, $R^8$ is 1-(4-chloro-phenyl)-cyclobutyl. In some embodiments, $R^8$ is 2-(pyridine-2-sulfonyl)-ethyl. In some embodiments, $R^8$ is 1-pyridin-2-yl-cyclopropylmethyl. In some embodiments, $R^8$ is 1-methyl-1,2,3,4-tetrahydro-quinolin-7-yl. In some embodiments, $R^8$ is benzyl. In some embodiments, $R^8$ is 3,5-dimethyl-pyrazin-2-yl. In some embodiments, $R^8$ is 1-(2-hydroxy-pyridin-3-yl)-1-methyl-ethyl. In some embodiments, $R^8$ is 1-(ethoxycarbonyl)cyclobutyl. In some embodiments, $R^8$ is 1-(tert-butoxycarbonyl)pyrrolidin-3-ylmethyl. In some embodiments, $R^8$ is quinolin-4-ylmethyl. In some embodiments, $R^8$ is 2-(4-fluoro-phenyl)-1-(2-hydroxy-ethylcarbamoyl)-1-methyl-ethyl. In some embodiments, $R^8$ is 2-morpholin-4-yl-pyridin-3-yl. In some embodiments, $R^8$ is 6-methyl-pyridin-2-yl. In some embodiments, $R^8$ is 3-difluoromethoxy-benzyl. In some embodiments, $R^8$ is 4-hydroxy-1-methyl-piperidin-4-ylmethyl. In some embodiments, $R^8$ is 1-(2,5-dimethylpyrrolidine-1-carbonyl)cyclopentyl. In some embodiments, $R^8$ is 2-methoxy-benzyl. In some embodiments, $R^8$ is 6-methyl-pyridin-2-ylmethyl. In some embodiments, $R^8$ is 3-chloro-pyridin-4-yl. In some embodiments, $R^8$ is 2-carboxypropan-2-yl. In some embodiments, $R^8$ is 6-chloro-pyridin-3-yl. In some embodiments, $R^8$ is 2-hydroxy-2-pyridin-3-yl-ethyl. In some embodiments, $R^8$ is 1-p-tolyl-cyclopropyl. In some embodiments, $R^8$ is 1-(3,3,3-trifluoro-propyl)-piperidin-4-yl. In some embodiments, $R^8$ is 4-methoxy-pyridin-2-yl. In some embodiments, $R^8$ is 3-azepan-1-yl-2,2-dimethyl-propyl. In some embodiments, $R^8$ is 1-(tert-butoxycarbonyl)azetidin-3-yl. In some embodiments, $R^8$ is 5-methyl-pyrazin-2-ylmethyl. In some embodiments, $R^8$ is 1-oxo-hexahydro-$1\lambda^4$-thiopyran-4-yl. In some embodiments, $R^8$ is 2-(2-chloro-phenyl)-ethyl. In some embodiments, $R^8$ is 3-chloro-5-trifluoromethyl-pyridin-2-ylmethyl. In some embodiments, $R^8$ is 2-hydroxy-1-hydroxymethyl-ethyl. In some embodiments, $R^8$ is (1-methyl-pyrrolidin-2-yl)-pyridin-2-yl. In some embodiments, $R^8$ is 5-fluoro-2-hydroxy-phenyl. In some embodiments, $R^8$ is methyl. In some embodiments, $R^8$ is 4-(methoxycarbonyl)-1-methylpiperidin-4-yl. In some embodiments, $R^8$ is 4-hydroxymethyl-1-methyl-piperidin-4-yl. In some embodiments, $R^8$ is 2-(2-hydroxymethyl-pyrrolidin-1-yl)-ethyl. In some embodiments, $R^8$ is 1-phenyl-cyclohexyl. In some embodiments, $R^8$ is 3-methyl-1,1-dioxo-tetrahydro-$1\lambda^6$-thiophen-3-yl. In some embodiments, $R^8$ is 1-cyano-cyclohexyl. In some embodiments, $R^8$ is 1-(5-methyl-[1,2,4]oxadiazol-3-yl)-cyclohexyl. In some embodiments, $R^8$ is 2-cyanopropan-2-yl. In some embodiments, $R^8$ is 3-methyl-1-phenylureido. In some embodiments, $R^8$ is 1-carbamoyl-2,2-dimethyl-propyl. In some embodiments, $R^8$ is tert-butyl amino. In some embodiments, $R^8$ is 2,2,2-trifluoro-1,1-dimethyl-ethyl. In some embodiments, $R^8$ is 2,2-dimethyl-1-methylcarbamoyl-propyl. In some embodiments, $R^8$ is 1-cyclopropyl-ethyl. In some embodiments, $R^8$ is amino. In some embodiments, $R^8$ is N-tert-butylmethylsulfonamido. In some embodiments, $R^8$ is 1,1-dimethyl-prop-2-ynyl. In some embodiments, $R^8$ is 2-methyl-1-(phosphonooxy)propan-2-yl. In some embodiments, $R^8$ is 1-tert-butyl-3-methylureido. In some embodiments, $R^8$ is 4-cyano-tetrahydro-pyran-4-yl. In some embodiments, $R^8$ is 1-methyl-cyclobutyl. In some embodiments, $R^8$ is 1-hydroxymethyl-2-methyl-propyl. In some embodiments, $R^8$ is cyclobutylamino. In some embodiments, $R^8$ is 1-cyano-cyclopentyl. In some embodiments, $R^8$ is cyano-dimethyl-methyl. In some embodiments, $R^8$ is 2,2-dimethyl-1-(methylcarbamoyl)-propyl. In some embodiments, $R^8$ is phenylamino. In some embodiments, $R^8$ is 1-hydroxymethyl-propyl. In some embodiments, $R^8$ is 1-methyl-1-(1H-tetrazol-5-yl)-ethyl. In some embodiments, $R^8$ is 3,3-dimethyl-1-(phosphonooxy)butan-2-yl). In some embodiments, $R^8$ is 2-hydroxy-1-tetrahydro-pyran-4-yl-ethyl. In some embodiments, $R^8$ is 1,2-dimethyl-propyl. In some embodiments, $R^8$ is 1-pyridin-2-yl-cyclobutyl. In some embodiments, $R^8$ is 1-hydroxymethyl-2-phenyl-ethyl. In some embodiments, $R^8$ is 4-methylcarbamoyl-tetrahydro-pyran-4-yl. In some embodiments, $R^8$ is 1-methyl-1-methylcarbamoyl-ethyl. In some embodiments, $R^8$ is 2,2-dimethyl-1-morpholin-4-ylmethyl-propyl. In some embodiments, $R^8$ is 1-methylcarbamoyl-cyclopent-3-enyl. In some embodiments, $R^8$ is 2-methoxy-2-oxo-1-(pyridin-2-yl)ethyl. In some embodiments, $R^8$ is methylcarbamoyl-pyridin-2-yl-methyl. In some embodiments, $R^8$ is 1-methylcarbamoyl-cyclopentyl. In some embodiments, $R^8$ is 1-(tert-butylcarbamoyl)-2,2-dimethyl-propyl. In some embodiments, $R^8$ is 2,2-dimethyl-1-(pyridin-2-ylcarbamoyl)-propyl. In some embodiments, $R^8$ is 1-(pyridin-2-ylcarbamoyl)-cyclobutyl. In some embodiments, $R^8$ is 1-methyl-carbamoyl-cyclobutyl. In some embodiments, $R^8$ is 2-(methylamino)-2-oxo-1-phenylethyl. In some embodiments, $R^8$ is pyrrolidin-1-yl. In some embodiments, $R^8$ is piperidin-1-yl. In some embodiments, $R^8$ is 2,6-dimethyl-piperidin-1-yl. In some embodiments, $R^8$ is 1-cyclopropyl-carbamoyl-2,2-dimethyl-propyl. In some embodiments, $R^8$ is 2,2-dimethyl-1-(2,2,2-trifluoro-ethylcarbamoyl)-propyl. In some embodiments, $R^8$ is 1-ethylcarbamoyl-2,2-dimethyl-propyl. In some embodiments, $R^8$ is 2-hydroxy-1-(tetrahydro-pyran-4-yl)-ethyl. In some embodiments, $R^8$ is N-cyclobutylmethylsulfonamido. In some embodiments, $R^8$ is N-phenylmethylsulfonamido. In some embodiments, $R^8$ is 1-cyclopropyl-2-hydroxy-ethyl. In some embodiments, $R^8$ is 1,2,2-trimethyl-propyl. In some embodiments, $R^8$ is 2-oxo-1-(pyridin-2-yl)-2-(2,2,2-trifluoroethylamino)ethyl. In some embodiments, $R^8$ is 2,2-dimethyl-1-pyridin-2-yl-propyl. In some embodiments, $R^8$ is 1-methoxy-3,3-dimethyl-1-oxobutan-2-yl. In some embodiments, $R^8$ is 1-carboxy-2,2-dimethylpropyl. In some embodiments, $R^8$ is 1-(hydroxymethyl-carbamoyl)-2,2-dimethyl-propyl. In some embodiments, $R^8$ is 1-dimethylcarbamoyl-2,2-dimethyl-propyl. In some embodiments, $R^8$ is 1-(azetidine-1-carbonyl)-2,2-dimethyl-propyl. In some embodiments, $R^8$ is 1-methoxycarbamoyl-2,2-dimethyl-propyl. In some embodiments, $R^8$ is 1-(methoxy-methyl-carbamoyl)-2,2-dimethyl-propyl. In some embodiments, $R^8$ is 1-tert-butoxy-carbamoyl-2,2-dimethyl-propyl. In some embodiments, $R^8$ is 2,2-dimethyl-1-pyridin-2-yl-propyl. In some embodiments, $R^8$ is fluoromethyl. In some embodiments, $R^8$ is 2,2,2-trifluoroethylamino. In some embodiments, $R^8$ is (1,1-dioxo-tetrahydro-$1\lambda^6$-thiophen-3-yl)amino. In some embodiments, $R^8$ is 1-hydroxycarbamoyl-2,2-dimethyl-propyl. In some embodiments, $R^8$ is 1-hydroxymethyl-2-methyl-butyl. In some embodiments, $R^8$ is 1-(2-hydroxy-ethylcarbamoyl)-2,2-dimethyl-propyl. In some embodiments, $R^8$ is 1,1-bis-hydroxymethyl-propyl. In some embodiments, $R^8$ is 1-(5-fluoro-pyridin-2-yl)-2,2-dimethyl-propyl. In some embodiments, $R^8$ is 4-hydroxymethyl-tetrahydro-2H-pyran-4-yl. In some embodiments, $R^8$ is 1-(2-(tert-butoxycarbonylamino)-3-methylbutanoyloxy)-2-methylpropan-2-yl. In some embodiments, $R^8$ is 1-(2-amino-3-methylbutanoyloxy)-3-methylbutan-2-yl. In some embodiments, $R^8$ is 1-(2-amino-3-methylbutanoyloxy)-2-methylpropan-2-yl. In some embodiments, $R^8$ is 2-hydroxy-1-(tetrahydro-2H-pyran-4-yl)-ethyl. In some embodiments, $R^8$ is 1-(4-carboxybutanoyloxy)-2-methylpropan-2-yl. In some embodiments, $R^8$ is 1-(4-carboxybutanoyloxy)-3-methylbutan-2-yl. In some embodiments, $R^8$ is 1-(4-carboxybutanoyloxy)-3,3-dimethylbutan-2-yl. In some embodiments, $R^8$ is 1-(2-amino-3-methylbutanoyloxy)-3,3-dimethylbutan-2-yl. In some embodiments, $R^8$ is 2-(2-amino-3-methylbutanoyloxy)-1-(tetrahydro-2H-pyran-4-yl)ethyl. In some embodiments, $R^8$ is 3,3,3-trifluoro-1-hydroxymethyl-propyl. In some embodiments, $R^8$ is 3-fluoro-1-methoxy-3-methyl-1-oxobutan-2-yl. In some embodiments, $R^8$ is 1-ethoxy-4,4,4-trifluoro-1-oxo-3-(trifluoromethyl)butan-2-yl. In some embodiments, $R^8$ is 2-fluoro-1-hydroxymethyl-2-methyl-propyl. In some embodiments, $R^8$ is 1-(2-(tert-butoxycarbonylamino)-3-methylbutanoyloxy)-3,3-dimethylbutan-2-yl. In some embodiments, $R^8$ is 4,4,4-trifluoro-1-methoxy-1-oxobutan-2-yl. In some embodiments, $R^8$ is 2-fluoro-1,1-dimethyl-ethyl. In some embodiments, $R^8$ is 3-fluoro-2-(fluoromethyl)-1-methoxy-1-oxopropan-2-yl. In some embodiments, $R^8$ is 2-fluoro-1-fluoromethyl-1-hydroxymethyl-ethyl. In some embodiments, $R^8$ is 3-hydroxy-1-methoxy-2-methyl-1-oxopropan-2-yl. In some embodiments, $R^8$ is 2-carboxy-1-hydroxypropan-2-yl. In some embodiments, $R^8$ is 2,2,2-trifluoroethylamino. In some embodiments, $R^8$ is 1-fluoromethyl-2-methyl-propyl. In some embodiments, $R^8$ is 1-fluoromethyl-2,2-dimethyl-propyl. In some embodiments, $R^8$ is 3-methyl-oxetan-3-yl. In some embodiments, $R^8$ is 1-fluoromethyl-cyclobutyl. In some embodiments, $R^8$ is 1,1-bis-hydroxymethyl-2-methyl-propyl. In some embodiments, $R^8$ is 1-trifluoromethyl-cyclopropyl. In some embodiments, $R^8$ is 1-methyl-cyclopropyl. In some embodiments, $R^8$ is 1-trifluoromethyl-cyclobutyl.

The Group $R^9$:

In some embodiments, $R^9$ is selected from H, $C_1$-$C_6$ alkyl, and $C_3$-$C_7$ cycloalkyl.

In some embodiments, $R^9$ is $C_1$-$C_6$ alkyl.

In some embodiments, $R^9$ is $C_3$-$C_7$ cycloalkyl.

In some embodiments, $R^9$ is selected from H, methyl, tert-butyl, and cyclobutyl.

In some embodiments, $R^9$ is H.

In some embodiments, $R^9$ is methyl.

In some embodiments, $R^9$ is tert-butyl.

In some embodiments, $R^9$ is cyclobutyl.

The Group $R_{10}$:

In some embodiments, $R^{10}$ is selected from: $C_1$-$C_6$ alkylene, heteroarylene, and heterocyclylene.

In some embodiments, $R^{10}$ is selected from: 1,1-dimethylethylene, 1,1-dimethylmethylene, ethylene, methylene, 1,4-piperidinylene, 2,5-pyrazinylene, and 2,4-pyridinylene.

In some embodiments, $R^{10}$ is $C_1$-$C_6$ alkylene.

In some embodiments, $R^{10}$ is selected from: 1,1-dimethylethylene, 1,1-dimethylmethylene, ethylene, and methylene.

In some embodiments, $R^{10}$ is 1,1-dimethylethylene

In some embodiments, $R^{10}$ is 1,1-dimethylmethylene.

In some embodiments, $R^{10}$ is ethylene.

In some embodiments, $R^{10}$ is methylene.

In some embodiments, $R^{10}$ is heteroarylene.

In some embodiments, $R^{10}$ is selected from: 2,5-pyrazinylene, and 2,4-pyridinylene.

In some embodiments, $R^{10}$ is heterocyclylene.

In some embodiments, $R^{10}$ is 1,4-piperidinylene.

In some embodiments, $R^{10}$ is absent.

The Group $R^{11}$:

In some embodiments, $R^{11}$ is selected from: —C(O)NH— and $C_1$-$C_6$ alkylene.

In some embodiments, $R^{11}$ is selected from: —C(O)NH— and methylene.

In some embodiments, $R^{11}$ is —C(O)NH—.

In some embodiments, $R^{11}$ is $C_1$-$C_6$ alkylene.

In some embodiments, $R^{11}$ is methylene.

In some embodiments, $R^{11}$ is absent.

The Group $R^{12}$:

In some embodiments, $R^{12}$ is $C_1$-$C_6$ alkylene.

In some embodiments, $R^{12}$ is methylene.

In some embodiments, $R^{12}$ is 1,1-dimethyl-methylene.

In some embodiments, $R^{12}$ is absent.

The Group $R^{13}$:

In some embodiments, $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl.

In some embodiments, $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: fluoro, bromo, chloro, iodo, methoxy, cyano, methyl, tert-butyl, isopropyl, hydroxyl, ethyl, heptafluoropropyl, cyclobutyl, trifluoromethyl, cyclopropyl, dimethylamino, methoxy, ethoxy, methylamino, propyl, amino, and methanesulfonyl.

In some embodiments, $R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: fluoro, bromo, chloro, methoxy, cyano, methyl, tert-butyl, isopropyl, hydroxyl, ethyl, heptafluoropropyl, cyclobutyl, trifluoromethyl, cyclopropyl, dimethylamino, methoxy, ethoxy, methylamino, propyl, amino, and methanesulfonyl.

In some embodiments, $R^{13}$ is selected from: 2,4-difluoro-phenyl, 2,4-dichloro-phenyl, 2-fluoro-4-methanesulfonyl-phenyl, 2,6-difluoro-phenyl, 2,5-difluoro-phenyl, 4-methoxy-phenyl, 4-cyano-phenyl, 4-fluoro-phenyl, phenyl, 2-fluoro-phenyl, 3-fluoro-phenyl, o-tolyl, tert-butyl, isopropyl, 2,2-dimethylpropyl, hydroxyl, 2-hydroxy-2-methyl-propyl, 1-oxo-hexahydro-1$\lambda^4$-thiopyran-4-yl, 1,1-dioxo-hexahydro-1$\lambda^6$-thiopyran-4-yl, tetrahydrothiopyran-4-yl, morpholin-4-yl, tetrahydro-pyran-4-yl, 1,1-dioxo-tetrahydro-1$\lambda^6$-thiophen-3-yl, pyrazin-2-yl, 5-ethyl-pyrazin-2-yl, 5-hydroxy-pyrazin-2-yl, 5-isopropyl-pyrazin-2-yl, 5-heptafluoropropyl-pyrazin-2-yl, 5-cyclobutyl-pyrazin-2-yl, 5-methyl-pyrazin-2-yl, 6-ethyl-pyrazin-2-yl, 5-trifluoromethyl-pyrazin-2-yl, cyclopropyl, 5-cyclopropyl-pyrazin-2-yl, 6-chloro-pyrazin-2-yl, 5-dimethylamino-pyrazin-2-yl, 4-cyano-phenyl, 6-methoxy-pyridazin-3-yl, 6-chloro-pyridazin-3-yl, pyrimidin-5-yl, 6-dimethylamino-pyrazin-2-yl, 6-methoxy-pyrazin-2-yl, 2-pyrimidin-4-yl, 5-bromo-pyrazin-2-yl, 5-hydroxy-pyrazin-2-yl, 5-methoxy-pyrazin-2-yl, 5-ethoxypyrazin-2-yl, 5-methylamino-pyrazin-2-yl, 5-bromo-pyridin-2-yl, pyridin-3-yl, 5-trifluoromethyl-pyridin-2-yl, 5-isopropyl-pyridin-2-yl, 5-isopropyl-pyridin-2-yl, 5-methyl-pyridin-2-yl, 5-ethyl-pyridin-2-yl, 5-methoxy-pyridin-2-yl, 4-trifluoromethyl-pyridin-2-yl, 5-cyano-pyridin-2-yl, 5-dimethylamino-pyridin-2-yl, 4-methyl-pyridin-2-yl, 5-chloro-4-methyl-pyridin-2-yl, 5-chloro-4-trifluoromethyl-pyridin-2-yl, 4-trifluoromethyl-pyridin-2-yl, 3-fluoro-pyridin-2-yl, 6-methyl-4-trifluoromethyl-pyridin-2-yl, 3-methyl-pyridin-2-yl, 5-propyl-pyridin-2-yl, 5-cyclopropyl-pyridin-2-yl, 5-fluoro-pyridin-2-yl, 3,5-difluoro-pyridin-2-yl, 6-bromo-pyridin-3-yl, 5-bromo-pyridin-3-yl, 5,6-difluoro-pyridin-3-yl, 6-chloro-pyridin-3-yl, 3-fluoro-pyridin-4-yl, 5-cyano-pyridin-3-yl, pyridin-4-yl, 2-chloro-pyridin-4-yl, 2-methoxy-pyridin-4-yl, 6-methyl-pyridin-3-yl, m-tolyl, thiazol-2-yl, cyclopentyl, 4-amino-pyridin-2-yl, 4-methoxy-pyridin-2-yl, 4-choro-pyridin-2-yl, 4-fluoro-pyridin-2-yl, 4-cyclopropyl-pyridin-2-yl, 4-bromo-pyridin-2-yl, 4-methanesulfonyl-pyridin-2-yl, 4-cyano-pyridin-2-yl, hydroxymethyl, 4-oxy-pyrazin-2-yl, 3-methyl-1,1-dioxo-tetrahydro-1$\lambda^6$-thiophen-5-chloro-3-fluoro-pyridin-2-yl, 3-fluoro-5-methoxy-pyridin-2-yl, 2-chloro-4-fluoro-phenyl, 6-fluoro-pyridin-3-yl, 6-cyano-pyridin-3-yl, 4-iodo-pyridin-2-yl, 1-oxy-pyridin-3-yl, and 4-hydroxy-pyridin-2-yl.

In some embodiments, $R^{13}$ is selected from: 2,4-difluoro-phenyl, 2,4-dichloro-phenyl, 2-fluoro-4-methanesulfonyl-phenyl, 2,6-difluoro-phenyl, 2,5-difluoro-phenyl, 4-methoxy-phenyl, 4-cyano-phenyl, 4-fluoro-phenyl, phenyl, 2-fluoro-phenyl, 3-fluoro-phenyl, o-tolyl, tert-butyl, isopropyl, 2,2-dimethylpropyl, hydroxyl, 2-hydroxy-2-methylpropyl, 1-oxo-hexahydro-1$\lambda^4$-thiopyran-4-yl, 1,1-dioxo-hexahydro-1$\lambda^6$-thiopyran-4-yl, tetrahydrothiopyran-4-yl, morpholin-4-yl, tetrahydro-pyran-4-yl, 1,1-dioxo-tetrahydro-1$\lambda^6$-thiophen-3-yl, pyrazin-2-yl, 5-ethyl-pyrazin-2-yl, 5-hydroxy-pyrazin-2-yl, 5-isopropyl-pyrazin-2-yl, 5-heptafluoropropyl-pyrazin-2-yl, 5-cyclobutyl-pyrazin-2-yl, 5-methyl-pyrazin-2-yl, 6-ethyl-pyrazin-2-yl, 5-trifluoromethyl-pyrazin-2-yl, cyclopropyl, 5-cyclopropyl-pyrazin-2-yl, 6-chloro-pyrazin-2-yl, 5-dimethylamino-pyrazin-2-yl, 4-cyano-phenyl, 6-methoxy-pyridazin-3-yl, 6-chloro-pyridazin-3-yl, pyrimidin-5-yl, 6-dimethylamino-pyrazin-2-yl, 6-methoxy-pyrazin-2-yl, 2-pyrimidin-4-yl, 5-bromo-pyrazin-2-yl, 5-hydroxy-pyrazin-2-yl, 5-methoxy-pyrazin-2-yl, 5-ethoxypyrazin-2-yl, 5-methylamino-pyrazin-2-yl, 5-bromo-pyridin-2-yl, pyridin-3-yl, 5-trifluoromethyl-pyridin-2-yl, 5-isopropyl-pyridin-2-yl, 5-isopropyl-pyridin-2-yl, 5-methyl-pyridin-2-yl, 5-ethyl-pyridin-2-yl, 5-methoxy-pyridin-2-yl, 4-trifluoromethyl-pyridin-2-yl, 5-cyano-pyridin-2-yl, 5-dimethylamino-pyridin-2-yl, 4-methyl-pyridin-2-yl, 5-chloro-4-methyl-pyridin-2-yl, 5-chloro-4-trifluoromethyl-pyridin-2-yl, 4-trifluoromethyl-pyridin-2-yl, 3-fluoro-pyridin-2-yl, 6-methyl-4-trifluoromethyl-pyridin-2-yl, 3-methyl-pyridin-2-yl, 5-propyl-pyridin-2-yl, 5-cyclopropyl-pyridin-2-yl, 5-fluoro-pyridin-2-yl, 3,5-difluoro-pyridin-2-yl, 6-bromo-pyridin-3-yl, 5-bromo-pyridin-3-yl, 5,6-difluoro-pyridin-3-yl, 6-chloro-pyridin-3-yl, 3-fluoro-pyridin-4-yl, 5-cyano-pyridin-3-yl, pyridin-4-yl, 2-chloro-pyridin-4-yl, 2-methoxy-pyridin-4-yl, 6-methyl-pyridin-3-yl, m-tolyl, thiazol-2-yl, cyclopentyl, 4-methoxy-pyridin-2-yl, 4-choro-pyridin-2-yl, 4-fluoro-pyridin-2-yl, 4-cyclopropyl-pyridin-2-yl, 4-bromo-pyridin-2-yl, 4-methanesulfonyl-pyridin-2-yl, 4-cyano-pyridin-2-yl, hydroxymethyl, and 4-oxy-pyrazin-2-yl.

In some embodiments, $R^{13}$ is 2,4-difluoro-phenyl. In some embodiments, $R^{13}$ is 2,4-dichloro-phenyl. In some embodiments, $R^{13}$ is 2-fluoro-4-methanesulfonyl-phenyl. In some embodiments, $R^{13}$ is 2,6-difluoro-phenyl. In some embodiments, $R^{13}$ is 2,5-difluoro-phenyl. In some embodiments, $R^{13}$ is 4-methoxy-phenyl. In some embodiments, $R^{13}$ is 4-cyano-phenyl. In some embodiments, $R^{13}$ is 4-fluoro-phenyl. In some embodiments, $R^{13}$ is phenyl. In some embodiments, $R^{13}$ is 2-fluoro-phenyl. In some embodiments, $R^{13}$ is 3-fluoro-phenyl. In some embodiments, $R^{13}$ is o-tolyl. In some embodiments, $R^{13}$ is tert-butyl. In some embodiments, $R^{13}$ is isopropyl. In some embodiments, $R^{13}$ is 2,2-dimethylpropyl. In some embodiments, $R^{13}$ is hydroxyl. In some embodiments, $R^{13}$ is 2-hydroxy-2-methylpropyl. In some embodiments, $R^{13}$ is 1-oxo-hexahydro-1$\lambda^4$-thiopyran-4-yl. In some embodiments, $R^{13}$ is 1,1-dioxo-hexahydro-1$\lambda^6$-thiopyran-4-yl. In some embodiments, $R^{13}$ is tetrahydrothiopyran-4-yl. In some embodiments, $R^{13}$ is morpholin-4-yl. In some embodiments, $R^{13}$ is tetrahydro-pyran-4-yl. In some embodiments, $R^{13}$ is 1,1-dioxo-tetrahydro-1$\lambda^6$-thiophen-3-yl. In some embodiments, $R^{13}$ is pyrazin-2-yl. In some embodiments, $R^{13}$ is 5-ethyl-pyrazin-2-yl. In some embodiments, $R^{13}$ is 5-hydroxy-pyrazin-2-yl. In some embodiments, $R^{13}$ is 5-isopropyl-pyrazin-2-yl. In some embodiments, $R^{13}$ is 5-heptafluoropropyl-pyrazin-2-yl. In some embodiments, $R^{13}$ is 5-cyclobutyl-pyrazin-2-yl. In some embodiments, $R^{13}$ is 5-methyl-pyrazin-2-yl. In some embodiments, $R^{13}$ is 6-ethyl-pyrazin-2-yl. In some embodiments, $R^{13}$ is 5-trifluoromethyl-pyrazin-2-yl. In some embodiments, $R^{13}$ is cyclopropyl. In some embodiments, $R^{13}$ is 5-cyclopropyl-pyrazin-2-yl. In some embodiments, $R^{13}$ is 6-chloro-pyrazin-2-yl. In some embodiments, $R^{13}$ is 5-dimethylamino-pyrazin-2-yl. In some embodiments, $R^{13}$ is 4-cyano-phenyl. In some embodiments, $R^{13}$ is 6-methoxy-pyridazin-3-yl. In some embodiments, $R^{13}$ is 6-chloro-pyridazin-3-yl. In some embodiments, $R^{13}$ is pyrimidin-5-yl. In some embodiments, $R^{13}$ is 6-dimethylamino-pyrazin-2-yl. In some embodiments, $R^{13}$ is 6-methoxy-pyrazin-2-yl. In some embodiments, $R^{13}$ is 2-pyrimidin-4-yl. In some embodiments, $R^{13}$ is 5-bromo-pyrazin-2-yl. In some embodiments, $R^{13}$ is 5-hydroxy-pyrazin-2-yl. In some embodiments, $R^{13}$ is 5-methoxy-pyrazin-2-yl. In some embodiments, $R^{13}$ is 5-ethoxypyrazin-2-yl. In some embodiments, $R^{13}$ is 5-methylamino-pyrazin-2-yl. In some embodiments, $R^{13}$ is 5-bromo-pyridin-2-yl. In some embodiments, $R^{13}$ is pyridin-3-yl. In some embodiments, $R^{13}$ is 5-trifluoromethyl-pyridin-2-yl. In some embodiments, $R^{13}$ is 5-isopropyl-pyridin-2-yl. In some embodiments, $R^{13}$ is 5-isopropyl-pyridin-2-yl. In some embodiments, $R^{13}$ is 5-methyl-pyridin-2-yl. In some embodiments, $R^{13}$ is 5-ethyl-pyridin-2-yl. In some embodiments, $R^{13}$ is 5-methoxy-pyridin-2-yl. In some embodiments, $R^{13}$ is 4-trifluoromethyl-pyridin-2-yl. In some embodiments, $R^{13}$ is 5-cyano-pyridin-2-yl. In some embodiments, $R^{13}$ is 5-dimethylamino-pyridin-2-yl. In some embodiments, $R^{13}$ is 4-methyl-pyridin-2-yl. In some embodiments, $R^{13}$ is 5-chloro-4-methyl-pyridin-2-yl. In some embodiments, $R^{13}$ is 5-chloro-4-trifluoromethyl-pyridin-2-yl. In some embodiments, $R^{13}$ is 4-trifluoromethyl-pyridin-2-yl. In some embodiments, $R^{13}$ is 3-fluoro-pyridin-2-yl. In some embodiments, $R^{13}$ is 6-methyl-4-trifluoromethyl-pyridin-2-yl. In some embodiments, $R^{13}$ is 3-methyl-pyridin-2-yl. In some embodiments, $R^{13}$ is 5-propyl-pyridin-2-yl. In some embodiments, $R^{13}$ is 5-cyclopropyl-pyridin-2-yl. In some embodiments, $R^{13}$ is 5-fluoro-pyridin-2-yl. In some embodiments, $R^{13}$ is 3,5-difluoro-pyridin-2-yl. In some embodiments, $R^{13}$ is 6-bromo-pyridin-3-yl. In some embodiments, $R^{13}$ is 5-bromo-pyridin-3-yl. In some embodiments, $R^{13}$ is 5,6-difluoro-pyridin-3-yl. In some embodiments, $R^{13}$ is 6-chloro-pyridin-3-yl. In some embodiments, $R^{13}$ is 3-fluoro-pyridin-4-yl. In some embodiments, $R^{13}$ is 5-cyano-pyridin-3-yl. In some embodiments, $R^{13}$ is pyridin-4-yl. In some embodiments, $R^{13}$ is 2-chloro-pyridin-4-yl. In some embodiments, $R^{13}$ is 2-methoxy-pyridin-4-yl. In some embodiments, $R^{13}$ is 6-methyl-pyridin-3-yl. In some embodiments, $R^{13}$ is m-tolyl. In some embodiments, $R^{13}$ is thiazol-2-yl. In some embodiments, $R^{13}$ is cyclopentyl. In some embodiments, $R^{13}$ is 4-amino-pyridin-2-yl. In some embodiments, $R^{13}$ is 4-methoxy-pyridin-2-yl. In some embodiments, $R^{13}$ is 4-choro-pyridin-2-yl. In some embodiments, $R^{13}$ is 4-fluoro-pyridin-2-yl. In some embodiments, $R^{13}$ is 4-cyclopropyl-pyridin-2-yl. In some embodiments, $R^{13}$ is 4-bromo-pyridin-2-yl. In some embodiments, $R^{13}$ is 4-methanesulfonyl-pyridin-2-yl. In some embodiments, $R^{13}$ is 4-cyano-pyridin-2-yl. In some embodiments, $R^{13}$ is hydroxymethyl. In some embodiments, $R^{13}$ is 4-oxy-pyrazin-2-yl. In some embodiments, $R^{13}$ is 3-methyl-1,1-dioxo-tetrahydro-1$\lambda^6$-thiophen-3-yl. In some embodiments, $R^{13}$ is 5-chloro-3-fluoro-pyridin-2-yl. In some embodiments, $R^{13}$ is 3-fluoro-5-methoxy-pyridin-2-yl. In some embodiments, $R^{13}$ is 2-chloro-4-fluoro-phenyl. In some embodiments, $R^{13}$ is 6-fluoro-pyridin-3-yl. In some embodiments, $R^{13}$ is 6-cyano-pyridin-3-yl. In some embodiments, $R^{13}$ is 4-iodo-pyridin-2-yl. In some embodiments, $R^{13}$ is 1-oxy-pyridin-3-yl. In some embodiments, $R^{13}$ is 4-hydroxy-pyridin-2-yl.

The Group $R^{14}$:

In some embodiments, $R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl.

In some embodiments, $R^{14}$ is selected from: $C_1$-$C_6$ alkylene and $C_3$-$C_7$ cycloalkylene; wherein said $C_1$-$C_6$ alkylene is optionally substituted with one or more substituents selected from: $C_1$-$C_6$ alkyl, aryl, heterocyclyl, and hydroxyl; wherein said $C_1$-$C_6$ alkyl is optionally substituted with one substituent selected from: halogen, and hydroxyl.

In some embodiments, $R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: methyl, tert-butyl, ethyl, tetrahydro-2H-pyranyl, isopropyl, benzyl, pyridinyl, hydroxymethyl, 4-fluoro-phenyl, tert-butoxycarbonyl, carboxy, methoxymethyl, hydroxyethyl, tetrahydrofuranyl, 3H-imidazolylmethyl, hydroxyl, pyrrolidinyl, cyclopropyl, sec-butyl, 2,2,2-trifluoroethyl, 2-fluoropropan-2-yl, 1,1,1,3,3,3-hexafluoropropan-2-yl, and fluoromethyl.

In some embodiments, $R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: methyl, tert-butyl, ethyl, tetrahydro-2H-pyranyl, isopropyl, benzyl, pyridinyl, hydroxymethyl, 4-fluoro-phenyl, tert-butoxycarbonyl, carboxy, methoxymethyl, hydroxyethyl, tetrahydrofuranyl, 3H-imidazolylmethyl, hydroxyl, pyrrolidinyl, and cyclopropyl.

In some embodiments, $R^{14}$ is selected from: $C_1$-$C_6$ alkylene and $C_3$-$C_7$ cycloalkylene; wherein said $C_1$-$C_6$ alkylene is optionally substituted with one or more substituents selected from: tetrahydro-2H-pyranyl, hydroxyl, 2,2,2-trifluoroethyl, and fluoromethyl.

In some embodiments, $R^{14}$ is selected from: methylene, ethylene, cyclopropylene, cyclobutylene, piperidinylene, pyridinylene, tetrahydropyranylene, thiazolylene, cyclohexylene, cyclopentylene, cyclopentenylene, dioxohexahydrothiopyranylene, pyrrolidinylene, tetrahydrothiophenylene, propylene, 3,3-oxetanylene, and —$SO_2$—; wherein said ethylene, methylene, piperidinylene, propylene, and pyrrolidinylene are each optionally substituted with one or more substituents selected from: methyl, tert-butyl, ethyl, tetrahydro-2H-pyranyl, isopropyl, benzyl, pyridinyl, hydroxymethyl, 4-fluoro-phenyl, tert-butoxycarbonyl, carboxy, methoxymethyl, hydroxyethyl, tetrahydro-furanyl, 3H-imidazolylmethyl, hydroxyl, pyrrolidinyl, cyclopropyl, sec-butyl, 2,2,2-trifluoroethyl, 2-fluoropropan-2-yl, 1,1,1,3,3,3-hexafluoropropan-2-yl, and fluoromethyl.

In some embodiments, $R^{14}$ is selected from: methylene, ethylene, cyclopropylene, cyclobutylene, piperidinylene, pyridinylene, tetrahydropyranylene, thiazolylene, cyclohexylene, cyclopentylene, cyclopentenylene, dioxohexahydrothiopyranylene, pyrrolidinylene, tetrahydrothiophenylene, propylene, and —$SO_2$—; wherein said ethylene, methylene, piperidinylene, propylene, and pyrrolidinylene are each optionally substituted with one or more substituents selected from: methyl, tert-butyl, ethyl, tetrahydro-2H-pyranyl, isopropyl, benzyl, pyridinyl, hydroxymethyl, 4-fluoro-phenyl, tert-butoxycarbonyl, carboxy, methoxymethyl, hydroxyethyl, tetrahydro-furanyl, 3H-imidazolylmethyl, hydroxyl, pyrrolidinyl, and cyclopropyl.

In some embodiments, $R^{14}$ is selected from: methylene, ethylene, 1,1-cyclopropylene, 1,1-dimethyl-methylene, 1,1-cyclobutylene, tert-butyl-methylene, 1-methyl-4,4-piperidinylene, 4,4-tetrahydro-2H-pyranylene, methyl-methylene, 1,1-cyclohexylene, 1,2-cyclohexylene, 1,1-dimethyl-ethylene, 1-tert-butyl-ethylene, 1-ethyl-ethylene, 1-methyl-ethylene, 1-(tetrahydro-2H-pyran-4-yl)-ethylene, isopropyl-methylene, 1,1-cyclopentylene, benzyl-methylene, 4,4-cyclopent-1-enylene, 1,1-dioxo-hexahydro-1$\lambda^6$-4,4-thiopyranylene, 1-tert-butoxycarbonyl-4,4-piperidinylene, 1-(pyridin-4-yl)-ethylene, 1-(pyridin-3-yl)-ethylene, 1-(pyridin-2-yl)-ethylene, 1-(4-fluoro-phenyl)-ethylene, 1-hydroxymethyl-1-methyl-ethylene, 1-carboxy-1-methyl-ethylene, 1-methoxymethyl-ethylene, 1-hydroxymethyl-ethylene, 1-(1-hydroxyethyl)-ethylene, 1,1-dimethyl-ethylene, 1-(tetrahydro-furan-3-yl)-ethylene, phenyl-methylene, 1-(3H-imidazol-4-ylmethyl)-ethylene, 1-(4-hydroxy-phenyl)-ethylene, benzyl-ethylene, (1-hydroxymethyl-2-methyl)-ethylene, 1-isopropyl-ethylene, pyridin-2-yl-methylene, 1,1-dimethyl-propylene, 2-hydroxy-propylene, (1-isobutyl-pyrrolidin-3-yl)-methylene, 1,3-azetidinylene, 1,3-pyrrolidinylene, 1,3-piperidinylene, 1,4-piperidinylene, 2,4-thiazolylene, 3,4-pyridinylene, 2,4-pyridinylene, 2,5-pyridinylene, —$SO_2$—, 2,5-pyridinylene, 1-cyclopropyl-ethylene, 1-(sec-butyl)-ethylene, 1-hydroxymethyl-1-ethyl-ethylene, 1-isopropyl-ethylene, 1-(2,2,2-trifluoroethyl)-ethylene, (2-fluoropropan-2-yl)-methylene, (1,1,1,3,3,3-hexafluoropropan-2-yl)-methylene, 1-(2-fluoropropan-2-yl)-ethylene, (2,2,2-trifluoroethyl)-methylene, 1,1-di(fluoromethyl)-ethylene, (hydroxymethyl)(methyl) methylene, (hydroxymethyl)(methyl)methylene, 3,3-oxetanylene, and 1-hydroxymethyl-1-isopropyl-ethylene.

In some embodiments, $R^{14}$ is selected from: methylene, ethylene, 1,1-cyclopropylene, 1,1-dimethyl-methylene, 1,1-cyclobutylene, tert-butyl-methylene, 1-methyl-4,4-piperidinylene, 4,4-tetrahydro-2H-pyranylene, methyl-methylene, 1,1-cyclohexylene, 1,2-cyclohexylene, 1,1-dimethyl-ethylene, 1-tert-butyl-ethylene, 1-ethyl-ethylene, 1-methyl-ethylene, 1-(tetrahydro-2H-pyran-4-yl)-ethylene, isopropyl-methylene, 1,1-cyclopentylene, benzyl-methylene, 4,4-cyclopent-1-enylene, 1,1-dioxo-hexahydro-1$\lambda^6$-4,4-thiopyranylene, 1-tert-butoxycarbonyl-4,4-piperidinylene, 1-(pyridin-4-yl)-ethylene, 1-(pyridin-3-yl)-ethylene, 1-(pyridin-2-yl)-ethylene, 1-(4-fluoro-phenyl)-ethylene, 1-hydroxymethyl-1-methyl-ethylene, 1-carboxy-1-methyl-ethylene, 1-methoxymethyl-ethylene, 1-hydroxymethyl-ethylene, 1-(1-hydroxyethyl)-ethylene, 1,1-dimethyl-ethylene, 1-(tetrahydro-furan-3-yl)-ethylene, phenyl-methylene, 1-(3H-imidazol-4-ylmethyl)-ethylene, 1-(4-hydroxy-phenyl)-ethylene, benzyl-ethylene, (1-hydroxymethyl-2-methyl)-ethylene, 1-isopropyl-ethylene, pyridin-2-yl-methylene, 1,1-dimethyl-propylene, 2-hydroxy-propylene, (1-isobutyl-pyrrolidin-3-yl)-methylene, 1,3-azetidinylene, 1,3-pyrrolidinylene, 1,3-piperidinylene, 1,4-piperidinylene, 2,4-thiazolylene, 3,4-pyridinylene, 2,4-pyridinylene, 2,5-pyridinylene, —$SO_2$—, 2,5-pyridinylene, and 1-cyclopropyl-ethylene.

In some embodiments, $R^{14}$ is selected from: 1,1-cyclopropylene, 1,1-dimethyl-methylene, 1,1-cyclobutylene, tert-butyl-methylene, 1,1-dimethyl-ethylene, 1-tert-butyl-ethylene, 1-(tetrahydro-2H-pyran-4-yl)-ethylene, isopropyl-methylene, 1-hydroxymethyl-1-methyl-ethylene, phenyl-methylene, 1-isopropyl-ethylene, 1-(2,2,2-trifluoroethyl)-ethylene, and 1,1-di(fluoromethyl)-ethylene.

In some embodiments, $R^{14}$ is methylene. In some embodiments, $R^{14}$ is ethylene. In some embodiments, $R^{14}$ is 1,1-cyclopropylene. In some embodiments, $R^{14}$ is 1,1-dimethyl-methylene. In some embodiments, $R^{14}$ is 1,1-cyclobutylene. In some embodiments, $R^{14}$ is tert-butyl-methylene. In some embodiments, $R^{14}$ is 1-methyl-4,4-piperidinylene. In some embodiments, $R^{14}$ is 4,4-tetrahydro-2H-pyranylene. In some embodiments, $R^{14}$ is methyl-methylene. In some embodiments, $R^{14}$ is 1,1-cyclohexylene. In some embodiments, $R^{14}$ is 1,2-cyclohexylene. In some embodiments, $R^{14}$ is 1,1-dimethyl-ethylene. In some embodiments, $R^{14}$ is 1-tert-butyl-ethylene. In some embodiments, $R^{14}$ is 1-ethyl-ethylene. In some embodiments, $R^{14}$ is 1-methyl-ethylene. In some embodiments, $R^{14}$ is 1-(tetrahydro-2H-pyran-4-yl)-ethylene. In some embodiments, $R^{14}$ is isopropyl-methylene. In some embodiments, $R^{14}$ is 1,1-cyclopentylene. In some embodiments, $R^{14}$ is benzyl-methylene. In some embodiments, $R^{14}$ is 4,4-cyclopent-1-enylene. In some embodiments, $R^{14}$ is 1,1-dioxo-hexahydro-1$\lambda^6$-4,4-thiopyranylene. In some embodiments, $R^{14}$ is 1-tert-butoxycarbonyl-4,4-piperidinylene. In some embodiments, $R^{14}$ is 1-(pyridin-4-yl)-ethylene. In some embodiments, $R^{14}$ is 1-(pyridin-3-yl)-ethylene. In some embodiments, $R^{14}$ is 1-(pyridin-2-yl)-ethylene. In some embodiments, $R^{14}$ is 1-(4-fluoro-phenyl)-ethylene. In some embodiments, $R^{14}$ is 1-hydroxymethyl-1-methyl-ethylene. In some embodiments, $R^{14}$ is 1-carboxy-1-methyl-ethylene. In some embodiments, $R^{14}$ is 1-methoxymethyl-ethylene. In some embodiments, $R^{14}$ is 1-hydroxymethyl-ethylene. In some embodiments, $R^{14}$ is 1-(1-hydroxyethyl)-ethylene. In some embodiments, $R^{14}$ is 1,1-dimethyl-ethylene. In some embodiments, $R^{14}$ is 1-(tetrahydro-furan-3-yl)-ethylene. In some embodiments, $R^{14}$ is phenyl-methylene. In some embodiments, $R^{14}$ is 1-(3H-imidazol-4-ylmethyl)-ethylene. In some embodiments, $R^{14}$ is 1-(4-hydroxy-phenyl)-ethylene. In some embodiments, $R^{14}$ is benzyl-ethylene. In some embodiments, $R^{14}$ is (1-hydroxymethyl-2-methyl)-ethylene. In some embodiments, $R^{14}$ is 1-isopropyl-ethylene. In some embodiments, $R^{14}$ is pyridin-2-yl-methylene. In some embodiments, $R^{14}$ is 1,1-dimethyl-propylene. In some embodiments, $R^{14}$ is 2-hydroxy-propylene. In some embodiments, $R^{14}$ is (1-isobutyl-pyrrolidin-3-yl)-methylene. In some embodiments, $R^{14}$ is 1,3-azetidinylene. In some embodiments, $R^{14}$ is 1,3-pyrrolidinylene. In some embodiments, $R^{14}$ is 1,3-piperidinylene. In some embodiments, $R^{14}$ is 1,4-piperidinylene. In some embodiments, $R^{14}$ is 2,4-thiazolylene. In some embodiments, $R^{14}$ is 3,4-pyridinylene. In some embodiments, $R^{14}$ is 2,4-pyridinylene. In some embodiments, $R^{14}$ is 2,5-pyridinylene. In some embodiments, $R^{14}$ is —SO$_2$—. In some embodiments, $R^{14}$ is 2,5-pyridinylene. In some embodiments, $R^{14}$ is 1-cyclopropyl-ethylene. In some embodiments, $R^{14}$ is 1-(sec-butyl)-ethylene. In some embodiments, $R^{14}$ is 1-hydroxymethyl-1-ethyl-ethylene. In some embodiments, $R^{14}$ is 1-isopropyl-ethylene. In some embodiments, $R^{14}$ is 1-(2,2,2-trifluoroethyl)-ethylene. In some embodiments, $R^{14}$ is (2-fluoropropan-2-yl)-methylene. In some embodiments, $R^{14}$ is (1,1,1,3,3,3-hexafluoropropan-2-yl)-methylene. In some embodiments, $R^{14}$ is 1-(2-fluoropropan-2-yl)-ethylene. In some embodiments, $R^{14}$ is (2,2,2-trifluoroethyl)-methylene. In some embodiments, $R^{14}$ is 1,1-di(fluoromethyl)-ethylene. In some embodiments, $R^{14}$ is (hydroxymethyl)(methyl)methylene. In some embodiments, $R^{14}$ is (hydroxymethyl)(methyl)methylene. In some embodiments, $R^{14}$ is 3,3-oxetanylene. In some embodiments, $R^{14}$ is 1-hydroxymethyl-1-isopropyl-ethylene.

In some embodiments, $R^{14}$ is absent.

The Group $R^{15}$:

In some embodiments, $R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl.

In some embodiments, $R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl.

In some embodiments, $R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with methyl.

In some embodiments, $R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with methyl.

In some embodiments, $R^{15}$ is selected from: pyrrolidinylene, piperidinylene, pyridinylene, azetidinylene, —C(O)NH—, —C(O)—, —C(O)O—, morpholinylene, methylene, ethylene, cyclopropylene, tetrahydropyranylene, cyclopentylene, tetrahydrothiophenylene, oxotetrahydrothiophenylene; wherein said piperidinylene is optionally substituted with methyl.

In some embodiments, $R^{15}$ is selected from: pyrrolidinylene, piperidinylene, pyridinylene, azetidinylene, —C(O)NH—, —C(O)—, morpholinylene, methylene, ethylene, cyclopropylene, tetrahydropyranylene, cyclopentylene, tetrahydrothiophenylene, oxotetrahydrothiophenylene; wherein said piperidinylene is optionally substituted with methyl.

In some embodiments, $R^{15}$ is selected from: 1,3-pyrrolidinylene, 1,4-piperidinylene, 2,6-pyridinylene, 1,3-azetidinylene, —C(O)NH—, —C(O)—, —C(O)O—, 1,2-pyrrolidinylene, 2,4-morpholinylene, ethylene, methylene, 1,1-cyclopentylene, 4,4-tetrahydro-2H-pyranylene, 3,3-tetrahydro-thiophenylene, 1,1-cyclopropylene, 1-methyl-4,4-piperidinylene, and 1-oxo-tetrahydro-1$\lambda^4$-3,3-thiophenylene.

In some embodiments, $R^{15}$ is selected from: 1,3-pyrrolidinylene, 1,4-piperidinylene, 2,6-pyridinylene, 1,3-azetidinylene, —C(O)NH—, —C(O)—, 1,2-pyrrolidinylene, 2,4-morpholinylene, ethylene, methylene, 1,1-cyclopentylene, 4,4-tetrahydro-2H-pyranylene, 3,3-tetrahydro-thiophenylene, 1,1-cyclopropylene, 1-methyl-4,4-piperidinylene, and 1-oxo-tetrahydro-1$\lambda^4$-3,3-thiophenylene.

In some embodiments, $R^{15}$ is selected from: —C(O)NH— and —C(O)O—.

In some embodiments, $R^{15}$ is 1,3-pyrrolidinylene. In some embodiments, $R^{15}$ is 1,4-piperidinylene. In some embodiments, $R^{15}$ is 2,6-pyridinylene. In some embodiments, $R^{15}$ is 1,3-azetidinylene. In some embodiments, $R^{15}$ is —C(O)NH—. In some embodiments, $R^{15}$ is —C(O)—. In some embodiments, $R^{15}$ is 1,2-pyrrolidinylene. In some embodiments, $R^{15}$ is 2,4-morpholinylene. In some embodiments, $R^{15}$ is ethylene. In some embodiments, $R^{15}$ is methylene. In some embodiments, $R^{15}$ is 1,1-cyclopentylene. In some embodiments, $R^{15}$ is 4,4-tetrahydro-2H-pyranylene. In some embodiments, $R^{15}$ is 3,3-tetrahydro-thiophenylene. In some embodiments, $R^{15}$ is 1,1-cyclopropylene. In some embodiments, $R^{15}$ is 1-methyl-4,4-piperidinylene. In some embodiments, $R^{15}$ is 1-oxo-tetrahydro-1$\lambda^4$-3,3-thiophenylene.

In some embodiments, $R^{15}$ is absent.

The Group $R^{16}$:

In some embodiments, $R^{16}$ is $C_1$-$C_6$ alkylene.

In some embodiments, $R^{16}$ is selected from: ethylene, methylene, isopropyl-methylene, and propylene.

In some embodiments, $R^{16}$ is selected from: methylene, isopropyl-methylene, and propylene.

In some embodiments, $R^{16}$ is selected from: ethylene, and methylene.

In some embodiments, $R^{16}$ is ethylene.

In some embodiments, $R^{16}$ is methylene.

In some embodiments, $R^{16}$ is absent.

The Group $R^{17}$:

In some embodiments, $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_3$-$C_7$ cycloalkylamino, $C_2$-$C_8$ dialkylamino, $C_1$-$C_6$ haloalkoxy, $C_1$-$C_6$ haloalkyl, halogen, heteroaryl, heterocyclyl, and hydroxyl.

In some embodiments, $R^{17}$ is selected from: H, $C_1$-$C_6$ alkyl, $C_1$-$C_6$ alkylamino, amino, aryl, carboxy, cyano, $C_1$-$C_6$ haloalkyl, heteroaryl, hydroxyl, and phosphonooxy; wherein said aryl is optionally substituted with one hydroxyl group.

In some embodiments, $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: amino, tert-butoxycarbonylamino, methyl, tert-butoxycarbonyl, ethyl, hydroxyl, isopropyl, tert-butyl, fluoro, chloro, methoxy, methanesulfonyl, carboxy, trifluoromethoxy, difluoromethoxy, dimethyl amino, methoxycarbonyl, ethoxycarbonyl, carboxy, carboxamide, trifluoromethyl, diethylamino, cyano, tert-butylamino, cyclopropyl, cyclobutyl, phenyl, bromo, 1-methyl-pyrrolidinyl, 2,2,2-trifluoroethyl, and 1,1-dioxo-tetrahydro-1$\lambda^6$-thiophen-3-yl.

In some embodiments, $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ di alkylamino, $C_2$-$C_8$ di alkyl sulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: amino, 1-tert-butoxycarbonylamino, methyl, 1-tert-butoxycarbonyl, ethyl, hydroxyl, isopropyl, tert-butyl, fluoro, chloro, methoxy, methanesulfonyl, carboxy, trifluoromethoxy, difluoromethoxy, dimethyl, methoxycarbonyl, ethoxycarbonyl, carboxy, carboxamide, trifluoromethyl, diethylamino, cyano, tert-butylamino, cyclopropyl, cyclobutyl, phenyl, bromo, and 1-methyl-pyrrolidinyl.

In some embodiments, $R^{17}$ is selected from: H, $C_1$-$C_6$ alkyl, $C_1$-$C_6$ alkylamino, amino, aryl, carboxy, cyano, $C_3$-$C_7$ cycloalkyl, $C_1$-$C_6$ haloalkyl, heteroaryl, heterocyclyl, hydroxyl, and phosphonooxy; wherein said aryl and $C_3$-$C_7$ cycloalkyl are each optionally substituted with one or more substituents selected from: hydroxyl and trifluoromethyl.

In some embodiments, $R^{17}$ is selected from: H, amino, 1-tert-butoxycarbonylamino, morpholin-4-yl, 4-methyl-piperidin-1-yl, piperidin-4-yl, 1-tert-butoxycarbonyl-piperidin-3-yl, tetrahydro-thiopyran-4-yl, 1-oxo-hexahydro-1$\lambda^4$-thiopyran-4-yl, tetrahydro-pyran-4-yl, pyrrolidin-1-yl, 1-tert-butoxycarbonyl-azetidin-3-yl, 2,6-dimethyl-morpholin-4-yl, piperidin-1-yl, 1-tert-butoxycarbonyl-piperidin-4-yl, 1,1-dioxo-hexahydro-1$\lambda^6$-thiopyran-4-yl, tetrahydro-furan-2-yl, 1-ethyl-pyrrolidin-2-yl, 1-methyl-pyrrolidin-2-yl, morpholin-2-yl, 1-methyl-piperidin-2-yl, 1-methyl-piperidin-4-yl, 4-hydroxy-1-methyl-piperidin-4-yl, thiomorpholin-4-yl, tetrahydro-furan-3-yl, 1-tert-butoxycarbonyl-pyrrolidin-4-yl, 1,2,2,6,6-pentamethyl-piperidin-4-yl, 1,1-dioxo-tetrahydro-1$\lambda^6$-thiophen-3-yl, 4-methyl-morpholin-2-yl, 4-tert-butoxycarbonyl-morpholin-2-yl, 1-isopropyl-piperidin-4-yl, 4-hydroxy-1,1-dioxo-tetrahydro-1$\lambda^6$-thiophen-3-yl, 3-methyl-1,1-dioxo-tetrahydro-1$\lambda^6$-thiophen-3-yl, phenyl, 2-hydroxy-indan-1-yl, indan-1-yl, cyclopentyl, 2-hydroxy-cyclopentyl, cyclobutyl, 2-hydroxy-cyclohexyl, 1,3,3-trimethyl-bicyclo[2.2.1]hept-2-yl, 6,6-dimethyl-bicyclo[3.1.1]hept-2-yl, 1-aza-bicyclo[2.2.2]oct-3-yl, 9-methyl-9-aza-bicyclo[3.3.1]non-1-yl, 3-azepan-1-yl, 2-fluoro-phenyl, 2-chloro-phenyl, 4-fluoro-phenyl, 4-chloro-phenyl, 3-fluoro-phenyl, 5-fluoro-2-methoxy-phenyl, 2-fluoro-4-methanesulfonyl-phenyl, 4-carboxy-2-fluoro-phenyl, 2,5-difluoro-phenyl, m-tolyl, o-tolyl, 2,5-dimethyl-phenyl, 2,3-dimethyl-phenyl, 4-hydroxy-3-methoxy-phenyl, 2,4-dimethoxy-phenyl, 2,3-dimethoxy-phenyl, 3,5-dimethoxy-phenyl, 4-methoxy-phenyl, 3-methoxy-phenyl, 2-methoxy-phenyl, 3-hydroxy-phenyl, 4-hydroxy-phenyl, 2-hydroxy-phenyl, 5-fluoro-2-hydroxy-phenyl, 3-trifluoromethoxy-phenyl, 4-difluoromethoxy-phenyl, 3-difluoromethoxy-phenyl, 4-fluoro-phenoxy, 2-dimethylamino-phenyl, 4-dimethylamino-phenyl, 6-fluoro-4H-benzo[1,3]dioxin-8-yl, benzo[1,3]dioxol-5-yl, pyrimidin-2-yl, pyrimidin-4-yl, 2,6-dimethyl-pyrimidin-4-yl, pyridazin-3-yl, 5-methyl-pyrazin-2-yl, 6-methoxy-pyrimidin-4-yl, pyrazin-2-yl, 3,5-dimethyl-pyrazin-2-yl, 5-fluoro-2-oxo-2,3-dihydro-pyrimidin-4-yl, hydroxyl, methoxycarbonyl, ethoxycarbonyl, carboxy, 1-piperidin-1-yl, carboxamide, methoxy, trifluoromethyl, methyl, tert-butyl, diethylamino, dimethylamino, cyano, tert-butylamino, cyclopropyl, pyridin-3-yloxy, 1H-tetrazol-5-yl, 5-methyl-[1,2,4]oxadiazol-3-yl, phosphonooxy, cyclobutylamino, phenylamino, 1-tert-butyl-3-methylureido, 3-methyl-1-phenylureido, N-tert-butylmethylsulfonamido, 1-cyclobutyl-3-methylureido, methylcarbamoyl, 5-hydroxy-1H-indol-3-yl, 1H-benzoimidazol-2-yl, 5,7-dimethyl-pyrazolo[1,5-a]pyrimidin-2-yl, 1H-benzoimidazol-2-yl, 2-(tert-butoxycarbonyl)-3,4-dihydro-1H-isoquinoline-2-yl, quinolin-3-yl, quinolin-4-yl, 2-methyl-quinolin-4-yl, benzooxazol-2-yl, 1-methyl-1,2,3,4-tetrahydro-quinolin-7-yl, 2,3-dihydro-benzofuran-3-yl, benzothiazol-2-yl, 1,4-dimethyl-1H-pyrrol-2-yl, 3-methyl-3H-imidazol-4-yl, 1H-imidazol-4-yl, 5-hydroxy-1H-pyrazol-3-yl, 1-methyl-1H-pyrazol-3-yl, 4-pyridin-2-yl-thiazol-2-yl, 5-methyl-thiazol-2-yl, oxazol-4-yl, 4-phenyl-thiazol-2-yl, 5-tert-butyl-isoxazol-3-yl, pyridin-2-yl, pyridin-3-yl, pyridin-4-yl, 3-hydroxy-pyridin-2-yl, 6-hydroxy-pyridin-3-yl, 3-hydroxy-pyridin-4-yl, 4-hydroxy-pyridin-2-yl, 6-hydroxy-pyridin-2-yl, 2-hydroxy-pyridin-3-yl, 2-methoxy-pyridin-3-yl, 5-methoxy-pyridin-2-yl, 4-methoxy-pyridin-2-yl, 2-methoxy-pyridin-4-yl, 6-methoxy-pyridin-2-yl, 6-methoxy-pyridin-3-yl, 3-fluoro-pyridin-2-yl, 2-fluoro-pyridin-3-yl, 6-fluoro-pyridin-2-yl, 5-fluoro-pyridin-2-yl, 6-fluoro-pyridin-3-yl, 3-fluoro-pyridin-4-yl, 3-methyl-pyridin-2-yl, 3-methyl-pyridin-4-yl, 6-methyl-pyridin-2-yl, 4-methyl-pyridin-2-yl, 6-methyl-pyridin-3-yl, 2-methyl-pyridin-3-yl, 5-trifluoromethyl-pyridin-2-yl, 6-trifluoromethyl-pyridin-3-yl, 4-trifluoromethyl-pyridin-2-yl, 3-chloro-5-trifluoromethyl-pyridin-2-yl, 4,6-dimethyl-pyridin-2-yl, 4,6-dimethyl-pyridin-2-yl, 3-chloro-5-methyl-pyridin-2-yl, 6-cyano-pyridin-3-yl, 3-cyano-5-methyl-pyridin-2-yl, 3-cyano-5-methyl-pyridin-2-yl, 3-chloro-5-methyl-pyridin-2-yl, 2-chloro-pyridin-3-yl, 5-chloro-pyridin-2-yl, 6-chloro-2-methyl-pyridin-3-yl, 6-chloro-pyridin-3-yl, 3-chloro-pyridin-4-yl, 6-bromo-2-methyl-pyridin-3-yl, 5-bromo-3-methyl-pyridin-2-yl, 6-carboxypyridin-2-yl, 6-methanesulfonyl-4-methyl-pyridin-3-yl, 6-methanesulfonyl-4-methyl-pyridin-3-yl, 6-methanesulfonyl-2-methyl-pyridin-3-yl, 6-methanesulfonyl-pyridin-3-yl, 2,6-dimethoxy-pyridin-3-yl, 5-fluoro-1-oxy-pyridin-2-yl, 1-oxy-pyridin-2-yl, 6-pyrrolidin-1-yl-pyridin-2-ylmethyl, 5-(1-methyl-pyrrolidin-2-yl)-pyridin-2-yl, 6-morpholin-4-yl-pyridin-2-yl, 6-morpholin-4-yl-pyridin-3-yl, ethynyl, tert-butyl(methyl)amino, 2,2,2-trifluoroethyl, N-cyclobutylmethylsulfonamido, N-phenylmethylsulfonamido, hydroxy(methyl)amino, methoxy(methyl)amino, azetidin-1-yl, tert-butoxy, fluoromethyl, 2,2,2-trifluoroethylamino, and (1,1-dioxo-tetrahydro-1$\lambda^6$-thiophen-3-yl)amino.

In some embodiments, $R^{17}$ is selected from: H, amino, 1-tert-butoxycarbonylamino, morpholin-4-yl, 4-methyl-piperidin-1-yl, piperidin-4-yl, 1-tert-butoxycarbonyl-piperidin-3-yl, tetrahydro-thiopyran-4-yl, 1-oxo-hexahydro-1$\lambda^4$-thiopyran-4-yl, tetrahydro-pyran-4-yl, pyrrolidin-1-yl, 1-tert-butoxycarbonyl-azetidin-3-yl, 2,6-dimethyl-morpholin-4-yl, piperidin-1-yl, 1-tert-butoxycarbonyl-piperidin-4-yl, 1,1-dioxo-hexahydro-1$\lambda^6$-thiopyran-4-yl, tetrahydro-furan-2-yl, 1-ethyl-pyrrolidin-2-yl, 1-methyl-pyrrolidin-2-yl, morpholin-2-yl, 1-methyl-piperidin-2-yl, 1-methyl-piperidin-4-yl, 4-hydroxy-1-methyl-piperidin-4-yl, thiomorpholin-4-yl, tetrahydro-furan-3-yl, 1-tert-butoxycarbonyl-pyrrolidin-4-yl, 1,2,2,6,6-pentamethyl-piperidin-4-yl, 1,1-dioxo-tetrahydro-1$\lambda^6$-thiophen-3-yl, 4-methyl-morpholin-2-yl, 4-tert-butoxycarbonyl-morpholin-2-yl, 1-isopropyl-piperidin-4-yl, 4-hydroxy-1,1-dioxo-tetrahydro-1$\lambda^6$-thiophen-3-yl, 3-methyl-1,1-dioxo-tetrahydro-1$\lambda^6$-thiophen-3-yl, phenyl, 2-hydroxy-indan-1-yl, indan-1-yl, cyclopentyl, 2-hydroxy-cyclopentyl, cyclobutyl, 2-hydroxy-cyclohexyl, 1,3,3-trimethyl-bicyclo[2.2.1]hept-2-yl, 6,6-dimethyl-bicyclo[3.1.1]hept-2-yl, 1-aza-bicyclo[2.2.2]oct-3-yl, 9-methyl-9-aza-bicyclo[3.3.1]non-1-yl, 3-azepan-1-yl, 2-fluoro-phenyl, 2-chloro-phenyl, 4-fluoro-phenyl, 4-chloro-phenyl, 3-fluoro-phenyl, 5-fluoro-2-methoxy-phenyl, 2-fluoro-4-methanesulfonyl-phenyl, 4-carboxy-2-fluoro-phenyl, 2,5-difluoro-phenyl, m-tolyl, o-tolyl, 2,5-dimethyl-phenyl, 2,3-dimethyl-phenyl, 4-hydroxy-3-methoxy-phenyl, 2,4-dimethoxy-phenyl, 2,3-dimethoxy-phenyl, 3,5-dimethoxy-phenyl, 4-methoxy-phenyl, 3-methoxy-phenyl, 2-methoxy-phenyl, 3-hydroxy-phenyl, 4-hydroxy-phenyl, 2-hydroxy-phenyl, 5-fluoro-2-hydroxy-phenyl, 3-trifluoromethoxy-phenyl, 4-difluoromethoxy-phenyl, 3-difluoromethoxy-phenyl, 4-fluoro-phenoxy, 2-dimethyl amino-phenyl, 4-dimethyl amino-phenyl, 6-fluoro-4H-benzo[1,3]dioxin-8-yl, benzo[1,3]dioxol-5-yl, pyrimidin-2-yl, pyrimidin-4-yl, 2,6-dimethyl-pyrimidin-4-yl, pyridazin-3-yl, 5-methyl-pyrazin-2-yl, 6-methoxy-pyrimidin-4-yl, pyrazin-2-yl, 3,5-dimethyl-pyrazin-2-yl, 5-fluoro-2-oxo-2,3-dihydro-pyrimidin-4-yl, hydroxyl, methoxycarbonyl, ethoxycarbonyl, carboxy, 1-piperidin-1-yl, carboxamide, methoxy, trifluoromethyl, methyl, tert-butyl, diethylamino, dimethylamino, cyano, tert-butylamino, cyclopropyl, pyridin-3-yloxy, 1H-tetrazol-5-yl, 5-methyl-[1,2,4]oxadiazol-3-yl, phosphonooxy, cyclobutylamino, phenylamino, 1-tert-butyl-3-methylureido, 3-methyl-1-phenylureido, N-tert-butylmethylsulfonamido, 1-cyclobutyl-3-methylureido, methylcarbamoyl, 5-hydroxy-1H-indol-3-yl, 1H-benzoimidazol-2-yl, 5,7-dimethyl-pyrazolo[1,5-a]pyrimidin-2-yl, 1H-benzoimidazol-2-yl, 2-(tert-butoxycarbonyl)-3,4-dihydro-1H-isoquinoline-2-yl, quinolin-3-yl, quinolin-4-yl, 2-methyl-quinolin-4-yl, benzooxazol-2-yl, 1-methyl-1,2,3,4-tetrahydro-quinolin-7-yl, 2,3-dihydro-benzofuran-3-yl, benzothiazol-2-yl, 1,4-dimethyl-1H-pyrrol-2-yl, 3-methyl-3H-imidazol-4-yl, 1H-imidazol-4-yl, 5-hydroxy-1H-pyrazol-3-yl, 1-methyl-1H-pyrazol-3-yl, 4-pyridin-2-yl-thiazol-2-yl, 5-methyl-thiazol-2-yl, oxazol-4-yl, 4-phenyl-thiazol-2-yl, 5-tert-butyl-isoxazol-3-yl, pyridin-2-yl, pyridin-3-yl, pyridin-4-yl, 3-hydroxy-pyridin-2-yl, 6-hydroxy-pyridin-3-yl, 3-hydroxy-pyridin-4-yl, 4-hydroxy-pyridin-2-yl, 6-hydroxy-pyridin-2-yl, 2-hydroxy-pyridin-3-yl, 2-methoxy-pyridin-3-yl, 5-methoxy-pyridin-2-yl, 4-methoxy-pyridin-2-yl, 2-methoxy-pyridin-4-yl, 6-methoxy-pyridin-2-yl, 6-methoxy-pyridin-3-yl, 3-fluoro-pyridin-2-yl, 2-fluoro-pyridin-3-yl, 6-fluoro-pyridin-2-yl, 5-fluoro-pyridin-2-yl, 6-fluoro-pyridin-3-yl, 3-fluoro-pyridin-4-yl, 3-methyl-pyridin-2-yl, 3-methyl-pyridin-4-yl, 6-methyl-pyridin-2-yl, 4-methyl-pyridin-2-yl, 6-methyl-pyridin-3-yl, 2-methyl-pyridin-3-yl, 5-trifluoromethyl-pyridin-2-yl, 6-trifluoromethyl-pyridin-3-yl, 4-trifluoromethyl-pyridin-2-yl, 3-chloro-5-trifluoromethyl-pyridin-2-yl, 4,6-dimethyl-pyridin-2-yl, 4,6-dimethyl-pyridin-2-yl, 3-chloro-5-methyl-pyridin-2-yl, 6-cyano-pyridin-3-yl, 3-cyano-5-methyl-pyridin-2-yl, 3-cyano-5-methyl-pyridin-2-yl, 3-chloro-5-methyl-pyridin-2-yl, 2-chloro-pyridin-3-yl, 5-chloro-pyridin-2-yl, 6-chloro-2-methyl-pyridin-3-yl, 6-chloro-pyridin-3-yl, 3-chloro-pyridin-4-yl, 6-bromo-2-methyl-pyridin-3-yl, 5-bromo-3-methyl-pyridin-2-yl, 6-carboxypyridin-2-yl, 6-methanesulfonyl-4-methyl-pyridin-3-yl, 6-methanesulfonyl-4-methyl-pyridin-3-yl, 6-methanesulfonyl-2-methyl-pyridin-3-yl, 6-methanesulfonyl-pyridin-3-yl, 2,6-dimethoxy-pyridin-3-yl, 5-fluoro-1-oxy-pyridin-2-yl, 1-oxy-pyridin-2-yl, 6-pyrrolidin-1-yl-pyridin-2-ylmethyl, 5-(1-methyl-pyrrolidin-2-yl)-pyridin-2-yl, 6-morpholin-4-yl-pyridin-2-yl, 6-morpholin-4-yl-pyridin-3-yl, ethynyl, tert-butyl(methyl)amino, 2,2,2-trifluoroethyl, N-cyclobutylmethylsulfonamido, N-phenylmethylsulfonamido, hydroxy(methyl)amino, methoxy(methyl)amino, azetidin-1-yl, and tert-butoxy.

In some embodiments, $R^{17}$ is selected from: is selected from: amino, 2-hydroxy-indan-1-yl, hydroxyl, carboxy, trifluoromethyl, methyl, tert-butyl, cyano, tert-butylamino, phosphonooxy, pyridin-2-yl, and fluoromethyl.

In some embodiments, $R^{17}$ is H. In some embodiments, $R^{17}$ is amino. In some embodiments, $R^{17}$ is 1-tert-butoxycarbonylamino. In some embodiments, $R^{17}$ is morpholin-4-yl. In some embodiments, $R^{17}$ is 4-methyl-piperidin-1-yl. In some embodiments, $R^{17}$ is piperidin-4-yl. In some embodiments, $R^{17}$ is 1-tert-butoxycarbonyl-piperidin-3-yl. In some embodiments, $R^{17}$ is tetrahydro-thiopyran-4-yl. In some embodiments, $R^{17}$ is 1-oxo-hexahydro-1$\lambda^4$-thiopyran-4-yl. In some embodiments, $R^{17}$ is tetrahydro-pyran-4-yl. In some embodiments, $R^{17}$ is pyrrolidin-1-yl. In some embodiments, $R^{17}$ is 1-tert-butoxycarbonyl-azetidin-3-yl. In some embodiments, $R^{17}$ is 2,6-dimethyl-morpholin-4-yl. In some embodiments, $R^{17}$ is piperidin-1-yl. In some embodiments, $R^{17}$ is 1-tert-butoxycarbonyl-piperidin-4-yl. In some embodiments, $R^{17}$ is 1,1-dioxo-hexahydro-1$\lambda^6$-thiopyran-4-yl. In some embodiments, $R^{17}$ is tetrahydro-furan-2-yl. In some embodiments, $R^{17}$ is 1-ethyl-pyrrolidin-2-yl. In some embodiments, $R^{17}$ is 1-methyl-pyrrolidin-2-yl. In some embodiments, $R^{17}$ is morpholin-2-yl. In some embodiments, $R^{17}$ is 1-methyl-piperidin-2-yl. In some embodiments, $R^{17}$ is 1-methyl-piperidin-4-yl. In some embodiments, $R^{17}$ is 4-hydroxy-1-methyl-piperidin-4-yl. In some embodiments, $R^{17}$ is thiomorpholin-4-yl. In some embodiments, $R^{17}$ is tetrahydro-furan-3-yl. In some embodiments, $R^{17}$ is 1-tert-butoxycarbonyl-pyrrolidin-4-yl. In some embodiments, $R^{17}$ is 1,2,2,6,6-pentamethyl-piperidin-4-yl. In some embodiments, $R^{17}$ is 1,1-dioxo-tetrahydro-1$\lambda^6$-thiophen-3-yl. In some embodiments, $R^{17}$ is 4-methyl-morpholin-2-yl. In some embodiments, $R^{17}$ is 4-tert-butoxycarbonyl-morpholin-2-yl. In some embodiments, $R^{17}$ is 1-isopropyl-piperidin-4-yl. In some embodiments, $R^{17}$ is 4-hydroxy-1,1-dioxo-tetrahydro-1$\lambda^6$-thiophen-3-yl. In some embodiments, $R^{17}$ is 3-methyl-1,1-dioxo-tetrahydro-1$\lambda^6$-thiophen-3-yl. In some embodiments, $R^{17}$ is phenyl. In some embodiments, $R^{17}$ is 2-hydroxy-indan-1-yl. In some embodiments, $R^{17}$ is indan-1-yl. In some embodiments, $R^{17}$ is cyclopentyl. In some embodiments, $R^{17}$ is 2-hydroxy-cyclopentyl. In some embodiments, $R^{17}$ is cyclobutyl. In some embodiments, $R^{17}$ is 2-hydroxy-cyclohexyl. In some embodiments, $R^{17}$ is 1,3,3-trimethyl-bicyclo[2.2.1]hept-2-yl. In some embodiments, $R^{17}$ is 6,6-dimethyl-bicyclo[3.1.1]hept-2-yl. In some embodiments, $R^{17}$ is 1-aza-bicyclo[2.2.2]oct-3-yl. In some embodiments, $R^{17}$ is 9-methyl-9-aza-bicyclo[3.3.1]non-1-yl. In some embodiments, $R^{17}$ is 3-azepan-1-yl. In some embodiments, $R^{17}$ is 2-fluoro-phenyl. In some embodiments, $R^{17}$ is 2-chloro-phenyl. In some embodiments, $R^{17}$ is 4-fluoro-phenyl. In some embodiments, $R^{17}$ is 4-chloro-phenyl. In some embodiments, $R^{17}$ is 3-fluoro-phenyl. In some embodiments, $R^{17}$ is 5-fluoro-2-methoxy-phenyl. In some embodiments, $R^{17}$ is 2-fluoro-4-methanesulfonyl-phenyl. In some embodiments, $R^{17}$ is 4-carboxy-2-fluoro-phenyl. In some embodiments, $R^{17}$ is 2,5-difluoro-phenyl. In some embodiments, $R^{17}$ is m-tolyl. In some embodiments, $R^{17}$ is o-tolyl. In some embodiments, $R^{17}$ is 2,5-dimethyl-phenyl. In some embodiments, $R^{17}$ is 2,3-dimethyl-phenyl. In some embodiments, $R^{17}$ is 4-hydroxy-3-methoxy-phenyl. In some embodiments, $R^{17}$ is 2,4-dimethoxy-phenyl. In some embodiments, $R^{17}$ is 2,3-dimethoxy-phenyl. In some embodiments, $R^{17}$ is 3,5-dimethoxy-phenyl. In some embodiments, $R^{17}$ is 4-methoxy-phenyl. In some embodiments, $R^{17}$ is 3-methoxy-phenyl. In some embodiments, $R^{17}$ is 2-methoxy-phenyl. In some embodiments, $R^{17}$ is 3-hydroxy-phenyl. In some embodiments, $R^{17}$ is 4-hydroxy-phenyl. In some embodiments, $R^{17}$ is 2-hydroxy-phenyl. In some embodiments, $R^{17}$ is 5-fluoro-2-hydroxy-phenyl. In some embodiments, $R^{17}$ is 3-trifluoromethoxy-phenyl. In some embodiments, $R^{17}$ is 4-difluoromethoxy-phenyl. In some embodiments, $R^{17}$ is 3-difluoromethoxy-phenyl. In some embodiments, $R^{17}$ is 4-fluoro-phenoxy. In some embodiments, $R^{17}$ is 2-dimethylamino-phenyl. In some embodiments, $R^{17}$ is 4-dimethylamino-phenyl. In some embodiments, $R^{17}$ is 6-fluoro-4H-benzo[1,3]dioxin-8-yl. In some embodiments, $R^{17}$ is benzo[1,3]dioxol-5-yl. In some embodiments, $R^{17}$ is pyrimidin-2-yl. In some embodiments, $R^{17}$ is pyrimidin-4-yl. In some embodiments, $R^{17}$ is 2,6-dimethyl-pyrimidin-4-yl. In some embodiments, $R^{17}$ is pyridazin-3-yl. In some embodiments, $R^{17}$ is 5-methyl-pyrazin-2-yl. In some embodiments, $R^{17}$ is 6-methoxy-pyrimidin-4-yl. In some embodiments, $R^{17}$ is pyrazin-2-yl. In some embodiments, $R^{17}$ is 3,5-dimethyl-pyrazin-2-yl. In some embodiments, $R^{17}$ is 5-fluoro-2-oxo-2,3-dihydro-pyrimidin-4-yl. In some embodiments, $R^{17}$ is hydroxyl. In some embodiments, $R^{17}$ is methoxycarbonyl. In some embodiments, $R^{17}$ is ethoxycarbonyl. In some embodiments, $R^{17}$ is carboxy. In some embodiments, $R^{17}$ is 1-piperidin-1-yl. In some embodiments, $R^{17}$ is carboxamide. In some embodiments, $R^{17}$ is methoxy. In some embodiments, $R^{17}$ is trifluoromethyl. In some embodiments, $R^{17}$ is methyl. In some embodiments, $R^{17}$ is tert-butyl. In some embodiments, $R^{17}$ is diethylamino. In some embodiments, $R^{17}$ is dimethylamino. In some embodiments, $R^{17}$ is cyano. In some embodiments, $R^{17}$ is tert-butylamino. In some embodiments, $R^{17}$ is cyclopropyl. In some embodiments, $R^{17}$ is pyridin-3-yloxy. In some embodiments, $R^{17}$ is 1H-tetrazol-5-yl. In some embodiments, $R^{17}$ is 5-methyl-[1,2,4]oxadiazol-3-yl. In some embodiments, $R^{17}$ is phosphonooxy. In some embodiments, $R^{17}$ is cyclobutylamino. In some embodiments, $R^{17}$ is phenylamino. In some embodiments, $R^{17}$ is 1-tert-butyl-3-methylureido. In some embodiments, $R^{17}$ is 3-methyl-1-phenylureido. In some embodiments, $R^{17}$ is N-tert-butylmethylsulfonamido. In some embodiments, $R^{17}$ is 1-cyclobutyl-3-methylureido. In some embodiments, $R^{17}$ is methylcarbamoyl. In some embodiments, $R^{17}$ is 5-hydroxy-1H-indol-3-yl. In some embodiments, $R^{17}$ is 1H-benzoimidazol-2-yl. In some embodiments, $R^{17}$ is 5,7-dimethyl-pyrazolo[1,5-a]pyrimidin-2-yl. In some embodiments, $R^{17}$ is 1H-benzoimidazol-2-yl. In some embodiments, $R^{17}$ is 2-(tert-butoxycarbonyl)-3,4-dihydro-1H-isoquinoline-2-yl. In some embodiments, $R^{17}$ is quinolin-3-yl. In some embodiments, $R^{17}$ is quinolin-4-yl. In some embodiments, $R^{17}$ is 2-methyl-quinolin-4-yl. In some embodiments, $R^{17}$ is benzooxazol-2-yl. In some embodiments, $R^{17}$ is 1-methyl-1,2,3,4-tetrahydro-quinolin-7-yl. In some embodiments, $R^{17}$ is 2,3-dihydro-benzofuran-3-yl. In some embodiments, $R^{17}$ is benzothiazol-2-yl. In some embodiments, $R^{17}$ is 1,4-dimethyl-1H-pyrrol-2-yl. In some embodiments, $R^{17}$ is 3-methyl-3H-imidazol-4-yl. In some embodiments, $R^{17}$ is 1H-imidazol-4-yl. In some embodiments, $R^{17}$ is 5-hydroxy-1H-pyrazol-3-yl. In some embodiments, $R^{17}$ is 1-methyl-1H-pyrazol-3-yl. In some embodiments, $R^{17}$ is 4-pyridin-2-yl-thiazol-2-yl. In some embodiments, $R^{17}$ is 5-methyl-thiazol-2-yl. In some embodiments, $R^{17}$ is oxazol-4-yl. In some embodiments, $R^{17}$ is 4-phenyl-thiazol-2-yl. In some embodiments, $R^{17}$ is 5-tert-butyl-isoxazol-3-yl. In some embodiments, $R^{17}$ is pyridin-2-yl. In some embodiments, $R^{17}$ is pyridin-3-yl. In some embodiments, $R^{17}$ is pyridin-4-yl. In some embodiments, $R^{17}$ is 3-hydroxy-pyridin-2-yl. In some embodiments, $R^{17}$ is 6-hydroxy-pyridin-3-yl. In some embodiments, $R^{17}$ is 3-hydroxy-pyridin-4-yl. In some embodiments, $R^{17}$ is 4-hydroxy-pyridin-2-yl. In some embodiments, $R^{17}$ is 6-hydroxy-pyridin-2-yl. In some embodiments, $R^{17}$ is 2-hydroxy-pyridin-3-yl. In some embodiments, $R^{17}$ is 2-methoxy-pyridin-3-yl. In some embodiments, $R^{17}$ is 5-methoxy-pyridin-2-yl. In some embodiments, $R^{17}$ is 4-methoxy-pyridin-2-yl. In some embodiments, $R^{17}$ is 2-methoxy-pyridin-4-yl. In some embodiments, $R^{17}$ is 6-methoxy-pyridin-2-yl. In some embodiments, $R^{17}$ is 6-methoxy-pyridin-3-yl. In some embodiments, $R^{17}$ is 3-fluoro-pyridin-2-yl. In some embodiments, $R^{17}$ is 2-fluoro-pyridin-3-yl. In some embodiments, $R^{17}$ is 6-fluoro-pyridin-2-yl. In some embodiments, $R^{17}$ is 5-fluoro-pyridin-2-yl. In some embodiments, $R^{17}$ is 6-fluoro-pyridin-3-yl. In some embodiments, $R^{17}$ is 3-fluoro-pyridin-4-yl. In some embodiments, $R^{17}$ is 3-methyl-pyridin-2-yl. In some embodiments, $R^{17}$ is 3-methyl-pyridin-4-yl. In some embodiments, $R^{17}$ is 6-methyl-pyridin-2-yl. In some embodiments, $R^{17}$ is 4-methyl-pyridin-2-yl. In some embodiments, $R^{17}$ is 6-methyl-pyridin-3-yl. In some embodiments, $R^{17}$ is 2-methyl-pyridin-3-yl. In some embodiments, $R^{17}$ is 5-trifluoromethyl-pyridin-2-yl. In some embodiments, $R^{17}$ is 6-trifluoromethyl-pyridin-3-yl. In some embodiments, $R^{17}$ is 4-trifluoromethyl-pyridin-2-yl. In some embodiments, $R^{17}$ is 3-chloro-5-trifluoromethyl-pyridin-2-yl. In some embodiments, $R^{17}$ is 4,6-dimethyl-pyridin-2-yl. In some embodiments, $R^{17}$ is 4,6-dimethyl-pyridin-2-yl. In some embodiments, $R^{17}$ is 3-chloro-5-methyl-pyridin-2-yl. In some embodiments, $R^{17}$ is 6-cyano-pyridin-3-yl. In some embodiments, $R^{17}$ is 3-cyano-5-methyl-pyridin-2-yl. In some embodiments, $R^{17}$ is 3-cyano-5-methyl-pyridin-2-yl. In some embodiments, $R^{17}$ is 3-chloro-5-methyl-pyridin-2-yl. In some embodiments, $R^{17}$ is 2-chloro-pyridin-3-yl. In some embodiments, $R^{17}$ is 5-chloro-pyridin-2-yl. In some embodiments, $R^{17}$ is 6-chloro-2-methyl-pyridin-3-yl. In some embodiments, $R^{17}$ is 6-chloro-pyridin-3-yl. In some embodiments, $R^{17}$ is 3-chloro-pyridin-4-yl. In some embodiments, $R^{17}$ is 6-bromo-2-methyl-pyridin-3-yl. In some embodiments, $R^{17}$ is 5-bromo-3-methyl-pyridin-2-yl. In some embodiments, $R^{17}$ is 6-carboxypyridin-2-yl. In some embodiments, $R^{17}$ is 6-methanesulfonyl-4-methyl-pyridin-3-yl. In some embodiments, $R^{17}$ is 6-methanesulfonyl-4-methyl-pyridin-3-yl. In some embodiments, $R^{17}$ is 6-methanesulfonyl-2-methyl-pyridin-3-yl. In some embodiments, $R^{17}$ is 6-methanesulfonyl-pyridin-3-yl. In some embodiments, $R^{17}$ is 2,6-dimethoxy-pyridin-3-yl. In some embodiments, $R^{17}$ is 5-fluoro-1-oxy-pyridin-2-yl. In some embodiments, $R^{17}$ is 1-oxy-pyridin-2-yl. In some embodiments, $R^{17}$ is 6-pyrrolidin-1-yl-pyridin-2-ylmethyl. In some embodiments, $R^{17}$ is 5-(1-methyl-pyrrolidin-2-yl)-pyridin-2-yl. In some embodiments, $R^{17}$ is 6-morpholin-4-yl-pyridin-2-yl. In some embodiments, $R^{17}$ is 6-morpholin-4-yl-pyridin-3-yl. In some embodiments, $R^{17}$ is ethynyl. In some embodiments, $R^{17}$ is tert-butyl(methyl)amino. In some embodiments, $R^{17}$ is 2,2,2-trifluoroethyl. In some embodiments, $R^{17}$ is N-cyclobutylmethylsulfonamido. In some embodiments, $R^{17}$ is N-phenylmethylsulfonamido. In some embodiments, $R^{17}$ is hydroxy(methyl)amino. In some embodiments, $R^{17}$ is methoxy(methyl)amino. In some embodiments, $R^{17}$ is azetidin-1-yl. In some embodiments, $R^{17}$ is tert-butoxy. In some embodiments, $R^{17}$ is fluoromethyl. In some embodiments, $R^{17}$ is 2,2,2-trifluoroethylamino. In some embodiments, $R^{17}$ is (1,1-dioxo-tetrahydro-1$\lambda^6$-thiophen-3-yl)amino.

Certain $R^{15}$ and $R^{17}$ Combinations:

In some embodiments, $R^{15}$ is selected from: —C(O)NH—, —C(O)—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_2$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkyl sulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl.

Certain Combinations:

In some embodiments, $R^1$, $R^2$, $R^3$, $R^4$, $R^5$, and $R^6$ are each independently selected from: H and $C_1$-$C_6$ alkyl.

In some embodiments, $R^1$ and $R^6$ are each independently selected from: H, and $C_1$-$C_6$ alkyl; and $R^2$, $R^3$, $R^4$, and $R^5$ are each H.

In some embodiments, $R^1$, $R^2$, $R^3$, $R^4$, $R^5$, and $R^6$ are each independently selected from: H, methyl, and isopropyl.

In some embodiments, $R^1$ is selected from: H and methyl; $R^2$, $R^3$, $R^4$, and $R^5$ are each H; and $R^6$ is selected from: H and is isopropyl.

In some embodiments, $R^1$ is methyl; $R^2$, $R^3$, $R^4$, and $R^5$ are each H; and $R^6$ is isopropyl.

In some embodiments, $R^1$, $R^2$, $R^3$, $R^4$, $R^5$, and $R^6$ are each H.

In some embodiments, $R^8$ and $R^9$ together with the nitrogen atom to which they are both bonded form group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

In some embodiments, $R^8$ and $R^9$ together with the nitrogen atom to which they are both bonded form 4-cyclohexylmethyl-piperazin-1-yl, hexahydro-pyrrolo[1,2-a]pyrazin-2-yl, 5,7-dihydro-pyrrolo[3,4-b]pyridin-6-yl, 4-methoxy-2,3-dihydro-indol-1-yl, 2-phenyl-pyrrolidin-1-yl, 2-pyridin-2-yl-thiomorpholin-4-yl, 2-hydroxymethyl-2,3-dihydro-indol-1-yl, 4-hydroxy-piperidin-1-yl, hexahydro-pyrrolo[1,2-a]pyrazin-2-yl, 7-(methoxycarbonyl)-3,4-dihydro-1H-isoquinolin-2-yl, 7-methoxy-3,4-dihydro-1H-isoquinolin-2-yl, 1,4,6,7-tetrahydro-imidazo[4,5-c]pyridin-5-yl, 5-fluoro-1,3-dihydro-isoindol-2-yl, 3-hydroxy-7,8-dihydro-5H-[1,6]naphthyridin-6-yl, 4-(tert-butoxycarbonyl)-2-(hydroxymethyl)piperazin-1-yl, 1,3-dihydro-isoindol-2-yl, 3-trifluoromethyl-5,6-dihydro-8H-[1,2,4]triazolo[4,3-a]pyrazin-7-yl, 4-morpholin-4-yl-piperidin-1-yl, 3,4-dihydro-1H-isoquinolin-2-yl, 4-(3-methoxy-pyridin-2-yl)-piperazin-1-yl, 3-hydroxy-piperidin-1-yl, 4-(3-chloro-phenyl)-piperazin-1-yl, 6-methoxy-3,4-dihydro-1H-isoquinolin-2-yl, morpholin-4-yl, 2-hydroxymethyl-pyrrolidin-1-yl, 1,3-dihydro-pyrrolo[3,4-c]pyridin-2-yl, 3-pyridin-4-yl-pyrrolidin-1-yl, 4-(pyridin-2-yloxy)-piperidin-1-yl, 3-pyridin-2-yl-pyrrolidin-1-yl, 7-methyl-3,4-dihydro-2H-[1,8]naphthyridin-1-yl, 3-pyridin-3-yl-pyrrolidin-1-yl, 3-hydroxy-pyrrolidin-1-yl, 4-(4,6-dimethyl-pyrimidin-2-yl)-piperazin-1-yl, 2-methyl-3,4-dihydro-2H-quinolin-1-yl, 2-phenyl-morpholin-4-yl or pyrazin-2-yl.

In some embodiments, $R^8$ and $R^9$ together with the nitrogen atom to which they are both bonded form 4-cyclohexylmethyl-piperazin-1-yl. In some embodiments, $R^8$ and $R^9$ together with the nitrogen atom to which they are both bonded form hexahydro-pyrrolo[1,2-a]pyrazin-2-yl. In some embodiments, $R^8$ and $R^9$ together with the nitrogen atom to which they are both bonded form 5,7-dihydro-pyrrolo[3,4-b]pyridin-6-yl. In some embodiments, $R^8$ and $R^9$ together with the nitrogen atom to which they are both bonded form 4-methoxy-2,3-dihydro-indol-1-yl. In some embodiments, $R^8$ and $R^9$ together with the nitrogen atom to which they are both bonded form 2-phenyl-pyrrolidin-1-yl. In some embodiments, $R^8$ and $R^9$ together with the nitrogen atom to which they are both bonded form 2-pyridin-2-yl-thiomorpholin-4-yl. In some embodiments, $R^8$ and $R^9$ together with the nitrogen atom to which they are both bonded form 2-hydroxymethyl-2,3-dihydro-indol-1-yl. In some embodiments, $R^8$ and $R^9$ together with the nitrogen atom to which they are both bonded form 4-hydroxypiperidin-1-yl. In some embodiments, $R^8$ and $R^9$ together with the nitrogen atom to which they are both bonded form hexahydro-pyrrolo[1,2-a]pyrazin-2-yl. In some embodiments, $R^8$ and $R^9$ together with the nitrogen atom to which they are both bonded form 7-(methoxycarbonyl)-3,4-dihydro-1H-isoquinolin-2-yl. In some embodiments, $R^8$ and $R^9$ together with the nitrogen atom to which they are both bonded form 7-methoxy-3,4-dihydro-1H-isoquinolin-2-yl. In some embodiments, $R^8$ and $R^9$ together with the nitrogen atom to which they are both bonded form 1,4,6,7-tetrahydro-imidazo[4,5-c]pyridin-5-yl. In some embodiments, $R^8$ and $R^9$ together with the nitrogen atom to which they are both bonded form 5-fluoro-1,3-dihydro-isoindol-2-yl. In some embodiments, $R^8$ and $R^9$ together with the nitrogen atom to which they are both bonded form 3-hydroxy-7,8-dihydro-5H-[1,6]naphthyridin-6-yl. In some embodiments, $R^8$ and $R^9$ together with the nitrogen atom to which they are both bonded form 4-(tert-butoxycarbonyl)-2-(hydroxymethyl)piperazin-1-yl. In some embodiments, $R^8$ and $R^9$ together with the nitrogen atom to which they are both bonded form 1,3-dihydro-isoindol-2-yl. In some embodiments, $R^8$ and $R^9$ together with the nitrogen atom to which they are both bonded form 3-trifluoromethyl-5,6-dihydro-8H-[1,2,4]triazolo[4,3-a]pyrazin-7-yl. In some embodiments, $R^8$ and $R^9$ together with the nitrogen atom to which they are both bonded form 4-morpholin-4-yl-piperidin-1-yl. In some embodiments, $R^8$ and $R^9$ together with the nitrogen atom to which they are both bonded form 3,4-dihydro-1H-isoquinolin-2-yl. In some embodiments, $R^8$ and $R^9$ together with the nitrogen atom to which they are both bonded form 4-(3-methoxy-pyridin-2-yl)-piperazin-1-yl. In some embodiments, $R^8$ and $R^9$ together with the nitrogen atom to which they are both bonded form 3-hydroxy-piperidin-1-yl. In some embodiments, $R^8$ and $R^9$ together with the nitrogen atom to which they are both bonded form 4-(3-chlorophenyl)-piperazin-1-yl. In some embodiments, $R^8$ and $R^9$ together with the nitrogen atom to which they are both bonded form 6-methoxy-3,4-dihydro-1H-isoquinolin-2-yl. In some embodiments, $R^8$ and $R^9$ together with the nitrogen atom to which they are both bonded form morpholin-4-yl. In some embodiments, $R^8$ and $R^9$ together with the nitrogen atom to which they are both bonded form 2-hydroxymethyl-pyrrolidin-1-yl. In some embodiments, $R^8$ and $R^9$ together with the nitrogen atom to which they are both bonded form 1,3-dihydro-pyrrolo[3,4-c]pyridin-2-yl. In some embodiments, $R^8$ and $R^9$ together with the nitrogen atom to which they are both bonded form 3-pyridin-4-yl-pyrrolidin-1-yl. In some embodiments, $R^8$ and $R^9$ together with the nitrogen atom to which they are both bonded form 4-(pyridin-2-yloxy)-piperidin-1-yl. In some embodiments, $R^8$ and $R^9$ together with the nitrogen atom to which they are both bonded form 3-pyridin-2-yl-pyrrolidin-1-yl. In some embodiments, $R^8$ and $R^9$ together with the nitrogen atom to which they are both bonded form 7-methyl-3,4-dihydro-2H-[1,8]naphthyridin-1-yl. In some embodiments, $R^8$ and $R^9$ together with the nitrogen atom to which they are both bonded form 3-pyridin-3-yl-pyrrolidin-1-yl. In some embodiments, $R^8$ and $R^9$ together with the nitrogen atom to which they are both bonded form 3-hydroxy-pyrrolidin-1-yl. In some embodiments, $R^8$ and $R^9$ together with the nitrogen atom to which they are both bonded form 4-(4,6-dimethyl-pyrimidin-2-yl)-piperazin-1-yl. In some embodiments, $R^8$ and $R^9$ together with the nitrogen atom to which they are both bonded form 2-methyl-3,4-dihydro-2H-quinolin-1-yl. In some embodiments, $R^8$ and $R^9$ together with the nitrogen atom to which they are both bonded form 2-phenyl-morpholin-4-yl or pyrazin-2-yl.

In some embodiments, the compound of Formula Ia, or a pharmaceutically acceptable salt, solvate, hydrate, and/or N-oxide thereof is selected from compounds of Formula Ie and pharmaceutically acceptable salts, solvates, hydrates, and N-oxides thereof:

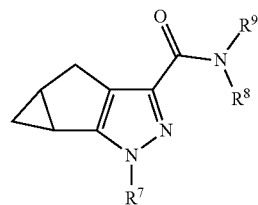

Ie wherein:
$R^7$ is —$R^{10}$—$R^{11}$—$R^{12}$—$R^{13}$; wherein
$R^{10}$ is selected from: $C_1$-$C_6$ alkylene, heteroarylene, and heterocyclylene; or $R^{10}$ is absent;
$R^{11}$ is selected from: —C(O)NH— and $C_1$-$C_6$ alkylene; or is absent;
$R^{12}$ is $C_1$-$C_6$ alkylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;
$R^8$ is —$R^{14}$—$R^{15}$—$R^{16}$—$R^{17}$; wherein
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;
$R^{15}$ is selected from: —C(O)NH—, —C(O)—, —C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{18}$ is absent;
$R^{16}$ is $C_1$-$C_6$ alkylene; or $R^{16}$ is absent; and
$R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_3$-$C_7$ cycloalkylamino, $C_2$-$C_8$ dialkylamino, $C_1$-$C_6$ haloalkoxy, $C_1$-$C_6$ haloalkyl, halogen, heteroaryl, heterocyclyl, and hydroxyl; and R$^9$ is selected from H, C$_1$-C$_6$ alkyl, and C$_3$-C$_7$ cycloalkyl; or R$^8$ and R$^9$ together with the nitrogen atom to which they are both bonded form a group selected from: heterocyclyl and heterobicyclyl, each optionally substituted with one or more substituents selected from: carbo-C$_1$-C$_6$-alkoxy, C$_1$-C$_6$ alkoxy, C$_1$-C$_6$ alkyl, aryl, carbo-C$_1$-C$_6$-alkoxy, C$_1$-C$_6$ haloalkyl, halogen, heteroaryl, heteroaryloxy, heterocyclyl, and hydroxyl; wherein said aryl, C$_1$-C$_6$ alkyl, and heteroaryl are optionally substituted with one substituent selected from: C$_3$-C$_7$ cycloalkyl, C$_1$-C$_6$ alkoxy, halogen, and hydroxyl.

In some embodiments, the compound of Formula Ia is selected from the following compounds and pharmaceutically acceptable salts, solvates, hydrates and/or N-oxides thereof:

Compound 151: (1aR,5aR)-2-(5-Chloro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

Compound 174: (1aR,5aR)-2-(2,4-Dichloro-phenyl)-1a,2,5,5a-tetrahydro-1H-2,3-diaza-cyclopropa[a]pentalene-4-carboxylic acid (1-hydroxymethyl-cyclopropyl)-amide;

Compound 264: (1aR,5aR)-2-(5-Cyano-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide;

Compound 309: (1aR,5aR)-2-(5-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

Compound 493: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide;

Compound 515: 1-(2,4-Difluoro-phenyl)-3b,4,4a,5-tetrahydro-1H-cyclopropa[3,4]cyclopenta[1,2-c]pyrazole-3-carboxylic acid (2-hydroxy-1,1-dimethyl-ethyl)-amide;

Compound 593: (1aR,5aR)-2-Pyrazin-2-yl-1a,2,5,5a-tetrahydro-1H-2,3-diaza-cyclopropa[a]pentalene-4-carboxylic acid tert-butylamide;

Compound 625: (1aR,5aR)-2-(4-Chloro-pyridin-2-yl)-1a,2,5,5a-tetrahydro-1H-2,3-diaza-cyclopropa[a]pentalene-4-carboxylic acid (cyano-dimethyl-methyl)-amide;

Compound 642: (1aR,5aR)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide;

Compound 644: (1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

Compound 646: Phosphoric acid mono-(2-{[(1aR,5aR)-2-(4-cyano-pyridin-2-yl)-1a,2,5,5a-tetrahydro-1H-2,3-diaza-cyclopropa[a]pentalene-4-carbonyl]-amino}-2-methyl-propyl) ester;

Compound 667: (1aR,5aR)-2-Pyrazin-2-yl-1a,2,5,5a-tetrahydro-1H-2,3-diaza-cyclopropa[a]pentalene-4-carboxylic acid [2,2-dimethyl-1-((S)-methylcarbamoyl)-propyl]-amide;

Compound 683: Phosphoric acid mono-{(S)-3,3-dimethyl-2-[((1aR,5aR)-2-pyrazin-2-yl-1a,2,5,5a-tetrahydro-1H-2,3-diaza-cyclopropa[a]pentalene-4-carbonyl)-amino]-butyl}ester;

Compound 684: (1aR,5aR)-2-Pyrazin-2-yl-1a,2,5,5a-tetrahydro-1H-2,3-diaza-cyclopropa[a]pentalene-4-carboxylic acid ((S)-2-hydroxy-1-tetrahydro-pyran-4-yl-ethyl)-amide;

Compound 690: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide;

Compound 696: (1aS,5aS)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide;

Compound 698: (1aR,5aR)-2-(4-Oxy-pyrazin-2-yl)-1a,2,5,5a-tetrahydro-1H-2,3-diaza-cyclopropa[a]pentalene-4-carboxylic acid (1-hydroxymethyl-cyclobutyl)-amide;

Compound 699: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide;

Compound 700: (1aS,5aS)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclobutyl)-amide;

Compound 703: Phosphoric acid mono-((S)-3,3-dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester;

Compound 704: (1aR,5aR)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide;

Compound 722: (1aR,5aR)-2-(4-Oxy-pyrazin-2-yl)-1a,2,5,5a-tetrahydro-1H-2,3-diaza-cyclopropa[a]pentalene-4-carboxylic acid ((S)-methylcarbamoyl-phenyl-methyl)-amide;

Compound 746: (S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric acid methyl ester;

Compound 764: (1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclopropyl)-amide;

Compound 765: (1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclobutyl)-amide;

Compound 766: (1aS,5aS)-2-(4-Oxy-pyrazin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide;

Compound 767: (1aS,5aS)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide;

Compound 820: (1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide;

Compound 821: (1aR,5aR)-2-(4-Oxy-pyrazin-2-yl)-1a,2,5,5a-tetrahydro-1H-2,3-diaza-cyclopropa[a]pentalene-4-carboxylic acid (1-methyl-cyclobutyl)-amide;

Compound 828: (1aR,5aR)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide;

Compound 841: (1aR,5aR)-2-(4-Oxy-pyrazin-2-yl)-1a,2,5,5a-tetrahydro-1H-2,3-diaza-cyclopropa[a]pentalene-4-carboxylic acid [(S)-2-hydroxy-1-(tetrahydro-pyran-4-yl)-ethyl]-amide;

Compound 844: (1aR,5aR)-Pentanedioic acid mono-((S)-3-methyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester;

Compound 848: (1aS,5aS)—(S)-2-Amino-3-methyl-butyric acid (S)-3,3-dimethyl-2-{[2-(4-oxy-pyrazin-2-yl)-1a,2,5,5a-tetrahydro-1H-2,3-diaza-cyclopropa[a]pentalene-4-carbonyl]-amino}-butyl ester;

Compound 889: (1aS,5aS)-2-(4-Chloro-pyridin-2-yl)-1a,2, 5,5a-tetrahydro-1H-2,3-diaza-cyclopropa[a]pentalene-4-carboxylic acid (2-fluoro-1-fluoromethyl-1-hydroxymethyl-ethyl)-amide;

Compound 891: (1aS,5aS)-2-(4-Cyano-pyridin-2-yl)-1a,2, 5,5a-tetrahydro-1H-2,3-diaza-cyclopropa[a]pentalene-4-carboxylic acid ((S)-3,3,3-trifluoro-1-hydroxymethyl-propyl)-amide;

Compound 896: (1aS,5aS)-2-(4-Oxy-pyrazin-2-yl)-1a,2,5, 5a-tetrahydro-1H-2,3-diaza-cyclopropa[a]pentalene-4-carboxylic acid ((S)-1-hydroxymethyl-2-methyl-propyl)-amide;

Compound 897: (1aS,5aS)-2-(4-Chloro-pyridin-2-yl)-1a,2, 5,5a-tetrahydro-1H-2,3-diaza-cyclopropa[a]pentalene-4-carboxylic acid (2-fluoro-1,1-dimethyl-ethyl)-amide;

Compound 902: (1aS,5aS)-2-(4-Oxy-pyrazin-2-yl)-1a,2,5, 5a-tetrahydro-1H-2,3-diaza-cyclopropa[a]pentalene-4-carboxylic acid N'-tert-butyl-hydrazide;

Compound 904: (1aS,5aS)-2-(4-Oxy-pyrazin-2-yl)-1a,2,5, 5a-tetrahydro-1H-2,3-diaza-cyclopropa[a]pentalene-4-carboxylic acid (2-fluoro-1,1-dimethyl-ethyl)-amide;

Compound 912: (1aS,5aS)-2-(4-Oxy-pyrazin-2-yl)-1a,2,5, 5a-tetrahydro-1H-2,3-diaza-cyclopropa[a]pentalene-4-carboxylic acid ((R)-1,2-dimethyl-propyl)-amide;

Compound 913: (1aS,5aS)-2-(4-Oxy-pyrazin-2-yl)-1a,2,5, 5a-tetrahydro-1H-2,3-diaza-cyclopropa[a]pentalene-4-carboxylic acid ((S)-2-hydroxy-1-phenyl-ethyl)-amide;

Compound 918: (1aR,5aR)-2-(4-Oxy-pyrazin-2-yl)-1a,2,5, 5a-tetrahydro-1H-2,3-diaza-cyclopropa[a]pentalene-4-carboxylic acid ((S)-1-fluoromethyl-2,2-dimethyl-propyl)-amide;

Compound 919: (1aS,5aS)-2-(4-Oxy-pyrazin-2-yl)-1a,2,5, 5a-tetrahydro-1H-2,3-diaza-cyclopropa[a]pentalene-4-carboxylic acid (2,2,2-trifluoro-1,1-dimethyl-ethyl)-amide;

Compound 920: (1aS,5aS)-2-(4-Oxy-pyrazin-2-yl)-1a,2,5, 5a-tetrahydro-1H-2,3-diaza-cyclopropa[a]pentalene-4-carboxylic acid ((1S,2S)-2-hydroxy-indan-1-yl)-amide;

Compound 921: (1aS,5aS)-2-(4-Oxy-pyrazin-2-yl)-1a,2,5, 5a-tetrahydro-1H-2,3-diaza-cyclopropa[a]pentalene-4-carboxylic acid ((1S,2R)-2-hydroxy-indan-1-yl)-amide;

Compound 924: (1aS,5aS)-2-(4-Oxy-pyrazin-2-yl)-1a,2,5, 5a-tetrahydro-1H-2,3-diaza-cyclopropa[a]pentalene-4-carboxylic acid (1-fluoromethyl-cyclobutyl)-amide;

Compound 926: (1aS,5aS)-2-Pyrazin-2-yl-1a,2,5,5a-tetrahydro-1H-2,3-diaza-cyclopropa[a]pentalene-4-carboxylic acid (1-trifluoromethyl-cyclobutyl)-amide;

Compound 927: (1aS,5aS)-2-Pyrazin-2-yl-1a,2,5,5a-tetrahydro-1H-2,3-diaza-cyclopropa[a]pentalene-4-carboxylic acid (2,2,2-trifluoro-1,1-dimethyl-ethyl)-amide;

Compound 930: (1aS,5aS)-2-Pyrazin-2-yl-1a,2,5,5a-tetrahydro-1H-2,3-diaza-cyclopropa[a]pentalene-4-carboxylic acid (1-trifluoromethyl-cyclopropyl)-amide; and Compound 931: (1aR,5aR)-2-(4-Fluoro-pyridin-2-yl)-1a,2, 5,5a-tetrahydro-1H-2,3-diaza-cyclopropa[a]pentalene-4-carboxylic acid (2-hydroxy-1,1-dimethyl-ethyl)-amide.

In some embodiments, the compound of Formula Ia is selected from the following compounds and pharmaceutically acceptable salts, solvates, hydrates and/or N-oxides thereof:

Compound 699: (1aS,5aS)-2-(4-Oxy-pyrazin-2-yl)-1a,2,5, 5a-tetrahydro-1H-2,3-diaza-cyclopropa[a]pentalene-4-carboxylic acid ((S)-1-hydroxymethyl-2,2-dimethyl-propyl)-amide;

Compound 764: (1aS,5aS)-2-(4-Oxy-pyrazin-2-yl)-1a,2,5, 5a-tetrahydro-1H-2,3-diaza-cyclopropa[a]pentalene-4-carboxylic acid (1-trifluoromethyl-cyclopropyl)-amide;

Compound 765: (1aS,5aS)-2-(4-Oxy-pyrazin-2-yl)-1a,2,5, 5a-tetrahydro-1H-2,3-diaza-cyclopropa[a]pentalene-4-carboxylic acid (1-trifluoromethyl-cyclobutyl)-amide;

Compound 919: (1aS,5aS)-2-(4-Oxy-pyrazin-2-yl)-1a,2,5, 5a-tetrahydro-1H-2,3-diaza-cyclopropa[a]pentalene-4-carboxylic acid (2,2,2-trifluoro-1,1-dimethyl-ethyl)-amide;

Compound 921: (1aS,5aS)-2-(4-Oxy-pyrazin-2-yl)-1a,2,5, 5a-tetrahydro-1H-2,3-diaza-cyclopropa[a]pentalene-4-carboxylic acid ((1S,2R)-2-hydroxy-indan-1-yl)-amide; and Compound 926: (1aS,5aS)-2-Pyrazin-2-yl-1a,2,5,5a-tetrahydro-1H-2,3-diaza-cyclopropa[a]pentalene-4-carboxylic acid (1-trifluoromethyl-cyclobutyl)-amide.

In some embodiments, the compound of Formula Ia is (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide or a pharmaceutically acceptable salt, solvate, and/or hydrate, thereof.

Provided is an anhydrous form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide. The physical properties of the crystalline form of (1aS,5aS)-2-(4-Oxy-pyrazin-2-yl)-1a,2, 5,5a-tetrahydro-1H-2,3-diaza-cyclopropa[a]pentalene-4-carboxylic acid ((S)-1-hydroxymethyl-2,2-dimethyl-propyl)-amide (anhydrous form) are summarized in the table below.

Figure 10:
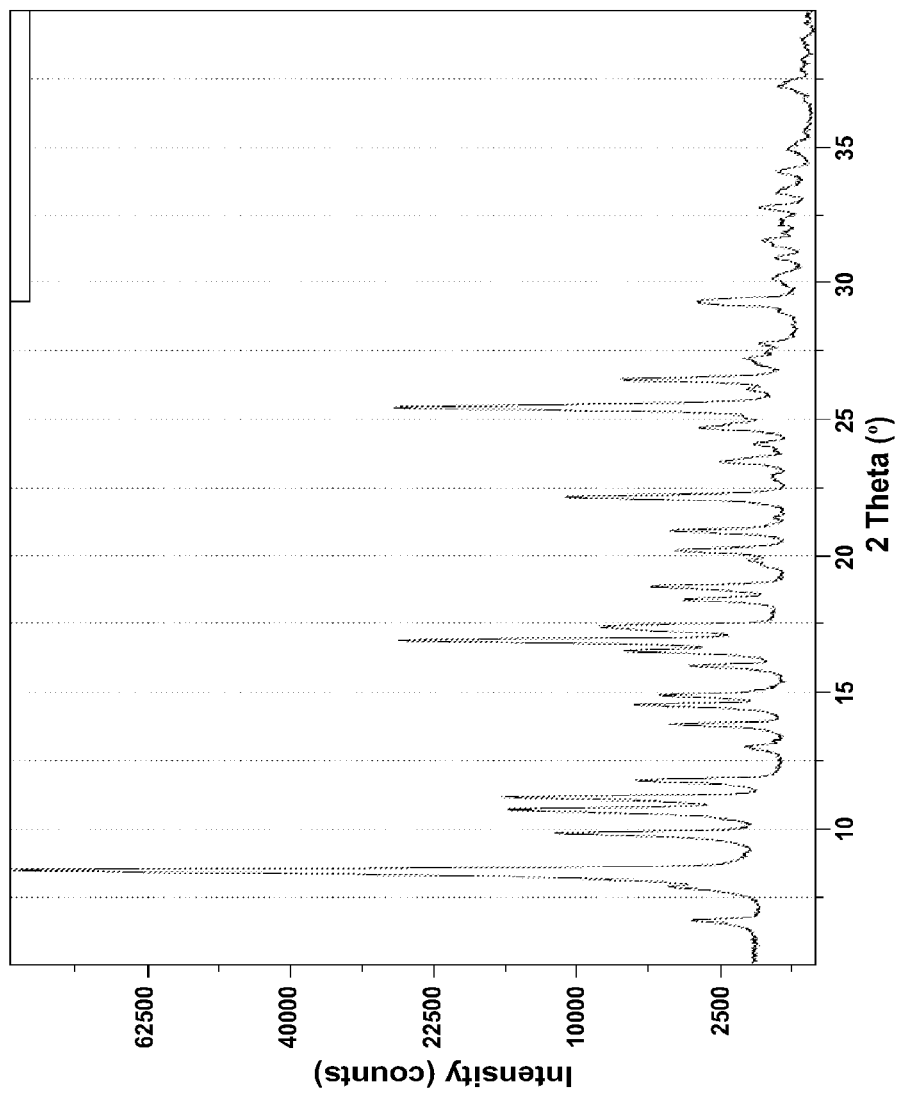
FIG. 10 shows a powder X-ray diffraction pattern (PXRD) for a sample containing an anhydrous crystalline form of Compound 699.

| | Compound 699 (Anhydrous Form) |
|---|---|
| PXRD | FIG. 10: Peaks of about ≥ 8.7% relative intensity at 8.5, 9.8, 10.7, 11.1, 11.8, 14.5, 16.5, 16.9, 17.4, 18.9, 22.1, and 25.4 °2θ |
| TGA | FIG. 11: Decrease in weight of about 0.24% out to about 150° C. |
| DSC | FIG. 11: Endotherm extrapolated onset temperature: about 162° C. |
| DMS | FIG. 12: The adsorption/desorption isotherm shows about 1.0% or less weight change from about 10% relative humidity (RH) to about 90% RH; and about 0.1% or less weight change after a 10% RH to 90% RH back to 10% RH cycle, See Example 9. |

Certain X-ray powder diffraction peaks for the anhydrous form of (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide are shown in the table below.

| Pos. [°2θ] | d-spacing [Å] | Rel. Int. [%] |
|---|---|---|
| 6.6 | 13.36534 | 4.4 |
| 7.9 | 11.2546 | 5.5 |
| 8.5 | 10.4588 | 100 |
| 9.8 | 9.01268 | 21.5 |
| 10.7 | 8.27929 | 28.3 |
| 11.1 | 7.94475 | 26.1 |
| 11.8 | 7.52225 | 10 |
| 13.8 | 6.40603 | 7.5 |
| 14.5 | 6.09847 | 11.3 |
| 14.9 | 5.95101 | 6 |
| 16 | 5.55637 | 5.8 |
| 16.5 | 5.37022 | 11.8 |
| 16.9 | 5.24987 | 26.7 |
| 17.3 | 5.13862 | 8.5 |
| 17.4 | 5.10045 | 14.8 |
| 18.4 | 4.8235 | 4.6 |

-continued

| Pos. [°2θ] | d-spacing [Å] | Rel. Int. [%] |
|---|---|---|
| 18.9 | 4.70416 | 8.7 |
| 20.2 | 4.40147 | 5.5 |
| 20.9 | 4.25028 | 4.4 |
| 22.1 | 4.01561 | 14.5 |
| 23.4 | 3.79482 | 3 |
| 24.7 | 3.60675 | 4.6 |
| 25.4 | 3.50373 | 26.6 |
| 26.5 | 3.36865 | 8.1 |
| 29.2 | 3.0526 | 2.8 |
| 29.3 | 3.04412 | 3.6 |

Also provided is an anhydrous crystalline form of (1aS, 5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

Also provided is an anhydrous crystalline form of (1aS, 5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide having an X-ray powder diffraction pattern comprising a peak, in terms of 2θ, at 8.5°±0.2°. In some embodiments, the anhydrous crystalline form has an X-ray powder diffraction pattern comprising peaks, in terms of 2θ, at 8.5°±0.2°, and 10.7°±0.2°. In some embodiments, the anhydrous crystalline form has an X-ray powder diffraction pattern comprising peaks, in terms of 2θ, at 8.5°±0.2°, 10.7°±0.2°, and 16.9°±0.2°. In some embodiments, the anhydrous crystalline form has an X-ray powder diffraction pattern comprising peaks, in terms of 2θ, at 8.5°±0.2°, 10.7°±0.2°, 16.9°±0.2°, 25.4°±0.2°, and 11.1°±0.2°. In some embodiments, the anhydrous crystalline form has an X-ray powder diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, and 17.4°±0.2°. In some embodiments, the anhydrous crystalline form has an X-ray powder diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, 17.4°±0.2°, 22.1°±0.2°, and 16.5°±0.2°. In some embodiments, the anhydrous crystalline form has an X-ray powder diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, 17.4°±0.2°, 22.1°±0.2°, 16.5°±0.2°, 14.5°±0.2°, 11.8°±0.2°, and 18.9°±0.2°. In some embodiments, the anhydrous crystalline form has an X-ray powder diffraction pattern substantially as shown in FIG. 10, wherein by "substantially" is meant that the reported peaks can vary by about ±0.2°2θ.

Figure 11:
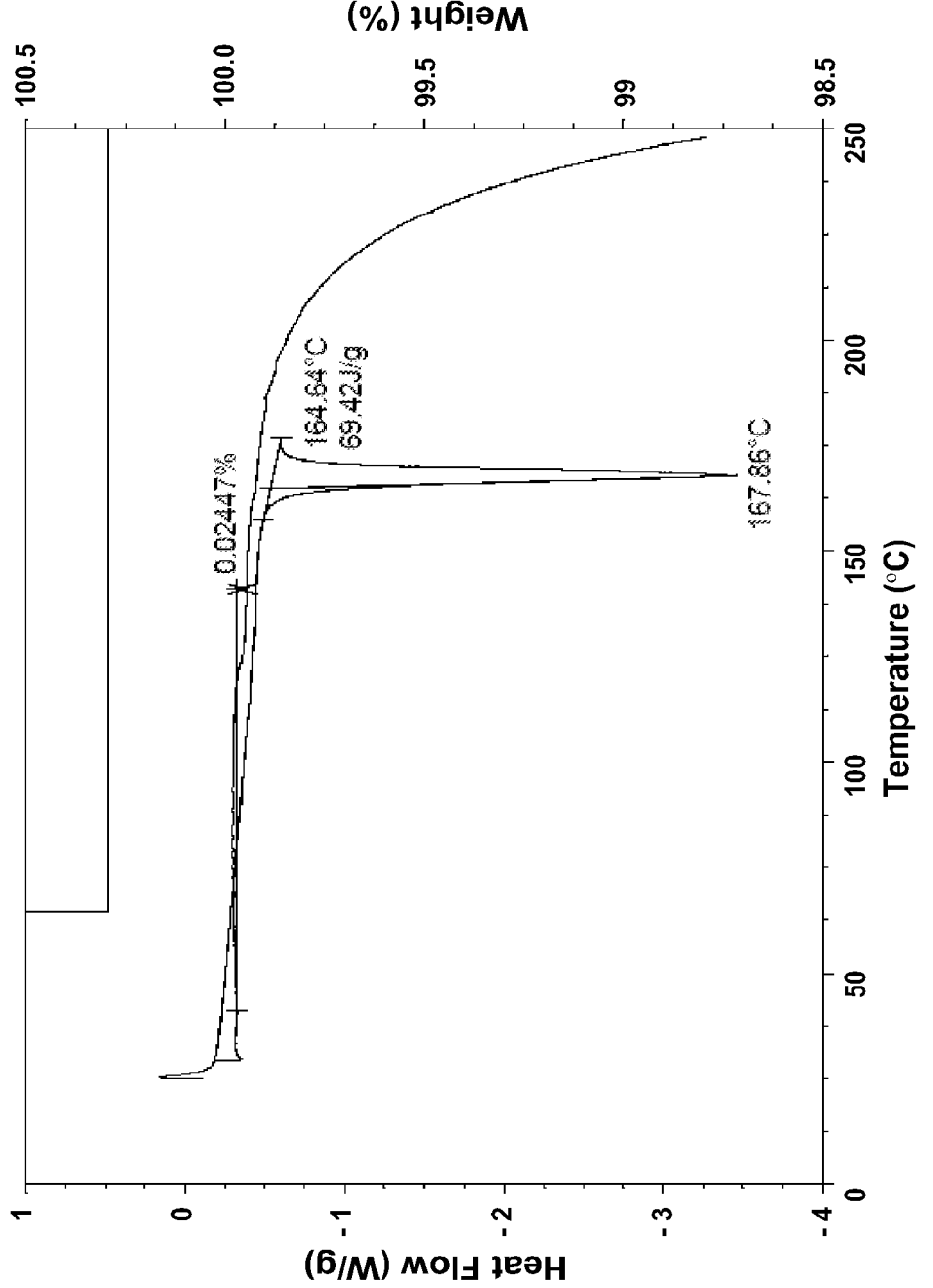
FIG. 11 shows a differential scanning calorimetry (DSC) thermogram for a sample containing an anhydrous crystalline form of Compound 699 and a thermogravimetric analysis (TGA) thermogram of a sample containing an anhydrous crystalline form of Compound 699.

In some embodiments, the anhydrous crystalline form has a differential scanning calorimetry thermogram comprising an endotherm with an extrapolated onset temperature between about 159.6° C. and about 169.6° C. In some embodiments, the anhydrous crystalline form has a differential scanning calorimetry thermogram comprising an endotherm with an extrapolated onset temperature between about 160.6° C. and about 168.6° C. In some embodiments, the anhydrous crystalline form has a differential scanning calorimetry thermogram comprising an endotherm with an extrapolated onset temperature between about 162.6° C. and about 166.6° C. In some embodiments, the anhydrous crystalline form has having a differential scanning calorimetry thermogram comprising an endotherm with an extrapolated onset temperature between about 163.6° C. and about 165.6° C. In some embodiments, the anhydrous crystalline form has a differential scanning calorimetry thermogram comprising an endotherm with an extrapolated onset temperature at about 164.6° C. In some embodiments, the anhydrous crystalline form has a differential scanning calorimetry thermogram substantially as shown in FIG. 11, wherein by "substantially" is meant that the reported DSC features can vary by about ±4° C. and that the reported DSC features can vary by about ±20 joules per gram.

In some embodiments, the anhydrous crystalline form has a thermogravimetric analysis profile showing about 0.5% weight loss below about 135° C. In some embodiments, the anhydrous crystalline form has a thermogravimetric analysis profile showing about 0.25% weight loss below about 135° C. In some embodiments, the anhydrous crystalline form has a thermogravimetric analysis profile showing about 0.05% weight loss below about 135° C. In some embodiments, the anhydrous crystalline form has a thermogravimetric analysis profile substantially as shown in FIG. 11, wherein by "substantially" is meant that the reported TGA features can vary by about ±5° C., and that that the reported TGA features can vary by about ±2% weight change.

Also provided is an anhydrous crystalline form having:
1) an X-ray powder diffraction pattern comprising peaks, in terms of 2θ, at 8.5°±0.2°, and 10.7°±0.2°;
2) a differential scanning calorimetry thermogram comprising an endotherm with an extrapolated onset temperature between about 159.6° C. and about 169.6° C.; and
3) a thermogravimetric analysis profile showing about 0.5% weight loss below about 135° C.

Also provided is an anhydrous crystalline form having:
1) an X-ray powder diffraction pattern comprising peaks, in terms of 2θ, at 8.5°±0.2°, 10.7°±0.2°, and 16.9°±0.2°;
2) a differential scanning calorimetry thermogram comprising an endotherm with an extrapolated onset temperature between about 160.6° C. and about 168.6° C.; and
3) a thermogravimetric analysis profile showing about 0.25% weight loss below about 135° C.

Also provided is an anhydrous crystalline form having:
1) an X-ray powder diffraction pattern comprising peaks, in terms of 2θ, at 8.5°±0.2°, 10.7°±0.2°, 16.9°±0.2°, 25.4°±0.2°, and 11.1°±0.2°;
2) a differential scanning calorimetry thermogram comprising an endotherm with an extrapolated onset temperature between about 162.6° C. and about 166.6° C.; and
3) a thermogravimetric analysis profile showing about 0.05% weight loss below about 135° C.

Also provided is an anhydrous crystalline form having:
1) an X-ray powder diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, and 17.4°±0.2°;
2) a differential scanning calorimetry thermogram comprising an endotherm with an extrapolated onset temperature between about 163.6° C. and about 165.6° C.; and
3) a thermogravimetric analysis profile showing about 0.05% weight loss below about 135° C.

Also provided is an anhydrous crystalline form having:
1) an X-ray powder diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, 17.4°±0.2°, 22.1°±0.2°, and 16.5°±0.2°;
2) a differential scanning calorimetry thermogram comprising an endotherm with an extrapolated onset temperature at about 164.6° C.; and 3) a thermogravimetric analysis profile showing about 0.05% weight loss below about 135° C.

Also provided is an anhydrous crystalline form having:
1) an X-ray powder diffraction pattern comprising peaks, in terms of 2θ, at 8.5°±0.2°, 10.7°±0.2°, 16.9°±0.2°, 25.4°±0.2°, 11.1°±0.2°, 9.8°±0.2°, 17.4°±0.2°, 22.1°±0.2°, 16.5°±0.2°, 14.5°±0.2°, 11.8°±0.2°, and 18.9°±0.2°;
2) a differential scanning calorimetry thermogram comprising an endotherm with an extrapolated onset temperature at about 164.6° C.; and
3) a thermogravimetric analysis profile showing about 0.05% weight loss below about 135° C.

Also provided is an anhydrous crystalline form having:
1) an X-ray powder diffraction pattern substantially as shown in FIG. 10;
2) a differential scanning calorimetry thermogram substantially as shown in FIG. 11; and
3) a thermogravimetric analysis profile substantially as shown in FIG. 11.

In some embodiments, the compound of Formula Ia, or a pharmaceutically acceptable salt, solvate, hydrate, and/or N-oxide thereof is (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide or a pharmaceutically acceptable salt, solvate, and/or hydrate thereof and the one or more known pharmaceutical agent is morphine.

Additionally, chemical genera and individual compounds, for example those compounds found in the above list including diastereoisomers and enantiomers thereof, encompass all pharmaceutically acceptable salts, solvates, and particularly hydrates, and N-oxides thereof:

The compounds of the Formula Ia may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]).

It is understood that the present invention embraces each diastereoisomer, each enantiomer and mixtures thereof of each compound and generic formulae disclosed herein just as if they were each individually disclosed with the specific stereochemical designation for each chiral carbon. Separation of the individual isomers (such as, by chiral HPLC, recrystallization of diastereoisomeric mixtures and the like) or selective synthesis (such as, by enantiomeric selective syntheses and the like) of the individual isomers is accomplished by application of various methods which are well known to practitioners in the art.

The combinations disclosed herein are useful in the treatment of cancer, and in the amelioration of symptoms thereof.

A number of human leukemia and lymphoma cell lines, including Jurkat, Molt-4 and Sup-T1, express $CB_2$ and not $CB_1$, and agonists of $CB_2$ induce apoptosis in these and primary acute lymphoblastic leukemia (ALL) cells (Nagarkatti, L. C. et al. US2004/0259936). See, also McKallip et al. *Blood* (2002) 100(2):627-634.

Similarly, $CB_2$ is expressed on glioblastoma cell lines and treatment with agonists of $CB_2$ induces apoptosis of these cells in vitro (Widmer, M. (2008) *J. Neurosci. Res.* 86(14): 3212-20).

Local administration of a selective $CB_2$ agonist induced a considerable regression of malignant tumors generated by inoculation of C6 glioma cells (Sánchez et al. *Cancer Res* 2001; 61:5784-5789.)

$CB_1$ and $CB_2$ are also expressed in normal skin and skin tumors of mice and humans. Local administration of a mixed $CB_1/CB_2$ agonist or a selective $CB_2$ agonist induced a considerable growth inhibition of malignant tumors generated by inoculation of epidermal tumor cells into nude mice (Casanova, et al. *J. Clin. Invest.* 111:43-50 (2003)).

Cannabinoid receptors are expressed in human pancreatic tumor cell lines and tumor biopsies at much higher levels than in normal pancreatic tissue Cannabinoids also reduced the growth of tumor cells in two animal models of pancreatic cancer. See, Carracedo et al. Cancer Res 2006; 66(13): 6748-55.

$CB_2$-mediated signaling is involved in the in vivo and in vitro growth inhibition of prostate cancer cells, which suggests that $CB_2$ agonists have potential therapeutic interest in the management of prostate cancer. (Inhibition of human tumour prostate PC-3 cell growth by cannabinoids R(+)-Methanandamide and JWH-015: Involvement of $CB_2$; Olea-Herrero, et al. *British Journal of Cancer* advance online publication 18 Aug. 2009; doi: 10.1038/sj.bjc. 6605248).

The most highly expressed gene in anaplastic thyroid carcinoma cell line was $CB_2$ which was expressed eightfold higher in anaplastic thyroid carcinoma cell line (ARO)/IL-12 cells than ARO cells (Shi et al. Cancer Gene Therapy (2008) 15, 101-107.)

Expression of $CB_1$ (24%) and $CB_2$ (55%) receptors have been found in non-small cell lung cancer (NSCLC) patients. Furthermore, treatment of NSCLC cell lines (A549 and SW-1573) with $CB_1/CB_2$ and $CB_2$-specific agonists significantly attenuated random as well as growth factor-directed in vitro chemotaxis and chemoinvasion in these cells. $CB_1$ and $CB_2$ agonists also significantly inhibited in vivo tumor growth and lung metastasis (~50%). See, Preet et al. Published OnlineFirst on Nov. 19, 2010 as 10.1158/1940-6207.

In addition, 91% of ErbB2-positive tumors express CB2 (Caffarel et al. *Molecular Cancer* 2010, 9:196).

Cannabinoids also have been found to exert antiproliferative properties in a variety of malignant tumors, including pancreatic ductal adenocarcinoma (Michalski et al. *Int J Cancer.* 2008 Feb. 15; 122(4): 742-750.)

Accordingly, $CB_2$-selective agonists are useful to attenuate the growth of a malignancy of the immune system, for example, leukemias, lymphomas, and solid tumors of the glial lineage. See, e.g., Pisanti et al. *Best Practice & Research Clinical Endocrinology & Metabolism* (2009) 23:117-131

In addition, as discussed above, $CB_1$-selective agonists and $CB_1/CB_2$ agonists are useful in providing relief from pain associated with cancer (GW Pharmaceuticals press release Jan. 19, 2005, Jun. 19, 2007).

The severity of the pain can be assessed with self-reported measures as is known in the art. Generally, pain is assessed at rest, with appropriate activity (e.g., ambulation, cough), at baseline (prior to administration of the compound of Formula Ia or a pharmaceutically acceptable salt, solvate, hydrate, and/or N-oxide thereof and at regular intervals thereafter. Some of the most commonly used pain assessment instruments include the visual analog scale (VAS), numeric rating scale (NRS), and categorical Likert scale. The VAS is a written assessment that typically utilizes a unmarked 100-mm line with the left end marked as "no pain" and the right end marked as "worst pain imaginable." Subjects put a mark on the line corresponding to their level of pain. The NRS can be applied in either written or verbal form and typically utilizes a rating from 0 (corresponding to "no pain") to 10 (corresponding to "worst pain imaginable"). Likert scales are typically four- or five-item instruments (e.g., ratings of "none", "mild", "moderate", "severe") that attempt to quantify pain.

It is understood that when the phrase "pharmaceutically acceptable salts, solvates and hydrates" is used when referring to a particular formula herein, it is intended to embrace solvates and/or hydrates of compounds of the particular formula, pharmaceutically acceptable salts of compounds of the particular formula as well as solvates and/or hydrates of pharmaceutically acceptable salts of compounds of the particular formula.

The compounds described herein can be administered in a wide variety of oral and parenteral dosage forms. It will be apparent to those skilled in the art that the following dosage forms may comprise, as the active component, either a compound described herein or a pharmaceutically acceptable salt or as a solvate or hydrate thereof. Moreover, various hydrates and solvates of the compounds described herein and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Brittan, Vol. 95, Marcel Dekker, Inc., New York, 1999, incorporated herein by reference in its entirety. Also provided are hydrates and solvates of compounds of Formula Ia and/or their pharmaceutical acceptable salts, as described herein, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, DE), Avantium Technologies (Amsterdam) and Aptuit (Greenwich, CT).

Polymorphism is the ability of a substance to exist as two or more crystalline phases that have different arrangements and/or conformations of the molecules in the crystal lattice. Polymorphs show the same properties in the liquid or gaseous state but they behave differently in the solid state.

Besides single-component polymorphs, drugs can also exist as salts and other multicomponent crystalline phases. For example, solvates and hydrates may contain an APT host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily.

By way of example, Stahly recently published a polymorph screens of 245 compounds consisting of a "wide variety of structural types" revealed that about 90% of them exhibited multiple solid forms. Overall, approximately half the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, *Crystal Growth & Design* (2007), 7(6), 1007-1026.)

As will be recognized, the steps of the methods described herein need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1: Syntheses

Illustrated syntheses for compounds described herein are shown in FIGS. 2 through 7 where the symbols have the same definitions as used throughout this disclosure.

The compounds and their syntheses are further illustrated by the following examples. The following examples are provided to further define the invention without, however, limiting the invention to the particulars of these examples. The compounds described herein, supra and infra, are named according to AutoNom version 2.2, AutoNom 2000, CS ChemDraw Ultra Version 7.0.1, or CS ChemDraw Ultra Version 9.0.7. In certain instances common names are used and it is understood that these common names would be recognized by those skilled in the art.

Chemistry: Proton nuclear magnetic resonance ($^1$H NMR) spectra were recorded on a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublets, ddd=doublet of doublet of doublets, dt=doublet of triplets, t=triplet, td=triplet of doublets, tt=triplet of triplets, q=quartet, m=multiplet, bs=broad singlet, bt=broad triplet. Microwave irradiations were carried out using a Smith Synthesizer™ or an Emrys Optimizer™ (Biotage). Thin-layer chromatography (TLC) was performed on silica gel 60 $F_{254}$ (Merck), preparatory thin-layer chromatography (prep TLC) was preformed on PK6F silica gel 60 Å 1 mm plates (Whatman) and column chromatography was carried out on a silica gel column using Kieselgel 60, 0.063-0.200 mm (Merck). Evaporation was done under reduced pressure on a Büchi rotary evaporator.

LCMS spec: HPLC-pumps: LC-LOAD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1.1: Preparation of (1aR,5aR)-2-(2,4-Difluoro-phenyl)-1a,2,5,5a-tetrahydro-1H-2,3-diaza-cyclopropa[a]pentalene-4-carboxylic Acid (Intermediate 1)

Step A: Preparation of (1aR,5aR)-2-(2,4-Difluoro-phenyl)-1a,2,5,5a-tetrahydro-1H-2,3-diaza-cyclo-propa[a]pentalene-4-carboxylic Acid Ethyl Ester. Method A To a solution of (1R,5S)-bicyclo[3.1.0]hexan-2-one (9.19 g, 96 mmol) and diethyl oxalate (12.98 mL, 96 mmol) in absolute ethanol (300 mL) was added a 1.0 M THF solution of potassium tert-butoxide (105 mL, 105 mmol). The resulting yellow solution was stirred at 20° C. for 2 h. (2,4-difluorophenyl)hydrazine hydrochloride (17.26 g, 96 mmol) was added followed by a 3.0 M aqueous solution of hydrogen chloride (96 mL, 287 mmol). The reaction was stirred at 40° C. for 18 h. The volume was reduced by about 200 mL, and then brine (300 mL) was added. The mixture was extracted with dichloromethane (3×250 mL). The combined organic extracts were dried (MgSO$_4$), filtered, and then concentrated. The residue was purified by silica gel flash chromatography to give the title compound as a yellow solid (18.4 g). LCMS m/z=305.3 [M+H]$^+$; $^1$H NMR (400 MHz, CDCl$_3$) δ ppm 0.49 (td, J=4.8, 3.3 Hz, 1H), 1.16 (td, J=7.8, 5.0 Hz, 1H), 1.38 (t, J=7.1 Hz, 3H), 2.11-2.16 (m, 1H), 2.24-2.30 (m, 1H), 2.90 (d, J=16.6 Hz, 1H), 3.03 (dd, J=16.4, 6.3 Hz, 1H), 4.38 (q, J=7.1 Hz, 2H), 6.97-7.02 (m, 2H), 7.66-7.72 (m, 1H).

Step B: Preparation of (1aR,5aR)-2-(2,4-Difluoro-phenyl)-1a,2,5,5a-tetrahydro-1H-2,3-diaza-cyclopropa[a]pentalene-4-carboxylic Acid. Method B To a solution of (1aR,5aR)-2-(2,4-difluoro-phenyl)-1a,2,5,5a-tetrahydro-1H-2,3-diaza-cyclopropa[a]pentalene-4-carboxylic acid ethyl ester (17.4 g, 57.2 mmol) in methanol (100 mL) and THF (100 mL) was added a 2.0 M aqueous solution of sodium hydroxide (86 mL, 172 mmol). The resulting orange solution was stirred at 23° C. for 3 h. The organic solvents were removed under reduced pressure. The remaining aqueous solution was diluted to 150 mL with water and then acidified to pH 2 by addition of 6 M HCl while stirring vigorously. The precipitate was collected by filtration, rinsed with water, and then dried under reduced pressure to give the title compound as a tan solid (15.62 g). LCMS m/z=277.3 [M+H]$^+$; $^1$H NMR (400 MHz, DMSO-d$_6$) δ ppm 0.41 (td, J=4.6, 3.4 Hz, 1H), 1.15 (td, J=7.8, 4.7 Hz, 1H), 2.16-2.21 (m, 1H), 2.23-2.29 (m, 1H), 2.76 (d, J=16.2 Hz, 1H), 2.90 (dd, J=16.4, 6.2 Hz, 1H), 7.27-7.32 (m, 1H), 7.56-7.62 (m, 1H), 7.75 (td, J=9.0, 5.9 Hz, 1H), 12.93 (bs, 1H).

Example 1.2: Preparation of (1aR,5aR)-2-(Pyrazin-2-yl)-1a,2,5,5a-tetrahydro-1H-2,3-diaza-cyclopropa[a]pentalene-4-carboxylic Acid (Intermediate 2)

Step A: Preparation of Potassium 2-Ethoxy-2-oxo-1-((1R,5R)-2-oxobicyclo[3.1.0]hexan-3-ylidene)ethanolate To a solution of (1R,5S)-bicyclo[3.1.0]hexan-2-one (10 g, 91 mmol) and diethyl oxalate (12.29 mL, 91 mmol) in absolute ethanol (250 mL) was added a 1.0 M THF solution of potassium tert-butoxide (91 mL, 91 mmol). The resulting yellow solution was stirred at 20° C. for 3 h. The mixture was diluted with diethyl ether (250 mL). The precipitate was collected by filtration, rinsed with diethyl ether, and then dried under reduced pressure to give the title compound as a yellow solid (16.7 g). LCMS m/z=197.2 [M+H]$^+$; $^1$H NMR (400 MHz, DMSO-d$_6$) δ ppm 0.14 (td, J=4.5, 3.4 Hz, 1H), 0.78 (td, J=8.0, 3.3 Hz, 1H), 1.15 (t, J=7.2 Hz, 3H), 1.26-1.31 (m, 1H), 1.41-1.47 (m, 1H), 2.27 (dd, J=14.2, 1.4 Hz, 1H), 2.39 (dd, J=14.2, 6.2 Hz, 1H), 3.91-4.01 (m, 2H).

Step B: Preparation of (1aR,5aR)-2-(Pyrazin-2-yl)-1a,2,5,5a-tetrahydro-1H-2,3-diaza-cyclopropa[a]pentalene-4-carboxylic Acid Ethyl Ester. Method C To a stirred suspension of 2-ethoxy-2-oxo-1-((1R,5R)-2-oxobicyclo[3.1.0]hexan-3-ylidene)ethanolate (300 mg, 1.28 mmol) in ethanol (5 mL) was added 2-hydrazinylpyrazine (141 mg, 1.28 mmol) followed by 6 N HCl (0.5 mL, 3.0 mmol). The reaction was stirred overnight at room temperature. The reaction was diluted with H$_2$O and extracted with DCM. The combined organic phases were washed with H$_2$O, dried over MgSO$_4$, and concentrated. Purification by silica gel flash chromatography gave the title compound (150 mg). LCMS m/z=271.2 [M+H]$^+$; $^1$H NMR (400 MHz, CDCl$_3$) δ ppm 0.47 (td, J=4.7 and 3.4 Hz, 1H), 1.22-1.28 (m, 1H), 1.39 (t, J=7.1 Hz, 3H), 2.26-2.30 (m, 1H), 2.77-2.82 (m, 1H), 2.87 (d, J=16.6 Hz, 1H), 2.98 (dd, J=16.6 and 6.3 Hz, 1H), 4.40 (q, J=7.1 Hz, 2H), 8.40 (dd, J=2.6 and 1.5 Hz, 1H), 8.51 (d, J=2.5 Hz, 1H), 9.39 (d, J=1.3 Hz, 1H).

Step C: Preparation of (1aR,5aR)-2-(Pyrazin-2-yl)-1a,2,5,5a-tetrahydro-1H-2,3-diaza-cyclopropa[a]pentalene-4-carboxylic Acid Method D To a solution of (1aR,5aR)-2-(pyrazin-2-yl)-1a,2,5,5a-tetrahydro-1H-2,3-diaza-cyclopropa[a]pentalene-4-carboxylic acid ethyl ester (150 mg, 0.56 mmol) in dioxane (2 mL) was added 1 N LiOH (1.1 mL, 1.11 mmol). The reaction was stirred for 1 h at 80° C., and cooled to room temperature. The reaction was acidified to pH 2 with 4 N HCl and diluted with H$_2$O to form precipitate. The resulting precipitate was collected by filtration, rinsed with water, and then dried to give the title compound as a white solid (100 mg). LCMS m/z=243.3 [M+H]$^+$; $^1$H NMR (400 MHz, DMSO-d$_6$) δ ppm 0.43 (td, J=4.5 and 3.4 Hz, 1H), 1.26 (td, J=7.7 and 4.4 Hz, 1H), 2.26-2.33 (m, 1H), 2.70-2.79 (m, 2H), 2.89 (dd, J=16.6 and 6.3 Hz, 1H), 8.60 (dd, J=2.6 and 1.5 Hz, 1H), 8.67 (d, J=2.6 Hz, 1H), 9.17 (d, J=1.4 Hz, 1H), 13.01 (s, 1H).

Example 1.3: Preparation of (1aR,5aR)-2-(2,4-Difluoro-phenyl)-1a,2,5,5a-tetrahydro-1H-2,3-diaza-cyclopropa[a]pentalene-4-carboxylic Acid (2-Hydroxy-1,1-dimethyl-ethyl)-amide (Compound 493)

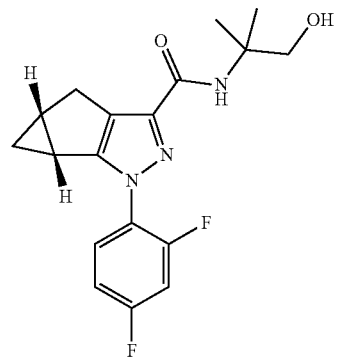 [SMILES: CC(C)(CO)NC(=O)c1nn(-c2ccc(F)cc2F)c2c1C[C@H]1C[C@@H]21]

To a stirred solution of Intermediate 1 (see Example 1.1, 2 g, 7.24 mmol), benzotriazole-1-yl-oxytripyrrolidinophosphonium hexafluorophosphate (PyBOP, 4.52 g, 8.69 mmol) and DIEA (2.52 mL, 14.48 mmol) in DMF (20 mL) was added 2-amino-2-methylpropan-1-ol (0.833 mL, 8.69 mmol). The reaction was stirred at room temperature overnight, then poured into water, and extracted with ethyl acetate. The combined organics were dried and concentrated. The residue was purified by silica gel column chromatography to give the title compound as a white solid (2.08 g). LCMS=348.4 [M+H]$^+$; $^1$H NMR (400 MHz, CDCl$_3$) δ ppm 0.48 (td, J=4.7, 3.3 Hz, 1H), 1.16 (td, J=7.8, 4.9 Hz, 1H), 1.371 (s, 3H), 1.376 (s, 3H), 2.08-2.13 (m, 1H), 2.25-2.31 (m, 1H), 2.94 (d, J=16.8 Hz, 1H), 3.04 (dd, J=16.4, 6.2 Hz, 1H), 3.68 (d, J=3.5 Hz, 2H), 4.81-4.84 (m, 1H), 6.88 (bs, 1H), 6.99-7.05 (m, 2H), 7.59-7.65 (m, 1H).

Example 1.4: Preparation of (1aR,5aR)-2-(5-Cyano-pyrazin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 264)

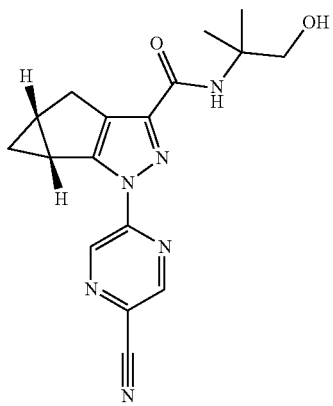 [SMILES: CC(C)(CO)NC(=O)c1nn(-c2cnc(C#N)cn2)c2c1C[C@H]1C[C@@H]21]

A heterogeneous mixture of (1aR,5aR)-2-(5-bromo-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide (40 mg, 0.10 mmol) and cyanocopper (13.7 mg, 0.15 mmol) in NMP (1.0 mL) in a heavy walled tube was heated at 200° C. under microwave irradiation for 2 h. The reaction was filtered and purified by preparative HPLC to give the title compound. LCMS m/z=339.6 [M+H]$^+$; $^1$H NMR (400 MHz, CDCl$_3$) δ ppm 0.46 (td, J=4.7 and 3.4 Hz, 1H), 1.29 (td, J=8.0 and 4.7 Hz, 1H), 1.42 (s, 3H), 1.43 (s, 3H), 2.30-2.37 (m, 1H), 2.71-2.77 (m, 1H), 2.92 (d, J=17.0 Hz, 1H), 3.01 (dd, J=16.8 and 6.2 Hz, 1H), 3.71 (s, 2H), 4.29 (s, 1H), 6.90 (s, 1H), 8.72 (d, J=1.4 Hz, 1H), 9.33 (d, J=1.4 Hz, 1H).

Example 1.5: Preparation of (1aR,5aR)-2-(5-Fluoro-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 309)

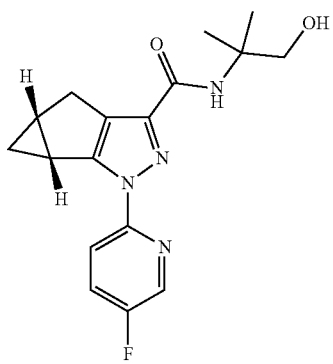 [SMILES: CC(C)(CO)NC(=O)c1nn(-c2ccc(F)cn2)c2c1C[C@H]1C[C@@H]21]

Step A: Preparation of (1aR,5aR)-2-(5-Fluoropyridin-2-yl)-1a,2,5,5a-tetrahydro-1H-2,3-diaza-cyclopropa[a]pentalene-4-carboxylic Acid Ethyl Ester To a solution of hydrazine monohydrate (3.13 mL, 64.6 mmol) in 1-butanol (8 mL) in a thick-walled glass tube was added 2-chloro-5-fluoropyridine (1.00 g, 7.60 mmol). The vessel was flushed with nitrogen then sealed. The solution was heated under microwave irradiation at 200° C. for 8 h. The reaction was concentrated under reduced pressure leaving an orange solid. The solid was taken up in ethyl acetate (30 mL), and the insoluble material was removed by filtration. The filtrate was concentrated to give an orange solid (0.8 g) as a 39:61 mixture of 5-fluoro-2-hydrazinylpyridine and 2-chloro-5-hydrazinylpyridine.

The title compound was prepared in a manner similar to that described in Method C using potassium 2-ethoxy-2-oxo-1-((1R,5R)-2-oxobicyclo[3.1.0]hexan-3-ylidene)ethanolate and mixture of 5-fluoro-2-hydrazinylpyridine and 2-chloro-5-hydrazinylpyridine. LCMS m/z=288.2 [M+H]$^+$.

Step B: Preparation of (1aR,5aR)-2-(5-Fluoropyridin-2-yl)-1a,2,5,5a-tetrahydro-1H-2,3-diaza-cyclopropa[a]pentalene-4-carboxylic Acid The title compound was prepared in a manner similar to that described in Method B using (1aR,5aR)-2-(5-fluoropyridin-2-yl)-1a,2,5,5a-tetrahydro-1H-2,3-diaza-cyclopropa[a]pentalene-4-carboxylic acid ethyl ester. LCMS m/z=260.2 [M+H]$^+$.

Step C: Preparation of (1aR,5aR)-2-(5-Fluoro-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide The title compound was prepared in a manner similar to that described in Method G using (1aR,5aR)-2-(5-fluoropyridin-2-yl)-1a,2,5,5a-tetrahydro-1H-2,3-diaza-cyclopropa[a]pentalene-4-carboxylic acid and 2-amino-2-methylpropan-1-ol. LCMS m/z=331.2 [M+H]$^+$; $^1$H NMR (400 MHz, CDCl$_3$) δ ppm 0.45 (td, J=4.7, 3.3 Hz, 1H), 1.24 (td, J=7.9, 4.8 Hz, 1H), 1.404 (s, 3H), 1.408 (s, 3H), 2.24-2.30 (m, 1H), 2.74-2.79 (m, 1H), 2.91 (d, J=16.7 Hz, 1H), 3.00 (dd, J=16.6, 6.2 Hz, 1H), 3.70 (d, J=6.2 Hz, 2H), 4.72 (t, J=6.3 Hz, 1H), 6.92 (s, 1H), 7.55 (ddd, J=9.1, 7.6, 3.0 Hz, 1H), 7.91 (dd, J=9.1, 3.9 Hz, 1H), 8.31 (d, J=2.8 Hz, 1H).

Example 1.6: Preparation of Phosphoric Acid mono-(2-{[(1aR,5aR)-2-(4-Cyano-pyridin-2-yl)-1a,2,5,5a-tetrahydro-1H-2,3-diaza-cyclopropa[a]pentalene-4-carbonyl]-amino}-2-methyl-propyl) Ester (Compound 646)

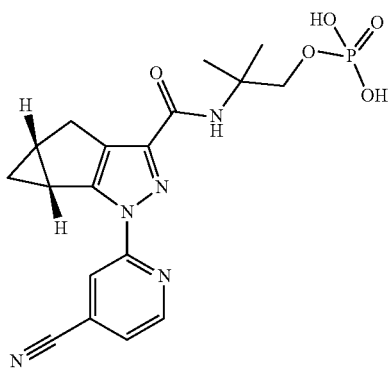 [SMILES: CC(C)(COP(=O)(O)O)NC(=O)c1nn(-c2cc(C#N)ccn2)c2c1C[C@H]1C[C@@H]21]

A solution of (1aR,5aR)-2-(4-cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide (500 mg, 1.482 mmol) in pyridine (10 mL) was cooled in a dry-ice/acetone bath until the mixture solidified. The cooling bath was removed and phosphoryl trichloride (0.691 mL, 7.41 mmol) was added as soon as the mixture melted (ca −42° C.). The cooling bath was replaced periodically, maintaining the temperature at −42° C. while stirring for 45 minutes. Still at −42° C., 50 mL 0.5 M aqueous HCl was added. The volume was reduced to 20 mL by distillation under reduced pressure (50° C. water bath). The remaining solution was purified by preparative HPLC to give a white solid (338 mg). The solid was suspended in water (10 mL) and acetonitrile (2 mL). Sodium carbonate (81.5 mg, 0.769 mmol) was added to form a solution. The resulting solution was lyophilized to give the sodium salt of the title compound as a white solid (385 mg). LCMS m/z=418.3 [M+H]$^+$; $^1$H NMR (400 MHz, D$_2$O) δ ppm 0.53-0.56 (m, 1H), 1.33-1.38 (m, 1H), 1.53 (s, 6H), 2.41-2.47 (m, 1H), 2.69-2.73 (m, 1H), 2.89 (d, J=16.4 Hz, 1H), 3.00 (dd, J=16.4, 6.2 Hz, 1H), 3.91 (d, J=4.2 Hz, 2H), 7.26 (d, J=4.2 Hz, 1H), 8.26-7.33 (s, 1H), 8.72 (d, J=4.6 Hz, 1H). $^{31}$P NMR (162 MHz, D$_2$O, no decoupling) δ ppm 3.36 (t, J=4.5 Hz, 1H).

Example 1.7: Preparation of (1aS,5aS)-2-Pyrazin-2-yl-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 696)

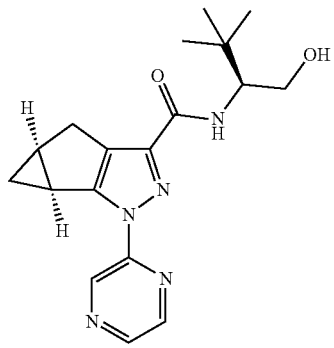 [SMILES: CC(C)(C)[C@@H](CO)NC(=O)c1nn(-c2cnccn2)c2c1C[C@@H]1C[C@H]21]

Step A: Preparation of (1aS,5aS)-2-(pyrazin-2-yl)-1a,2,5,5a-tetrahydro-1H-2,3-diaza-cyclopropa[a]pentalene-4-carboxylic Acid The title compound was prepared in a manner similar to that described in Example 1.2. LCMS m/z=243.1 [M+H]$^+$; $^1$H NMR (400 MHz, DMSO-d$_6$) δ ppm 0.43 (td, J=4.6, 3.2 Hz, 1H), 1.26 (td, J=8.0, 4.6 Hz, 1H), 2.27-2.33 (m, 1H), 2.71-2.75 (m, 1H), 2.75 (d, J=16.7 Hz, 1H), 2.89 (dd, J=16.4, 6.4 Hz, 1H), 8.61 (dd, J=2.5, 1.4 Hz, 1H), 8.67 (d, J=2.7 Hz, 1H), 9.17 (d, J=1.4 Hz, 1H), 12.99 (s, 1H).

Step B: Preparation of (1aS,5aS)-2-Pyrazin-2-yl-1a,2,5,5a-tetrahydro-1H-2,3-diaza-cyclopropa[a]pentalene-4-carboxylic Acid ((S)-1-Hydroxymethyl-2,2-dimethyl-propyl)-amide The title compound was prepared in a manner similar to that described in Method G, using (1aS,5aS)-2-(pyrazin-2-yl)-1a,2,5,5a-tetrahydro-1H-2,3-diaza-cyclopropa[a]pentalene-4-carboxylic acid and (S)-2-amino-3,3-dimethylbutan-1-ol. LCMS m/z=342.2 [M+H]$^+$; $^1$H NMR (400 MHz, CDCl$_3$) δ ppm 0.48 (td, J=4.6, 3.4 Hz, 1H), 1.05 (s, 9H), 1.24 (td, J=8.0, 4.7 Hz, 1H), 2.26-2.32 (m, 1H), 2.74-2.78 (m, 1H), 2.94 (d, J=16.8 Hz, 1H), 3.01 (dd, J=16.7, 6.1 Hz, 1H), 3.67-3.72 (m, 1H), 3.93-3.98 (m, 2H), 7.08 (d, J=8.5 Hz, 1H), 8.42 (dd, J=1.4, 0.9 Hz, 1H), 8.51 (d, J=2.7 Hz, 1H), 9.26 (d, J=1.1 Hz, 1H).

Example 1.8: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 699). Method PPP

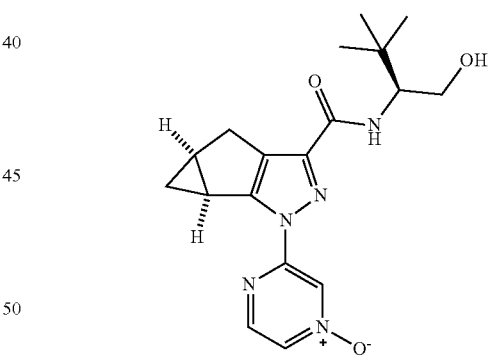

To a solution of (1aS,5aS)-2-pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide (900 mg, 2.64 mmol) in chloroform (10 mL) was added 3-chlorobenzoperoxoic acid (1772 mg, 7.91 mmol). The reaction was stirred at 23° C. for 3 h. Additional MCPBA (1.2 g) was added and stirring was continued at room temperature for 18 h. The mixture was purified by silica gel column chromatography to give the title compound (550 mg) as a white solid. LCMS m/z=358.3 [M+H]$^+$; $^1$H NMR (400 MHz, CDCl$_3$) δ ppm 0.49 (td, J=4.6, 3.3 Hz, 1H), 1.03 (s, 9H), 1.27 (td, J=8.0, 4.9 Hz, 1H), 2.08 (bs, 1H), 2.27-2.33 (m, 1H), 2.71-2.76 (m, 1H), 2.93 (d, J=16.8 Hz, 1H), 3.00 (dd, J=16.7, 6.1 Hz, 1H), 3.65-3.71 (m, 1H), 3.92-3.97 (m, 2H), 6.97 (d, J=8.5 Hz, 1H), 7.99 (dd, J=4.0, 1.4 Hz, 1H), 8.28 (d, J=4.2 Hz, 1H), 8.78 (dd, J=1.4, 0.8 Hz, 1H).

A sample was recrystallized from CH$_2$Cl$_2$/hexane to give a crystalline solvate. A thermogravimetric analysis (TGA) thermogram for this solvate showed a loss of ~5% weight occurring with a melting endotherm at 164° C.

A non-solvated form of Compound 699 was slurried in CH$_2$Cl$_2$ and stirred at −28° C. overnight. The suspension was filtered using a centrifuge filter and air dried prior to powder X-ray diffraction pattern (PXRD) analysis. The PXRD pattern showed the material following CH$_2$Cl$_2$ slurry to be indistinguishable from the original solvate form resulting from recrystallized from CH$_2$Cl$_2$/hexane. The differential scanning calorimetry (DSC) thermogram and thermogravimetric analysis (TGA) thermogram for the crystalline CH$_2$Cl$_2$ solvate obtained from recrystallization using CH$_2$Cl$_2$/hexane is shown in FIG. 11; and the PXRD pattern for each of the crystalline CH$_2$Cl$_2$ solvates obtained from two the different methods (i.e., recrystallization using CH$_2$Cl$_2$/hexane; and non-solvated Compound 699 slurried in CH$_2$Cl$_2$) is shown as an overlay in FIG. 12.

Example 1.9: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1-Pyridin-2-yl-cyclobutyl)-amide (Compound 700)

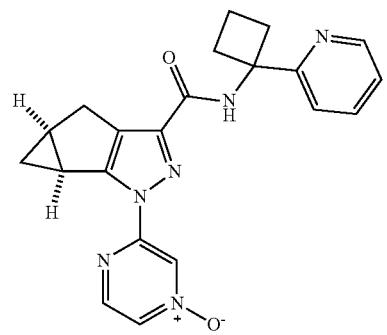 [SMILES: O=C(NC1(c2ccccn2)CCC1)c1nn(-c2c[n+]([O-])ccn2)c2c1C[C@@H]1C[C@H]21]

The title compound was prepared in a manner similar to that described in Method G, using (1aS,5aS)-2-(4-oxy-pyrazin-2-yl)-1a,2,5,5a-tetrahydro-1H-2,3-diaza-cyclopropa[a]pentalene-4-carboxylic acid and 1-(pyridin-2-yl)cyclobutanamine. LCMS m/z=389.4 [M+H]$^+$; $^1$H NMR (400 MHz, CDCl$_3$) δ ppm 0.46 (td, J=4.7, 3.4 Hz, 1H), 1.25 (td, J=7.8, 4.8 Hz, 1H), 1.97-2.08 (m, 1H), 2.19-2.31 (m, 2H), 2.70-2.78 (m, 3H), 2.84-2.92 (m, 3H), 2.98 (dd, J=16.7, 6.2 Hz, 1H), 7.19 (t, J=5.7 Hz, 1H), 7.62 (d, J=8.0 Hz, 1H), 7.72 (t, J=7.2 Hz, 1H), 7.98 (dd, J=4.2, 1.5 Hz, 1H), 8.00-8.04 (m, 1H), 8.28 (d, J=4.2 Hz, 1H), 8.61-8.63 (m, 1H), 8.85 (s, 1H).

Example 1.10: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid (1-Hydroxymethyl-cyclobutyl)-amide (Compound 698)

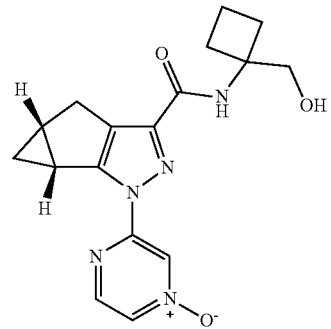 [SMILES: O=C(NC1(CO)CCC1)c1nn(-c2c[n+]([O-])ccn2)c2c1C[C@H]1C[C@@H]21]

The title compound was prepared in a manner similar to that described in Example 1.57. LCMS m/z=342.3 [M+H]$^+$; $^1$H NMR (400 MHz, CDCl$_3$) δ ppm 0.46 (dd, J=8.0 and 4.7 Hz, 1H), 1.28 (td, J=7.9 and 5.0 Hz, 1H), 1.87-2.07 (m, 2H), 2.22-2.37 (m, 5H), 2.71-2.76 (m, 1H), 2.90 (d, J=17.0 Hz, 1H), 2.99 (dd, J=16.7 and 6.2 Hz, 1H), 3.89 (s, 2H), 7.15 (s, NH, 1H), 8.00 (dd, J=4.1 and 1.5 Hz, 1H), 8.28 (d, J=4.1 Hz, 1H), 8.80 (s, 1H).

Example 1.11: Preparation of Phosphoric Acid mono-((S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) Ester (Compound 703)

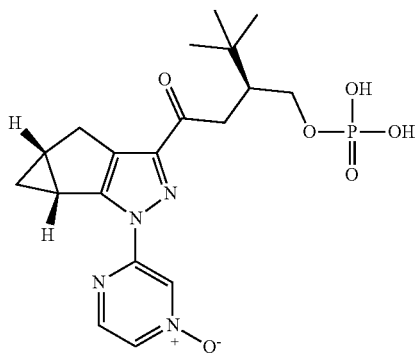

To a solution of phosphoric acid mono-{(S)-3,3-dimethyl-2-[((1aR,5aR)-2-pyrazin-2-yl-1a,2,5,5a-tetrahydro-1H-2,3-diaza-cyclopropa[a]pentalene-4-carbonyl)-amino]-butyl}ester (500 mg, 1.074 mmol) in formic acid (5 mL) was added hydrogen peroxide (35% in water, 0.31 mL, 3.22 mmol). The reaction was stirred at 45° C. for 6 h and concentrated. The residue was purified by preparative HPLC to give the title compound (284 mg) as a white solid. LCMS m/z=438.4 [M+H]$^+$; $^1$H NMR (400 MHz, CDCl$_3$) δ ppm 0.54 (dd, J=8.0 and 4.7 Hz, 1H), 1.05 (s, 9H), 1.25 (td, J=7.9 and 5.0 Hz, 1H), 2.27-2.33 (m, 1H), 2.70-2.74 (m, 1H), 2.90 (d, J=17.2 Hz, 1H), 2.99 (dd, J=16.7 and 6.2 Hz, 1H), 4.11-4.16 (m, 1H), 4.22-4.34 (m, 2H), 7.55 (d, J=10.2 Hz, NH, 1H), 8.02 (dd, J=4.1 and 1.5 Hz, 1H), 8.38 (d, J=4.1 Hz, 1H), 9.32 (s, 1H).

Example 1.12: Preparation of (1aR,5aR)-2-Pyrazin-2-yl-1a,2,5,5a-tetrahydro-1H-2,3-diaza-cyclopropa[a]pentalene-4-carboxylic Acid (2-Hydroxy-1-tetrahydro-pyran-4-yl-ethyl)-amide (Mixture of Compound 684 and Compound 685)

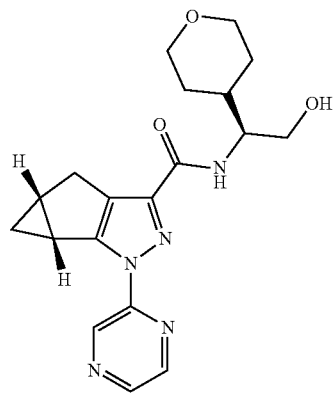

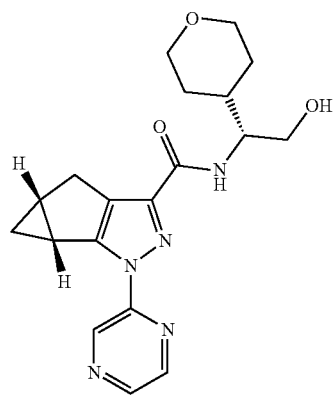

The title compound was prepared in a manner similar to that described in Method G using Intermediate 2 and 2-amino-2-(tetrahydro-2H-pyran-4-yl)ethanol. LCMS m/z=370.2 [M+H]$^+$; $^1$H NMR (400 MHz, CDCl$_3$) δ ppm 0.46-0.50 (m, 1H), 1.26 (td, J=7.8 and 4.6 Hz, 1H), 1.42-1.54 (m, 2H), 1.72 (d, J=12.6 Hz, 2H), 1.98-2.09 (m, 1H), 2.27-2.34 (m, 1H), 2.51 (bs, 1H), 2.73-2.79 (m, 1H), 2.94 (d, J=16.8 Hz, 1H), 3.01 (dd, J=16.4 and 6.1 Hz, 1H), 3.36-3.45 (m, 2H), 3.82-3.89 (m, 3H), 4.01 (dd, J=11.2 and 4.0 Hz, 2H), 7.11 (d, J=7.6 Hz, 1H), 8.42 (dd, J=2.5 and 1.5 Hz, 1H), 8.51 (d, J=2.4 Hz, 1H), 9.26 (d, J=1.4 Hz, 1H).

Resolution via Chiral HPLC.

- Column: normal phase preparative Chiralcel OD®, 5 cm ID×50 cm L, 20 μm particle size
- Eluent: 90% hexane/10% IPA
- Gradient: isocratic
- Flow: 60 mL/min
- Detector: 280 nm
- Retention Times: 1$^{st}$ diastereomer—31 min; 2$^{nd}$ diastereomer—35 min.

Example 1.13: Preparation of (1aR,5aR)-2-(4-Chloro-pyridin-2-yl)-1a,2,5,5a-tetrahydro-1H-2,3-diaza-cyclopropa[a]pentalene-4-carboxylic Acid (Cyano-dimethyl-methyl)-amide (Compound 625). Method JJJ

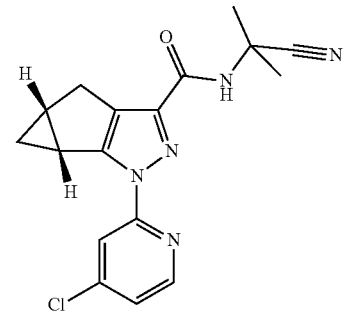 [SMILES: CC(C)(C#N)NC(=O)c1nn(-c2cc(Cl)ccn2)c2c1C[C@H]1C[C@@H]21]

A mixture of (1aR,5aR)-2-(4-bromo-pyridin-2-yl)-1a,2,5,5a-tetrahydro-1H-2,3-diaza-cyclopropa[a]pentalene-4-carboxylic acid (cyano-dimethyl-methyl)-amide (0.800 g, 2.071 mmol), lithium chloride (0.878 g, 20.71 mmol) and tetrabutylammonium bromide (0.334 g, 1.036 mmol) in DMA (10 mL) was heated in a heavy-walled sealed tube under microwave irradiation at 180° C. for 11 h. The mixture was purified by preparative HPLC to give the title compound (160 mg) as a white solid. LCMS m/z=342.1 [M+H]$^+$; $^1$H NMR (400 MHz, CDCl$_3$) δ ppm 0.45 (td, J=4.6, 3.4 Hz, 1H), 1.26 (td, J=8.0, 4.9 Hz, 1H), 1.839 (s, 3H), 1.844 (s, 3H), 2.25-2.31 (m, 1H), 2.78-2.82 (m, 1H), 2.94 (d, J=16.8 Hz, 1H), 3.02 (dd, J=16.7, 6.1 Hz, 1H), 6.91 (s, 1H), 7.23 (dd, J=5.4, 1.9 Hz, 1H), 7.92 (d, J=1.8 Hz, 1H) 8.37 (d, J=5.3 Hz, 1H).

Example 1.14: Preparation of (1aR,5aR)-2-Pyrazin-2-yl-1a,2,5,5a-tetrahydro-1H-2,3-diaza-cyclopropa[a]pentalene-4-carboxylic Acid [2,2-Dimethyl-1-((S)-methylcarbamoyl)-propyl]-amide (Compound 667)

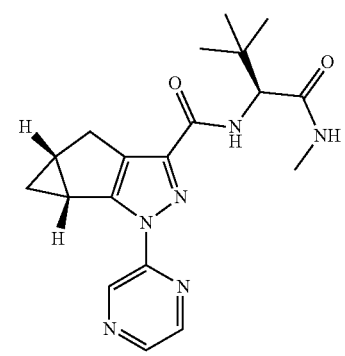 [SMILES: CNC(=O)[C@@H](NC(=O)c1nn(-c2cnccn2)c2c1C[C@H]1C[C@@H]21)C(C)(C)C]

The title compound was prepared in a manner similar to that described in Method G using Intermediate 2 and (S)-2-amino-N,3,3-trimethylbutanamide. LCMS m/z=369.3 [M+H]$^+$; $^1$H NMR (400 MHz, DMSO-d$_6$) δ ppm 0.41 (td, J=4.4 and 3.5 Hz, 1H), 0.96 (s, 9H), 1.23-1.28 (m, 1H), 2.25-2.34 (m, 1H), 2.60 (d, J=4.5 Hz, 3H), 2.68-2.74 (m, 1H), 2.75 (d, J=16.3 Hz, 1H), 2.90 (dd, J=16.2 and 6.4 Hz, 1H), 4.33 (d, J=9.7 Hz, 1H), 7.52 (d, J=9.7 Hz, 1H), 8.10-8.15 (m, 1H), 8.60 (dd, J=2.5 and 1.5 Hz, 1H), 8.66 (d, J=2.6 Hz, 1H), 9.27 (d, J=1.4 Hz, 1H).

Example 1.15: Preparation of (1aR,5aR)-2-Pyrazin-2-yl-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 642)

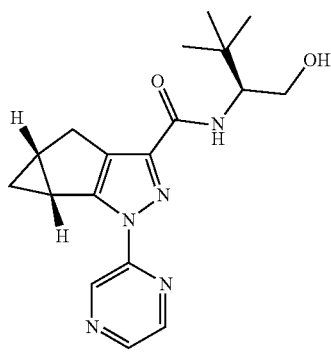 [SMILES: CC(C)(C)[C@@H](CO)NC(=O)c1nn(-c2cnccn2)c2c1C[C@H]1C[C@@H]21]

The title compound was prepared as described in Method G using Intermediate 2 and (S)-2-amino-3,3-dimethylbutan-1-ol. LCMS m/z=342.3 [M+H]$^+$; $^1$H NMR (400 MHz, DMSO-d$_6$) δ ppm 0.41 (td, J=4.4 and 3.3 Hz, 1H), 0.93 (s, 9H), 1.23-1.28 (m, 1H), 2.25-2.34 (m, 1H), 2.69-2.74 (m, 1H), 2.75 (d, J=16.0 Hz, 1H), 2.90 (dd, J=16.2 and 6.4 Hz, 1H), 3.50-3.58 (m, 1H), 3.62-3.67 (m, 1H), 3.76-3.82 (m, 1H), 4.52 (t, J=5.0 Hz, 1H), 7.54 (d, J=9.8 Hz, 1H), 8.58 (dd, J=2.5 and 1.5 Hz, 1H), 8.64 (d, J=2.6 Hz, 1H), 9.39 (d, J=1.4 Hz, 1H).

Example 1.16: Preparation of Phosphoric Acid mono-{(S)-3,3-Dimethyl-2-[((1aR,5aR)-2-pyrazin-2-yl-1a,2,5,5a-tetrahydro-1H-2,3-diaza-cyclopropa[a]pentalene-4-carbonyl)-amino]-butyl}Ester (Compound 683)

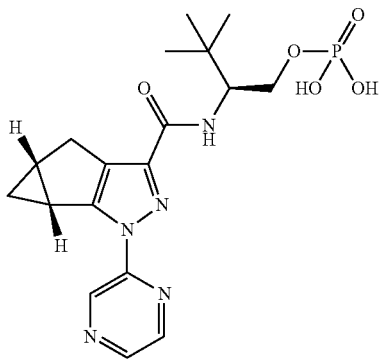 [SMILES: CC(C)(C)[C@@H](COP(=O)(O)O)NC(=O)c1nn(-c2cnccn2)c2c1C[C@H]1C[C@@H]21]

A mixture of (1aR,5aR)-2-pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide (600 mg, 1.757 mmol) in pyridine (5 mL) was cooled in a dry-ice/acetone bath until it solidified (pyridine mp=−42° C.). The cooling bath was removed and POCl$_3$ (0.819 ml, 8.79 mmol) was added as soon as the mixture was melted. The mixture was stirred at −42° C. for 2 h and an HCl solution (3.0 M, 15 mL) was added. The mixture was filtered and the filtrate was purified by prep-HPLC to give a white solid (260 mg). A solution of the solid (240 mg, 0.570 mmol) in H$_2$O/AcCN (4 mL/3 mL) was mixed with a solution of Na$_2$CO$_3$ (57.3 mg, 0.541 mmol) in H$_2$O (3 mL). The mixture was dried to give the sodium salt of the title compound (258 mg) as a white solid. LCMS m/z=422.3 [M+H]$^+$; $^1$H NMR (400 MHz, D$_2$O) δ ppm 0.42-0.47 (m, 1H), 0.99 (s, 9H), 1.21-1.27 (m, 1H), 2.29-2.36 (m, 1H), 2.57-2.62 (m, 1H), 2.80 (d, J=16.4 Hz, 1H), 2.92 (dd, J=16.4 and 6.4 Hz, 1H), 3.77-3.83 (m, 1H), 3.98-4.08 (m, 2H), 8.48-8.51 (m, 2H), 9.06 (s, 1H).

Example 1.17: Preparation of (1aS,5aS)-2-(Pyrazin-2-yl)-1a,2,5,5a-tetrahydro-1H-2,3-diaza-cyclopropa[a]pentalene-4-carboxylic Acid (Intermediate 4)

Step A: Preparation of (1S,5R)-Bicyclo[3.1.0]hexan-2-one

To a stirred solution of (S)-2-(but-3-enyl)oxirane (100 g, 1019 mmol) and 2,2,6,6-tetramethylpiperidine (86 mL, 509 mmol) in MTBE (1000 mL) cooled in a dry ice/acetone bath, was added dropwise a 2.5 M hexane solution of BuLi (489 mL, 1223 mmol) at a rate to maintain the internal temperature at −12 to −5° C. (time of addition=1 h). After addition was complete, the reaction was stirred one hour at −5 to 0° C. and quenched with 3 M aqueous HCl (545 mL) dropwise (internal temperature rose to 3° C.). The layers were separated and the organic layer was washed with 3 M HCl (200 mL). The combined aqueous layers were extracted with MTBE (2×500 mL). The combined organic layers were washed with brine (3×300 mL) and concentrated to give a pale yellow solution (ca. 1000 mL). To this solution in a 5 L 3-neck round bottom flask equipped with an overhead stirrer was added an aqueous solution of dibasic potassium phosphate (216 g, 1240 mmol), monobasic potassium phosphate (12.8 g, 94 mmol), and potassium bromide (18.19 g, 153 mmol) in water (407 mL). The mixture was cooled to −20° C. in a dry-ice/isopropanol bath. TEMPO (4.30 g, 27.5 mmol) was added. The temperature was allowed to warm to 0° C. and aqueous sodium hypochlorite (1.54 M, 1059 mL, 1630 mmol) was added dropwise over 70 min while maintaining the internal temperature between −10 and 0° C. Stirring was continued at 0° C. for another hour. Sodium sulfite (50 g) was added to quench excess sodium hypochlorite (temperature rose to 12° C.). The layers were separated and the aqueous layer was extracted twice more with MTBE (500 mL then 250 mL). The combined organic layers (total volume ca. 1600 mL) were dried (MgSO$_4$) then filtered. The solution was concentrated (ca. 300 mL). The residue was distilled (2 torr/36° C., note: receiving flask was cooled in dry ice/acetone bath) to give the title compound (65.8 g) as a light orange oil. $^1$H NMR (400 MHz, CDCl$_3$) δ 0.93 (td, J=4.6, 3.3 Hz, 1H), 1.20 (td, J=8.0, 4.8 Hz, 1H), 1.74-1.79 (m, 1H), 1.98-2.19 (m, 5H).

Step B: Preparation of 2-Hydrazinylpyrazine

Under nitrogen atmosphere, 2-chloropyrazine (96 mL, 1073 mmol) was added dropwise to 35 wt % aqueous hydrazine (544 mL, 6009 mmol) at 65° C. over 1 h. After the addition, stirring was continued at 63-67° C. for 16 h and the reaction mixture was let stand at room temperature for two days. The mixture was filtered to remove a small amount of precipitate, then extracted with 10% iPrOH/dichloromethane (5×250 mL). The combined organic extracts were dried (MgSO$_4$), filtered, then concentrated under reduced pressure. The resulting solid was triturated with isopropyl acetate (600 mL). The solid was collected by filtration, rinsed with isopropyl acetate, then dried in vacuo to give the title compound (60 g) as a pale yellow solid. LCMS m/z=111.2 [M+H]$^+$; $^1$H NMR (400 MHz, DMSO-d$_6$) δ 4.21 (s, 2H), 7.70 (d, J=2.8 Hz, 1H), 7.89 (s, 1H), 7.93 (dd, J=2.8, 1.5 Hz, 1H), 8.10 (d, J=1.5 Hz, 1H).

Step C: Preparation of (1aS,5aS)-2-(Pyrazin-2-yl)-1a,2,5,5a-tetrahydro-1H-2,3-diaza-cyclopropa[a]pentalene-4-carboxylic Acid Ethyl Ester. Method KKK To a solution of (1S,5R)-bicyclo[3.1.0]hexan-2-one (52.9 g, 539 mmol) and diethyl oxalate (0.073 L, 539 mmol) in absolute ethanol (0.9 L) (not denatured with methanol) was added a THF solution of potassium tert-butoxide (1.0 M, 0.539 L, 539 mmol) over 15 min (maintaining the temperature below 43° C.). The resulting yellow solution was stirred at 40° C. for 3.5 h. 2-Hydrazinylpyrazine (59.4 g, 539 mmol) was added followed by a 6.0 M aqueous solution of hydrogen chloride (0.270 L, 1618 mmol). The reaction was stirred at 50° C. for 1.5 h. The mixture was poured into ice-water (5 L). A precipitate appeared immediately. After sitting for 30 minutes in an ice bath, the solid was collected by filtration, rinsed with water (5×1 L), and dried to give the title compound (106 g) as an off-white solid $^1$H NMR. LCMS m/z=271.2 [M+H]$^+$; $^1$H NMR (400 MHz, CDCl$_3$) δ 0.47 (td, J=4.7, 3.3 Hz, 1H), 1.27 (td, J=8.0, 4.9 Hz, 1H), 1.41 (t, J=7.1 Hz, 3H), 2.26-2.32 (m, 1H), 2.77-2.82 (m, 1H), 2.88 (dd, J=16.7, 1.4 Hz, 1H), 2.99 (dd, J=16.6, 6.4 Hz, 1H), 4.40 (q, J=7.1 Hz, 2H), 8.41 (dd, J=2.5, 1.5 Hz, 1H), 8.52 (d, J=2.5 Hz, 1H), 9.40 (d, J=1.5 Hz, 1H).

Step D: Preparation of (1aS,5aS)-2-(Pyrazin-2-yl)-1a,2,5,5a-tetrahydro-1H-2,3-diaza-cyclopropa[a]pentalene-4-carboxylic Acid (Intermediate 4). Method LLL To a suspension of (1aS,5aS)-2-(pyrazin-2-yl)-1a,2,5,5a-tetrahydro-1H-2,3-diaza-cyclopropa[a]pentalene-4-carboxylic acid ethyl ester (106 g, 392 mmol) in MeOH (300 mL) and THF (300 mL) was added a 2.0 M aqueous solution of NaOH (235 mL, 471 mmol). The reaction was stirred at 23° C. for 20 h. The organic solvents were removed on rotovap. The remaining aqueous solution was diluted to ~1.5 L with H$_2$O then acidified to pH ~2 with 6 M HCl (ca. 95 mL). The resulting fine precipitate was collected by filtration, rinsed with water, and dried to give the title compound (95 g) as a white solid. LCMS m/z=243.1 [M+H]$^+$; $^1$H NMR (400 MHz, DMSO-d$_6$) δ 0.43 (td, J=4.6, 3.2 Hz, 1H), 1.26 (td, J=8.0, 4.4 Hz, 1H), 2.27-2.33 (m, 1H), 2.71-2.75 (m, 1H), 2.76 (d, J=16.8 Hz, 1H), 2.89 (dd, J=16.4, 6.4 Hz, 1H), 8.61 (dd, J=2.7, 1.5 Hz, 1H), 8.67 (d, J=2.5 Hz, 1H), 9.17 (d, J=1.5 Hz, 1H), 13.02 (s, 1H).

Example 1.18: Preparation of (1aS,5aS)-2-(Pyrazin-2-yl)-1a,2,5,5a-tetrahydro-1H-2,3-diaza-cyclopropa[a]pentalene-4-carboxylic Acid N-Oxide (Intermediate 5)

To a suspension of (1aS,5aS)-2-(pyrazin-2-yl)-1a,2,5,5a-tetrahydro-1H-2,3-diaza-cyclopropa[a]pentalene-4-carboxylic acid (68.8 g, 284 mmol) in formic acid (688 mL) at room temperature was added a 50 wt % aqueous solution of hydrogen peroxide (82 mL, 1420 mmol). The mixture was heated to 64° C. The reaction was stirred at 58 to 64° C. for 3 h. Another 8 mL 50% H$_2$O$_2$ was added and stirring continued another hour at 60° C. The mixture was cooled to room temperature and diluted with water (1 L). After cooling in an ice-bath for 1 h, the precipitate was collected by filtration, rinsed with water, and dried in vacuo to give a pale yellow solid (56.7 g) which contains about 2% starting material. The material was re-subjected to reaction conditions aforementioned to give the title compound (45 g). LCMS m/z=259.2 [M+H]$^+$; $^1$H NMR (400 MHz, DMSO-d$_6$) δ 0.42 (td, J=4.4, 3.3 Hz, 1H), 1.27 (td, J=7.8, 4.7 Hz, 1H), 2.27-2.33 (m, 1H), 2.68-2.73 (m, 1H), 2.75 (dd, J=16.9, 1.5 Hz, 1H), 2.88 (dd, J=16.4, 6.4 Hz, 1H), 8.33 (dd, J=4.2, 1.5 Hz, 1H), 8.50 (dd, J=4.2, 0.6 Hz, 1H), 8.54 (dd, J=1.5, 0.6 Hz, 1H), 13.08 (s, 1H).

Example 1.19: Preparation of (1aR,5aR)-2-(Pyrazin-2-yl)-1a,2,5,5a-tetrahydro-1H-2,3-diaza-cyclopropa[a]pentalene-4-carboxylic Acid The title compound was prepared in a manner similar to that described in Example 1.17 using (R)-2-(but-3-enyl)oxirane. LCMS m/z=243.3 [M+H]$^+$; $^1$H NMR (400 MHz, DMSO-d$_6$) 0.43 (td, J=4.5 and 3.4 Hz, 1H), 1.26 (td, J=7.7 and 4.4 Hz, 1H), 2.26-2.33 (m, 1H), 2.70-2.79 (m, 2H), 2.89 (dd, J=16.6 and 6.3 Hz, 1H), 8.60 (dd, J=2.6 and 1.5 Hz, 1H), 8.67 (d, J=2.6 Hz, 1H), 9.17 (d, J=1.4 Hz, 1H), 13.01 (s, 1H).

Example 1.20: Preparation of (1aR,5aR)-2-(Pyrazin-2-yl)-1a,2,5,5a-tetrahydro-1H-2,3-diaza-cyclopropa[a]pentalene-4-carboxylic Acid N-Oxide (Intermediate 6)

The title compound was prepared in a manner similar to that described in Example 1.18 using Intermediate 2. LCMS m/z=259.3 [M+H]$^+$; $^1$H NMR (400 MHz, DMSO-d$_6$) 0.43 (td, J=4.6 and 3.3 Hz, 1H), 1.28 (td, J=7.9 and 4.8 Hz, 1H), 2.27-2.33 (m, 1H), 2.68-2.73 (m, 1H), 2.75 (d, J=16.7 Hz, 1H), 2.88 (dd, J=16.5 and 6.4 Hz, 1H), 8.33 (dd, J=4.2 and 1.5 Hz, 1H), 8.50 (d, J=4.2 Hz, 1H), 8.55 (d, J=1.0 Hz, 1H), 13.10 (bs, 1H).

Example 1.21: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid (1-Methyl-cyclobutyl)-amide (Compound 821). Method UU

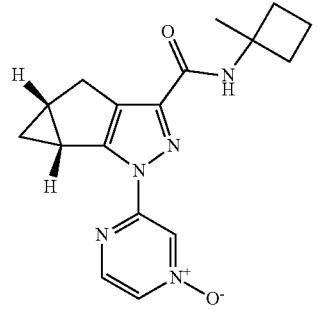 [SMILES: CC1(NC(=O)c2nn(-c3c[n+]([O-])ccn3)c3c2C[C@H]2C[C@@H]32)CCC1]

A solution of Intermediate 6 (200 mg, 0.77 mmol), HATU (300 mg, 0.78 mmol), and Et$_3$N (0.15 mL, 1.17 mmol) in acetonitrile (5 mL) was stirred for 10 min at room temperature. 1-Methylcyclobutanamine (70 mg, 0.82 mmol) was added into the solution, and the mixture was stirred for 2 h at room temperature. The reaction was diluted with DCM, washed with H$_2$O and 1 N HCl, dried with anhydrous MgSO$_4$, and concentrated. The residue was purified by column chromatography to give the title compound (120 mg). LCMS m/z=326.3 [M+H]$^+$; $^1$H NMR (400 MHz, CDCl$_3$) δ 0.44-0.48 (m, 1H), 1.26 (td, J=7.8, 4.8 Hz, 1H), 1.56 (s, 3H), 1.83-1.97 (m, 2H), 2.06-2.14 (m, 2H), 2.26-2.33 (m, 1H), 2.41-2.50 (m, 2H), 2.69-2.74 (m, 1H), 2.92 (d, J=16.6 Hz, 1H), 3.00 (dd, J=16.6, 6.0 Hz, 1H), 6.87 (s, 1H), 7.97 (dd, J=4.0, 1.4 Hz, 1H), 8.28 (d, J=4.2 Hz, 1H), 8.78 (s, 1H).

Example 1.22: Preparation of (1aS,5aS)-2-(4-Chloro-pyridin-2-yl)-1a,2,5,5a-tetrahydro-1H-2,3-diaza-cyclopropa[a]pentalene-4-carboxylic Acid (2-Fluoro-1,1-dimethyl-ethyl)-amide (Compound 897). Method MMM

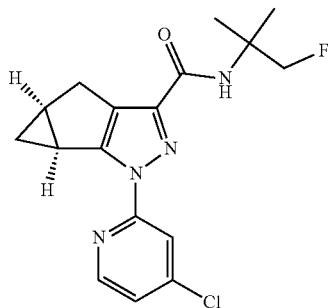 [SMILES: CC(C)(CF)NC(=O)c1nn(-c2cc(Cl)ccn2)c2c1C[C@@H]1C[C@H]21]

Step A: Preparation of (1aS,5aS)-2-(4-Chloro-pyridin-2-yl)-1a,2,5,5a-tetrahydro-1H-2,3-diaza-cyclopropa[a]pentalene-4-carboxylic Acid Ethyl Ester The title compound was prepared in a manner similar to that described in Example 1.18, Step C, using (1S,5R)-bicyclo[3.1.0]hexan-2-one and 4-chloro-2-hydrazinylpyridine. LCMS m/z=348.0 [M+H]$^+$.

Step B: Preparation of (1aS,5aS)-2-(4-Chloro-pyridin-2-yl)-1a,2,5,5a-tetrahydro-1H-2,3-diaza-cyclopropa[a]pentalene-4-carboxylic Acid To a solution of (1aS,5aS)-2-(4-bromo-pyridin-2-yl)-1a,2,5,5a-tetrahydro-1H-2,3-diaza-cyclopropa[a]pentalene-4-carboxylic acid ethyl ester (2.1 g, 6.0 mmol) in acetonitrile (30 mL) was added concentrated HCl (1.4 mL, 18.0 mmol). The reaction was stirred for 6 h at 80° C. The reaction was cooled down and diluted with H$_2$O. The solid precipitate was filtered, washed with H$_2$O, and dried to give a solid (1.7 g). The solid aforementioned was dissolved in dioxane (10 mL). After addition of 1 N LiOH (9.0 mL), the reaction was stirred at 40° C. for 4 h. The reaction was cooled down to room temperature, diluted with H$_2$O, and acidified with 4 N HCl to form a precipitate. The solid was filtered, washed with H$_2$O, and dried to give the title compound. LCMS m/z=276.1 [M+H]$^+$.

Step C: Preparation of (1aS,5aS)-2-(4-Chloro-pyridin-2-yl)-1a,2,5,5a-tetrahydro-1H-2,3-diaza-cyclopropa[a]pentalene-4-carboxylic Acid (2-Fluoro-1,1-dimethyl-ethyl)-amide (Compound 897)

The title compound was prepared in a manner similar to that described in Method UU using (1aS,5a5)-2-(4-chloro-pyridin-2-yl)-1a,2,5,5a-tetrahydro-1H-2,3-diaza-cyclopropa[a]pentalene-4-carboxylic acid and 1-fluoro-2-methylpropan-2-amine hydrochloride. LCMS m/z=349.2 [M+H]$^+$; $^1$H NMR (400 MHz, CDCl$_3$) δ 0.42-0.47 (m, 1H), 1.24 (td, J=7.9, 4.8 Hz, 1H), 1.48 (s, 3H), 1.49 (s, 3H), 2.22-2.29 (m, 1H), 2.76-2.82 (m, 1H), 2.90 (d, J=16.8 Hz, 1H), 2.99 (dd, J=16.6, 6.2 Hz, 1H), 4.56 (d, J=47 Hz, 2H), 6.80 (s, 1H), 7.20 (dd, J=5.4, 1.9 Hz, 1H), 7.93 (d, J=1.8 Hz, 1H), 8.35 (d, J=5.4 Hz, 1H).

Example 1.23: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (2,2,2-Trifluoro-1,1-dimethyl-ethyl)-amide (Compound 919)

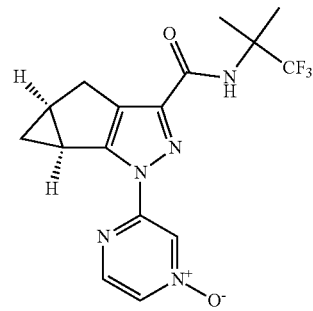 [SMILES: CC(C)(NC(=O)c1nn(-c2c[n+]([O-])ccn2)c2c1C[C@@H]1C[C@H]21)C(F)(F)F]

The title compound was prepared in a manner similar to that described in Method UU using Intermediate 5 and 1,1,1-trifluoro-2-methylpropan-2-amine. LCMS m/z=368.3 [M+H]$^+$; $^1$H NMR (400 MHz, CDCl$_3$) δ 0.44-0.49 (m, 1H), 1.27 (td, J=8.0, 4.8 Hz, 1H), 1.70 (s, 6H), 2.27-2.34 (m, 1H), 2.71-2.76 (m, 1H), 2.91 (d, J=17.0 Hz, 1H), 3.00 (dd, J=16.7, 6.4 Hz, 1H), 6.81 (s, 1H), 7.99 (dd, J=4.2, 1.6 Hz, 1H), 8.28 (dd, J=4.2, 0.6 Hz, 1H), 8.77 (dd, J=1.5, 0.7 Hz, 1H).

Example 1.24: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((1S,2S)-2-Hydroxy-indan-1-yl)-amide (Compound 920)

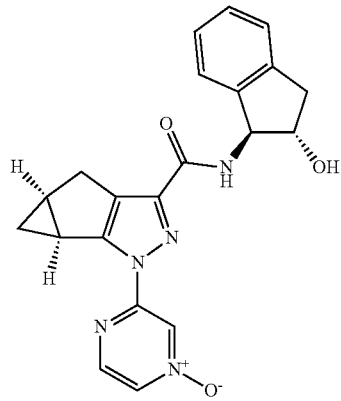 [SMILES: O=C(N[C@H]1c2ccccc2C[C@@H]1O)c1nn(-c2c[n+]([O-])ccn2)c2c1C[C@@H]1C[C@H]21]

The title compound was prepared in a manner similar to that described in Method UU using Intermediate 5 and (1S,2S)-1-amino-2,3-dihydro-1H-inden-2-ol. LCMS m/z=390.4 [M+H]+; 1H NMR (400 MHz, CDCl3) δ 0.48-0.52 (m, 1H), 1.30 (td, J=7.9, 5.0 Hz, 1H), 2.30-2.37 (m, 1H), 2.73-2.79 (m, 1H), 2.96 (d, J=16.9 Hz, 1H), 2.99-3.03 (m, 1H), 3.05 (dd, J=16.7, 6.2 Hz, 1H), 3.37 (dd, J=15.7, 7.7 Hz, 1H), 4.46 (s, 1H), 4.55 (q, J=7.7 Hz, 1H), 5.26 (t, J=5.8 Hz, 1H), 7.26-7.34 (m, 5H), 7.95 (dd, J=4.0, 1.6 Hz, 1H), 8.28 (dd, J=4.2, 0.6 Hz, 1H), 8.75 (dd, J=1.5, 0.7 Hz, 1H).

Example 1.25: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((1S,2R)-2-Hydroxy-indan-1-yl)-amide (Compound 921)

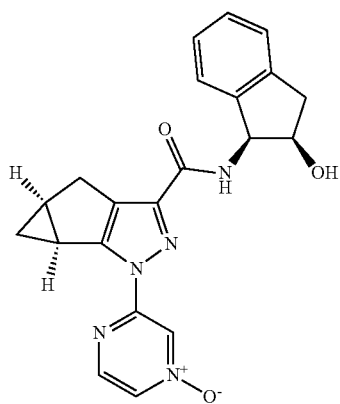 [SMILES: O=C(N[C@H]1c2ccccc2C[C@H]1O)c1nn(-c2c[n+]([O-])ccn2)c2c1C[C@@H]1C[C@H]21]

The title compound was prepared in a manner similar to that described in Method UU using Intermediate 5 and (1S,2R)-1-amino-2,3-dihydro-M-inden-2-ol. LCMS m/z=390.3 [M+H]+; 1H NMR (400 MHz, CDCl3) δ 0.46-0.51 (m, 1H), 1.28 (td, J=8.0, 5.1 Hz, 1H), 2.27-2.33 (m, 1H), 2.67-2.73 (m, 1H), 2.96 (d, J=16.8 Hz, 1H), 3.00-3.07 (m, 2H), 3.24 (dd, J=16.5, 5.4 Hz, 1H), 4.76 (td, J=5.2, 2.2 Hz, 1H), 5.55 (dd, J=8.4, 5.2 Hz, 1H), 7.20-7.34 (m, 4H), 7.56 (d, J=8.4 Hz, 1H), 7.79 (dd, J=4.2, 1.6 Hz, 1H), 8.19 (dd, J=4.0, 0.6 Hz, 1H), 8.84 (dd, J=1.4, 0.6 Hz, 1H).

Example 1.26: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid [2-Hydroxy-1-(tetrahydro-pyran-4-yl)-ethyl]-amide (Compound 841)

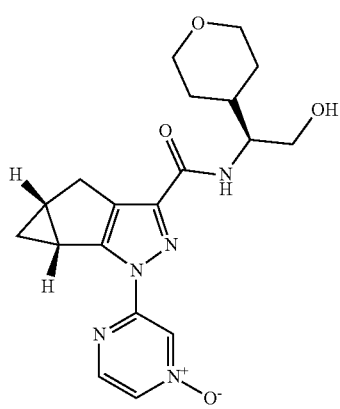 [SMILES: O=C(N[C@H](CO)C1CCOCC1)c1nn(-c2c[n+]([O-])ccn2)c2c1C[C@H]1C[C@@H]21]

The title compound was prepared in a manner similar to that described in Method UU using Intermediate 6 and 2-amino-2-(tetrahydro-2H-pyran-4-yl)ethanol. The crude reaction mixture was purified by preparative HPLC to give a white solid. LCMS m/z=386.2 [M+H]+; 1H NMR (400 MHz, CDCl3) δ 0.47 (td, J=4.6 and 3.2 Hz, 1H), 1.23-1.29 (m, 1H), 1.40-1.54 (m, 2H), 1.65-1.75 (m, 2H), 1.95-2.05 (m, 1H), 2.27-2.33 (m, 1H), 2.30-2.40 (m, 1H), 2.70-2.75 (m, 1H), 2.89-3.04 (m, 2H), 3.36-3.45 (m, 2H), 3.82-3.91 (m, 3H), 4.00 (dd, J=11.3 and 3.8 Hz, 2H), 7.05 (d, J=8.3 Hz, 1H), 7.99 (d, J=4.1 and 0.9 Hz, 1H), 8.28 (d, J=4.1 Hz, 1H), 8.80 (d, J=0.5 Hz, 1H).

Resolution Via Chiral HPLC

Column: Chiralcel OD preparative column, 5 cm ID×50 cm L

Injection: ~60 mg

Fluent: 50% IPA/Hexanes

Gradient: isocratic

Flow: 60 mL/min

Detector: 280 nm

Retention Time: 1st diastereomer—37.0 min, 2nd diastereomer—44.2 min

Example 1.27: Preparation of (1aS,5aS)-2-Pyrazin-2-yl-1a,2,5,5a-tetrahydro-1H-2,3-diaza-cyclopropa[a]pentalene-4-carboxylic Acid (2,2,2-Trifluoro-1,1-dimethyl-ethyl)-amide (Compound 927)

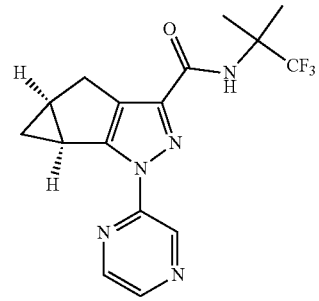 [SMILES: CC(C)(NC(=O)c1nn(-c2cnccn2)c2c1C[C@@H]1C[C@H]21)C(F)(F)F]

The title compound was prepared in a manner similar to that described in Method UU using Intermediate 4 and 1,1,1-trifluoro-2-methylpropan-2-amine. LCMS m/z=352.4 [M+H]+; 1H NMR (400 MHz, CDCl3) δ 0.47 (td, J=4.6 and 3.2 Hz, 1H), 1.23-1.29 (m, 1H), 1.71 (s, 6H), 2.27-2.33 (m, 1H), 2.74-2.80 (m, 1H), 2.93 (d, J=17.1 Hz, 1H), 3.00 (dd, J=16.6 and 6.2 Hz, 1H), 6.94 (s, 1H), 8.42 (dd, J=2.5 and 1.5 Hz, 1H), 8.52 (d, J=2.5 Hz, 1H), 9.25 (d, J=1.4 Hz, 1H).

Example 1.28: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1-Trifluoromethyl-cyclobutyl)-amide (Compound 765)

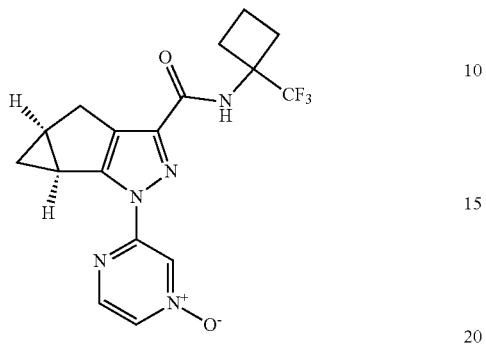

Step A: Preparation of 1-(Trifluoromethyl)cyclobutanamine Hydrochloride 1-(Trifluoromethyl)cyclobutanecarboxylic acid (1 g, 5.95 mmol) and triethylamine (0.912 mL, 6.54 mmol) in anhydrous tert-butanol (20 mL) was stirred at room temperature in the presence of 4 Å molecular sieves powder. To the mixture was added diphenyl phosphorazidate (1.801 g, 6.54 mmol). The reaction mixture was refluxed under $N_2$ for 2 days, filtered, then concentrated in vacuo. The oily residue was stirred in ether, ether layer was isolated. The procedure was repeated three times. The combined organics were washed with 5% citric acid, saturated aqueous $NaHCO_3$ twice, brine, dried over anhydrous $Na_2SO_4$, and concentrated to give tert-butyl 1-(trifluoromethyl)cyclobutylcarbamate (713 mg) as a white solid. The solid was dissolved in 1.25 N HCl in methanol solution (10 mL), stirred at 50° C. overnight, and concentrated to give the title compound (493 mg). $^1$H NMR (400 MHz, DMSO-$d_6$) δ 1.87-1.97 (m, 1H), 2.04-2.15 (m, 1H), 2.44-2.50 (m, 4H), 9.40 (br, 3H).

Step B: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1-Trifluoromethyl-cyclobutyl)-amide (Compound 765)

The title compound was prepared in a manner similar to that described in Method UU using Intermediate 5 and 1-(trifluoromethyl)cyclobutanamine hydrochloride. LCMS m/z=380.4 [M+H]$^+$; $^1$H NMR (400 MHz, CDCl$_3$) δ 0.47 (td, J=4.6, 3.2 Hz, 1H), 1.23-1.29 (m, 1H), 2.04-2.14 (m, 2H), 2.27-2.33 (m, 1H), 2.62-2.69 (m, 4H), 2.71-2.76 (m, 1H), 2.92 (d, J=17.1 Hz, 1H), 3.00 (dd, J=16.8 and 6.2 Hz, 1H), 6.92 (s, 1H), 7.99 (dd, J=4.1 and 1.5 Hz, 1H), 8.29 (dd, J=4.1 and 0.6 Hz, 1H), 8.81 (dd, J=1.5 and 0.6 Hz, 1H).

Example 1.29: Preparation of (1aS,5aS)-2-Pyrazin-2-yl-1a,2,5,5a-tetrahydro-1H-2,3-diaza-cyclopropa[a]pentalene-4-carboxylic Acid (1-Trifluoromethyl-cyclobutyl)-amide (Compound 926)

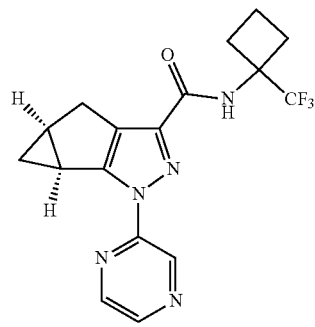 [SMILES: O=C(NC1(C(F)(F)F)CCC1)c1nn(-c2cnccn2)c2c1C[C@@H]1C[C@H]21]

The title compound was prepared in a manner similar to that described in Method UU using Intermediate 4 and 1-(trifluoromethyl)cyclobutanamine hydrochloride. LCMS m/z=364.4 [M+H]$^+$; $^1$H NMR (400 MHz, CDCl$_3$) δ 0.47 (td, J=4.6, 3.2 Hz, 1H), 1.23-1.29 (m, 1H), 2.04-2.14 (m, 2H), 2.27-2.33 (m, 1H), 2.64-2.70 (m, 4H), 2.74-2.80 (m, 1H), 2.93 (d, J=16.9 Hz, 1H), 3.02 (dd, J=16.6 and 6.2 Hz, 1H), 6.99 (s, 1H), 8.42 (dd, J=2.5 and 1.5 Hz, 1H), 8.52 (d, J=2.5 Hz, 1H), 9.26 (d, J=1.4 Hz, 1H).

Example 1.30: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1-Trifluoromethyl-cyclopropyl)-amide (Compound 764)

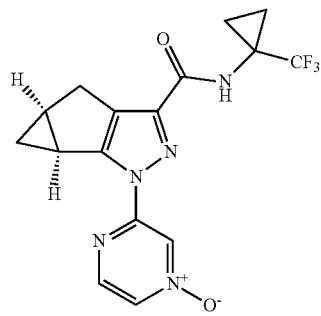 [SMILES: O=C(NC1(C(F)(F)F)CC1)c1nn(-c2c[n+]([O-])ccn2)c2c1C[C@@H]1C[C@H]21]

Step A: Preparation of 1-(Trifluoromethyl)cyclopropanamine Hydrochloride

The title compound was prepared in a manner similar to that described in Example 1.28, Step A, using 1-(trifluoromethyl)cyclopropanecarboxylic acid.

Step B: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1-Trifluoromethyl-cyclopropyl)-amide (Compound 764)

The title compound was prepared in a manner similar to that described in Method UU using Intermediate 5 and 1-(trifluoromethyl)cyclopropanamine hydrochloride. LCMS m/z=366.4 [M+H]⁺; ¹H NMR (400 MHz, CDCl₃) δ 0.47 (td, J=4.6, 3.2 Hz, 1H), 1.23-1.29 (m, 3H), 1.39-1.43 (m, 2H), 2.27-2.33 (m, 1H), 2.70-2.75 (m, 1H), 2.92 (d, J=17.0 Hz, 1H), 3.00 (dd, J=16.8 and 6.2 Hz, 1H), 7.28 (s, 1H), 8.00 (dd, J=4.1 and 1.5 Hz, 1H), 8.29 (dd, J=4.1 and 0.6 Hz, 1H), 8.81 (dd, J=1.5 and 0.6 Hz, 1H).

Example 1.31: Preparation of (1aS,5aS)-2-Pyrazin-2-yl-1a,2,5,5a-tetrahydro-1H-2,3-diaza-cyclopropa[a]pentalene-4-carboxylic Acid (1-Trifluoromethyl-cyclopropyl)-amide (Compound 930)

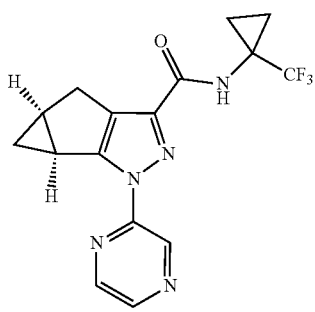 [SMILES: O=C(NC1(C(F)(F)F)CC1)c1nn(-c2cnccn2)c2c1C[C@@H]1C[C@H]21]

The title compound was prepared in a manner similar to that described in Method UU using Intermediate 4 and 1-(trifluoromethyl)cyclopropanamine hydrochloride. LCMS m/z=350.2 [M+H]⁺; ¹H NMR (400 MHz, CDCl₃) δ 0.47 (td, J=4.6, 3.2 Hz, 1H), 1.23-1.29 (m, 3H), 1.39-1.43 (m, 2H), 2.27-2.33 (m, 1H), 2.74-2.80 (m, 1H), 2.94 (d, J=16.8 Hz, 1H), 3.02 (dd, J=16.7 and 6.2 Hz, 1H), 7.31 (s, 1H), 8.42 (dd, J=2.5 and 1.5 Hz, 1H), 8.52 (d, J=2.5 Hz, 1H), 9.26 (d, J=1.4 Hz, 1H).

Example 1.32: Preparation of (1aR,5aR)-Pentanedioic Acid mono-((S)-3-Methyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) Ester (Compound 844) and its Sodium Salt

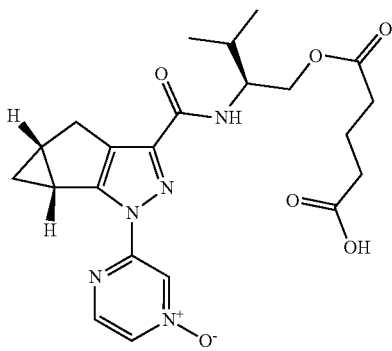 [SMILES: CC(C)[C@@H](COC(=O)CCCC(=O)O)NC(=O)c1nn(-c2c[n+]([O-])ccn2)c2c1C[C@H]1C[C@@H]21]

To a solution of (1aR,5aR)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide (Compound 690) (100 mg, 0.291 mmol), DMAP (17.79 mg, 0.146 mmol) and triethylamine (79 µL, 0.582 mmol) in DCM (5 mL) was added dihydro-2H-pyran-2,6(3H)-dione (100 mg, 0.874 mmol). The reaction mixture was stirred at room temperature overnight, then concentrated. The residue was purified by preparative HPLC. The combined fractions were extracted with DCM. The organic layers were washed with water twice, dried over anhydrous Na₂SO₄, and concentrated to give the title compound as a white solid (95 mg). LCMS m/z=458.4 [M+H]⁺; ¹H NMR (400 MHz, DMSO-d₆) δ 0.42 (td, J=4.6, 3.2 Hz, 1H), 0.91 (d, J=6.8 Hz, 3H), 0.93 (d, J=6.8 Hz, 3H), 1.23-1.27 (m, 1H), 1.65-1.72 (m, 2H), 1.85-1.92 (m, 1H), 2.18 (t, J=7.5 Hz, 2H), 2.30 (t, J=7.4 Hz, 2H), 2.27-2.33 (m, 1H), 2.65-2.70 (m, 1H), 2.75 (d, J=16.8 Hz, 1H), 2.86 (dd, J=16.5 and 6.4 Hz, 1H), 3.92-4.02 (m, 1H), 4.08 (dd, J=11.0 and 8.2 Hz, 1H), 4.25 (dd, J=11.0 and 4.2 Hz, 1H), 8.05 (d, J=9.2 Hz, 1H), 8.29 (dd, J=4.1 and 1.5 Hz, 1H), 8.47 (d, J=4.1 Hz, 1H), 8.81 (d, J=1.3, 1H), 12.0 (br, 1H).

(1aR,5aR)-Pentanedioic acid mono-((S)-3-methyl-2-{[(1aR,5aR)-2-(4-oxy-pyrazin-2-yl)-1a,2,5,5a-tetrahydro-1H-2,3-diazacyclopropa[a]pentalene-4-carbonyl]-amino}-butyl) ester (165 mg, 0.36 mmol) was dissolved in THF (5 mL), heated at 40° C. for 5 min, 0.1 N NaOH solution (3.6 mL, 0.36 mmol) was added slowly, stirred for 30 min while cooled down, then concentrated. The residue was lyophilized to give the sodium salt as white solid (165 mg). LCMS m/z=458.2 [M+H—Na]⁺; ¹H NMR (400 MHz, d₆-DMSO) δ 0.42 (td, J=4.6, 3.2 Hz, 1H), 0.91 (d, J=6.8 Hz, 3H), 0.93 (d, J=6.8 Hz, 3H), 1.23-1.27 (m, 1H), 1.55-1.62 (m, 2H), 1.80 (t, J=7.0 Hz, 2H), 1.85-1.92 (m, 1H), 2.24 (t, J=7.4 Hz, 2H), 2.25-2.33 (m, 1H), 2.65-2.70 (m, 1H), 2.75 (d, J=16.7 Hz, 1H), 2.86 (dd, J=16.5 and 6.5 Hz, 1H), 3.91-3.99 (m, 1H), 4.05 (dd, J=11.0 and 7.6 Hz, 1H), 4.22 (dd, J=11.0 and 4.3 Hz, 1H), 8.15 (d, J=9.1 Hz, 1H), 8.28 (dd, J=4.2 and 1.5 Hz, 1H), 8.47 (d, J=4.1 Hz, 1H), 9.06 (d, J=1.6 Hz, 1H).

Example 1.33: Preparation of (1aR,5aR)-2-(4-Cyano-pyridin-2-yl)-1a,2,5,5a-tetrahydro-1H-2,3-diaza-cyclopropa[a]pentalene-4-carboxylic Acid (2-Hydroxy-1-hydroxymethyl-1-methyl-ethyl)-amide (Compound 820)

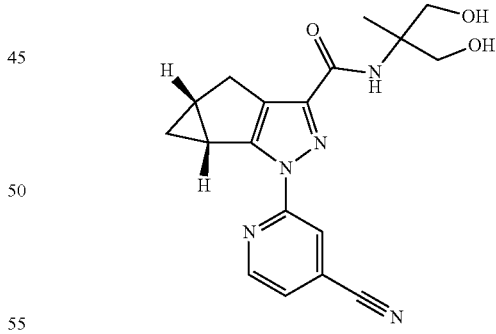

Step A: Preparation of 4-Bromo-2-hydrazinylpyridine

To a solution of 4-bromo-2-fluoropyridine (23.75 g, 135 mmol) in ethanol (120 mL) was added hydrazine monohydrate (65.5 mL, 1350 mmol). The mixture was stirred at 45° C. for 16 h then concentrated. The resulting solid was triturated with water, collected by filtration, rinsed with water, and dried under vacuum, to give the title compound (23.2 g) as a white solid. LCMS m/z=188.0 [M+H]⁺; ¹H NMR (400 MHz, DMSO-d$_6$) δ 4.19 (s, 2H), 6.69 (dd, J=5.3, 1.8 Hz, 1H), 6.92 (d, J=1.7 Hz, 1H), 7.69 (s, 1H), 7.84 (d, J=5.3 Hz, 1H).

Step B: Preparation of (1aR,5aR)-2-(4-Bromo-pyridin-2-yl)-1a,2,5,5a-tetrahydro-1H-2,3-diaza-cyclopropa[a]pentalene-4-carboxylic Acid Ethyl Ester The title compound was prepared as described in Method KKK, using (1R,5S)-bicyclo[3.1.0]hexan-2-one and 4-bromo-2-hydrazinylpyridine. LCMS m/z=348.2

Step C: Preparation of (1aR,5aR)-2-(4-Bromo-pyridin-2-yl)-1a,2,5,5a-tetrahydro-1H-2,3-diaza-cyclopropa[a]pentalene-4-carboxylic Acid To a solution of (1aR,5aR)-2-(4-bromo-pyridin-2-yl)-1a,2,5,5a-tetrahydro-1H-2,3-diaza-cyclopropa[a]pentalene-4-carboxylic acid ethyl ester (9.0 g, 25.8 mmol) in THF (50 mL) and MeOH (50.0 mL) was added a 2.0 M aqueous solution of sodium hydroxide (25.8 mL, 51.7 mmol). The reaction was stirred at 23° C. for 2 h then concentrated to remove the organic solvents. The remaining residue was diluted to 150 mL with water. This solution was filtered to remove trace insoluble impurities then acidified to pH ~3 with 6 M HCl. The resulting precipitate was collected by filtration, rinsed with water, then dried under vacuum to give the title compound (8.3 g) as a white solid. LCMS m/z=320.0 [M+H]$^+$.

Step D: Preparation of (1aR,5aR)-2-(4-Cyano-pyridin-2-yl)-1a,2,5,5a-tetrahydro-1H-2,3-diaza-cyclopropa[a]pentalene-4-carboxylic Acid (1aR,5aR)-2-(4-Bromo-pyridin-2-yl)-1a,2,5,5a-tetrahydro-1H-2,3-diaza-cyclopropa[a]pentalene-4-carboxylic Acid (1.00 g, 3.12 mmol) was dissolved in DMA (10 mL). 60 wt % sodium hydride (0.125 g, 3.12 mmol) was added and the mixture was stirred vigorously for 5 min. Nitrogen was bubbled through the mixture for 10 min. Zinc(II) cyanide (0.734 g, 6.25 mmol) and palladium tetrakistriphenylphosphine (0.180 g, 0.156 mmol) were added. The reaction was microwaved at 120° C. for 1 h. The reaction was diluted with ethyl acetate (20 mL) and methanol (5 mL), filtered, then concentrated. The residue was purified by HPLC to give the title compound (0.557 g) as a white solid. LCMS m/z=267.2 [M+H]$^+$.

Step E: Preparation of (1aR,5aR)-2-(4-Cyano-pyridin-2-yl)-1a,2,5,5a-tetrahydro-1H-2,3-diaza-cyclopropa[a]pentalene-4-carboxylic Acid (2-Hydroxy-1-hydroxymethyl-1-methyl-ethyl)-amide (Compound 820)

To a solution of (1aR,5aR)-2-(4-cyano-pyridin-2-yl)-1a,2,5,5a-tetrahydro-1H-2,3-diaza-cyclopropa[a]pentalene-4-carboxylic acid (100 mg, 0.376 mmol), 2-amino-2-methyl-propane-1,3-diol (39.5 mg, 0.376 mmol), and triethylamine (0.105 mL, 0.751 mmol) in DMF (2 mL) was added HATU (157 mg, 0.413 mmol). The reaction was stirred at 23° C., for 30 min then concentrated. The residue was purified by silica gel flash column chromatography to give the title compound (125 mg) as a white solid. LCMS m/z=354.3 [M+H]$^+$; $^1$H NMR (400 MHz, CDCl$_3$) δ 0.46 (td, J=4.7, 3.3 Hz, 1H), 1.27 (td, J=8.0, 4.9 Hz, 1H), 1.36 (s, 3H), 2.27-2.33 (m, 1H), 2.78-2.89 (m, 2H), 3.00 (dd, J=16.8, 6.4 Hz, 1H), 3.72-3.77 (m, 4H), 3.87-3.94 (m, 2H), 7.23 (m, 1H), 7.42 (dd, J=5.1, 1.0 Hz, 1H), 8.16-8.17 (m, 1H), 8.62 (d, J=5.1 Hz, 1H).

Example 1.34: Preparation of (1aS,5aS)-2-(4-Oxypyrazin-2-yl)-1a,2,5,5a-tetrahydro-1H-2,3-diaza-cyclopropa[a]pentalene-4-carboxylic Acid N'-tert-Butyl-hydrazide (Compound 902). Method TT

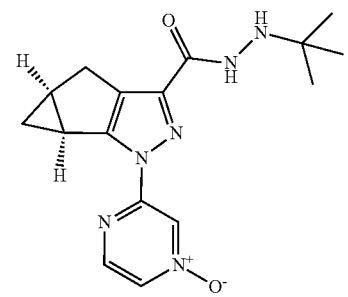 [SMILES: CC(C)(C)NNC(=O)c1nn(-c2c[n+]([O-])ccn2)c2c1C[C@@H]1C[C@H]21]

To a solution of Intermediate 5 (129 mg, 0.5 mmol) and HATU (190 mg, 0.500 mmol) in DMF (4 mL) was added triethylamine (126 mg, 1.250 mmol) followed by tert-butylhydrazine (44.1 mg, 0.500 mmol) at room temperature. The reaction was stirred for 16 h. The reaction mixture was diluted with water (100 mL) and extracted with EtOAc (70 mL). The organic layer was concentrated and the residue was purified by silica gel column chromatography to give the title compound (87 mg) as a while solid. LCMS m/z=329.3 [M+H]$^+$; $^1$H NMR (400 MHz, CDCl$_3$) δ 0.49 (dd, J=8.0 and 4.7 Hz, 1H), 1.17 (s, 9H), 1.25-1.31 (m, 1H), 2.29-2.33 (m, 1H), 2.72-2.77 (m, 1H), 2.93 (d, J=16.8 Hz, 1H), 3.01 (dd, J=17.0 and 6.2 Hz, 1H), 8.00 (dd, J=4.1 and 1.4 Hz, 1H), 8.29 (d, J=4.1 Hz, 1H), 8.80 (d, J=1.4 Hz, 1H).

Example 1.35: Preparation of (1aS,5aS)-2-(4-Oxypyrazin-2-yl)-1a,2,5,5a-tetrahydro-1H-2,3-diaza-cyclopropa[a]pentalene-4-carboxylic Acid ((S)-1-Hydroxymethyl-2-methyl-propyl)-amide (Compound 896)

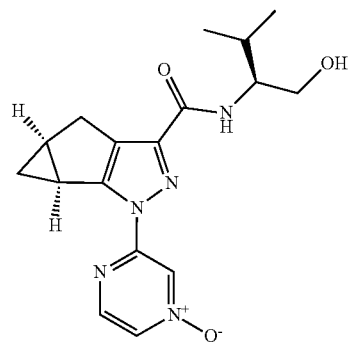 [SMILES: CC(C)[C@@H](CO)NC(=O)c1nn(-c2c[n+]([O-])ccn2)c2c1C[C@@H]1C[C@H]21]

The title compound was prepared in a manner similar to that described in Method TT. LCMS m/z=344.1 [M+H]$^+$; $^1$H NMR (400 MHz, CDCl$_3$) δ 0.48 (dd, J=8.0 and 4.7 Hz, 1H), 1.02 (t, J=7.1 Hz, 6H), 1.28 (td, J=8.0 and 5.0 Hz, 1H), 1.98-2.04 (m, 1H), 2.28-2.32 (m, 1H), 2.71-2.75 (m, 1H), 2.93 (d, J=16.8 Hz, 1H), 3.00 (dd, J=16.7 and 6.3 Hz, 1H), 3.74-3.88 (m, 3H), 6.97 (d, J=8.1 Hz, NH, 1H), 7.99 (dd, J=4.1 and 1.5 Hz, 1H), 8.28 (d, J=4.1 Hz, 1H), 8.79 (d, J=1.5 Hz, 1H).

Example 1.36: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-2,2-Dimethyl-1-pyridin-2-yl-propyl)-amide (Compound 767). Method AAA

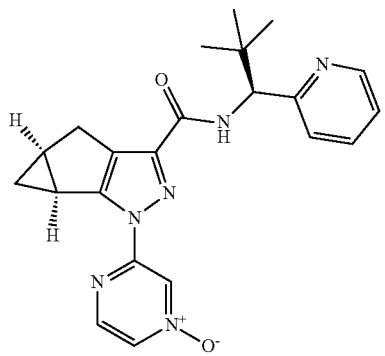 [SMILES: CC(C)(C)[C@H](NC(=O)c1nn(-c2c[n+]([O-])ccn2)c2c1C[C@@H]1C[C@H]21)c1ccccn1]

Step A: Preparation of (R)—N—((S)-2,2-Dimethyl-1-(pyridin-2-yl)propyl)-3,3,3-trifluoro-2-methoxy-2-phenylpropanamide and (R)—N—((R)-2,2-Dimethyl-1-(pyridin-2-yl)propyl)-3,3,3-trifluoro-2-methoxy-2-phenylpropanamide To an ice-cooled solution of racemic 2,2-dimethyl-1-(pyridin-2-yl)propan-1-amine (1.0 g, 6.09 mmol) and triethylamine (0.849 mL, 6.09 mmol) in dichloromethane (20 mL) was added a dichloromethane (5 mL) solution of (S)-3,3,3-trifluoro-2-methoxy-2-phenylpropanoyl chloride (1.148 mL, 6.09 mmol). The solution was stirred at 23° C. for 30 min then loaded onto a silica column. Purification by silica gel flash column chromatography gave the title compound as diastereomers: First-eluting diastereomer (0.56 g) and second-eluting diastereomer (0.504 g) as yellow oils.

First-eluting diastereomer: LCMS m/z=381.4 [M+H]$^+$; $^1$H NMR (400 MHz, CDCl$_3$) δ 0.83 (s, 9H), 3.40 (q, J=1.7 Hz, 3H), 4.93 (d, J=9.5 Hz, 1H), 7.16-7.20 (m, 2H), 7.38-7.42 (m, 3H), 7.61 (td, J=7.7, 1.8 Hz, 1H), 7.65-7.68 (m, 2H), 7.96 (d, J=9.5 Hz, 1H), 8.55 (dt, J=4.5, 1.3 Hz, 1H).

Second-eluting diastereomer: LCMS m/z=381.4 [M+H]$^+$; $^1$H NMR (400 MHz, CDCl$_3$) δ 0.96 (s, 9H), 3.44 (q, J=1.4 Hz, 3H), 4.90 (d, J=9.5 Hz, 1H), 7.14-7.17 (m, 2H), 7.23-7.31 (m, 3H), 7.41 (d, J=7.3 Hz, 2H), 7.59 (td, J=7.7, 1.8 Hz, 1H), 8.16 (d, J=9.4 Hz, 1H), 8.50 (dt, J=5.3, 1.8 Hz, 1H).

Step B: Preparation of (S)-2,2-Dimethyl-1-(pyridin-2-yl)propan-1-amine and (R)-2,2-Dimethyl-1-(pyridin-2-yl)propan-1-amine Solutions of (R)—N—((S)-2,2-dimethyl-1-(pyridin-2-yl)propyl)-3,3,3-trifluoro-2-methoxy-2-phenylpropanamide (0.56 g, 1.472 mmol) or (R)—N—((R)-2,2-dimethyl-1-(pyridin-2-yl)propyl)-3,3,3-trifluoro-2-methoxy-2-phenylpropanamide (0.56 g, 1.472 mmol) in 48 wt % aqueous hydrogen bromide (5.02 mL, 44.2 mmol) were heated under microwave irradiation at 160° C. for 2 h. The mixtures were diluted with water (25 mL), extracted with dichloromethane (3×25 mL), and the dichloromethane extracts discarded. The aqueous solutions were basified with 2 M aqueous NaOH (25 mL) then extracted with dichloromethane (3×25 mL). These extracts were dried (MgSO$_4$), filtered, then concentrated to give enantiomeric 2,2-dimethyl-1-(pyridin-2-yl)propan-1-amine derived from first-eluting diastereomer (0.175 g) and enantiomeric 2,2-dimethyl-1-(pyridin-2-yl)propan-1-amine derived from second-eluting diastereomer (0.200 g) as yellow oils.

Enantiomer derived from first-eluting Mosher amide: LCMS m/z=165.3 [M+H]$^+$;

Enantiomer derived from second-eluting Mosher amide: LCMS m/z=165.3 [M+H]$^+$.

Step C: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-2,2-Dimethyl-1-pyridin-2-yl-propyl)-amide To a solution of Intermediate 5 (200 mg, 0.774 mmol), (S)-2,2-dimethyl-1-(pyridin-2-yl)propan-1-amine (127 mg, 0.774 mmol), and triethylamine (0.216 mL, 1.549 mmol) in DMF (3 mL) was added HATU (324 mg, 0.852 mmol). The reaction was stirred at 23° C. for 1 h then diluted with DMSO (2 mL). The mixture was purified by preparative HPLC to give the title compound (183 mg) as a white solid. LCMS m/z=405.4 [M+H]$^+$. $^1$H NMR (400 MHz, CDCl$_3$) δ 0.38 (td, J=4.7, 3.3 Hz, 1H), 0.99 (s, 9H), 1.23 (td, J=8.0, 4.8 Hz, 1H), 2.24-2.31 (m, 1H), 2.71-2.75 (m, 1H), 2.88 (dd, J=16.7, 1.8 Hz, 1H), 3.03 (dd, J=16.7, 6.4 Hz, 1H), 5.02 (d, J=9.5 Hz, 1H), 7.15-7.20 (m, 2H), 7.59 (td, J=7.7, 1.8 Hz, 1H), 7.99 (dd, J=4.0, 1.4 Hz, 1H), 8.18 (d, J=9.5 Hz, 1H), 8.28 (d, J=4.2 Hz, 1H), 8.61-8.62 (m, 1H), 8.92-8.93 (m, 1H).

Example 1.37: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((R)-2,2-Dimethyl-1-pyridin-2-yl-propyl)-amide (Compound 766)

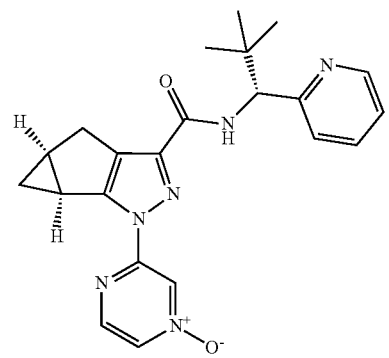 [SMILES: CC(C)(C)[C@@H](NC(=O)c1nn(-c2c[n+]([O-])ccn2)c2c1C[C@@H]1C[C@H]21)c1ccccn1]

To a solution of Intermediate 5 (200 mg, 0.774 mmol), (R)-2,2-dimethyl-1-(pyridin-2-yl)propan-1-amine (127 mg, 0.774 mmol), and triethylamine (0.216 mL, 1.549 mmol) in DMF (3 mL) was added HATU (324 mg, 0.852 mmol). The reaction was stirred at 23° C. for 1 h then diluted with DMSO (2 mL). The mixture was purified by preparative HPLC to give the title compound (230 mg) as a white solid. LCMS m/z=405.4 [M+H]$^+$; $^1$H NMR (400 MHz, CDCl$_3$) δ 0.50 (td, J=4.8, 3.3 Hz, 1H), 0.99 (s, 9H), 1.26 (td, J=7.8, 4.9

Hz, 1H), 2.24-2.30 (m, 1H), 2.69-2.74 (m, 1H), 2.94-2.95 (m, 2H), 5.02 (d, J=9.5 Hz, 1H), 7.15-7.20 (m, 2H), 7.59 (td, J=7.7, 1.9 Hz, 1H), 7.99 (dd, J=4.2, 1.5 Hz, 1H), 8.18 (d, J=9.5 Hz, 1H), 8.28 (d, J=4.2 Hz, 1H), 8.61-8.63 (m, 1H), 8.92-8.93 (m, 1H).

Example 1.38: Preparation of (1aS,5aS)—(S)-2-Amino-3-methyl-butyric Acid (S)-3,3-Dimethyl-2-{[2-(4-oxy-pyrazin-2-yl)-1a,2,5,5a-tetrahydro-1H-2,3-diaza-cyclopropa[a]pentalene-4-carbonyl]-amino}-butyl Ester (Compound 848)

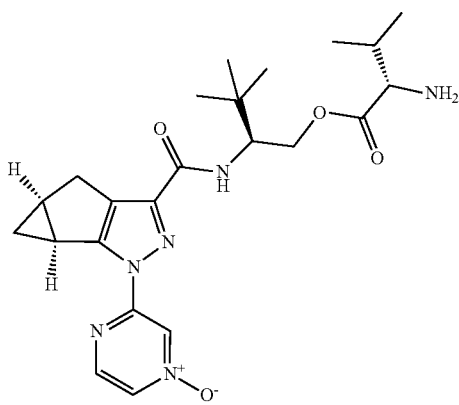 [SMILES: CC(C)[C@H](N)C(=O)OC[C@@H](NC(=O)c1nn(-c2c[n+]([O-])ccn2)c2c1C[C@@H]1C[C@H]21)C(C)(C)C]

Step A: Preparation of (1aS,5aS)-2-Pyrazin-2-yl-1a,2,5,5a-tetrahydro-1H-2,3-diaza-cyclopropa[a]pentalene-4-carboxylic Acid ((S)-1-Hydroxymethyl-2,2-dimethyl-propyl)-amide To a solution of Intermediate 4 (1.4 g, 5.78 mmol) and triethylamine (1.611 mL, 11.56 mmol) in DMF (15 mL) was added HATU (2.242 g, 5.90 mmol). The reaction was stirred at 23° C. for 5 min, then (S)-2-amino-3,3-dimethylbutan-1-ol (0.711 g, 6.07 mmol) was added. The reaction was stirred at 23° C. for 15 min then concentrated. The residue was purified by silica gel column chromatography to give the title compound (1.97 g) as a white solid. LCMS m/z=342.2 [M+H]$^+$; $^1$H NMR (400 MHz, CDCl$_3$) δ 0.48 (td, J=4.6, 3.4 Hz, 1H), 1.05 (s, 9H), 1.24 (td, J=8.0, 4.7 Hz, 1H), 2.26-2.32 (m, 1H), 2.74-2.78 (m, 1H), 2.94 (d, J=16.8 Hz, 1H), 3.01 (dd, J=16.7, 6.1 Hz, 1H), 3.67-3.72 (m, 1H), 3.93-3.98 (m, 2H), 7.08 (d, J=8.5 Hz, 1H), 8.42 (dd, J=1.4, 0.9 Hz, 1H), 8.51 (d, J=2.7 Hz, 1H), 9.26 (d, J=1.1 Hz, 1H).

Step B: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide To a solution of (1aS,5aS)-2-pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide (900 mg, 2.64 mmol) in chloroform (10 mL) was added 3-chlorobenzoperoxoic acid (1772 mg, 7.91 mmol). The reaction was stirred at 23° C. for 3 h. Another 1.2 g mCPBA was added and stirring was continued at room temperature for 18 h. The mixture was purified by silica gel column chromatography to give the title compound (550 mg) as a white solid. LCMS m/z=358.3 [M+H]$^+$; $^1$H NMR (400 MHz, CDCl$_3$) δ 0.49 (td, J=4.6, 3.3 Hz, 1H), 1.03 (s, 9H), 1.27 (td, J=8.0, 4.9 Hz, 1H), 2.08 (bs, 1H), 2.27-2.33 (m, 1H), 2.71-2.76 (m, 1H), 2.93 (d, J=16.8 Hz, 1H), 3.00 (dd, J=16.7, 6.1 Hz, 1H), 3.65-3.71 (m, 1H), 3.92-3.97 (m, 2H), 6.97 (d, J=8.5 Hz, 1H), 7.99 (dd, J=4.0, 1.4 Hz, 1H), 8.28 (d, J=4.2 Hz, 1H), 8.78 (dd, J=1.4, 0.8 Hz, 1H).

Step C: Preparation of (S)-2-tert-Butoxycarbonylamino-3-methyl-butyric Acid (S)-3,3-Dimethyl-2-{[(1aS,5aS)-2-(4-oxy-pyrazin-2-yl)-1a,2,5,5a-tetrahydro-1H-2,3-diaza-cyclopropa[a]pentalene-4-carbonyl]-amino}-butyl Ester To a solution of aS,5aS)-2-(4-Oxy-pyrazin-2-yl)-1a,2,5,5a-tetrahydro-1H-2,3-diaza-acid ((S)-1-hydroxymethyl-2,2-dimethyl-propyl)-amide (500 mg, 1.399 mmol), (S)-2-(tert-butoxycarbonylamino)-3-methylbutanoic acid (1003 mg, 4.62 mmol), triethylamine (1.170 mL, 8.39 mmol), and DMAP (68.4 mg, 0.560 mmol) in 1,2-dichloroethane (10 mL) was added N1-((ethylimino)methylene)-N3,N3-dimethylpropane-1,3-diamine. The mixture was stirred at 60° C. for 2 h. The mixture was purified by silica gel column chromatography to give the title compound (495 mg) as a white solid. LCMS m/z=557.5.

Step D: Preparation of (1aS,5aS)—(S)-2-Amino-3-methyl-butyric Acid (S)-3,3-Dimethyl-2-{[2-(4-oxy-pyrazin-2-yl)-1a,2,5,5a-tetrahydro-1H-2,3-diaza-cyclopropa[a]pentalene-4-carbonyl]-amino}-butyl Ester To (S)-2-tert-butoxycarbonylamino-3-methyl-butyric acid (S)-3,3-dimethyl-2-{[(1aS,5aS)-2-(4-oxy-pyrazin-2-yl)-1a,2,5,5a-tetrahydro-1H-2,3-diaza-cyclopropa[a]pentalene-4-carbonyl]-amino}-butyl ester (495 mg, 0.889 mmol) was added HCl (4 M in dioxane, 5.56 mL, 22.23 mmol). The reaction was stirred at 23° C. for 1 h then concentrated. The off-white solid was taken up in 2:1 water/acetonitrile (10 mL) then freeze-dried to give the HCl salt of the title compound (437 mg) as a white solid. LCMS m/z=457.3 [M+H]$^+$; $^1$H NMR (400 MHz, DMSO-d$_6$) δ 0.44 (td, J=4.4, 3.4 Hz, 1H), 0.78 (d, J=7.0 Hz, 3H), 0.81 (d, J=7.1 Hz, 3H), 0.97 (s, 9H), 1.27 (td, J=7.8, 4.7 Hz, 1H), 1.98-2.06 (m, 1H), 2.27-2.33 (m, 1H), 2.65-2.69 (m, 1H), 2.73-2.84 (m, 2H), 3.85 (d, J=4.2 Hz, 1H), 4.12 (td, J=10.2, 2.3 Hz, 1H), 4.33 (dd, J=8.2, 2.9 Hz, 1H), 4.47 (t, J=10.9 Hz, 1H), 8.08 (d, J=9.7 Hz, 1H), 8.29 (dd, J=4.2, 1.5 Hz, 1H), 8.33 (s, 3H), 8.48 (d, J=4.2 Hz, 1H), 9.11-9.12 (m, 1H).

Example 1.39: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((R)-1,2-Dimethyl-propyl)-amide (Compound 912)

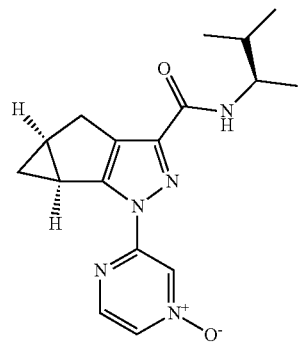 [SMILES: CC(C)[C@@H](C)NC(=O)c1nn(-c2c[n+]([O-])ccn2)c2c1C[C@@H]1C[C@H]21]

The title compound was prepared in a manner similar to that described in Method UU using Intermediate 5 and (R)-3-methylbutan-2-amine. LCMS m/z=328.3 [M+H]$^+$; $^1$H NMR (400 MHz, CDCl$_3$) δ 0.46-0.50 (m, 1H), 0.96 (d, J=6.8 Hz, 3H), 0.97 (d, J=6.7 Hz, 3H), 1.19 (d, J=6.9 Hz, 3H), 1.26 (td, J=8.2, 4.8 Hz, 1H), 1.75-1.87 (m, 1H), 2.26-2.33 (m, 1H), 2.70-2.75 (m, 1H), 2.94 (d, J=16.8 Hz, 1H), 3.01 (dd, J=16.6, 6.0 Hz, 1H), 3.95-4.05 (m, 1H), 6.64 (d, J=9.0 Hz, 1H), 7.98 (dd, J=4.0, 1.4 Hz, 1H), 8.28 (d, J=4.0 Hz, 1H), 8.78-8.80 (m, 1H).

Example 1.40: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid ((R)-1,2-Dimethyl-propyl)-amide (Compound 828)

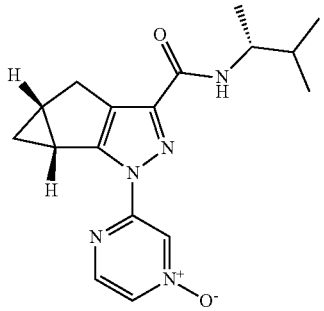 [SMILES: CC(C)[C@@H](C)NC(=O)c1nn(-c2c[n+]([O-])ccn2)c2c1C[C@H]1C[C@@H]21]

The title compound was prepared in a manner similar to that described in Method UU using Intermediate 6 and (R)-3-methylbutan-2-amine. LCMS m/z=328.3 [M+H]$^+$; $^1$H NMR (400 MHz, CDCl$_3$) δ 0.44-0.48 (m, 1H), 0.95 (d, J=6.8 Hz, 3H), 0.97 (d, J=6.9 Hz, 3H), 1.18 (d, J=6.9 Hz, 3H), 1.26 (td, J=8.0, 4.9 Hz, 1H), 1.75-1.88 (m, 1H), 2.26-2.33 (m, 1H), 2.70-2.75 (m, 1H), 2.93 (d, J=17.1 Hz, 1H), 3.02 (dd, J=16.7, 6.2 Hz, 1H), 3.95-4.05 (m, 1H), 6.64 (d, J=8.9 Hz, 1H), 7.98 (dd, J=4.0, 1.4 Hz, 1H), 8.28 (d, J=4.0 Hz, 1H), 8.79-8.80 (m, 1H).

Example 1.41: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (2-Fluoro-1,1-dimethyl-ethyl)-amide (Compound 904)

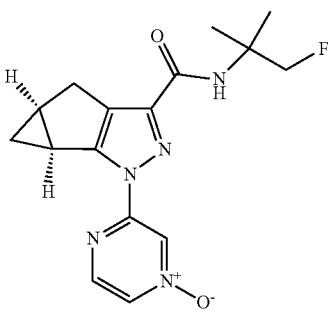 [SMILES: CC(C)(CF)NC(=O)c1nn(-c2c[n+]([O-])ccn2)c2c1C[C@@H]1C[C@H]21]

The title compound was prepared in a manner similar to that described in Method UU using Intermediate 5 and 1-fluoro-2-methylpropan-2-amine. LCMS m/z=332.2 [M+H]$^+$; $^1$H NMR (400 MHz, CDCl$_3$) δ 0.44-0.48 (m, 1H), 1.27 (td, J=8.0, 5.0 Hz, 1H), 1.46 (s, 3H), 1.47 (s, 3H), 2.26-2.34 (m, 1H), 2.703-2.76 (m, 1H), 2.91 (d, J=16.9 Hz, 1H), 3.00 (dd, J=16.6, 6.2 Hz, 1H), 4.54 (d, J=47.5 Hz, 2H), 6.73 (s, 1H), 7.98 (dd, J=4.0, 1.5 Hz, 1H), 8.28 (d, J=4.2 Hz, 1H), 8.78-8.79 (m, 1H).

Example 1.42: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-2-Hydroxy-1-phenyl-ethyl)-amide (Compound 913)

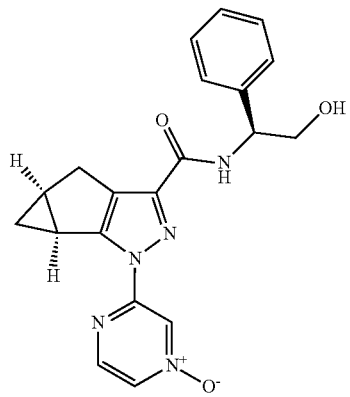 [SMILES: O=C(N[C@H](CO)c1ccccc1)c1nn(-c2c[n+]([O-])ccn2)c2c1C[C@@H]1C[C@H]21]

The title compound was prepared in a manner similar to that described in Method UU using Intermediate 5 and (S)-2-amino-2-phenylethanol. LCMS=378.3 [M+H]$^+$; $^1$H NMR (400 MHz, CDCl$_3$) δ 0.43-0.47 (m, 1H), 1.26 (td, J=7.8, 4.9 Hz, 1H), 2.26-2.33 (m, 1H), 2.55 (bs, 1H), 2.70-2.76 (m, 1H), 2.90 (d, J=16.9 Hz, 1H), 3.00 (dd, J=16.7, 6.3 Hz, 1H), 3.95-4.04 (m, 2H), 5.18-5.24 (m, 1H), 7.29-7.35 (m, 1H), 7.36-7.41 (m, 4H), 7.44 (d, J=7.4 Hz, 1H), 7.98 (dd, J=4.2, 1.5 Hz, 1H), 8.28 (d, J=4.2 Hz, 1H), 8.80 (d, J=1.1 Hz, 1H).

Example 1.43: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid ((S)-1-Fluoromethyl-2,2-dimethyl-propyl)-amide (Compound 918)

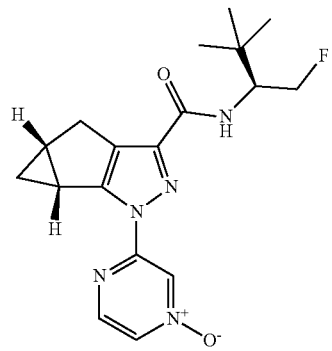 [SMILES: CC(C)(C)[C@@H](CF)NC(=O)c1nn(-c2c[n+]([O-])ccn2)c2c1C[C@H]1C[C@@H]21]

The title compound was prepared in a manner similar to that described in Method UU, using Intermediate 6 and (S)-1-fluoro-3,3-dimethylbutan-2-amine hydrochloride. LCMS m/z=360.2 [M+H]$^+$; $^1$H NMR (400 MHz, CDCl$_3$) δ

0.50 (td, J=4.6 and 3.2 Hz, 1H), 1.05 (s, 9H), 1.25-1.30 (m, 1H), 2.27-2.35 (m, 1H), 2.72-2.77 (m, 1H), 2.93 (d, J=16.9 Hz, 1H), 3.01 (dd, J=16.6 and 6.2 Hz, 1H), 4.03-4.15 (m, 1H), 4.48-4.74 (m, 2H), 7.04 (d, J=10.0 Hz, 1H), 7.99 (dd, J=4.1 and 1.5 Hz, 1H), 8.28 (d, J=4.1 Hz, 1H), 8.81 (d, J=1.5 Hz, 1H).

Example 1.44: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid (1-Fluoromethyl-cyclobutyl)-amide (Compound 924)

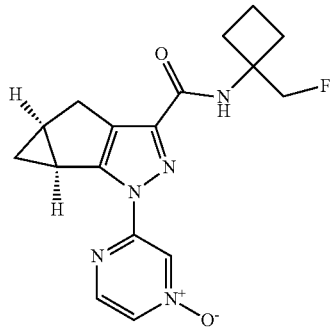 [SMILES: O=C(NC1(CF)CCC1)c1nn(-c2c[n+]([O-])ccn2)c2c1C[C@@H]1C[C@H]21]

The title compound was prepared in a manner similar to that described in Method UU, using Intermediate 5 and 1-(fluoromethyl)cyclobutanamine hydrochloride, which was prepared in a similar manner to that described in Example 1.58, Step A to Step E, using (1-aminocyclobutyl)methanol. LCMS m/z=344.2 [M+H]$^+$; $^1$H NMR (400 MHz, CDCl$_3$) δ 0.48 (td, J=4.6 and 3.2 Hz, 1H), 1.24-1.29 (m, 1H), 1.85-1.95 (m, 1H), 2.00-2.10 (m, 1H), 2.27-2.47 (m, 5H), 2.70-2.75 (m, 1H), 2.91 (d, J=17.3 Hz, 1H), 3.00 (dd, J=16.7 and 6.2 Hz, 1H), 4.68 (d, J=47.8 Hz, 2H), 6.98 (s, 1H), 7.97 (dd, J=4.1 and 1.5 Hz, 1H), 8.28 (dd, J=4.1 and 0.7 Hz, 1H), 8.80 (dd, J=1.5 and 0.7 Hz, 1H).

Example 1.45: Preparation of (1aR,5aR)-2-(4-Fluoro-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 931)

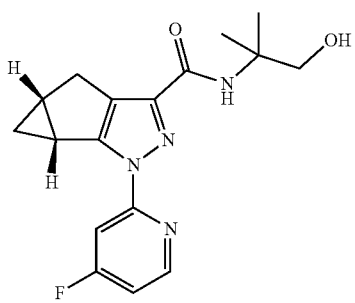 [SMILES: CC(C)(CO)NC(=O)c1nn(-c2cc(F)ccn2)c2c1C[C@H]1C[C@@H]21]

Step A: Preparation of 2-Hydrazinyl-4-iodopyridine

To a solution of 2-fluoro-4-iodopyridine (7.00 g, 31.4 mmol) in ethanol (60 mL) was added hydrazine monohydrate (15.23 mL, 314 mmol). The mixture was stirred at 40° C. for 15 h then concentrated. The resulting residue was triturated with 1:1 hexanes/ether. The remaining solid was further triturated with water then dried under vacuum to give the title compound (6.6 g) as a tan solid. LCMS m/z=235.9 [M+H]$^+$. $^1$H NMR (400 MHz, DMSO-d$_6$) δ 4.15 (s, 2H), 6.86 (dd, J=5.2, 1.5 Hz, 1H), 7.13 (d, J=1.5 Hz, 1H), 7.56 (s, 1H), 7.67 (d, J=5.3 Hz, 1H).

Step B: Preparation of (1aR,5aR)-2-(4-Iodo-pyridin-2-yl)-1a,2,5,5a-tetrahydro-1H-2,3-diaza-cyclopropa[a]pentalene-4-carboxylic Acid Ethyl Ester To a solution of (1R,5S)-bicyclo[3.1.0]hexan-2-one (2.045 g, 21.27 mmol) and diethyl oxalate (2.91 mL, 21.27 mmol) in absolute ethanol (100 mL) was added a 1.0 M THF solution of potassium 2-methylpropan-2-olate (21.27 mL, 21.27 mmol). The mixture was stirred at 40° C. for 4 h. 2-Hydrazinyl-4-iodopyridine (5.00 g, 21.27 mmol) was added followed by a 3.0 M aqueous solution of hydrogen chloride (21.27 mL, 63.8 mmol). The reaction was stirred at 45° C., for 16 h. Brine (150 mL) was added. The mixture was extracted with dichloromethane (3×50 mL). The combined organic extracts were washed with brine (100 mL), dried (MgSO$_4$), filtered, and then concentrated. The residue was purified by silica gel flash chromatography to give the title compound (5.8 g) as a white solid. LCMS m/z=396.1 [M+H]$^+$; $^1$H NMR (400 MHz, CDCl$_3$) δ 0.44 (td, J=4.7, 3.5 Hz, 1H), 1.25 (td, J=8.0, 5.1 Hz, 1H), 1.40 (t, J=7.1 Hz, 3H), 2.22-2.29 (m, 1H), 2.80-2.85 (m, 1H), 2.85 (d, J=17.1 Hz, 1H), 2.97 (dd, J=16.9, 6.6 Hz, 1H), 4.39 (q, J=7.1 Hz, 2H), 7.57 (dd, J=5.2, 1.4 Hz, 1H), 8.10 (d, J=5.2 Hz, 1H), 8.48 (s, 1H).

Step C: Preparation of (1aR,5aR)-2-(4-Iodo-pyridin-2-yl)-1a,2,5,5a-tetrahydro-1H-2,3-diaza-cyclopropa[a]pentalene-4-carboxylic Acid To a solution of (1aR,5aR)-2-(4-iodo-pyridin-2-yl)-1a,2,5,5a-tetrahydro-1H-2,3-diaza-cyclopropa[a]pentalene-4-carboxylic acid ethyl ester in MeOH (10.00 mL) and THF (10.00 mL) was added a 2 M aqueous solution of sodium hydroxide (5.20 mL, 10.40 mmol). The mixture was stirred at room temperature for 2 h then concentrated. The remaining solid was dissolved in water (30 mL). The solution was acidified to pH ~2 by addition of 6 M aqueous HCl. The resulting precipitate was collected by filtration, rinsed with water, then dried to give the title compound (190 mg) as a white solid. LCMS m/z=368.1 [M+H]$^+$.

Step D: Preparation of (1aR,5aR)-2-(4-Fluoro-pyridin-2-yl)-1a,2,5,5a-tetrahydro-1H-2,3-diaza-cyclopropa[a]pentalene-4-carboxylic Acid To a solution of (1aR,5aR)-2-(4-iodo-pyridin-2-yl)-1a,2,5,5a-tetrahydro-1H-2,3-diaza-cyclopropa[a]pentalene-4-carboxylic acid (174 mg, 0.47 mmol) in DMSO (2.5 mL) was added cesium fluoride (500 mg, 3.29 mmol). The mixture was heated under microwave irradiation at 200° C. for 60 min. The mixture was purified by preparative HPLC to give the title compound as a white solid (85 mg). LCMS m/z=260.1 [M+H]$^+$.

Step E: Preparation of (1aR,5aR)-2-(4-Fluoro-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide To a solution of (1aR,5aR)-2-(4-fluoro-pyridin-2-yl)-1a,2,5,5a-tetrahydro-1H-2,3-diaza-cyclopropa[a]pentalene-4- carboxylic acid (68 mg, 0.262 mmol), 2-amino-2-methyl-propan-1-ol (23.38 mg, 0.262 mmol), and triethylamine (0.073 mL, 0.525 mmol) in DMF (1 mL) was added HATU (105 mg, 0.275 mmol). The reaction was stirred at 23° C. for 20 min then concentrated. The residue was purified by silica gel column chromatography to give the title compound (80 mg) as a white solid. LCMS m/z=331.3 [M+H]+; 1H NMR (400 MHz, CDCl3) δ 0.46 (td, J=4.6, 3.4 Hz, 1H), 1.26 (td, J=7.8, 4.9 Hz, 1H), 1.41 (s, 3H), 1.42 (s, 3H), 2.24-2.30 (m, 1H), 2.79-2.84 (m, 1H), 2.91 (d, J=16.8 Hz, 1H), 3.00 (dd, J=16.6, 6.3 Hz, 1H), 3.70 (d, J=6.4 Hz, 2H), 4.69 (t, J=6.3 Hz, 1H), 6.93-6.98 (m, 2H), 7.63 (dd, J=10.1, 2.4 Hz, 1H), 8.43 (dd, J=8.5, 5.7 Hz, 1H).

Example 1.46: Preparation of 1-(2,4-Difluoro-phenyl)-3b,4,4a,5-tetrahydro-1H-cyclopropa[3,4]cyclopenta[1,2-c]pyrazole-3-carboxylic Acid (2-Hydroxy-1,1-dimethyl-ethyl)-amide (Compound 515)

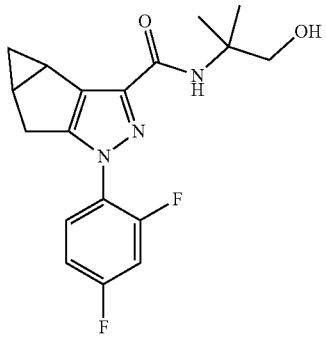 [SMILES: CC(C)(CO)NC(=O)c1nn(-c2ccc(F)cc2F)c2c1C1CC1C2]

The title compound was prepared in a manner similar to that described in Method X using 2-amino-2-methylpropan-1-ol. LCMS m/z=348.2 [M+H]+.

Example 1.47: Preparation of (1aR,5aR)-2-(5-Chloro-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 151)

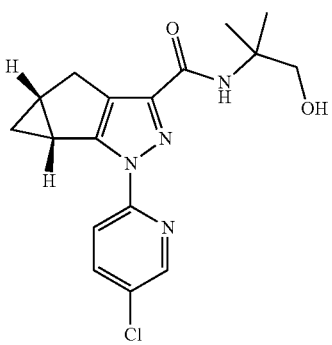 [SMILES: CC(C)(CO)NC(=O)c1nn(-c2ccc(Cl)cn2)c2c1C[C@H]1C[C@@H]21]

The title compound was prepared in a manner similar to that described in Method G using 2-amino-2-methylpropane-1,3-diol and (1aR,5aR)-2-(5-Chloropyridin-2-yl)-1a,2,5,5a-tetrahydro-1H-2,3-diaza-cyclopropa[a]pentalene-4-carboxylic acid. The aforementioned acid was prepared in a similar method as described in Method A and B using (1R,5S)-bicyclo[3,1,0]hexan-2-one and 5-chloro-2-hydrazinylpyridine. LCMS m/z=347.2 [M+H]+; 1H NMR (400 MHz, CDCl3) δ ppm 0.45 (td, J=4.7, 3.3 Hz, 1H), 1.25 (td, J=8.3, 4.4 Hz, 1H), 1.406 (s, 3H), 1.410 (s, 3H), 2.24-2.30 (m, 1H), 2.75-2.80 (m, 1H), 2.90 (d, J=16.6 Hz, 1H), 3.00 (dd, J=16.6, 6.4 Hz, 1H), 3.70 (s, 2H), 4.63 (bs, 1H), 6.92 (s, 1H), 7.78 (dd, J=8.7, 2.5 Hz, 1H), 7.87 (dd, J=8.8, 0.6 Hz, 1H), 8.41 (dd, J=2.5, 0.6 Hz, 1H).

Example 1.48: Preparation of (1aR,5aR)-2-(2,4-Dichloro-phenyl)-1a,2,5,5a-tetrahydro-1H-2,3-diaza-cyclopropa[a]pentalene-4-carboxylic Acid (1-Hydroxymethyl-cyclopropyl)-amide (Compound 174)

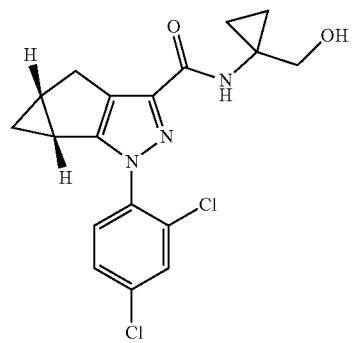 [SMILES: O=C(NC1(CO)CC1)c1nn(-c2ccc(Cl)cc2Cl)c2c1C[C@H]1C[C@@H]21]

The title compound was prepared in a manner similar to that described in Method G using (1aR,5aR)-2-(2,4-dichloro-phenyl)-1a,2,5,5a-tetrahydro-1H-2,3-diaza-cyclopropa[a]pentalene-4-carboxylic acid and (1-hydroxymethyl-cyclopropyl)-amine. LCMS m/z=378.2 [M+H]+; 1H NMR (400 MHz, CDCl3) δ ppm 0.51 (td, J=4.6 and 3.4 Hz, 1H), 0.90-1.03 (m, 4H), 1.14-1.21 (m, 1H), 2.00-2.07 (m, 1H), 2.27-2.37 (m, 1H), 2.97 (d, J=16.6 Hz, 1H), 3.06 (dd, J=16.6 and 6.3 Hz, 1H), 3.71 (s, 2H), 7.28 (bs, 1H), 7.40 (dd, J=8.5 and 2.1 Hz, 1H), 7.44 (d, J=8.5 Hz, 1H), 7.58 (d, J=2.1 Hz, 1H).

Example 1.49: Preparation of (1aR,5aR)-2-Pyrazin-2-yl-1a,2,5,5a-tetrahydro-1H-2,3-diaza-cyclopropa[a]pentalene-4-carboxylic Acid tert-Butylamide (Compound 593)

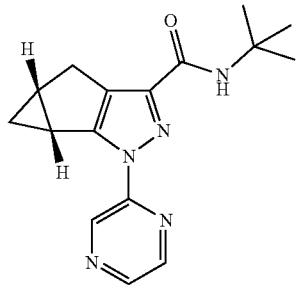 [SMILES: CC(C)(C)NC(=O)c1nn(-c2cnccn2)c2c1C[C@H]1C[C@@H]21]

The title compound was prepared in a manner similar to that described in Method G using Intermediate 2 and tert-butyl amine. LCMS m/z=298.3 [M+H]+; 1H NMR (400 MHz, CDCl3) δ 0.47 (td, J=4.6 and 3.3 Hz, 1H), 1.22-1.27 (m, 1H), 1.48 (s, 9H), 2.25-2.32 (m, 1H), 2.71-2.76 (m, 1H), 2.93 (d, J=16.7 Hz, 1H), 3.02 (dd, J=16.6 and 6.2 Hz, 1H), 6.79 (s, 1H), 8.42 (br, 1H), 8.49 (d, J=2.0 Hz, 1H), 9.25 (s, 1H).

Example 1.50: Preparation of (1aR,5aR)-2-(4-Cyano-pyridin-2-yl)-1a,2,5,5a-tetrahydro-1H-2,3-diaza-cyclopropa[a]pentalene-4-carboxylic Acid (2-Hydroxy-1,1-dimethyl-ethyl)-amide (Compound 644)

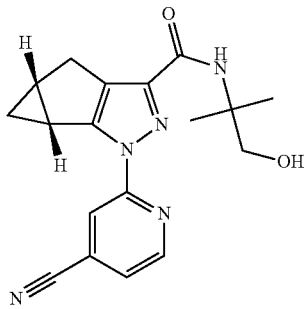 [SMILES: CC(C)(CO)NC(=O)c1nn(-c2cc(C#N)ccn2)c2c1C[C@H]1C[C@@H]21]

The title compound was prepared in a manner similar to that described in Method T using (1aR,5aR)-2-(5-bromo-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide and dicyanozine. LCMS m/z=338.3 [M+H]$^+$; $^1$H NMR (400 MHz, CDCl$_3$) δ ppm 0.47 (dd, J=4.6 and 3.4 Hz, 1H), 1.25-1.31 (m, 1H), 1.45 (s, 6H), 2.26-2.34 (m, 1H), 2.78-2.84 (m, 1H), 2.93 (d, J=16.1 Hz, 1H), 3.02 (dd, J=16.7 and 6.3 Hz, 1H), 3.73 (s, 2H), 6.93-6.97 (bs, 1H), 7.43 (dd, J=5.0 and 1.2 Hz, 1H), 8.17 (s, 1H), 8.63 (d, J=5.0, 1H).

Example 1.51: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2-methyl-propyl)-amide (Compound 690)

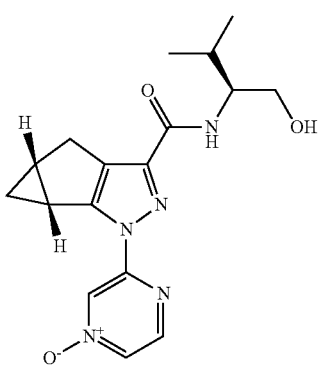 [SMILES: CC(C)[C@@H](CO)NC(=O)c1nn(-c2c[n+]([O-])ccn2)c2c1C[C@H]1C[C@@H]21]

The title compound was prepared in a manner similar to that described in Method CCC. LCMS m/z=344.3 [M+H]$^+$; $^1$H NMR (400 MHz, CDCl$_3$) δ ppm 0.47 (dd, J=8.0 and 4.7 Hz, 1H), 1.02 (t, J=7.2 Hz, 6H), 1.28 (td, J=8.0 and 5.0 Hz, 1H), 2.00-2.05 (m, 1H), 2.28-2.32 (m, 1H), 2.72-2.77 (m, 1H), 2.95 (d, J=17.3 Hz, 1H), 3.02 (dd, J=16.7 and 6.3 Hz, 1H), 3.73-3.89 (m, 3H), 6.98 (d, J=8.3 Hz, NH, 1H), 7.99 (dd, J=4.1 and 1.5 Hz, 1H), 8.28 (d, J=4.1 Hz, 1H), 8.80 (s, 1H).

Example 1.52: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid ((S)-2,2-Dimethyl-1-methylcarbamoyl-propyl)-amide (Compound 704)

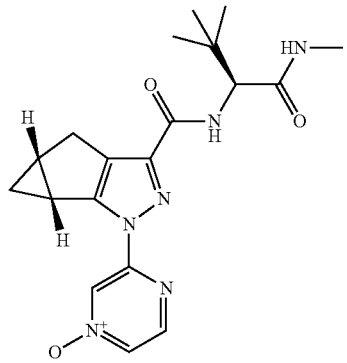 [SMILES: CNC(=O)[C@@H](NC(=O)c1nn(-c2c[n+](O)ccn2)c2c1C[C@H]1C[C@@H]21)C(C)(C)C]

The title compound was prepared in a manner similar to that described in Method CCC. LCMS m/z=385.3 [M+H]$^+$; $^1$H NMR (400 MHz, CDCl$_3$) δ ppm 0.44 (dd, J=8.0 and 4.7 Hz, 1H), 1.24-1.29 (m, 1H), 2.26-2.32 (m, 1H), 2.72-2.77 (m, 1H), 2.82 (d, J=4.8 Hz, 3H), 2.88 (d, J=16.7 Hz, 1H), 3.01 (dd, J=16.5 and 6.5 Hz, 1H), 4.30 (d, J=9.5 Hz, 1H), 5.90 (q, J=4.4 Hz, NH, 1H), 7.44 (d, J=9.5 Hz, NH, 1H), 8.00 (dd, J=4.1 and 1.5 Hz, 1H), 8.28 (d, J=4.1 Hz, 1H), 8.84 (s, 1H).

Example 1.53: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid ((S)-Methylcarbamoyl-phenyl-methyl)-amide (Compound 722)

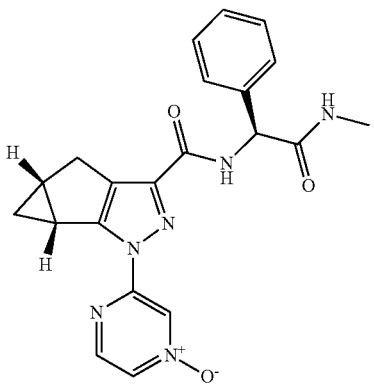 [SMILES: CNC(=O)[C@@H](NC(=O)c1nn(-c2c[n+]([O-])ccn2)c2c1C[C@H]1C[C@@H]21)c1ccccc1]

(S)-2-Amino-N-methyl-2-phenylacetamide was prepared in a manner similar to that described in Method HHH and III using (S)-2-(tert-butoxycarbonylamino)-2-phenylacetic acid and methylamine. The title compound was prepared in a manner similar to that described in Method G using (1aR, 5aR)-2-(4-oxy-pyrazin-2-yl)-1a,2,5,5a-tetrahydro-1H-2,3- diaza-cyclopropa[a]pentalene-4-carboxylic acid and (S)-2-amino-N-methyl-2-phenylacetamide. LCMS m/z=405.3 [M+H]+; 1H NMR (400 MHz, CDCl3) δ ppm 0.40-0.47 (m, 1H), 1.21-1.29 (m, 1H), 2.23-2.31 (m, 1H), 2.69-2.75 (m, 1H), 2.83 (dd, J=4.9 and 1.9 Hz, 3H), 2.87 (d, J=16.9 Hz, 1H), 2.92-3.00 (m, 1H), 5.50 (d, J=6.8 Hz, 1H), 5.69 (bs, 1H), 7.30-7.41 (m, 3H), 7.43-7.48 (m, 2H), 7.97 (dd, J=4.0 and 1.4 Hz, 1H), 7.98-8.03 (m, 1H), 8.26 (d, J=4.0 Hz, 1H), 8.83-8.85 (m, 1H).

Example 1.54: Preparation of (S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric Acid Methyl Ester (Compound 746)

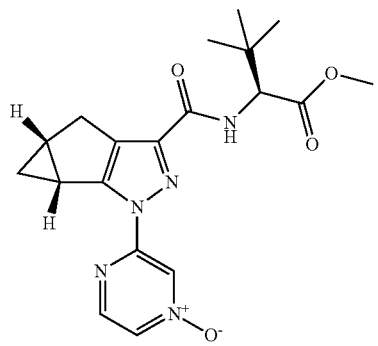 [SMILES: COC(=O)[C@@H](NC(=O)c1nn(-c2c[n+]([O-])ccn2)c2c1C[C@H]1C[C@@H]21)C(C)(C)C]

The title compound was prepared in a manner similar to that described in Method CCC, using (1aR,5aR)-2-(4-oxy-pyrazin-2-yl)-1a,2,5,5a-tetrahydro-1H-2,3-diaza-cyclopropa[a]pentalene-4-carboxylic acid and (S)-methyl 2-amino-3,3-dimethylbutanoate. LCMS m/z=386.2 [M+H]+; 1H NMR (400 MHz, CDCl3) δ ppm 0.44 (dd, J=8.0 and 4.7 Hz, 1H), 1.06 (s, 9H), 1.24-1.29 (m, 1H), 2.26-2.32 (m, 1H), 2.72-2.77 (m, 1H), 2.90 (d, J=16.8 Hz, 1H), 3.02 (dd, J=16.7 and 6.4 Hz, 1H), 3.75 (s, 3H), 4.58 (d, J=9.6 Hz, 1H), 7.28 (d, J=9.6 Hz, NH, 1H), 8.00 (dd, J=4.1 and 1.4 Hz, 1H), 8.29 (d, J=4.1 Hz, 1H), 8.83 (d, J=1.3 Hz, 1H).

Example 1.55: Preparation of (1aS,5aS)-2-(4-Chloro-pyridin-2-yl)-1a,2,5,5a-tetrahydro-1H-2,3-diaza-cyclopropa[a]pentalene-4-carboxylic Acid (2-Fluoro-1-fluoromethyl-1-hydroxymethyl-ethyl)-amide (Compound 889)

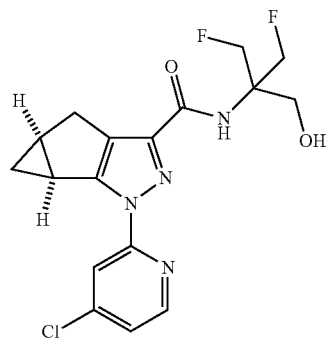 [SMILES: O=C(NC(CO)(CF)CF)c1nn(-c2cc(Cl)ccn2)c2c1C[C@@H]1C[C@H]21]

Step A: Preparation of Methyl 2-Amino-3-fluoro-2-(fluoromethyl)propanoate

The title compound was prepared as described in *Synthesis* 1994 vol. 7 pp. 701-702.

Step B: Preparation of 2-{[(1aS,5aS)-2-(4-Chloro-pyridin-2-yl)-1a,2,5,5a-tetrahydro-1H-2,3-diaza-cyclopropa[a]pentalene-4-carbonyl]-amino}-3-fluoro-2-fluoromethyl-propionic Acid Methyl Ester To a solution of (1aS,5aS)-2-(4-chloro-pyridin-2-yl)-1a,2,5,5a-tetrahydro-1H-2,3-diaza-cyclopropa[a]pentalene-4-carboxylic acid (100 mg, 0.363 mmol), methyl 2-amino-3-fluoro-2-(fluoromethyl)propanoate hydrochloride (76 mg, 0.399 mmol) and triethylamine (0.101 mL, 0.725 mmol) in DMF (2 mL) was added HATU (138 mg, 0.363 mmol). The reaction was stirred at 50° C. for 2 h, then concentrated. The residue was purified by silica gel flash chromatography to give the title compound as a white solid. LCMS m/z=411.2 [M+H]+; 1H NMR (400 MHz, CDCl3) δ 0.46 (td, J=4.7, 3.3 Hz, 1H), 1.25 (td, J=7.8, 4.7 Hz, 1H), 2.24-2.30 (m, 1H), 2.79-2.84 (m, 1H), 2.89 (d, J=16.8 Hz, 1H), 2.99 (dd, J=16.4, 6.2 Hz, 1H), 3.89 (s, 3H), 4.81-5.12 (m, 4H), 7.22 (dd, J=5.3, 1.8 Hz, 1H), 7.51 (s, 1H), 7.98 (d, J=1.8 Hz, 1H), 8.36 (d, J=5.3 Hz, 1H).

Step C: Preparation of (1aS,5aS)-2-(4-Chloro-pyridin-2-yl)-1a,2,5,5a-tetrahydro-1H-2,3-diaza-cyclopropa[a]pentalene-4-carboxylic Acid (2-Fluoro-1-fluoromethyl-1-hydroxymethyl-ethyl)-amide To a solution of 2-{[(1aS,5aS)-2-(4-chloro-pyridin-2-yl)-1a,2,5,5a-tetrahydro-1H-2,3-diaza-cyclopropa[a]pentalene-4-carbonyl]-amino}-3-fluoro-2-fluoromethyl-propionic acid methyl ester (130 mg, 0.316 mmol) in THF (2 mL) and MeOH (0.200 mL) was added sodium borohydride (23.94 mg, 0.633 mmol). The reaction was stirred at 23° C. for 2 h. Saturated aqueous NaHCO3 (15 mL) was added. The mixture was extracted with dichloromethane (3×15 mL). The combined organic extracts were dried (MgSO4), filtered, then concentrated. The residue was purified by silica gel flash chromatography to give the title compound (106 mg) as a white solid. LCMS m/z=383.2 [M+H]+; 1H NMR (400 MHz, CDCl3) δ 0.46 (td, J=4.6, 3.5 Hz, 1H), 1.27 (td, J=8.0, 4.9 Hz, 1H), 2.25-2.31 (m, 1H), 2.80-2.85 (m, 1H), 2.89 (d, J=16.9 Hz, 1H), 2.99 (dd, J=16.6, 6.3 Hz, 1H), 3.96 (d, J=5.9 Hz, 2H), 4.25 (t, J=6.8 Hz, 1H), 4.55-4.84 (m, 4H), 7.23 (dd, J=5.3, 1.8 Hz, 1H), 7.27 (s, 1H), 7.92 (d, J=1.6 Hz, 1H), 8.36 (d, J=5.3 Hz, 1H).

Example 1.56: Preparation of (1aS,5aS)-2-(4-Cyano-pyridin-2-yl)-1a,2,5,5a-tetrahydro-1H-2,3-diaza-cyclopropa[a]pentalene-4-carboxylic Acid ((S)-3,3,3-Trifluoro-1-hydroxymethyl-propyl)-amide (Compound 891)

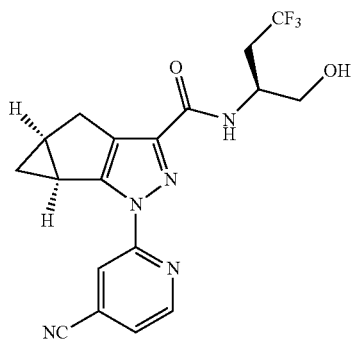 [SMILES: N#Cc1ccnc(-n2nc(C(=O)N[C@H](CO)CC(F)(F)F)c3c2[C@H]2C[C@H]2C3)c1]

Step A: Preparation of (1aS,5aS)-2-(4-Bromo-pyridin-2-yl)-1a,2,5,5a-tetrahydro-1H-2,3-diaza-cyclopropa[a]pentalene-4-carboxylic Acid To a solution of (1aS,5aS)-2-(4-bromo-pyridin-2-yl)-1a,2,5,5a-tetrahydro-1H-2,3-diaza-cyclopropa[a]pentalene-4-carboxylic acid ethyl ester (1.00 g, 2.87 mmol) in methanol (5 mL) and THF (5.00 mL) was added a 2.0 M aqueous solution of sodium hydroxide (2.87 mL, 5.74 mmol). The reaction was stirred at 23° C. for 2 h. The organic solvents were removed by distillation. The remaining aqueous solution was diluted with water (20 mL) then acidified to pH ~2 by addition of 6 M aq. HCl. The resulting precipitate was collected by filtration, rinsed with water, then dried under vacuum to give the title compound (0.87 g) as a white solid. LCMS m/z=320.0 [M+H]$^+$.

Step B: Preparation of (1aS,5aS)-2-(4-Cyano-pyridin-2-yl)-1a,2,5,5a-tetrahydro-1H-2,3-diaza-cyclopropa[a]pentalene-4-carboxylic Acid (1aS,5aS)-2-(4-Bromo-pyridin-2-yl)-1a,2,5,5a-tetrahydro-1H-2,3-diaza-cyclopropa[a]pentalene-4-carboxylic acid (0.87 g, 2.72 mmol) was dissolved in DMA (10 mL). Sodium hydride (0.109 g, 2.72 mmol) was added, and nitrogen was bubbled through the mixture for 10 min. Zinc(II) cyanide (0.638 g, 5.44 mmol) and palladium tetrakistriphenylphosphine (0.157 g, 0.136 mmol) were added. The reaction was stirred under microwave heating in a sealed tube at 120° C. for 2 h. Water (25 mL) and 6 M aqueous HCl (1 mL) were added. The mixture was extracted with 25% iPrOH/dichloromethane (3×25 mL) (The biphasic mixture was filtered after the first extraction to clear up an emulsion). The combined organic extracts were dried (MgSO$_4$), filtered, then concentrated. The residue was purified by flash chromatography to give the title compound (0.68 g) as a tan solid. LCMS m/z=267.0 [M+H]$^+$.

Step C: Preparation of (S)-2-Amino-4,4,4-trifluorobutan-1-ol

To an ice-cooled solution of (S)-2-(tert-butoxycarbonylamino)-4,4,4-trifluorobutanoic acid (1.0 g, 3.89 mmol) and N-ethyl-N-isopropylpropan-2-amine (0.813 mL, 4.67 mmol) in THF (15 mL) was added dropwise ethyl chloroformate (0.409 mL, 4.28 mmol). The cooling bath was removed and the mixture was stirred at 23° C. for 2 h. The mixture was filtered to remove the white precipitate, and the filtrate was treated with a 2 M THF solution of lithium borohydride (1.944 mL, 3.89 mmol) resulting in vigorous gas evolution. The mixture was stirred at room temperature for 2 h. Brine (25 mL) was added. The mixture was extracted with ethyl acetate (3×25 mL). The combined organic extracts were dried (MgSO$_4$), filtered, then concentrated under vacuum. The residue was purified by silica gel flash chromatography to give (S)-tert-butyl 4,4,4-trifluoro-1-hydroxybutan-2-ylcarbamate (0.80 g) as a white solid. This solid was treated with 4 M HCl in dioxane (10 mL) for 60 min then concentrated to give the HCl salt of the title compound (0.54 g) as a white solid. $^1$H NMR (400 MHz, CD$_3$OD) δ 2.55-2.79 (m, 2H), 3.42 (bs, 1H), 3.54 (dd, J=11.6, 5.6 Hz, 1H), 3.66 (dd, J=11.6, 3.9 Hz, 1H), 3.53 (bs, 1H), 8.27 (bs, 3H).

Step D: Preparation of (1aS,5aS)-2-(4-Cyano-pyridin-2-yl)-1a,2,5,5a-tetrahydro-1H-2,3-diaza-cyclopropa[a]pentalene-4-carboxylic Acid ((S)-3,3,3-Trifluoro-1-hydroxymethyl-propyl)-amide To a solution of (1aS,5aS)-2-(4-cyano-pyridin-2-yl)-1a,2,5,5a-tetrahydro-1H-2,3-diaza-cyclopropa[a]pentalene-4-carboxylic acid (75 mg, 0.282 mmol) and triethylamine (0.118 mL, 0.845 mmol) in DMF (1 mL) was added HATU (118 mg, 0.310 mmol). The reaction was stirred at 23° C., for 5 min, then was added (S)-2-amino-4,4,4-trifluorobutan-1-ol hydrochloride (55.6 mg, 0.310 mmol). The reaction was stirred at 23° C. for 30 min, then concentrated. The residue was purified by silica gel flash chromatography to give the title compound (86 mg) as a white solid. LCMS m/z=392.4 [M+H]$^+$; $^1$H NMR (400 MHz, CDCl$_3$) δ 0.47 (td, J=4.7, 3.2 Hz, 1H), 1.27 (td, J=8.1, 4.8 Hz, 1H), 2.26-2.32 (m, 1H), 2.54-2.69 (m, 3H), 2.77-2.82 (m, 1H), 2.93 (d, J=16.8 Hz, 1H), 3.01 (dd, J=16.6, 6.1 Hz, 1H), 3.88 (d, J=2.9 Hz, 2H), 4.33-4.41 (m, 1H), 7.23 (d, J=8.2 Hz, 1H), 7.41 (dd, J=5.1, 1.4 Hz, 1H), 8.17 (t, J=0.8 Hz, 1H), 8.62 (dd, J=5.1, 0.6 Hz, 1H).

Example 1.57: Preparation of (1aR,5aR)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 629)

To a solution of (1aR,5aR)-2-pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide (1.024 g, 3.0 mmol) in formic acid (10 mL) was added hydrogen peroxide (35% in water, 0.582 mL, 6.00 mmol). The reaction was stirred at 45° C. for 72 h and concentrated. The residue was dissolved in THF/MeOH (40 mL/40 mL) and added lithium hydroxide (1.437 g, 60.0 mmol) in water (5 mL). The reaction was stirred at room temperature for 1 h and neutralized with NH$_4$Cl solution. After removal of the organic solvent, the mixture was extracted with EtOAc. The organics were purified by silica gel column chromatography. The resulting oil was treated with ACN (5 mL) and concentrated to give the title compound (0.49 g) as a white solid. LCMS m/z=358.4 [M+H]$^+$; $^1$H NMR (400 MHz, CDCl$_3$) δ ppm 0.47 (dd, J=8.0 and 4.7 Hz, 1H), 1.05 (s, 9H), 1.28 (td, J=7.9 and 5.0 Hz, 1H), 2.28-2.32 (m, 1H), 2.72-2.76 (m, 1H), 2.92 (d, J=17.0 Hz, 1H), 3.02 (dd, J=16.7 and 6.4 Hz, 1H), 3.67 (dd, J=11.9 and 8.8 Hz, 1H), 3.92-3.98 (m, 2H), 6.97 (d, J=8.7 Hz, NH, 1H), 8.00 (dd, J=4.1 and 1.5 Hz, 1H), 8.28 (d, J=4.1 Hz, 1H), 8.79 (s, 1H).

Example 1.58: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Fluoromethyl-2,2-dimethyl-propyl)-amide (Compound 916)

Step A: Preparation of (S)-2-(Benzylamino)-3,3-dimethylbutan-1-ol (S)-2-Amino-3,3-dimethylbutan-1-ol (4.01 g, 34.2 mmol) was dissolved in benzene (120 mL). Benzaldehyde (3.65 mL, 35.9 mmol) and p-TsOH monohydrate (1.302 mg, 6.84 μmol) were added. The reaction mixture was heated at reflux for 5 h using Dean-Stark to remove water, the mixture was then concentrated. The residue was dissolved in anhydrous MeOH (100 mL), cooled down in an ice-water bath, and added sodium borohydride (1.942 g, 51.3 mmol) slowly. The reaction mixture was stirred for 30 min, quenched with 1 N NaOH solution, diluted with water, and extracted with ethyl acetate. The combined organics were washed with water, dried over anhydrous $Na_2SO_4$, filtered, then concentrated to give the title compound (5.77 g) as a colorless oil without further purification. LCMS m/z=208.2 [M+H]$^+$; $^1$H NMR (400 MHz, $CDCl_3$) δ 0.88 (s, 9H), 2.33 (dd, J=6.4 and 4.7 Hz, 1H), 3.34 (dd, J=10.6 and 6.4 Hz, 1H), 3.59 (dd, J=10.6 and 4.7 Hz, 1H), 3.76 and 3.85 (dd, J=12.8 Hz, 2H), 7.20-7.27 (m, 5H).

Step B: Preparation of (4S)-4-(tert-Butyl)-3-(phenylmethyl)-1,2,3-oxathiazolidine-2-oxide (S)-2-(Benzylamino)-3,3-dimethylbutan-1-ol (5.77 g, 27.8 mmol) in dry DCM (100 mL) was cooled down to −20° C., DIEA (19.39 ml, 111 mmol) was added, followed by thionyl chloride (2.228 ml, 30.6 mmol) in DCM (10 mL). The reaction mixture was stirred for 1 h at this temperature, then concentrated. The residue was purified by column chromatography to give the title compound (6.26 g) as a diastereomeric mixture. LCMS m/z=254.0 [M+H]$^+$.

Step C: Preparation of (4S)-4-(tert-Butyl)-3-(phenylmethyl)-1,2,3-oxathiazolidine-2,2-dioxide To a solution of (4S)-4-(tert-butyl)-3-(phenylmethyl)-1,2,3-oxathiazolidine-2-oxide (6.26 g, 24.71 mmol) in acetonitrile (30 mL) and water (30 mL) at 0° C. was added ruthenium chloride hydrate (5.13 mg, 0.025 mmol), followed by sodium periodate (7.93 g, 37.1 mmol). The reaction mixture was slowly warmed to room temperature and stirred for 3 h, diluted with water, extracted with ethyl acetate. The combined organics were washed with water, dried over anhydrous $Na_2SO_4$, filtered then concentrated to give the title compound (6.22 g) as an off-white solid. LCMS m/z=270.2 [M+H]$^+$; $^1$H NMR (400 MHz, $CDCl_3$) δ 1.00 (s, 9H), 3.25-3.30 (m, 1H), 4.31-4.40 (m, 2H), 4.47 and 4.55 (dd, J=15.2 Hz, 2H), 7.30-7.48 (m, 5H).

Step D: Preparation of (S)—N-Benzyl-1-fluoro-3,3-dimethylbutan-2-amine

To a solution of (4S)-4-(tert-butyl)-3-(phenylmethyl)-1,2,3-oxathiazolidine-2,2-dioxide (6.22 g, 23.09 mmol) in THF (100 mL) was added a 1 M solution of tetrabutylammonium fluoride in THF (46.2 ml, 46.2 mmol) at 0° C. The reaction mixture was warmed to room temperature and stirred overnight. Solvent was evaporated, and ether (50 mL) and 20% $H_2SO_4$ aqueous solution (20 mL) were added. The reaction mixture was stirred for 2 h at room temperature, diluted with water, neutralized with solid $NaHCO_3$ slowly then extracted with ethyl acetate. The combined organics were dried over anhydrous $Na_2SO_4$, filtered, then concentrated. The residue was purified by column chromatography to give the title compound (4.13 g) as a light yellow oil. LCMS m/z=210.4 [M+H]$^+$; $^1$H NMR (400 MHz, $CDCl_3$) δ 0.96 (s, 9H), 2.41 (dt, J=24.7 and 4.3 Hz, 1H), 3.76 (d, J=13.1 Hz, 1H), 4.01 (d, J=13.1 Hz, 1H), 4.39-4.72 (m, 2H), 7.23-7.38 (m, 5H).

Step E: Preparation of (S)-1-Fluoro-3,3-dimethylbutan-2-amine Hydrochloride

To a solution of (S)—N-benzyl-1-fluoro-3,3-dimethylbutan-2-amine (4.12 g, 19.68 mmol) in methanol (50 mL) was added 10% palladium on carbon (2.095 g, 1.968 mmol). The reaction mixture was shaken under $H_2$ atmosphere (60 Psi) for 24 h, a 1.25 M solution of HCl in ethanol (31.5 mL, 39.4 mmol) was added. The reaction mixture was stirred at room temperature for 1 h. The solid was filtered through Celite, washed with methanol. The filtrate was concentrated to give the title compound (3.1 g). $^1$H NMR (400 MHz, DMSO-$d_6$) δ 0.96 (s, 9H), 3.11-3.20 (m, 1H), 4.55-4.82 (m, 2H), 8.26 (s, 3H).

Step F: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Fluoromethyl-2,2-dimethyl-propyl)-amide The title compound was prepared in a manner similar to that described in Method UU, using Intermediate 5 and (S)-1-fluoro-3,3-dimethylbutan-2-amine hydrochloride. LCMS m/z=360.2 [M+H]$^+$; $^1$H NMR (400 MHz, $CDCl_3$) δ 0.50 (td, J=4.6 and 3.2 Hz, 1H), 1.05 (s, 9H), 1.25-1.30 (m, 1H), 2.27-2.35 (m, 1H), 2.72-2.77 (m, 1H), 2.95 (dt, J=16.8 and 0.7 Hz, 1H), 3.01 (dd, J=16.6 and 5.8 Hz, 1H), 4.03-4.15 (m, 1H), 4.48-4.74 (m, 2H), 7.04 (d, J=10.1 Hz, 1H), 7.99 (dd, J=4.1 and 1.5 Hz, 1H), 8.28 (dd, J=4.1 and 0.6 Hz, 1H), 8.80 (dd, J=1.5 and 0.7 Hz, 1H).

Example 1.59: Preparation of (1aS,5aS)-2-(4-Oxy-pyrazin-2-yl)-1a,2,5,5a-tetrahydro-1H-2,3-diaza-cyclopropa[a]pentalene-4-carboxylic Acid ((S)-1-Hydroxymethyl-2,2-dimethyl-propyl)-amide (Compound 699, Anhydrous Form)

To a 4 L reactor equipped with an overhead stirrer, chiller/heater, and a dropping funnel was added (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide (Compound 699, 145 g, 406 mmol), acetonitrile (205 mL, 3925 mmol), and water (290 mL). The mixture was heated to 60° C. and then stirred for 60 min. To the resulting reaction was added an additional amount of water (2900 mL), cooled to 0° C., and allowed to stir for 4 h. The mixture was filtered, the solids washed with water and dried under vacuum at 50° C. to provide Compound 699 as the anhydrous form, the material was characterized by PXRD (FIG. 10), DSC/TGA (FIG. 11), and DMS (FIG. 12.

Example 2: Homogeneous Time-Resolved Fluorescence (HTRF®) Assay for Direct cAMP Measurement A: $CB_2$ Assay Compounds were screened for agonists and inverse agonists of $CB_2$ receptor (e.g., human $CB_2$ receptor) using the HTRF® assay for direct cAMP measurement (Gabriel et al., *ASSAY and Drug Development Technologies*, 1:291-303, 2003) in recombinant CHO-K1 cells stably transfected with the $CB_2$ receptor. CHO-K1 cells were obtained from ATCC® (Manassas, VA; Catalog #CCL-61). An agonist of the $CB_2$ receptor was detected in the HTRF® assay for direct cAMP measurement as a compound which decreased cAMP concentration. An inverse agonist of the $CB_2$ receptor was detected in the HTRF® assay for direct cAMP measurement as a compound which increased cAMP concentration. The HTRF® assay also was used to determine $EC_{50}$ values for $CB_2$ receptor agonists and inverse agonists.

B: $CB_1$ Assay

Compounds were also screened for agonists and inverse agonists of the $CB_1$ receptor (e.g., human $CB_1$ receptor) using HTRF® assay for direct cAMP measurement (Gabriel et al., *ASSAY and Drug Development Technologies*, 1:291-303, 2003) in recombinant CHO-K1 cells stably transfected with the $CB_1$ receptor. CHO-K1 cells were obtained from ATCC® (Manassas, VA; Catalog #CCL-61). An agonist of the $CB_1$ receptor was detected in the HTRF® assay for direct cAMP measurement as a compound which decreased cAMP concentration. An inverse agonist of the $CB_1$ receptor was detected in the HTRF® assay for direct cAMP measurement as a compound which increased cAMP concentration. The HTRF® assay also was used to determine $EC_{50}$ values for $CB_1$ receptor agonists and inverse agonists.

Principle of the assay: The HTRF® assay kit was purchased from Cisbio-US, Inc. (Bedford, MA; Catalog #62AM4PEC). The HTRF® assay supported by the kit is a competitive immunoassay between endogenous cAMP produced by the CHO-K1 cells and tracer cAMP labeled with the dye d2. The tracer binding is visualized by a monoclonal anti-cAMP antibody labeled with Cryptate. The specific signal (i.e., fluorescence resonance energy transfer, FRET) is inversely proportional to the concentration of unlabeled cAMP in the standard or sample.

Standard curve: The fluorescence ratio (665 nm/620 nm) of the standards (0.17 to 712 nM cAMP) included in the assay was calculated and used to generate a cAMP standard curve according to the kit manufacturer's instructions. The fluorescence ratio of the samples (test compound or compound buffer) was calculated and used to deduce respective cAMP concentrations by reference to the cAMP standard curve.

Setup of the assay: HTRF® assay was carried out using a two-step protocol essentially according to the kit manufacturer's instructions, in 20 µL total volume per well in 384-well plate format (ProxiPlates; PerkinElmer, Fremont, CA; catalog #6008280). To each of the experimental wells was transferred 1500 recombinant CHO-K1 cells in 5 µL phosphate buffered saline containing calcium chloride and magnesium chloride (PBS+; Invitrogen, Carlsbad, CA; catalog #14040) followed by test compound in 5 µL assay buffer (PBS+ supplemented with 0.2% BSA, 4 µM forskolin and 1 mM IBMX (Sigma-Aldrich, St. Louis, MO; catalog #s A8806, F6886 and I5879 respectively). The plate was then incubated at room temperature for 1 h. To each well was then added 5 µL cAMP-d2 conjugate in lysis buffer and 5 µL Cryptate conjugate in lysis buffer according to the kit manufacturer's instructions. The plate was then further incubated at room temperature for 1 h, after which the assay plate was read.

Assay readout: The HTRF® readout was accomplished using a PHERAstar (BMG Labtech Inc., Durham, NC) or an EnVision™ (Perkin Elmer, Fremont CA) microplate reader. Certain compounds described herein had $hCB_1$ $EC_{50}$ values ranging from about 279 pM to about 76.47 µM in this assay and $hCB_2$ $EC_{50}$ values ranging from about 170 pM to about 44.72 µM in this assay. Certain other compounds described herein had $hCB_2$ $EC_{50}$ values ranging from about 94 pM to about 2.7 nM in this assay.

Example 3: PathHunter β-Arrestin Assay

A: $CB_2$ Assay

Compounds were screened for agonists of the human $CB_2$ receptor using the DiscoveRx PathHunter β-arrestin assay which measures the β-arrestin binding to the $CB_2$ receptor upon its activation. $CB_2$ was cloned into the pCMV-PK vector (DiscoveRx, Fremont, CA; catalog #93-0167) and transfected into the CHO-K1 EA-Arrestin parental cell line (DiscoveRx, Fremont, CA; catalog #93-0164). CHO-K1 positive clones stably expressing the $CB_2$-ProLink fusion protein were identified by their responses to the $CB_2$ agonist CP55,940. Clone #61 was chosen for its big agonist window and homogenous expression as detected by anti-HA flow cytometry.

Principle of the assay: The PathHunter-arrestin assay measures the interaction of β-arrestin with activated GPCRs using Enzyme Fragment Complementation (Yan et al., *J. Biomol. Screen.* 7: 451-459, 2002). A small, 42 amino acid β-galactosidase fragment, Prolink, is fused to the c-terminus of a GPCR, and β-arrestin is fused to the larger β-galactosidase fragment, EA (Enzyme Acceptor). Binding of β-arrestin to the activated GPCR causes the complementation of the two enzyme fragments, forming an active β-galactosidase enzyme which can be measured using the chemiluminescent PathHunter Flash Detection Kit (DiscoveRx, Fremont, CA: catalog #93-0001).

The assay: The stable CHO-K1 cells expressing $CB_2$-Prolink fusion protein were plated over night in 384-well plates (Optiplate 384-Plus, PerkinElmer, Fremont CA; catalog #6007299) at 5000 cells/5 µL/well in the Opti-MEM medium (Invitrogen, Carlsbad, CA; catalog #31985088) with 1% FBS. 5 uL of test compound diluted in Opti-MEM supplemented with 1% BSA was transferred to each well of the Optiplate. The plates were then incubated at 37° C./5% $CO_2$ for two hours. 12 µL of substrate prepared from the PathHunter Flash Detection Kit (DiscoveRx, Fremont, CA: catalog #93-0001) was transferred to each well of the Optiplate. The plate was then incubated in the dark at room temperature for 2 h, after which the assay plate was read.

Assay readout: β-Arrestin assay readout was accomplished using a PHERAstar (BMG Labtech Inc., Durham, NC) or an EnVision™ (PerkinElmer, Fremont CA) microplate reader.

B: $CB_1$ Assay

Compounds were screened for agonists of the human $CB_1$ receptor using the DiscoveRx PathHunter β-arrestin assay which measures the β-arrestin binding to the $CB_1$ receptor upon its activation. $CB_1$ was cloned into the pCMV-PK vector (DiscoveRx, Fremont, CA; catalog #93-0167) and transfected into the CHO-K1 EA-Arrestin parental cell line (DiscoveRx, Fremont, CA; catalog #93-0164). CHO-K1 positive clones stably expressing the $CB_1$-ProLink fusion protein were identified by their responses to the $CB_1$ agonist CP55,940. Clone #3 was chosen for its big agonist window and homogenous expression as detected by anti-HA flow cytometry Principle of the assay: The PathHunter β-arrestin assay measures the interaction of β-arrestin with activated GPCRs using Enzyme Fragment Complementation (Yan et al., *J. Biomol. Screen.* 7: 451-459, 2002). A small, 42 amino acid β-galactosidase fragment, Prolink, is fused to the c-terminus of a GPCR, and β-arrestin is fused to the larger β-galactosidase fragment, EA (Enzyme Acceptor). Binding of β-arrestin to the activated GPCR causes the complementation of the two enzyme fragments, forming an active β-galactosidase enzyme which can be measured using the chemiluminiescent PathHunter Flash Detection Kit (DiscoveRx, Fremont, CA: catalog #93-0001).

The assay: The stable CHO-K1 cells expressing $CB_1$-Prolink fusion protein were plated over night in 384-well plates (Optiplate 384-Plus, PerkinElmer, Fremont CA; catalog #6007299) at 5000 cells/5 μL/well in the Opti-MEM medium (Invitrogen, Carlsbad, CA; catalog #31985088) with 1% FBS. 5 uL of test compound diluted in Opti-MEM supplemented with 1% BSA was transferred to each well of the Optiplate. The plates were then incubated at 37° C./5% $CO_2$ for two h. 12 μL of substrate prepared from the PathHunter Flash Detection Kit (DiscoveRx, Fremont, CA: catalog #93-0001) was transferred to each well of the Optiplate. The plate was then incubated in the dark at room temperature for 2 h, after which the assay plate was read.

Assay readout: β-Arrestin assay readout was accomplished using a PHERAstar (BMG LABTECH Inc., Durham, NC) or EnVision (PerkinElmer, Fremont CA) microplate reader.

Certain compounds described herein had $hCB_1$ $EC_{50}$ values ranging from about 2.6 nM to about 89.06 μM in this assay and $hCB_2$ $EC_{50}$ values ranging from about 643 pM to about 7 μM in this assay. Certain other compounds described herein had $hCB_1$ $EC_{50}$ values ranging from about 10.9 nM to about 100 μM in this assay and $hCB_2$ $EC_{50}$ values ranging from about 384 pM to about 100 μM in this assay.

Each of Compounds 151, 174, 309, 515, 593, 625, 642, 644, 646, 667, 683, 684, 690, 696, 698, 699, 700, 703, 704, 722, 746, 764, 765, 766, 767, 820, 821, 828, 841, 848, 889, 891, 896, 897, 902, 904, 912, 913, 918, 919, 920, 921, 924, 926, 927, 930, and 931 had an $hCB_2EC_{50}$ value ranging from about 0.72 nM to about 3 μM. Compounds 264, 493, and 844 were not tested in this assay.

Certain compounds described herein and their corresponding $hCB_2EC_{50}$ values are shown below.

| Cmpd No. | $EC_{50}$ |
|---|---|
| 699 | 5.4 nM |
| 764 | 5.9 nM |
| 765 | 1.1 nM |
| 919 | 2.8 nM |
| 921 | 2.2 nM |
| 926 | 4.1 nM |

Example 4: Radioligand Binding Assay

Preparation of Membranes: HEK293 cells stably expressing human $CB_2$ receptor were collected, washed in ice cold PBS, and centrifuged at 48,000×g for 20 min at 4° C. The cell pellet was then collected, resuspended in wash buffer (20 mM HEPES, pH 7.4 and 1 mM EDTA), homogenized on ice using a Brinkman Polytron, and centrifuged at 48,000×g for 20 min at 4° C. The resultant pellet was resuspended in ice cold 20 mM HEPES, pH 7.4, homogenized again on ice, recentrifuged for 20 min at 4° C., and membrane pellets were then stored at −80° C. until needed.

[$^3$H]CP55,940 and [$^3$H]WIN55,212-2 Radioligand Binding Assays: Radioligand binding assays for human $CB_2$ receptors were performed using two different agonist radioligands, [$^3$H]CP55,940 and [$^3$H]WIN55,212-2 and similar assay conditions. For both assays, nonspecific binding was determined in the presence of 10 μM unlabeled compound. Competition experiments consisted of addition of 20 μL of assay buffer (50 mM Tris, pH 7.4, 2.5 mM EDTA, 5 mM $MgCl_2$, and 0.5 mg/mL of fatty acid free BSA) containing test compound (concentrations ranging from 1 pM to 100 μM), 25 μL of radioligand (1 nM final assay concentration for [$^3$H]CP55,904 and [$^3$H]WIN55,212-2), and 50 μL of membranes (20 μg/mL final protein for both assays). Incubations were conducted for 1 h at room temperature, assay plates were filtered under reduced pressure over GF/B filters, washed with assay buffer and dried overnight in a 50° C. oven. Then, 25 μL of BetaScint scintillation cocktail was added to each well, and plates were read in a Packard TopCount scintillation counter.

Certain compounds described herein had $hCB_1$ $K_i$ values ranging from about 124 nM to about 19.36 μM in this assay and $hCB_2$ $K_i$ values ranging from about 3.22 nM to about 4.69 μM in this assay.

Example 5: Paclitaxel-Induced Allodynia in Sprague Dawley Rats

The mitotic inhibitor, paclitaxel (Taxol®) is one of the most effective and frequently used chemotherapeutic agents for the treatment of solid tumors as well as ovarian and breast cancers. Therapy however is often associated with the unwanted side affects of painful peripheral neuropathy.

Animals: Male Sprague Dawley rats [200-250 g] (Harlan Laboratories Inc., Livermore, CA) were housed three per cage and maintained in a humidity-controlled (40-60%) and temperature-controlled (68-72° F.) facility on a 12 h:12 h light/dark cycle (lights on at 6:30 am) with free access to food (Harlan Teklad, Orange, CA, Rodent Diet 8604) and water. Rats were allowed one week of habituation to the animal facility before starting treatment.

Induction of Allodynia: Rats were treated intraperitoneally, with 2 mg/kg of paclitaxel (Sigma Aldrich, Saint Louis, MO) in 10% Cremophor vehicle (500 μL) on days 0, 2, 4, and 6.

Clinical scoring: Tactile allodynia was tested using von Frey filaments. Briefly, the von Frey assay was performed using the standardized up down method with von Frey filaments, that determine the tactile sensitivity of the paw. By applying the increasingly or decreasingly thicker filaments to the paw in a logarithmic scale of actual force, a linear scale of perceived intensity is determined.

Drug treatment: Eight days after the start of paclitaxel dosing, a baseline measurement (von Frey assay) was performed prior to dosing of compounds. The paclitaxel treated groups of rats (6 per group) were dosed orally, with vehicle (PEG400) or 10 mg/kg Compound 493. As a positive control, rats were dosed intraperitoneally with 100 mg/kg gabapentin in water. The dosing volume for oral and peritoneal treatment was 500 μL. The von Frey assay was performed to measure the efficacy of the test compound 30, 60 and 180 minutes after dosing. An increase in paw withdrawal threshold (PWT) by treatment with Compound 493 in comparison with vehicle and gabapentin was indicative of the test compound exhibiting therapeutic efficacy in paclitaxel model of cancer pain. The time course shows maximum efficacy at 1 h post-dosing. See FIG. 1.

Example 6: Powder X-Ray Diffraction

Powder X-ray Diffraction (PXRD) data were collected on an X'Pert PRO MPD powder diffractometer (PANalytical, Inc.) with a Cu source set at 45 kV and 40 mA, Cu(Kα) radiation and an X'Celerator detector. Samples were added to the sample holder and smoothed flat with a spatula and weigh paper. With the samples spinning, X-ray diffractograms were obtained by a 12-min scan over the 2-theta range 5-40°2θ. Diffraction data were viewed and analyzed with the X'Pert Data Viewer Software, version 1.0a and X'Pert HighScore Software, version 1.0b.

Example 7: Differential Scanning Calorimetry

Differential scanning calorimetry (DSC) studies were conducted using a TA Instruments, Q2000 at a heating rate 10° C./min. The instruments were calibrated for temperature and energy using the melting point and enthalpy of fusion of an indium standard. Thermal events (desolvation, melting, etc.) were evaluated using Universal Analysis 2000 software, version 4.1D, Build 4.1.0.16.

Example 8: Thermal Gravimetric Analysis

Thermogravimetric analyses (TGA) were conducted using a TA Instruments TGA Q500 or Q5000 at a heating rate 10° C./min. The instruments were calibrated using a standard weight for the balance, and Alumel and Nickel standards for the furnace (Curie point measurements). Thermal events such as weight-loss are calculated using the Universal Analysis 2000 software, version 4.1D, Build 4.1.0.16.

Example 9: Dynamic Moisture-Sorption Analysis

A dynamic moisture-sorption (DMS) study was conducted using a dynamic moisture-sorption analyzer, VII Corporation, SGA-100. The instrument was calibrated using polyvinyl pyrrolidone (PVP) and NaCl. Samples were prepared for DMS analysis by placing 5 mg to 20 mg of a sample in a tared sample holder. The sample was placed on the hang-down wire of the VTI balance. A drying step was run, typically at 40° C. and 0.5-1% RH for 1 h. The isotherm temperature is 25° C. Defined % RH holds typically ranged from 10% RH to 90% RH, with intervals of 10 to 20% RH. A % weight change smaller than 0.010% over 10 min, or up to 2 h, whichever occurred first, was required before continuing to the next % RH hold. The water content of the sample equilibrated as described above was determined at each % RH hold.

Figure 12:
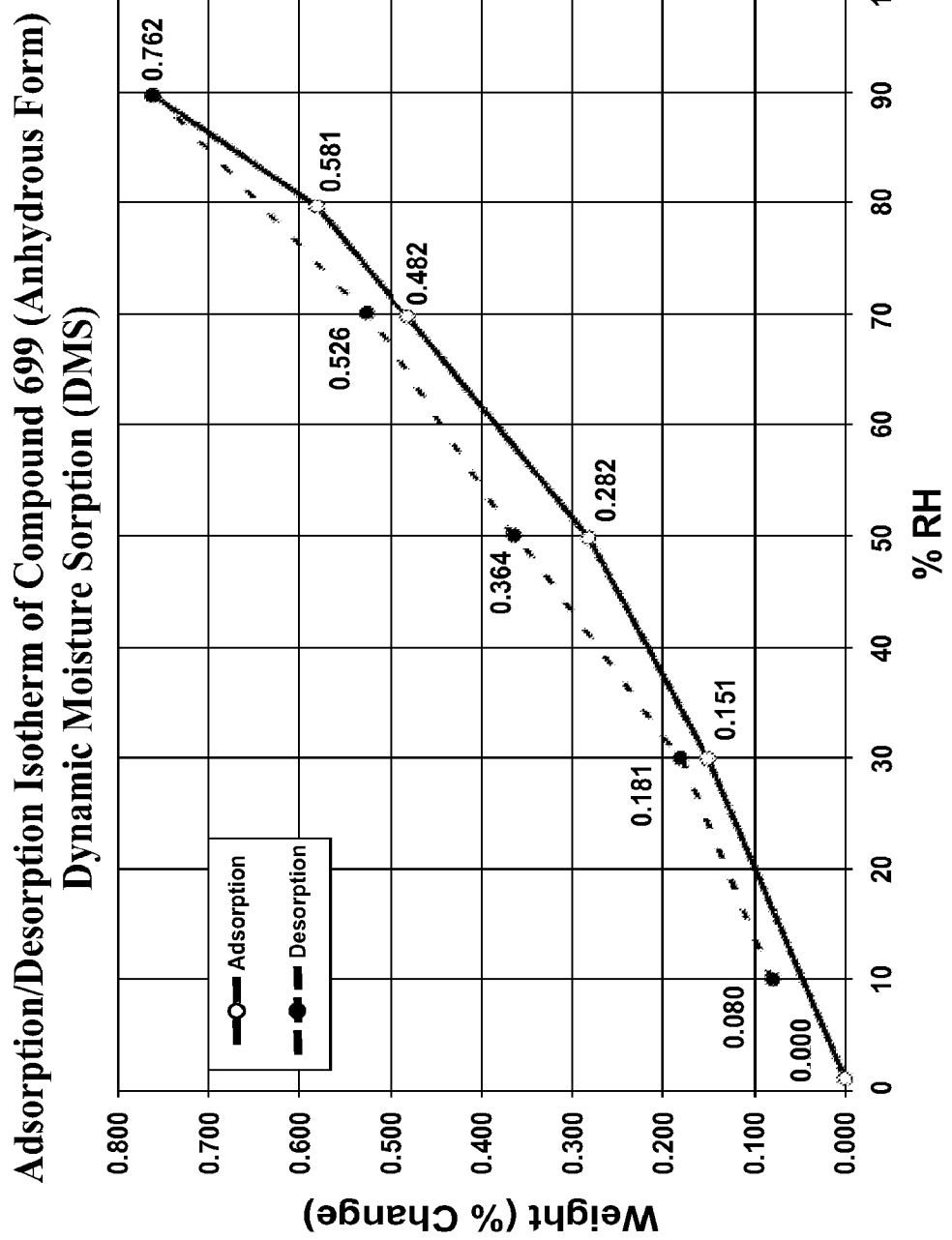
FIG. 12 shows an adsorption and desorption isotherm, Dyanmic Moisture Sorption (DMS), for a sample containing anhydrous crystalline form of Compound 699.

The DMS profile (adsorption/desorption isotherm) for the anhydrous crystalline form of Compound 699 is shown in FIG. 12. The corresponding data in tabular form is provided below:

| Elapsed Time (min) | Weight (mg) | Weight (% Change) | Sample Temperature | Sample RH (%) |
|---|---|---|---|---|
| 46.6 | 9.6782 | 0 | 25.46 | 1.1 |
| 71.4 | 9.6928 | 0.151 | 25.32 | 29.94 |
| 91.1 | 9.7055 | 0.282 | 25.31 | 49.86 |
| 111.2 | 9.7248 | 0.482 | 25.3 | 69.77 |
| 129.1 | 9.7344 | 0.581 | 25.29 | 79.70 |
| 160.1 | 9.7519 | 0.762 | 25.3 | 89.72 |
| 180.1 | 9.7291 | 0.526 | 25.30 | 70.11 |
| 200.1 | 9.7134 | 0.364 | 25.3 | 50.07 |
| 218.6 | 9.6957 | 0.181 | 25.29 | 29.99 |
| 234.4 | 9.6859 | 0.080 | 25.29 | 10.06 |

Those skilled in the art will recognize that various modifications, additions, substitutions, and variations to the illustrative examples set forth herein can be made without departing from the spirit of the invention and are, therefore, considered within the scope of the invention.

The invention claimed is:

1. A pharmaceutical composition, comprising a compound selected from compounds of Formula Ia and pharmaceutically acceptable salts, solvates, hydrates, and N-oxides thereof:

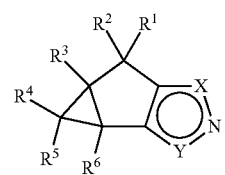

Ia wherein:
$R^1$, $R^2$, $R^3$, $R^4$, $R^5$, and $R^6$ are each independently selected from: H and $C_1$-$C_6$ alkyl;
X is $NR^7$ and Y is $CC(O) N(R^8) R^9$; or
X is $CC(O) N(R^8) R^9$ and Y is $NR^7$;
$R^7$ is —$R^{10}$—$R^{11}$—$R^{12}$-$R^{13}$, wherein:
$R^{10}$ is selected from: $C_1$-$C_6$ alkylene, heteroarylene, and heterocyclylene; or $R^{10}$ is absent;
$R^{11}$ is selected from: —C(O) NH— and $C_1$-$C_6$ alkylene; or $R^{11}$ is absent;
$R^{12}$ is $C_1$-$C_6$ alkylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;
$R^8$ is —$R^{14}$—$R^{15}$—$R^{16}$—$R^{17}$, wherein:
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;
$R^{15}$ is selected from: —C(O) NH—, —C(O)—, —C(O) O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;
$R^{16}$ is $C_1$-$C_6$ alkylene; or $R^{16}$ is absent; and
$R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and
$R^9$ is selected from: H, $C_1$-$C_6$ alkyl, and $C_3$-$C_7$ cycloalkyl; or
$R^8$ and $R^9$ together with the nitrogen atom to which they are both bonded form a group selected from: heterocyclyl and heterobicyclyl, each optionally substituted with one or more substituents selected from: Carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl,
and one or more anticancer agents selected from the group consisting of acivicin, aclarubicin, acodazole hydrochloride, acronine, adozelesin, aldesleukin, altretamine, ambomycin, ametantrone acetate, aminoglutethimide, amsacrine, anthramycin, asparaginase, asperlin, 4zacytidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, hydroxyurea, idarubicin hydrochloride, ifosfamide, ilmofosine, interleukin II, recombinant interleukin II, interferon alfa-2a, interferon alfa-2b, interferon alfa-n1, interferon alfa-n3, interferon beta-I a, interferon gamma-I b, iproplatin, irinotecan hydrochloride, lanreotide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, and zorubicin hydrochloride; in an amount that is therapeutically effective in treating cancer in an individual, wherein the cancer is not prostate cancer, leukemia, lymphoma, or a CNS tumor.

2. A kit comprising the pharmaceutical composition according to claim 1.

3. The kit according to claim 2, wherein said kit comprises a first package comprising the pharmaceutical composition comprising a compound selected from compounds of Formula Ia and pharmaceutically acceptable salts, solvates, hydrates, and N-oxides thereof:

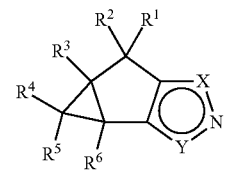

Ia wherein:
$R^1$, $R^2$, $R^3$, $R^4$, $R^5$, and $R^6$ are each independently selected from: H and $C_1$-$C_6$ alkyl;
X is $NR^7$ and Y is $CC(O)$ $N(R^8)$ $R^9$; or
X is $CC(O)$ $N(R^8)$ $R^9$ and Y is $NR^7$;
$R^7$ is —$R^{10}$—$R^{11}$—$R^{12}$—$R^{13}$, wherein:
$R^{10}$ is selected from: $C_1$-$C_6$ alkylene, heteroarylene, and heterocyclylene; or $R^{10}$ is absent;
$R^{11}$ is selected from: —$C(O)$ NH— and $C_1$-$C_6$ alkylene; or $R^{11}$ is absent;
$R^{12}$ is $C_1$-$C_6$ alkylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;

$R^8$ is $-R^{14}-R^{15}-R^{16}-R^{17}$, wherein:

$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;

$R^{15}$ is selected from: —C(O) NH—,—C(O)—,—C(O)O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;

$R^{16}$ is $C_1$-$C_6$ alkylene; or $R^{16}$ is absent; and $R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, amino, aryl, arylamino, aryloxy, $C_5$-$C_{11}$ bicycloalkyl, $C_3$-$C_7$ cycloalkyl, $C_3$-$C_7$ cycloalkylamino, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_2$-$C_8$ dialkylamino, $C_1$-$C_6$ haloalkoxy, $C_1$-$C_6$ haloalkyl, halogen, heteroaryl, heterocyclyl, and hydroxyl; and $R^9$ is selected from: H, $C_1$-$C_6$ alkyl, and $C_3$-$C_7$ cycloalkyl; or $R^8$ and $R^9$ together with the nitrogen atom to which they are both bonded form a group selected from: heterocyclyl and heterobicyclyl, each optionally substituted with one or more substituents selected from: Carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl, and a second package comprising one or more anticancer agents selected from the group consisting of acivicin, aclarubicin, acodazole hydrochloride, acronine, adozelesin, aldesleukin, altretamine, ambomycin, ametantrone acetate, aminoglutethimide, amsacrine, anthramycin, asparaginase, asperlin, 7zacytidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, hydroxyurea, idarubicin hydrochloride, ifosfamide, ilmofosine, interleukin II, recombinant interleukin II, interferon alfa-2a, interferon alfa-2b, interferon alfa-n1, interferon alfa-n3, interferon beta-I a, interferon gamma-I b, iproplatin, irinotecan hydrochloride, lanreotide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, and zorubicin hydrochloride or a pharmaceutical composition thereof.

4. The pharmaceutical composition according to claim 1, wherein the amount of the compound selected from compounds of Formula Ia and pharmaceutically acceptable salts, solvates, hydrates, and N-oxides thereof alone and the amount of the one or more known anticancer agents alone are therapeutically ineffective.

5. The pharmaceutical composition according to claim 1, wherein the compound selected from compounds of Formula Ia and pharmaceutically acceptable salts, solvates, hydrates, and N-oxides thereof and the one or more known anticancer agents are admixed with a pharmaceutically acceptable carrier.

6. The pharmaceutical composition according to claim 1, wherein the individual is a human.

7. The pharmaceutical composition according to claim 1, wherein the compound selected from compounds of Formula Ia and pharmaceutically acceptable salts, solvates, hydrates, and N-oxides thereof and the one or more known anticancer agents are each admixed with a different pharmaceutically acceptable carrier.

8. The pharmaceutical composition according to claim 1, wherein the cancer is chosen from: astrocytoma, brain cancers, breast cancer, colorectal cancer, glioblastoma multiforme, glioma, intestinal cancer, liver cancer, lung cancer, skin, neuroglioma, pancreatic cancer, and thyroid cancer.

9. The pharmaceutical composition according to claim 1, wherein the cancer is chosen from: pancreatic cancer, lung cancer, and breast cancer.

10. The pharmaceutical composition according to claim 1, wherein the cancer is melanoma.

11. The pharmaceutical composition according to claim 9, wherein the breast cancer is estrogen receptor (ER)-negative breast tumor.

12. The pharmaceutical composition according to claim 1, wherein the compound selected from compounds of Formula Ia and pharmaceutically acceptable salts, solvates, hydrates, and N-oxides thereof is selected from compounds of Formula Ie and pharmaceutically acceptable salts, solvates, hydrates, and N-oxides thereof:

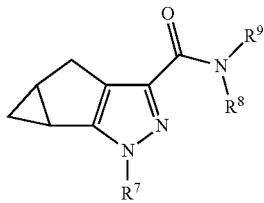

Ie wherein:
$R^7$ is —$R^{10}$—$R^{11}$—$R^{12}$—$R^{13}$, wherein:
$R^{10}$ is selected from: $C_1$-$C_6$ alkylene, heteroarylene, and heterocyclylene; or $R^{10}$ is absent;
$R^{11}$ is selected from: —C(O) NH— and $C_1$-$C_6$ alkylene; or $R^{11}$ is absent;
$R^{12}$ is $C_1$-$C_6$ alkylene; or $R^{12}$ is absent; and
$R^{13}$ is selected from: $C_1$-$C_6$ alkyl, aryl, $C_3$-$C_7$ cycloalkyl, heteroaryl, heterocyclyl, and hydroxyl; wherein said $C_1$-$C_6$ alkyl, aryl, and heteroaryl are each optionally substituted with one or two substituents selected from: $C_1$-$C_6$ alkoxy, $C_1$-$C_6$ alkyl, $C_1$-$C_6$ alkylamino, $C_1$-$C_6$ alkylsulfonyl, amino, $C_3$-$C_7$ cycloalkyl, cyano, $C_2$-$C_8$ dialkylamino, $C_1$-$C_6$ haloalkyl, halogen, and hydroxyl;
$R^8$ is —$R^{14}$—$R^{15}$—$R^{16}$-$R^{17}$, wherein:
$R^{14}$ is selected from: $C_1$-$C_6$ alkylene, $C_3$-$C_7$ cycloalkenylene, $C_3$-$C_7$ cycloalkylene, heteroarylene, and heterocyclylene; wherein said $C_1$-$C_6$ alkylene and heterocyclylene are each optionally substituted with one or more substituents selected from: $C_1$-$C_6$ alkoxycarbonyl, $C_1$-$C_6$ alkyl, $C_3$-$C_7$ cycloalkyl, aryl, carboxy, heteroaryl, heterocyclyl, and hydroxyl; wherein said $C_1$-$C_6$ alkyl and aryl are optionally substituted with one substituent selected from: $C_1$-$C_6$ alkoxy, aryl, halogen, heteroaryl, and hydroxyl; or $R^{14}$ is absent;
$R^{15}$ is selected from: —C(O) NH—,—C(O)—,—C(O) O—, $C_1$-$C_6$ alkylene, $C_3$-$C_7$ cycloalkylene, heteroarylene, and heterocyclylene; wherein said heterocyclylene is optionally substituted with $C_1$-$C_6$ alkyl; or $R^{15}$ is absent;
$R^{16}$ is $C_1$-$C_6$ alkylene; or $R^{16}$ is absent; and
$R^{17}$ is selected from: H, $C_1$-$C_6$ alkoxy, $C_1$-$C_6$ alkyl, $C_1$-$C_6$ alkylamino, $C_1$-$C_6$ alkylcarboxamide, $C_2$-$C_6$ alkynyl, ureyl, amino, aryl, arylamino, arylcarbonyl, aryloxy, carbo-$C_1$-$C_6$-alkoxy, carboxamide, carboxy, cyano, $C_3$-$C_7$ cycloalkyl, $C_5$-$C_{11}$ bicycloalkyl, $C_3$-$C_7$ cycloalkylamino, $C_2$-$C_8$ dialkylamino, $C_2$-$C_8$ dialkylsulfonamide, $C_1$-$C_6$ haloalkyl, heteroaryl, heteroaryloxy, heterobicyclyl, heterocyclyl, hydroxyl, and phosphonooxy; wherein said $C_1$-$C_6$ alkylamino, aryl, arylamino, aryloxy, $C_5$-$C_{11}$ bicycloalkyl, $C_3$-$C_7$ cycloalkyl, heteroaryl, heterobicyclyl, heterocyclyl, and ureyl are each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylsulfonyl, amino, aryl, carboxy, cyano, $C_3$-$C_7$ cycloalkyl, $C_3$-$C_7$ cycloalkylamino, $C_2$-$C_8$ dialkylamino, $C_1$-$C_6$ haloalkoxy, $C_1$-$C_6$ haloalkyl, halogen, heteroaryl, heterocyclyl, and hydroxyl; and
$R^9$ is selected from: H, $C_1$-$C_6$ alkyl, and $C_3$-$C_7$ cycloalkyl; or
$R^8$ and $R^9$ together with the nitrogen atom to which they are both bonded form a group selected from: heterocyclyl and heterobicyclyl, each optionally substituted with one or more substituents selected from: carbo-$C_1$-$C_6$-alkoxy, $C_1$-$C_6$ alkoxy, $C_1$-$C_6$ alkyl, aryl, carbo-$C_1$-$C_6$-alkoxy, $C_1$-$C_6$ haloalkyl, halogen, heteroaryl, heteroaryloxy, heterocyclyl, and hydroxyl; wherein said aryl, $C_1$-$C_6$ alkyl, and heteroaryl are optionally substituted with one substituent selected from: $C_3$-$C_7$ cycloalkyl, $C_1$-$C_6$ alkoxy, halogen, and hydroxyl.

13. The pharmaceutical composition according to claim 1, wherein the compound selected from compounds of Formula Ia and pharmaceutically acceptable salts, solvates, hydrates, and N-oxides thereof is selected from the following compounds and pharmaceutically acceptable salts, solvates, and hydrates thereof:

Compound 151: (1aR,5aR)-2-(5-Chloro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

Compound 174: (1aR,5aR)-2-(2,4-Dichloro-phenyl)-1a,2,5,5a-tetrahydro-1H-2,3-diaza-cyclopropa[a]pentalene-4-carboxylic acid (1-hydroxymethyl-cyclopropyl)-amide;

Compound 264: (1aR,5aR)-2-(5-Cyano-pyrazin-2-yl)-1a,2,5,5a-tetrahydro-1H-2,3-diaza-cyclopropa[a]pentalene-4-carboxylic acid (2-hydroxy-1,1-dimethyl-ethyl)-amide;

Compound 309: (1aR,5aR)-2-(5-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

Compound 493: (1aR,5aR)-2-(2,4-Difluoro-phenyl)-1a,2,5,5a-tetrahydro-1H-2,3-diaza-cyclopropa[a]pentalene-4-carboxylic acid (2-hydroxy-1,1-dimethyl-ethyl)-amide;

Compound 515: 1-(2,4-Difluoro-phenyl)-3b,4,4a,5-tetrahydro-1H-cyclopropa[3,4] cyclopenta[1,2-c]pyrazole-3-carboxylic acid (2-hydroxy-1,1-dimethyl-ethyl)-amide;

Compound 593: (1aR,5aR)-2-Pyrazin-2-yl-1a,2,5,5a-tetrahydro-1H-2,3-diaza-cyclopropa[a]pentalene-4-carboxylic acid tert-butylamide;

Compound 625: (1aR,5aR)-2-(4-Chloro-pyridin-2-yl)-1a,2,5,5a-tetrahydro-1H-2,3-diaza-cyclopropa[a]pentalene-4-carboxylic acid (cyano-dimethyl-methyl)-amide;

Compound 642: (1aR,5aR)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide;

Compound 644: (1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide;

Compound 646: Phosphoric acid mono-(2-{[(1aR,5aR)-2-(4-cyano-pyridin-2-yl)-1a,2,5,5a-tetrahydro-1H-2,3-diaza-cyclopropa[a]pentalene-4-carbonyl]-amino}-2-methyl-propyl) ester;

Compound 667: (1aR,5aR)-2-Pyrazin-2-yl-1a,2,5,5a-tetrahydro-1H-2,3-diaza-cyclopropa[a]pentalene-4-carboxylic acid [2,2-dimethyl-1-((S)-methylcarbamoyl)-propyl]-amide;

Compound 683: Phosphoric acid mono-{(S)-3,3-dimethyl-2-[((1aR,5aR)-2-pyrazin-2-yl-1a,2,5,5a-tetrahydro-1H-2,3-diaza-cyclopropa[a]pentalene-4-carbonyl)-amino]-butyl}ester;

Compound 684: (1aR,5aR)-2-Pyrazin-2-yl-1a,2,5,5a-tetrahydro-1H-2,3-diaza-cyclopropa[a]pentalene-4-carboxylic acid ((S)-2-hydroxy-1-tetrahydro-pyran-4-yl-ethyl)-amide;

Compound 690: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide;

Compound 696: (1aS,5aS)-2-Pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide;

Compound 698: (1aR,5aR)-2-(4-Oxy-pyrazin-2-yl)-1a,2,5,5a-tetrahydro-1H-2,3-diaza-cyclopropa[a]pentalene-4-carboxylic acid (1-hydroxymethyl-cyclobutyl)-amide;

Compound 699: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide;

Compound 700: (1aS,5aS)-2-(4-Oxy-pyrazin-2-yl)-1a,2,5,5a-tetrahydro-1H-2,3-diaza-cyclopropa[a]pentalene-4-carboxylic acid (1-pyridin-2-yl-cyclobutyl)-amide;

Compound 703: Phosphoric acid mono-((S)-3,3-dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester;

Compound 704: (1aR,5aR)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-methylcarbamoyl-propyl)-amide;

Compound 722: (1aR,5aR)-2-(4-Oxy-pyrazin-2-yl)-1a,2,5,5a-tetrahydro-1H-2,3-diaza-cyclopropa[a]pentalene-4-carboxylic acid ((S)-methylcarbamoyl-phenyl-methyl)-amide;

Compound 746: (S)-3,3-Dimethyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyric acid methyl ester;

Compound 764: (1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclopropyl)-amide;

Compound 765: (1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclobutyl)-amide;

Compound 766: (1aS,5aS)-2-(4-Oxy-pyrazin-2-yl)-1a,2,5,5a-tetrahydro-1H-2,3-diaza-cyclopropa[a]pentalene-4-carboxylic acid ((R)-2,2-dimethyl-1-pyridin-2-yl-propyl)-amide;

Compound 767: (1aS,5aS)-2-(4-Oxy-pyrazin-2-yl)-1a,2,5,5a-tetrahydro-1H-2,3-diaza-cyclopropa[a]pentalene-4-carboxylic acid ((S)-2,2-dimethyl-1-pyridin-2-yl-propyl)-amide;

Compound 820: (1aR,5aR)-2-(4-Cyano-pyridin-2-yl)-1a,2,5,5a-tetrahydro-1H-2,3-diaza-cyclopropa[a]pentalene-4-carboxylic acid (2-hydroxy-1-hydroxymethyl-1-methyl-ethyl)-amide;

Compound 821: (1aR,5aR)-2-(4-Oxy-pyrazin-2-yl)-1a,2,5,5a-tetrahydro-1H-2,3-diaza-cyclopropa[a]pentalene-4-carboxylic acid (1-methyl-cyclobutyl)-amide;

Compound 828: (1aR,5aR)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide;

Compound 841: (1aR,5aR)-2-(4-Oxy-pyrazin-2-yl)-1a,2,5,5a-tetrahydro-1H-2,3-diaza-cyclopropa[a]pentalene-4-carboxylic acid [(S)-2-hydroxy-1-(tetrahydro-pyran-4-yl)-ethyl]-amide;

Compound 844: (1aR,5aR)-Pentanedioic acid mono-((S)-3-methyl-2-{[(1aR,5aR)-2-(4-oxy-pyrazin-2-yl)-1a,2,5,5a-tetrahydro-1H-2,3-diaza-cyclopropa[a]pentalene-4-carbonyl]-amino}-butyl) ester;

Compound 848: (1aS,5aS)—(S)-2-Amino-3-methyl-butyric acid(S)-3,3-dimethyl-2-{[2-(4-oxy-pyrazin-2-yl)-1a,2,5,5a-tetrahydro-1H-2,3-diaza-cyclopropa[a]pentalene-4-carbonyl]-amino}-butyl ester;

Compound 889: (1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1-fluoromethyl-1-hydroxymethyl-ethyl)-amide;

Compound 891: (1aS,5aS)-2-(4-Cyano-pyridin-2-yl)-1a,2,5,5a-tetrahydro-1H-2,3-diaza-cyclopropa[a]pentalene-4-carboxylic acid ((S)-3,3,3-trifluoro-1-hydroxymethyl-propyl)-amide;

Compound 896: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2-methyl-propyl)-amide;

Compound 897: (1aS,5aS)-2-(4-Chloro-pyridin-2-yl)-1a,2,5,5a-tetrahydro-1H-2,3-diaza-cyclopropa[a]pentalene-4-carboxylic acid (2-fluoro-1,1-dimethyl-ethyl)-amide;

Compound 902: (1aS,5aS)-2-(4-Oxy-pyrazin-2-yl)-1a,2,5,5a-tetrahydro-1H-2,3-diaza-cyclopropa[a]pentalene-4-carboxylic acid N'-tert-butyl-hydrazide;

Compound 904: (1aS,5aS)-2-(4-Oxy-pyrazin-2-yl)-1a,2,5,5a-tetrahydro-1H-2,3-diaza-cyclopropa[a]pentalene-4-carboxylic acid (2-fluoro-1,1-dimethyl-ethyl)-amide;

Compound 912: (1aS,5aS)-2-(4-Oxy-pyrazin-2-yl)-1a,2,5,5a-tetrahydro-1H-2,3-diaza-cyclopropa[a]pentalene-4-carboxylic acid ((R)-1,2-dimethyl-propyl)-amide;

Compound 913: (1aS,5aS)-2-(4-Oxy-pyrazin-2-yl)-1a,2,5,5a-tetrahydro-1H-2,3-diaza-cyclopropa[a]pentalene-4-carboxylic acid ((S)-2-hydroxy-1-phenyl-ethyl)-amide;

Compound 918: (1aR,5aR)-2-(4-Oxy-pyrazin-2-yl)-1a,2,5,5a-tetrahydro-1H-2,3-diaza-cyclopropa[a]pentalene-4-carboxylic acid ((S)-1-fluoromethyl-2,2-dimethyl-propyl)-amide;

Compound 920: (1aS,5aS)-2-(4-Oxy-pyrazin-2-yl)-1a,2,5,5a-tetrahydro-1H-2,3-diaza-cyclopropa[a]pentalene-4-carboxylic acid ((1S,2S)-2-hydroxy-indan-1-yl)-amide;

Compound 921: (1aS,5aS)-2-(4-Oxy-pyrazin-2-yl)-1a,2,5,5a-tetrahydro-1H-2,3-diaza-cyclopropa[a]pentalene-4-carboxylic acid ((1S,2R)-2-hydroxy-indan-1-yl)-amide;

Compound 924: (1aS,5aS)-2-(4-Oxy-pyrazin-2-yl)-1a,2,5,5a-tetrahydro-1H-2,3-diaza-cyclopropa[a]pentalene-4-carboxylic acid (1-fluoromethyl-cyclobutyl)-amide;

Compound 926: (1aS,5aS)-2-Pyrazin-2-yl-1a,2,5,5a-tetrahydro-1H-2,3-diaza-cyclopropa[a]pentalene-4-carboxylic acid (1-trifluoromethyl-cyclobutyl)-amide;

Compound 927: (1aS,5aS)-2-Pyrazin-2-yl-1a,2,5,5a-tetrahydro-1H-2,3-diaza-cyclopropa[a]pentalene-4-carboxylic acid (2,2,2-trifluoro-1,1-dimethyl-ethyl)-amide;

Compound 930: (1aS,5aS)-2-Pyrazin-2-yl-1a,2,5,5a-tetrahydro-1H-2,3-diaza-cyclopropa[a]pentalene-4-carboxylic acid (1-trifluoromethyl-cyclopropyl)-amide; and Compound 931: (1aR,5aR)-2-(4-Fluoro-pyridin-2-yl)-1a,2,5,5a-tetrahydro-1H-2,3-diaza-cyclopropa[a]pentalene-4-carboxylic acid (2-hydroxy-1,1-dimethyl-ethyl)-amide.

14. The pharmaceutical composition according to claim 1, wherein the compound selected from compounds of Formula Ia and pharmaceutically acceptable salts, solvates, hydrates, and N-oxides thereof is selected from the following compound and pharmaceutically acceptable salts, solvates, and hydrates thereof:

Compound 696: (1aS,5aS)-2-Pyrazin-2-yl-1$^a$,2,5,5$^a$-tetrahydro-1H-2,3-diaza-cyclopropa[a]pentalene-4-carboxylic acid ((S)-1-hydroxymethyl-2,2-dimethyl-propyl)-amide.

15. The pharmaceutical composition according to claim 1, wherein the compound selected from compounds of Formula Ia and pharmaceutically acceptable salts, solvates, hydrates, and N-oxides thereof is selected from the following compound and pharmaceutically acceptable salts, solvates, and hydrates thereof:

Compound 699: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

16. The pharmaceutical composition according to claim 1, wherein the compound selected from compounds of Formula Ia and pharmaceutically acceptable salts, solvates, hydrates, and N-oxides is an anhydrous crystalline form of:

Compound 699: (1aS,5aS)-2-(4-Oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

17. The pharmaceutical composition according to claim 1, wherein the compound selected from compounds of Formula Ia and pharmaceutically acceptable salts, solvates, hydrates, and N-oxides thereof is selected from the following compound and pharmaceutically acceptable salts, solvates, and hydrates thereof:

Compound 764: (1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclopropyl)-amide.

18. The pharmaceutical composition according to claim 1, wherein the compound selected from compounds of Formula Ia and pharmaceutically acceptable salts, solvates, hydrates, and N-oxides thereof is selected from the following compound and pharmaceutically acceptable salts, solvates, and hydrates thereof:

Compound 765: (1aS,5aS)-2-(4-Oxy-pyrazin-2-yl)-1a,2,5,5a-tetrahydro-1H-2,3-diaza-cyclopropa[a]pentalene-4-carboxylic acid (1-trifluoromethyl-cyclobutyl)-amide.

19. The pharmaceutical composition according to claim 1, wherein the compound selected from compounds of Formula Ia and pharmaceutically acceptable salts, solvates, hydrates, and N-oxides thereof is selected from the following compound and pharmaceutically acceptable salts, solvates, and hydrates thereof:

Compound 921: (1aS,5aS)-2-(4-Oxy-pyrazin-2-yl)-1a,2,5,5a-tetrahydro-1H-2,3-diaza-cyclopropa[a]pentalene-4-carboxylic acid ((1S,2R)-2-hydroxy-indan-1-yl)-amide.

20. The pharmaceutical composition according to claim 1, wherein the compound selected from compounds of Formula Ia and pharmaceutically acceptable salts, solvates, hydrates, and N-oxides thereof is selected from the following compound and pharmaceutically acceptable salts, solvates, and hydrates thereof:

Compound 926: (1aS,5aS)-2-Pyrazin-2-yl-1a,2,5,5a-tetrahydro-1H-2,3-diaza-cyclopropa[a]pentalene-4-carboxylic acid (1-trifluoromethyl-cyclobutyl)-amide.

\* \* \* \* \*